United States Patent
Chorn et al.

(10) Patent No.: US 9,732,342 B2
(45) Date of Patent: Aug. 15, 2017

(54) SEGMENTED MICRO RNA MIMETICS

(71) Applicant: SIRNA THERAPEUTICS, INC., Cambridge, MA (US)

(72) Inventors: Guillaume Chorn, San Francisco, CA (US); Lee Lim, San Francisco, CA (US); Lihong Zhao, Walnut Creek, CA (US)

(73) Assignee: SIRNA THERAPEUTICS, INC., Cambridge, MA (US)

(*) Notice: Subject to any disclaimer, the term of this patent is extended or adjusted under 35 U.S.C. 154(b) by 0 days.

(21) Appl. No.: 14/747,264

(22) Filed: Jun. 23, 2015

(65) Prior Publication Data

US 2015/0376613 A1 Dec. 31, 2015

Related U.S. Application Data

(63) Continuation of application No. 13/391,703, filed as application No. PCT/US2010/046551 on Aug. 24, 2010, now Pat. No. 9,096,850.

(60) Provisional application No. 61/236,486, filed on Aug. 24, 2009.

(51) Int. Cl.
  *C12N 15/11* (2006.01)
  *C12N 15/113* (2010.01)

(52) U.S. Cl.
  CPC .......... *C12N 15/113* (2013.01); *C12N 15/111* (2013.01); *C12N 15/1138* (2013.01); *C12N 2310/113* (2013.01); *C12N 2310/141* (2013.01); *C12N 2310/3231* (2013.01); *C12N 2310/33* (2013.01); *C12N 2310/332* (2013.01); *C12N 2310/3517* (2013.01); *C12N 2310/533* (2013.01); *C12N 2320/51* (2013.01); *C12N 2320/52* (2013.01)

(58) Field of Classification Search
None
See application file for complete search history.

(56) References Cited

U.S. PATENT DOCUMENTS

| | | |
|---|---|---|
| 2005/0059005 A1 | 3/2005 | Tuschl et al. |
| 2007/0275921 A1 | 11/2007 | Swayze et al. |
| 2008/0085869 A1* | 4/2008 | Yamada ............... C07H 19/00 514/44 A |
| 2009/0182136 A1 | 7/2009 | Wengel et al. |
| 2010/0022618 A1* | 1/2010 | Liang .................... C12N 15/111 514/44 A |

FOREIGN PATENT DOCUMENTS

| | | |
|---|---|---|
| WO | 2007017162 A2 | 2/2007 |
| WO | 2007056153 A2 | 5/2007 |
| WO | 2008049078 A1 | 4/2008 |

OTHER PUBLICATIONS

Bramsen, JB et al., Nucleic Acids Research, vol. 35, No. 17, (2007), pp. 5886-5897, "Improved silencing properties using small internally segmented interfering RNAs".
International Preliminary Report on Patentability from International Application No. PCT/US2010/046551 dated Feb. 28, 2012.
International Search Report for PCT/US2010/046551 dated Nov. 23, 2010.
Leuschner, PJ et al., EMBO Reports, vol. 7, No. 3 (2006), pp. 314-320, "Cleavage of the siRNA passenger strand during RISC assembly in human cells".

* cited by examiner

*Primary Examiner* — Kate Poliakova-Georgantas
(74) *Attorney, Agent, or Firm* — Lando & Anastasi, LLP

(57) ABSTRACT

This invention relates generally to segmented oligonucleotides capable of modulating gene expression. Specifically, the instant invention relates to segmented microRNA (miRNA) oligonucleotides, including segmented miRNA precursors and segmented pre-microRNAs. The invention also relates to compositions comprising such segmented oligonucleotides, as well as to methods of making and using such oligonucleotides for diagnosis and treatment of diseases associated or causally linked to aberrant levels or activities of gene expression, including aberrant levels of coding and/or non-coding RNA.

19 Claims, 33 Drawing Sheets

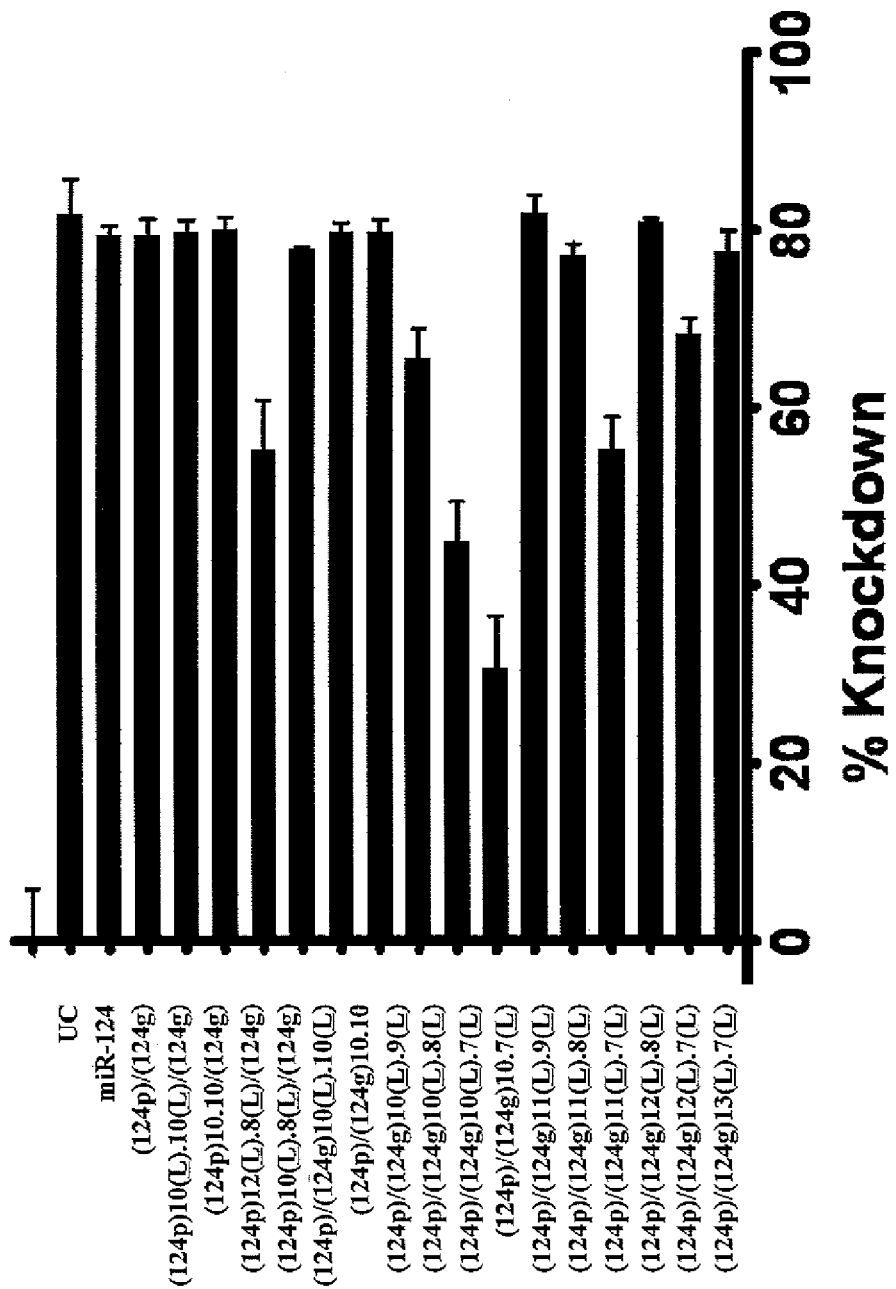
Figure 7 – Knockdown of CD164 by segmented miR-124

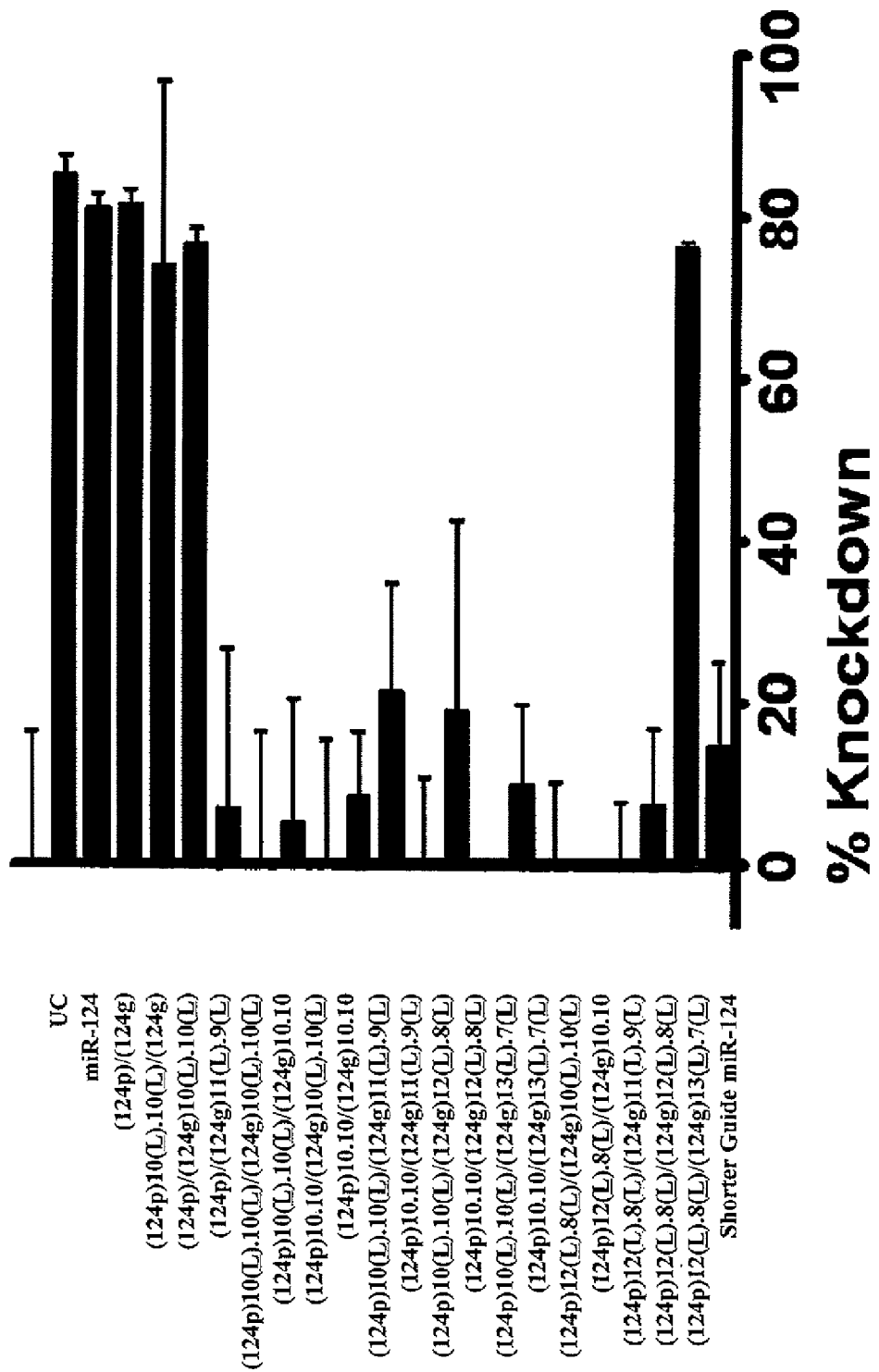
Figure 8 – Knockdown of VAMP3 by segmented miR-124

Knockdown of CD164 by segmented miR-124 but not by segmented miR-34

Knockdown of TK1 by segmented miR-34 but not by segmented miR-124

Knockdown of CD164 by segmented miR-124 comprising inverted abasic internal ends Knockdown of VAMP3 by segmented miR-124 comprising inverted abasic internal ends Knockdown of CD164 by segmented miR-124 comprising abasic-filled gaps

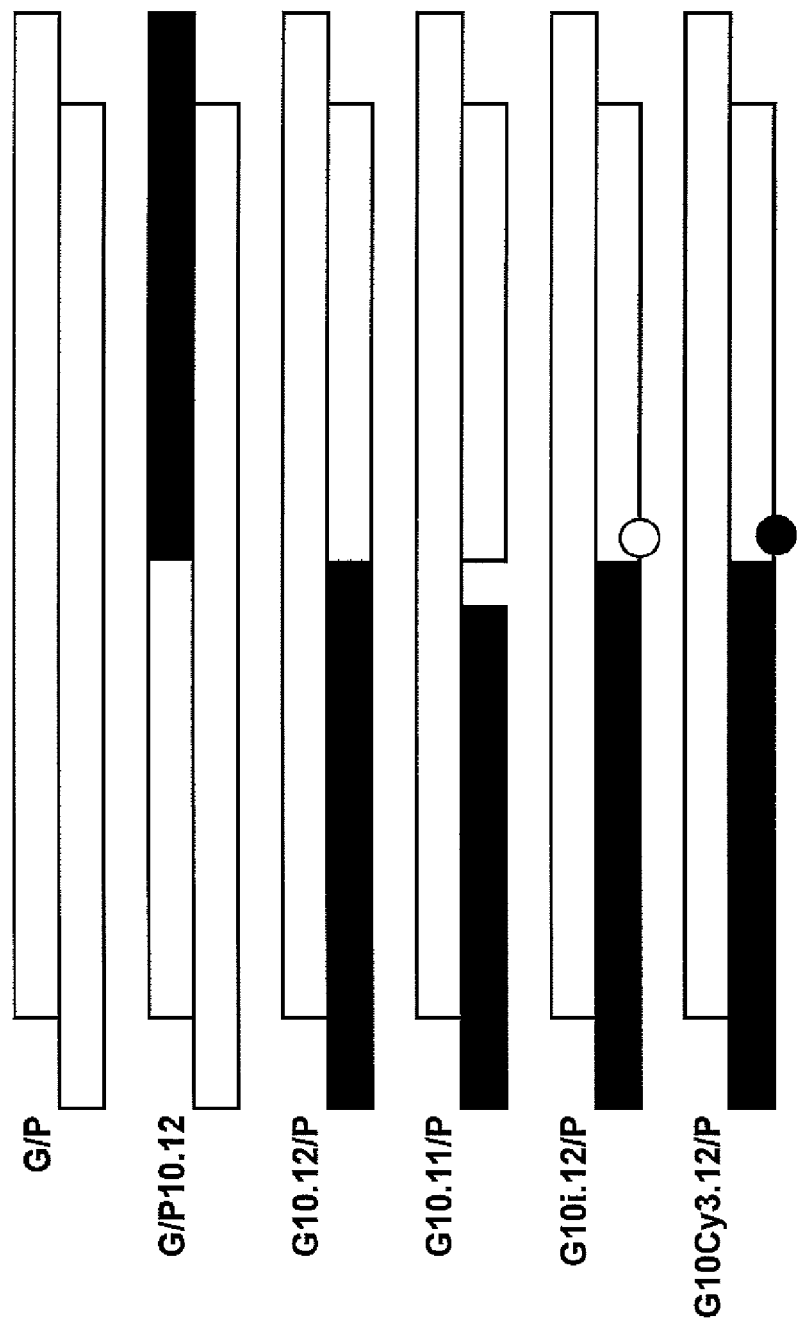

Figure 12B

KD of CD164 by Segmented miR-124

2xFL
```
UCGAGCAUAUACUGGCAUUCACCGGCGUGCCCUUAAUUGUUUAAAA    SEQ ID NO: 1308
              ||||||||||||||||||
           ACCGUAAGUGGGCGCACGGAAUU                 SEQ ID NO: 1091
```

2x7a
```
UCGAGCAUAUACUUAAUGUUUUCAAACGCCCUUAAUUGUUUAAAA     SEQ ID NO: 1309
                        ||||||||
           ACCGUAAGUGGGCGCACGGAAUU                 SEQ ID NO: 1091
```

2x7aMutant
```
UCGAGCAUAUACUUAAUGUUUUCAAACGCUUAAUUGUUUAAAA       SEQ ID NO: 1310
                        ||||
           ACCGUAAGUGGGCGCACGGAAUU                 SEQ ID NO: 1091
```

2x7a3p
```
UCGAGCAUAUACUUAAUUUCACCAAACGCCCUUAAUUGUUUAAAA     SEQ ID NO: 1310
              ||||    ||||||
           ACCGUAAGUGGGCGCACGGAAUU                 SEQ ID NO: 1091
```

SEGMENTED MICRO RNA MIMETICS

PRIORITY APPLICATIONS

This application is a continuation of U.S. patent application Ser. No. 13/391,703, filed Aug. 24, 2010, which is a National Stage Entry of PCT Application No. PCT/US10/46551, filed Aug. 24, 2010 which claims the benefit of U.S. Patent Application No. 61/236,486 filed Aug. 24, 2009.

TECHNICAL FIELD

This invention relates generally to segmented oligonucleotides capable of modulating gene expression. Specifically, the instant invention relates to segmented microRNA (miRNA) mimetic oligonucleotides, including segmented miRNA precursors and segmented pre-microRNAs. The invention also relates to compositions comprising such segmented oligonucleotides, as well as to methods of making and using such oligonucleotides for diagnosis and treatment of diseases associated or causally linked to aberrant levels or activities of gene expression, including aberrant levels of coding and/or non-coding RNA.

BACKGROUND

Segmented oligonucleotides based on short interfering RNA (siRNA) have been evaluated for RNA interference (RNAi) activity. Leuschner et al., (2006 EMBO 7:314) described an RNA-induced silencing complex which has a discontinued passenger (or sense) strand and a 2'-0-methyl modified nucleotide at position 9 of the passenger strand (5' to 3'), the natural cleavage site. Bramsen et al., (2007 Nucleic Acids Res. 35:5886) described an RNAi-active siRNA molecule comprising an internally segmented passenger strand, where the nick or gap is not necessarily located at the natural cleavage site, stabilized with locked nucleic acid (LNA) modifications at a number of positions. See also, e.g., Wengel et al., PCT Publication WO 2007/107162 A2; Quay et al., PCT Publication WO 2008/049078. None of Leuschner, Bramsen, Wengel and Quay described RNAi-active molecules having discontinued guide (or antisense) strands. In fact, Bramsen and Wengel indicated that duplexes designed to contain discontinuities in the guide strands completely eliminated silencing of the target.

The mechanistic difference between miRNA-mediated RNAi and siRNA-mediated RNAi can make certain modifications and/or designs suitable for one but not the other. Thus, there remains a heightened interest in formulating new and advantageous design features suitable for miRNA mimetics.

SUMMARY OF THE INVENTION

The specification describes certain segmented double-stranded miRNA mimetics having at least one non-contiguous (or discontinuous) strand comprising a miRNA sequence, which can be introduced or applied to cells, tissues, and/or organisms to mediate RNAi. These molecules are referred to herein as segmented miRNA mimetics, which comprise a guide strand and a passenger strand. The guide strand comprises at least two contiguous stretches of nucleotides separated by a discontinuity. The passenger strand can be fully contiguous, or alternatively can also comprise at least two contiguous stretches of nucleotides separated by a discontinuity. Segmented miRNA mimetics of the invention therefore have at least one non-contiguous guide strand comprising one or more miRNA sequences, or a portion thereof, including the seed sequence of such miRNA sequences. Non-limiting examples of miRNA sequences are those selected from the miRBase as of the filing date of the present invention; see for example Griffiths-Jones (2006) miRBase: the microRNA sequence database. *Methods in Molecular Biology* 342: 129-138 and miRBase release 13.0; http://micrirna.sanger.ac.uk/. A segmented miRNA of the invention therefore can include one or more miRNA sequences selected from SEQ ID NOs: 1-1090 of Table I, including portions thereof, such as the seed sequences.

A segmented miRNA mimetic of the invention comprises at least one discontinuity in the guide strand, and optionally at least one discontinuity in the passenger strand that can be the same or different as the discontinuity in the guide strand. Such discontinuities include nicks, gaps, substitutions, and/or insertions. Segmented miRNA mimetic can comprise mixtures of different discontinuities in one or both strands.

A segmented miRNA mimetic of the invention comprises about 12 to about 26 nucleotides in each strand, and further comprises about 10 to about 26 base pairs between the strands. Thus, a prototypical segmented miRNA mimetic of the invention generally comprises two strands having complementarity to form a duplex, each strand having between about 12 to about 26 nucleotides, wherein the guide strand comprises any of SEQ ID NOs: 1-1090 or a portion thereof, and wherein the guide strand further comprises at least on discontinuity.

Segmented miRNA mimetics of the invention can be administered to a cell, a tissue or an organism to supplement or increase the levels of their corresponding endogenous miRNAs and hence potentiate RNAi activity against their corresponding miRNAs targets. Because each endogenous miRNA typically has multiple targets, an exogenously introduced segmented miRNA mimetic of the invention does not necessarily share the same number, identity or type of targets with its corresponding endogenous miRNA. However, the exogenously-introduced segmented miRNA mimetic exerts activity on at least one (i.e., one or more or all) of the targets of its corresponding endogenous miRNA.

A segmented miRNA mimetic can be chemically modified at the nucleic acid base, phosphodiester backbone, or sugar to achieve, for instance, increased stability and/or reduced immunogenicity, and other pharmaceutically desirable attributes, including properties that would allow for enhanced delivery or lower toxicity. Methods of chemically modifying oligonucleotides to achieve such ends are known in the art. For instance, numerous such methods are set forth in McSwiggen, et al., U.S. Publication No. 2006/0211642.

In a further aspect, the specification provides a composition comprising one or more (i.e., in the number of individual molecules and/or in types) segmented mlRNA mimetics in a pharmaceutically acceptable carrier or diluent. In another aspect, the specification provides a method of introducing or applying one or more segmented miRNA mimetics to cells (regardless of whether the RNAi or other gene modulation process takes place inside the cells, outside the cells, or on the cell-membrane), tissues, organisms, or reconstituted in vitro systems, to increase the levels of corresponding endogenous miRNAs. Embodiments of the invention include methods of modulating gene expression, biologic pathways, or physiologic pathways in cells, cultures, tissues, or organisms such as subjects or patients, comprising administering one or more segmented miRNA mimetics of the invention in an amount that is sufficient to modulate the expression of one or more genes that are regulated by the corresponding endogenous miRNAs. In a specific embodiment, more than one type of segmented miRNA mimetic is administered. For example, a number of different segmented miRNA mimetics of the invention can be administered concurrently, in sequence, or in an ordered progression.

In certain embodiments, administration of the composition(s) can be enteral or parenteral. In certain aspects, enteral administration is oral. In further aspects, parenteral administration is intralesional, intravascular, intracranial, intrapleural, intratumoral, intraperitoneal, intramuscular, intralymphatic, intraglandular, subcutaneous, topical, intracronchial, intratracheal, intranasal, inhaled, or instilled. Compositions of the invention can be administered regionally or locally, and not necessarily directed into a lesion.

Embodiments of the invention can include obtaining or assessing a gene expression profile or miRNA profile of a target cell, tissue, or organism prior to selecting the mode of treatment, by, for example, administration of one or more segmented miRNA mimetics. In certain aspects of the invention, one or more segmented miRNA mimetics can modulate a single gene. In a further aspect, one or more genes in one or more genetic, cellular, or biologic/physiologic pathways can be modulated by a single segmented miRNA mimetic or a complement thereof, alone or in combination with other miRNAs or mimetics, or with other nucleic acid-based gene modulators, such as siRNAs, antisense molecules, ribozyme molecules, and the like.

A further aspect of the invention is directed to a method of modulating a cellular pathway comprising administering to the cell an amount of a segmented miRNA mimetic, alone or in combination with other miRNAs, mimetics, siRNAs, or other suitable nucleic-acid based or non-nucleic acid based agents capable of modulating one or more relevant genes in the same or associated pathways. In a related aspect, the invention is directed to methods of modulating a cellular pathway comprising administering to the cell a segmented miRNA mimetic in an amount sufficient to modulate the gene expression, function, status, or state of a cellular pathway, in particular a pathway that is known to include one or more genes associated with the corresponding endogenous miRNA. Modulation of a cellular pathway includes, but is not limited to, modulating the expression of one or more genes associated with the pathway. Modulation of a gene includes inhibiting its function, also called "down-regulate a gene," or providing an agonist to augment its functional, also called "up-regulating a gene." What is modulated is either the expression level or activity of a gene or its related gene product or protein.

Compositions and methods comprising a segmented miRNA mimetic are also useful for treating diseases or disorders associated with aberrant expression levels or activity of one or more corresponding miRNA targets. These diseases and/or disorders include, for example, hyperproliferative disorders (e.g., cancer), inflammatory conditions (e.g., arthritis), respiratory diseases, pulmonary diseases, cardiovascular diseases, autoimmune diseases, allergic disorders, neurologic diseases, infectious diseases (e.g., viral infections), renal diseases, transplant rejections, or any other conditions that respond to such modulation.

Still a further embodiment includes methods of treating a patient with a pathological condition comprising one or more steps: (a) administering to the patient an isolated or a synthetic segmented miRNA mimetic of the invention in an amount sufficient to modulate the expression of a cellular pathway; and (b) administering a second therapy, wherein the modulation of the cellular pathway in (a) sensitizes the patient to the second therapy. A cellular pathway can include, but is not limited to, one or more pathways that are known to be associated with known miRNAs listed in the miRBase as of the date of filing of the instant application. A second therapy can include administration of one or more miRNAs or mimetics targeting the same or different mRNAs, or one or more other therapeutic nucleic acids. A second therapy can also be one selected from other standard therapies, such as chemotherapy, radiation therapy, drug therapy, immunotherapy, and the like.

The invention also features a kit or article of manufacture comprising one or more segmented miRNA mimetics, typically in a pharmaceutical composition, and instructions for administering the composition to treat a pathological condition. Optionally, the kit or article of manufacture can contain one or more other pharmaceutical compositions or agents and instructions for their use in conjunction with the pharmaceutical composition comprising the segmented miRNA mimetics.

In yet a further aspect of the invention, one or more segmented miRNA mimetics of the invention can be included in a kit or article of manufacture for assessment or diagnosing of a pathological condition or the risk of developing a pathological condition.

It is contemplated that any method or composition described herein can be implemented with respect to any other method or composition described herein and that different embodiments can be combined.

BRIEF DESCRIPTION OF THE DRAWINGS

FIGS. 1-6 illustrate examples of different structural features of segmented miRNA mimetics. It will be apparent to the skilled person in the art that the various structural features illustrated in these figures can be combined. For example, a particular pattern of the overhangs can be combined with a molecule comprising one or more discontinuities at particular positions, which can or can not be linked, by phosphodiester bonds or non-phosphodiester connectors. Therefore, these figures should be interpreted as merely representative but non-limiting, such that, for example, the nature and position of the discontinuities can be changed and additional features, such as, for example, overhangs and nucleotide analogs, can be introduced to the same molecules.

FIG. 1A shows 3 representative segmented miRNA mimetics, comprising nicks or gaps in the guide (the lower strand), or in both the passenger (upper strand) and the guide strands. Each box represents a nucleotide (including a nucleotide analog), or a non-nucleotide substitute moiety. Each line connecting the boxes represents a phosphodiester bond or non-phosphodiester connector. Distinct contiguous stretches of nucleotides in a given strand are colored/shaded differently to facilitate the identification of the nick or gap positions. FIG. 1B shows a representative conformation of a segmented miRNA mimetic, wherein the passenger strand is uninterrupted and wherein the guide strand comprises a gap of 1 nucleotide. A similar motif comprising a nick instead of a gap is contemplated by the instant invention. FIG. 1C shows a representative segmented miRNA mimetic wherein each of the passenger strand and the guide strand comprises a nick. Some of the discontinuities in this figure are shown as nicks. However, those skilled in the art would appreciate that gaps can be present at similar positions, and other types of discontinuities such as substitutions and insertions are also contemplated. Moreover, those skilled in the art would appreciate that a gap can be a stretch of 1 to about 10 contiguous vacant nucleotide positions.

FIG. 3 illustrates that one or more discontinuities (nicks or gaps are shown, but also substitutions and insertions) can be present in the guide strand, or in both the passenger and the guide strands.

FIG. 5 illustrates that one or more suitable non-nucleotide substitutions or insertions can be used to connect a pair of neighboring contiguous stretches of nucleotides in the passenger strand, the guide strand, or both the passenger and guide strands.

FIG. 6 illustrates certain segmented miRNA mimetics comprising inverted abasic modifications at the internal ends. The molecules are named according to the starting and ending positions of the discontinuities.

FIGS. 7-20 show experimental data obtained from the examples herein.

FIG. 7 illustrates RNAi activity against an endogenous miR-124 target, CD164. RNAi activity of various segmented miRNA mimetics derived from miR-124 ("segmented miR-124") was measured. Levels of knockdown achieved by the segmented miR-124 constructs and by the corresponding non-segmented miR-124 mimetic, comprising the endogenous mature miR-124 sequence as its guide strand, were determined. The segmented miR-124 constructs can comprise one or more locked nucleic acid ("LNA") nucleotides in one or both strands, each represented by an underlined nucleotide in Table III herein, although the LNAs are not necessarily placed at the underlined nucleotide positions.

FIG. 8 illustrates RNAi activity against another endogenous miR-124 target, VAMP3. RNAi activity of various segmented miR-124 mimetics was measured. Levels of knockdown achieved by the segmented miR-124 constructs and by the corresponding non-segmented miR-124 mimetic, comprising the endogenous mature miR-124 sequence as its guide strand, were determined. The segmented miR-124 constructs can comprise one or more LNA nucleotides in one or both strands, each represented by an underlined nucleotide in Table IV herein, although the LNAs are not necessarily placed at the underlined nucleotide positions.

FIGS. 12A and 12B demonstrate that miR-124 activity tolerates segmentation of the passenger or guide strands. FIG. 12A includes schematic illustrations of miR-124 duplex designs, wherein the top strand represents the passenger strand and the bottom strand represents the guide strand. The gray-shade change indicates the site of a break in the strand backbone. The dark gray circle in the G10Cy3.12/P schematic represents a 5'-Cy3 label, and the light gray circle in the G10i.12/P schematic indicates a 5' inverted abasic nucleotide. FIG. 12B illustrates the dose-dependent response of CD164, a known miR-124 target, to various concentrations of the designs shown in FIG. 12A in HCT-116 cells as measured by RT-qPCR. UC3 corresponds to the negative control oligomer. EC50s for each curve are as follows: G/P, 0.12 nM; G/P10.12, 0.29 nm; G10.12/P, 0.22 nM; G10.11/P, 0.53 nM; G10i.12/P, 0.21 nM: G10Cy3.12/P, 0.45 nm.

FIG. 13A is a graphic illustration of the microarray signature 24 hours after transfection of 10 nM G10.12/P, plotted as expression ratio (relative to mock transfection) versus fluorescence intensity. Significantly down regulated probes (P<1e-6) are seen as gray data points below the black data points and unregulated probes are seen as gray data points above the black data points. Hypergeometric analysis of the hexamer content of the down regulated UTRs showed that the most significantly enriched hexamer (P<1e-20) was GCCTTA, corresponding to positions 2-7 of the transfected miR-124. FIG. 13B provides a comparison of gene expression data from G10.12/P transfected cells and G/P transfected cells. Expression ratio of the G/P transfection versus the mock transfection is plotted on the x-axis and the G10.12/P expression ratio versus mock transfection on the y-axis. The weighted correlation coefficient was calculated as 0.9, illustrating the similar effects of both RNA complexes on gene expression.

FIGS. 14A, 14B, 14C, and 14D illustrate that the activity of an unsegmented miR-124 guide strand is enhanced by additional complementarity beyond the seed sequence, but activity of a segmented guide strand is not. FIG. 14A is a schematic of miR-124 target sites that were duplicated and inserted into dual luciferase reporter vectors. FIG. 14B illustrates that G/P miR-124 exhibits suppression of activity from a reporter with a seed sequence match, which is enhanced by reporters containing additional complementarity to the 3' end of the guide strand (2×7a3p) or full-length complementarity. The EC50s for the curves: 2×7a, 0.39 nM; 2×7a3p, 0.08 nM; 2×FL, 0.09 nM. The EC50s for the curves are: 2×7a, 0.41 nM; 2×7a3p, 0.06 nM; 2×FL, 0.09 nM. FIG. 14C illustrates that segmentation of the passenger strand preserves the trends seen in FIG. 14B. FIG. 14D shows that activity from reporters with 3' complementarity is identical to that observed from the seed-only reporter when the guide strand is segmented. The EC50s for the curves are: 2×7a, 0.89 nM; 2×7a3p, 0.61 nM; 2×FL, 0.80 nM.

FIG. 15A is a miR-124 precursor schematic. FIG. 15B is a graph showing CD164 knockdown as measured by RT-qPCR. Activity of the unsegmented precursor is comparable to that of the mature miRNA, while activity of the segmented precursor is reduced but is significantly above background. The EC50s for the curves are: G/P, 0.14 nM; hairpin precursor, 0.31 nM; segmented precursor, 1.48 nM.

FIG. 16 illustrates that a segmented guide strand exhibits decreased knockdown for targets containing 3' supplementary pairing. Microarray data shown in FIG. 13B was further analyzed, specifically to analyze 1057 downregulated genes that contain TargetScan seed matches. The TargetScan 3' pairing score was then calculated for these genes, and the downregulation of the top quartile of 3' scores (containing a high degree of 3' pairing) was compared with the downregulation of the bottom quartile of 3' scores. The cumulative distribution of the difference in downregulation (between G/P and G10.10/P) is plotted for the top and bottom quartiles. A Kolmogorov-Smirnov test (p=0.02) shows that the top quartile of genes shows less knockdown in G10.10/P versus G/P, as compared with the bottom quartile.

FIG. 17A illustrates knockdown of CD164 expression by segmented miR-124 mimetics comprising deletions and c3 or c6 substitutions, while

FIG. 18A illustrates knockdown of CD164 expression by segmented miR-124 comprising c3 substitutions, while

FIG. 19A illustrates knockdown of CD164 expression by segmented miR-124 comprising c6 substitutions, while

FIG. 20A illustrates knockdown of CD164 expression by segmented miR-124 comprising c3 and c6 insertions, while

DETAILED DESCRIPTION OF THE INVENTION

Definitions

Figure 1A:
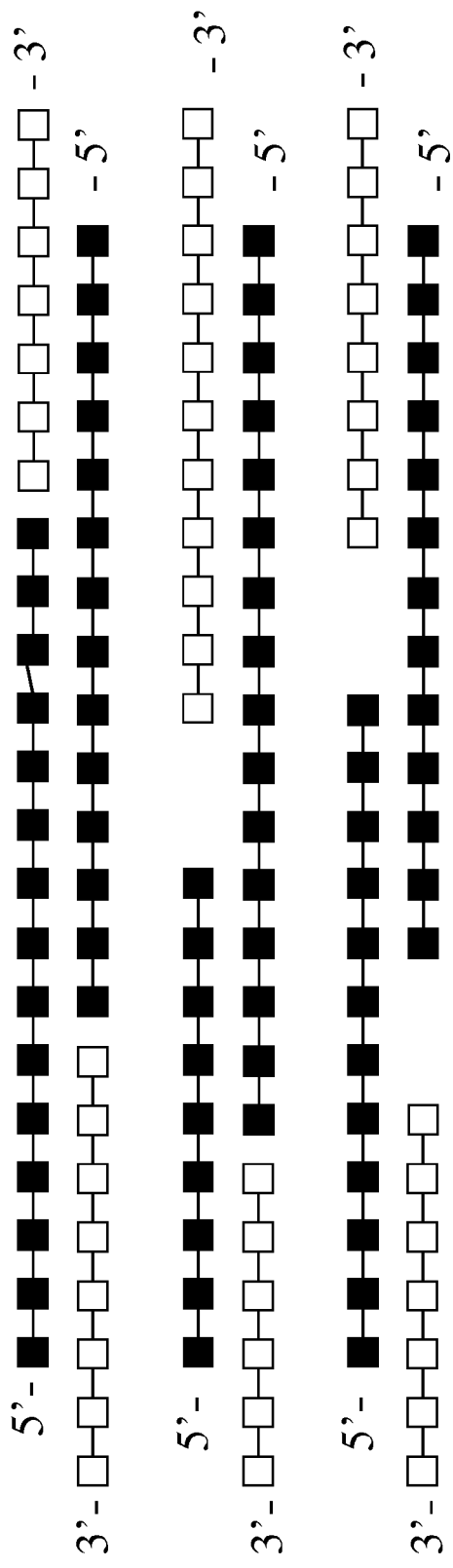
FIGS. 1A, 1B, and 1C illustrate the basic structural features of a segmented miRNA mimetic.
Figure 1B:
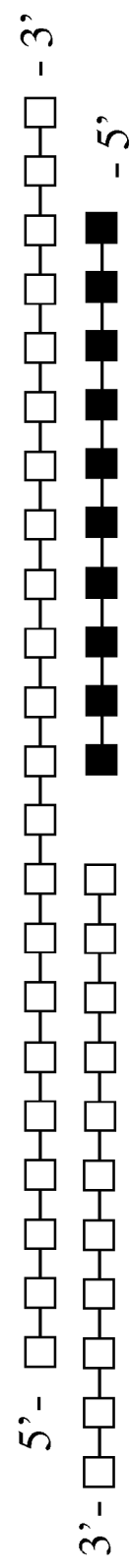
Figure 1C:
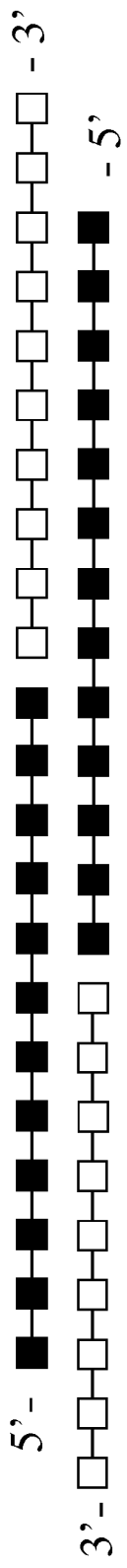
Figure 2A:
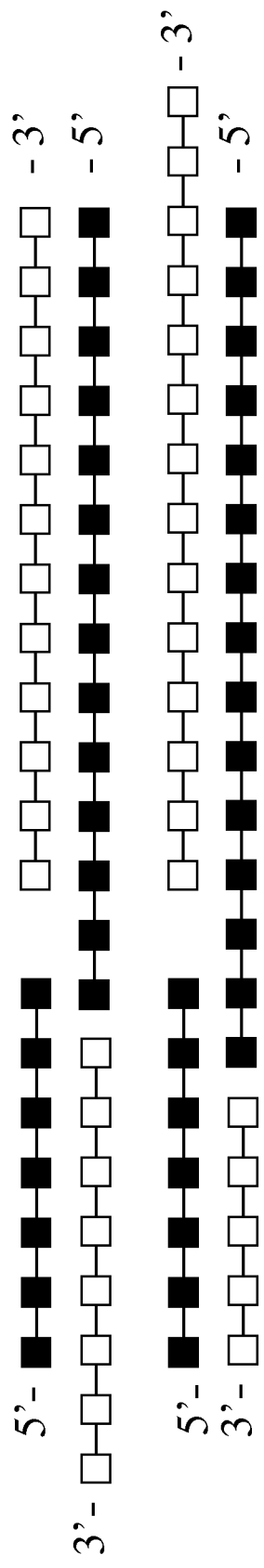
FIG. 2A illustrates various overhangs and blunt ends can be utilized in the design of a segmented miRNA mimetic of the invention. The discontinuities are shown in this figure as nicks or gaps of a single nucleotide, but other kinds of discontinuities, including larger gaps of one or more (e.g., up to 10) nucleotides, as well as substitutions and/or insertions are also contemplated.
Figure 2B:
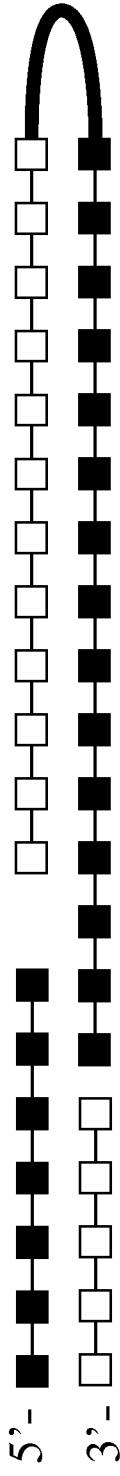
FIG. 2B illustrates a representative segmented miRNA mimetic wherein one set of the terminal ends are connected by a linker.
Figure 3:
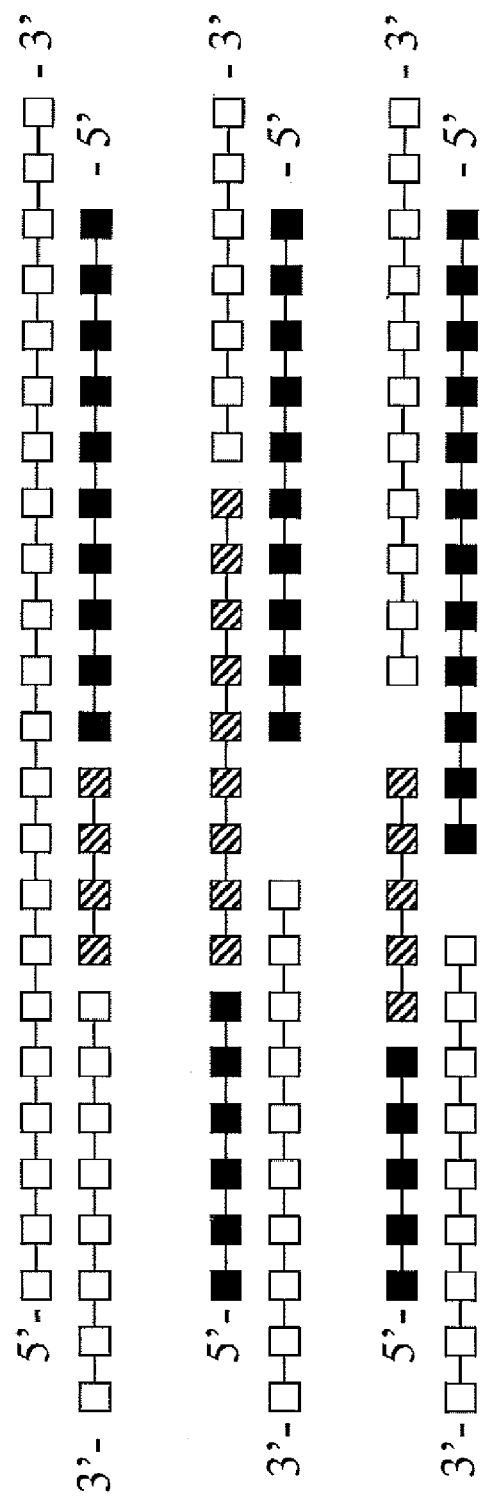
Figure 4A:
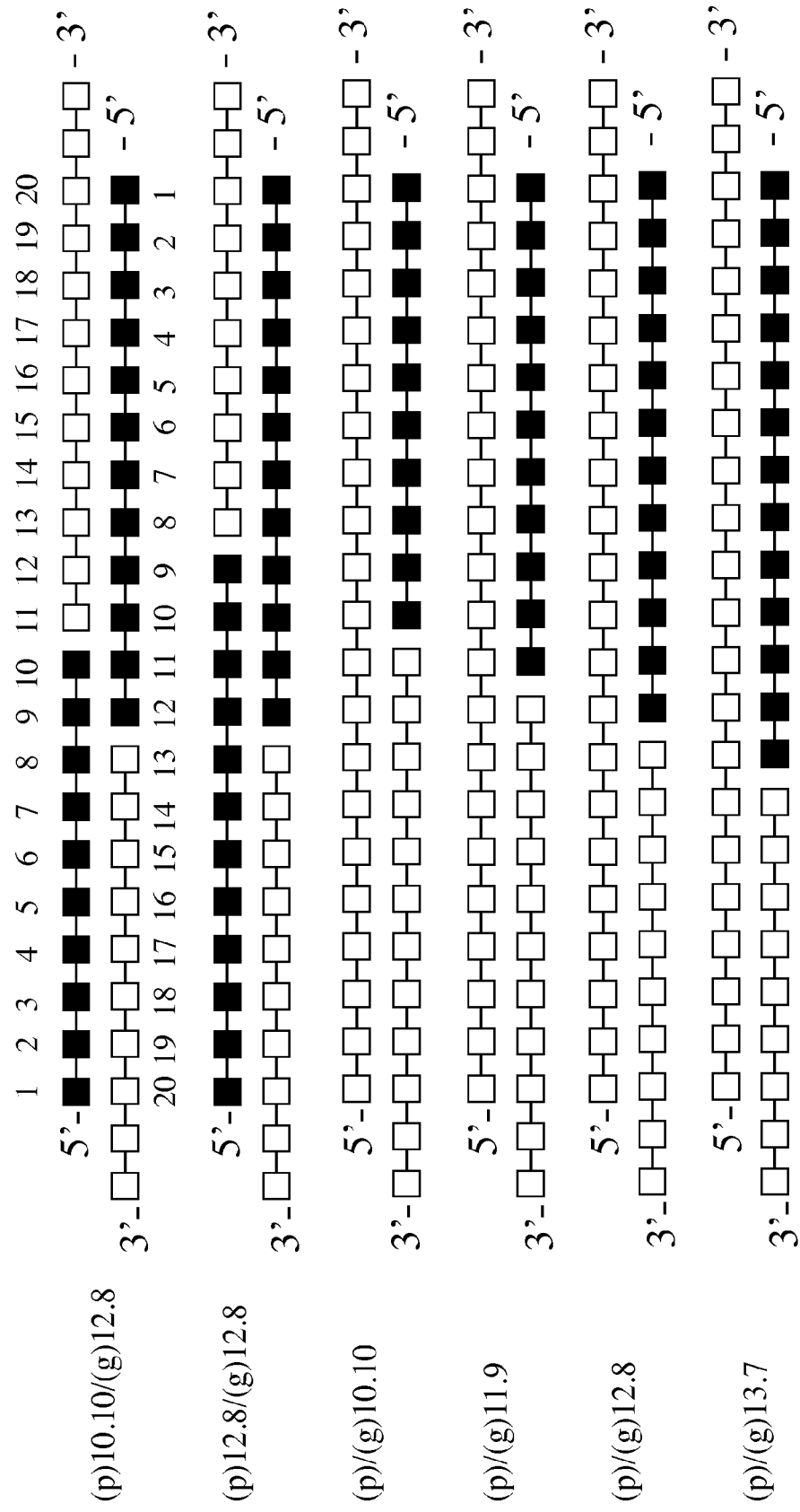
FIGS. 4A and 4B illustrate that the sizes or positions of the discontinuities on the guide strand, or both the passenger and guide strands can vary. The molecules are named according to the starting and ending positions of the discontinuities from the 5'-end.
Figure 4B:
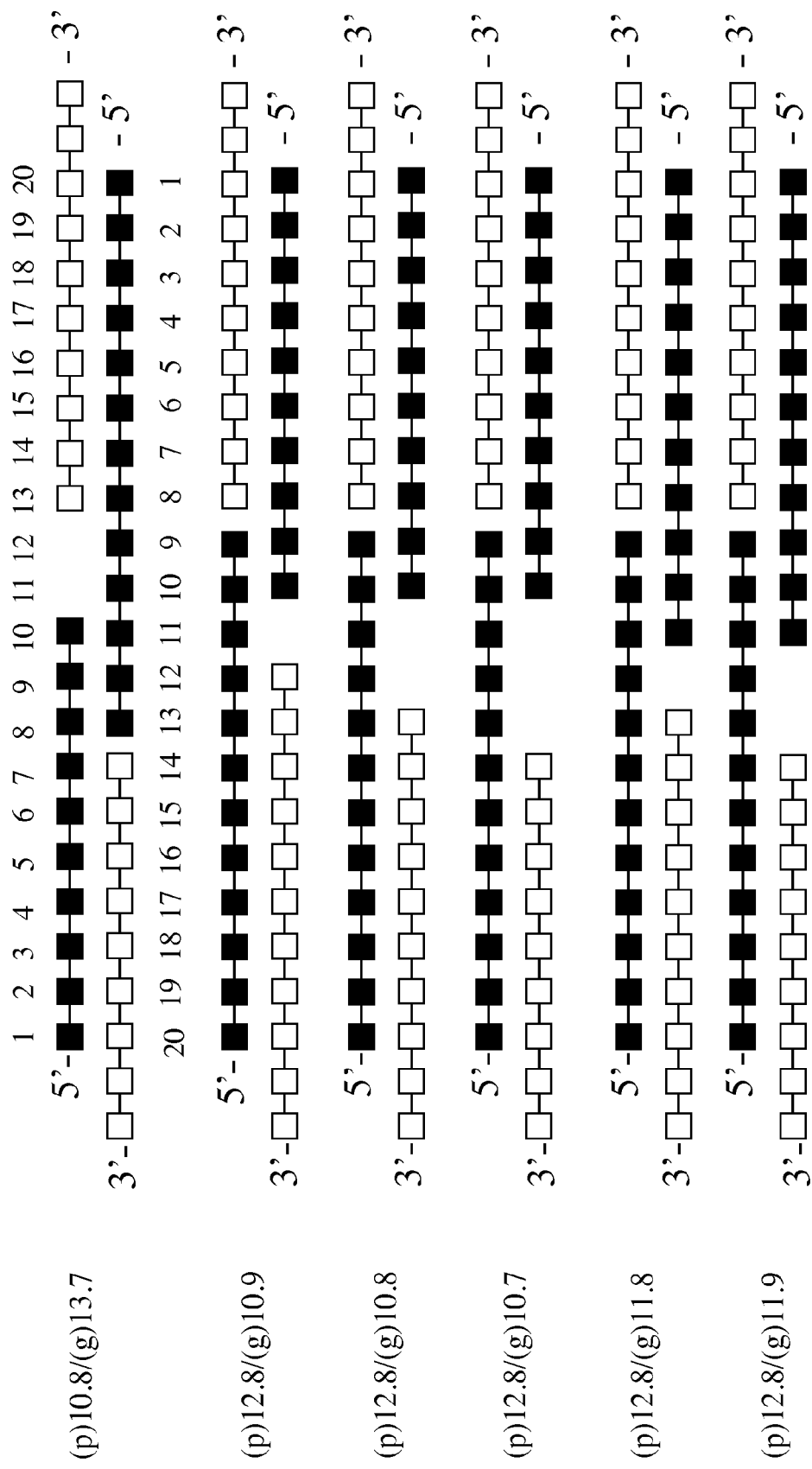
Figure 5:
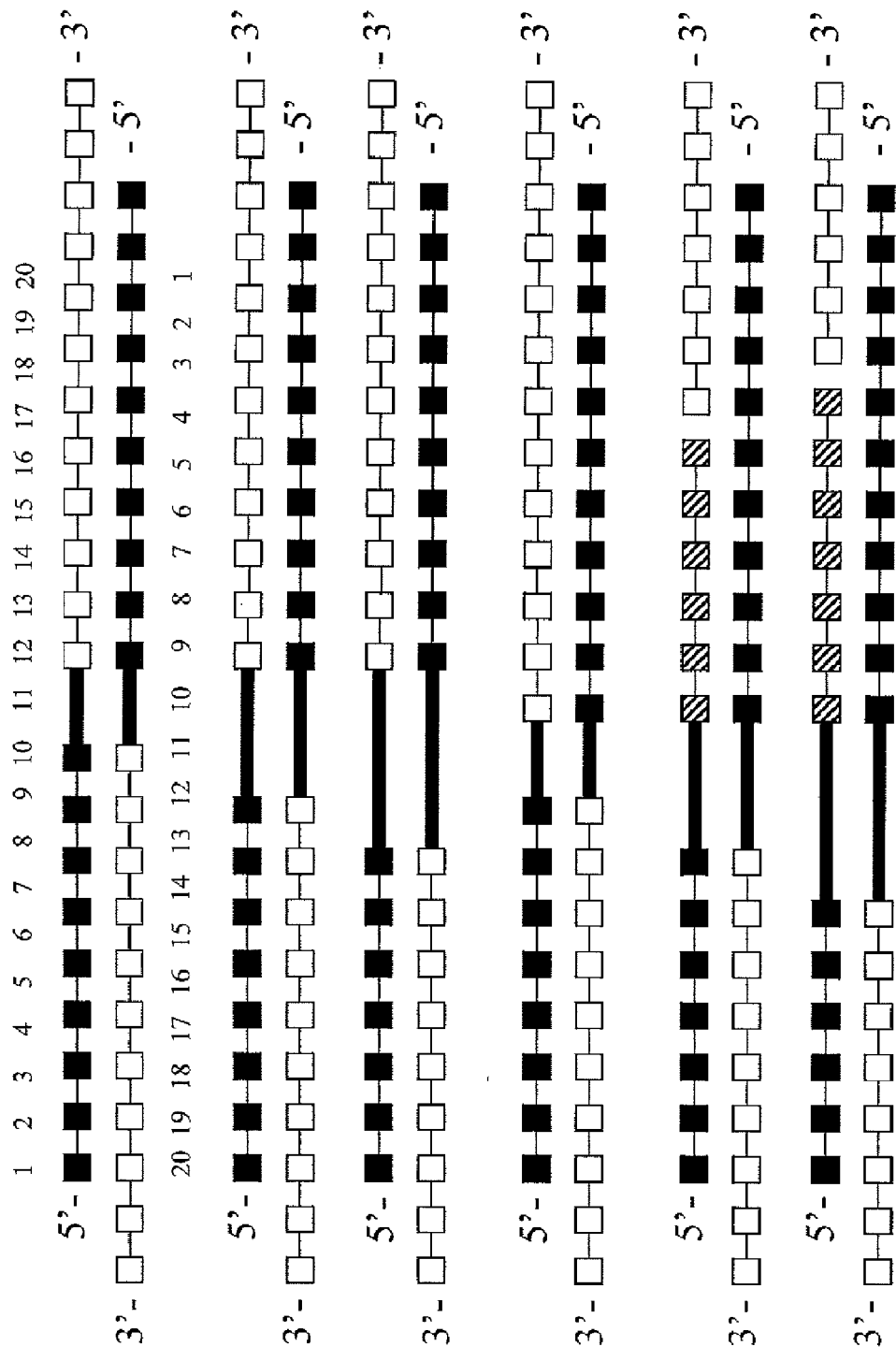
Figure 6:
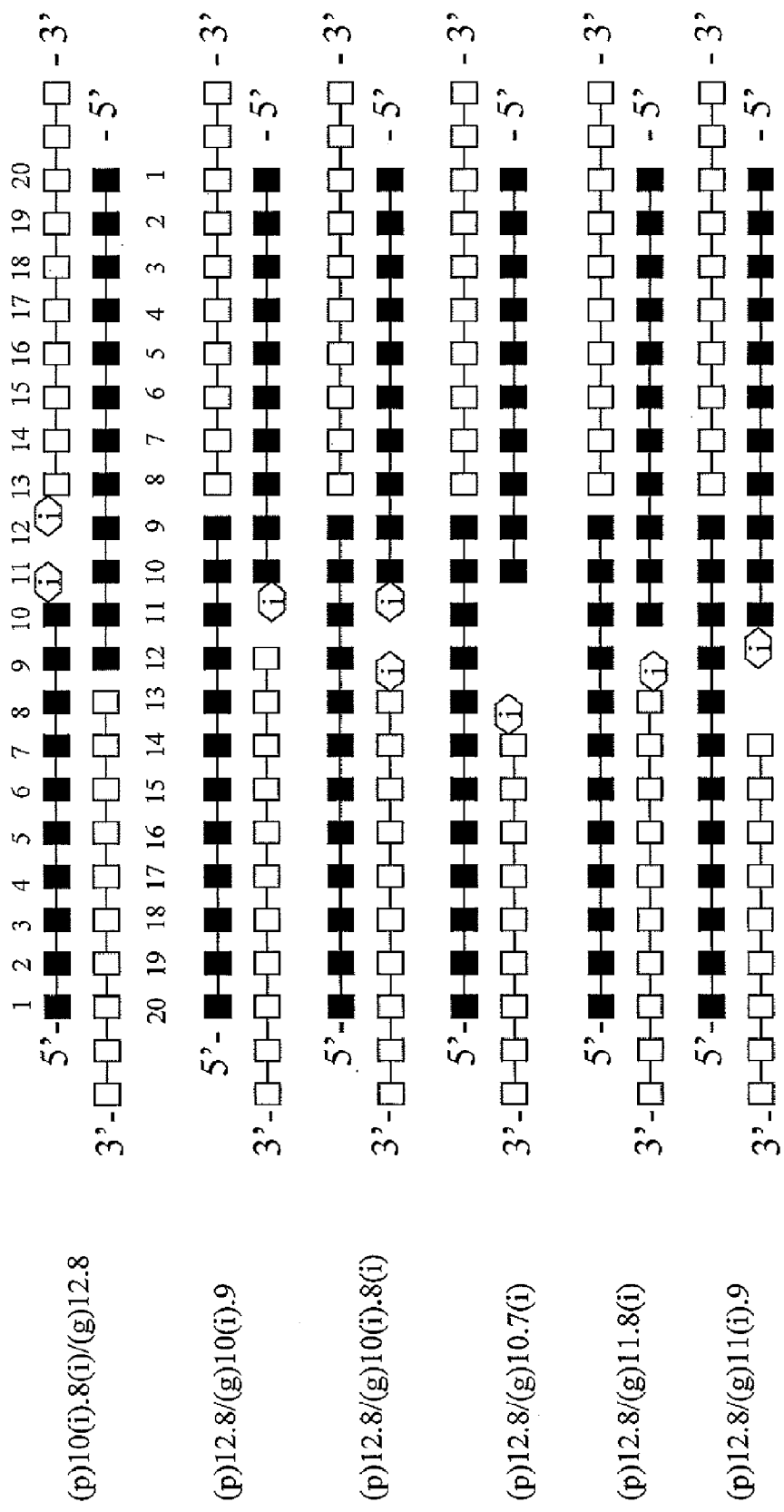

As used in this specification and the appended claims, the singular forms "a," "an" and "the" include plural referents unless the content clearly dictates otherwise. Thus, for example, reference to "a cell" includes a combination of two or more cells, and the like.

"About" as used herein indicates that a value includes the standard deviation of error for the device or method being employed to determine the value.

"Analog" as used herein refers to its meaning as is generally accepted in the art. The term generally refers to a compound that is structurally similar to a parent compound (e.g., a nucleotide), but differs in composition (e.g., one or more atom(s) or functional group(s) is/are different, added, or removed). The analog can have different chemical or physical properties than the original parent compound and can have improved biological or chemical activity. For example, the analog can be more hydrophilic or it can have altered activity of the parent compound. The analog can be a naturally or non-naturally occurring (e.g., chemically-modified or recombinant) variant of the original parent compound. An example of an RNA analog is an RNA molecule comprising a nucleotide analog. An example of a nucleotide analog is a nucleotide that is chemically modified at the sugar, base or nucleoside, as is generally known in the art.

The term "aptamer" as used herein refers to its meaning as is generally accepted in the art. The term generally refers to a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al, 1995 Annu. Rev. Biochem. 64:163; Brody and Gold, 2000 J. Biotechnol. 74:5; Sun, 2000 Curr. Opin. Mol. Ther. 2: 100; Kusser, J. 2000 Biotechnol. 74:21; Hermann and Patel, 2000 Science 257:820; and Jayasena, 1999 Clinical Chem. 45:1628).

As described herein, a "base pair" can be formed between two nucleotides, a nucleotide and a modified nucleotide, two modified nucleotides, a nucleotide and a nucleotide analog, two nucleotide analogs, a nucleotide and a non-nucleotide substitute moiety, or two non-nucleotide substitute moieties. In a specific embodiment, a non-nucleotide substitute can comprise any chemical moiety that is capable of associating with a component of the cellular RNAi machinery, such as, for example, the PAZ domain, the PIWI domain, and/or other Argonaute protein domains associated with the RISC. Non-traditional Watson-Crick base pairs are also understood as "non-canonical base pairs," which is meant any non-Watson Crick base pair, such as mismatches and/or wobble base pairs, including flipped mismatches, single hydrogen bond mismatches, trans-type mismatches, triple base interactions, and quadruple base interactions. Non-limiting examples of such non-canonical base pairs include, but are not limited to, AC reverse Hoogsteen, AC wobble, AU reverse Hoogsteen, GU wobble, AA N7 amino, CC 2-carbonyl-amino(H1)-N3-amino(H2), GA sheared, UC 4-carbonyl-amino, UU imino-carbonyl, AC reverse wobble, AU Hoogsteen, AU reverse Watson Crick, CG reverse Watson Crick, GC N3-amino-amino N3, AA N1-amino symmetric, AA N7-amino symmetric, GA N7-N1 amino-carbonyl, GA+ carbonyl-amino N7-N1, GG N1-carbonyl symmetric, GG N3-amino symmetric, CC carbonyl-amino symmetric, CC N3-amino symmetric, UU 2-carbonyl-imino symmetric, UU 4-carbonyl-imino symmetric, AA amino-N3, AA N1-amino, AC amino 2-carbonyl, AC N3-amino, AC N7-amino, AU amino-4-carbonyl, AU N1-imino, AU N3-imino, AU N7-imino, CC carbonyl-amino, GA amino-N1, GA amino-N7, GA carbonyl-amino, GA N3-amino, GC amino-N3, GC carbonyl-amino, GC N3-amino, GC N7-amino, GG amino-N7, GG carbonyl-imino, GG N7-amino, GU amino-2-carbonyl, GU carbonyl-imino, GU imino-2-carbonyl, GU N7-imino, psiU imino-2-carbonyl, UC 4-carbonyl-amino, UC imino-carbonyl, UU imino-4-carbonyl, AC C2-H—N3, GA carbonyl-C2-H, UU imino-4-carbonyl 2 carbonyl-C5-H, AC amino(A) N3(C)-carbonyl, GC imino amino-carbonyl, Gpsi imino-2-carbonyl amino-2-carbonyl, and GU imino amino-2-carbonyl base pairs.

The term "biodegradable" as used herein refers to its meaning as is generally accepted in the art. The term generally refers to degradation in a biological system, for example enzymatic degradation or chemical degradation.

The term "biodegradable linker" as used herein refers to its meaning as is generally accepted in the art. The term generally refers to a nucleic acid or non-nucleic acid linker molecule that is designed as a biodegradable linker to connect one molecule to another molecule, for example, connecting a biologically active molecule to a segmented miRNA mimetic of the invention or to either the passenger and/or guide strands of a segmented miRNA mimetic of the invention. The biodegradable linker can be attached to a segmented miRNA mimetic of the invention at one or more of the terminal ends, internal ends, or any other nucleotide positions that is not vacant. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biologically active molecule" as used herein refers to its meaning as is generally accepted in the art. The term generally refers to compounds or molecules that are capable of eliciting or modifying a biological response in a system. Non-limiting examples of biologically active molecules either alone or in combination with other molecules contemplated by the instant invention include therapeutically active molecules such as antibodies, hormones, antivirals, peptides, proteins, chemotherapeutics, small molecules, vitamins, co-factors, nucleosides, nucleotides, oligonucleotides, enzymatic nucleic acids, guide nucleic acids, triplex forming oligonucleotides, 2,5-A chimeras, siRNA, miRNA mimetics, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

By "capable of participating in RNAi against endogenous RNA targets of their corresponding naturally-occurring miRNAs" is meant that, when RNAi activity is measured by a suitable in vivo or in vitro assay or method, a segmented miRNA mimetic molecule of the invention demonstrates at least 5% or more of the knockdown effect against a target of its corresponding naturally-occurring miRNA as compared to the knockdown effect achieved by a non-segmented miRNA mimetic molecule directed to the same target under same experimental conditions. Preferably, a segmented miRNA mimetic molecule of the invention is capable of achieving 25% or more, 35% or more, 50% or more, 55% or more, 60% or more, 65% or more, 70% or more, 75% or more, 80% or more, 85% or more, 90% or more, 95% or more, 99% or more, or even 100% or more (i.e., equal or more potent RNAi activity) knockdown of the target than a non-segmented miRNA mimetic against the same target.

The term "cap structure" as used herein refers to its meaning as is generally accepted in the art. The term generally refers to chemical modifications, which have been incorporated into the ends of oligonucleotide (see, for example, Matulic-Adamic et al., U.S. Pat. No. 5,998,203, incorporated by reference herein). These terminal modifications can protect certain nucleic acid molecules from exonuclease degradation, and can impart certain advantages in delivery and/or cellular localization.

As used herein, the term "complementary" (or "complementarity") refers to its meaning as is generally accepted in the art. The term generally refers to nucleic acid sequences that are capable of base-pairing according to the standard Watson-Crick complementarity rules, that is purines will base pair with pyrimidines to form combinations: guanine paired with cytosine (G:C); and adenine paired with either thymine (A:T) in the case of DNA, or adenine paired with uracil (A:U) in the case of RNA. Base-pairing according to the Standard Waston-Crick complementarity rules can include base pairs formed between modified or nucleotide analogs. Aside from forming hydrogen bond(s) with each other according to the traditional Waston-Crick rules, a nucleic acid sequence can form other non-traditional types of base pairing with another nucleic acid sequence, and as such, the two nucleic acid sequences can also be called "complementary." As used herein, the term "complementary" thus encompasses any "base-pairing," which can be by hydrogen bonds or by any other interactions, of nucleotides, modified nucleotides, analogs, and/or non-nucleotides that provide sufficient binding free energy between the strands to allow the relevant function of the segmented miRNA mimetic, e.g., RNAi activity, to proceed. Determination of binding free energies for nucleic acid molecules is known in the art (see, e.g., Turner et al., 1987 CSH Symp. Quant. Biol. LII:123; Frier et al., 1986 Proc. Nat. Acad. Sci. USA 83:9373; Turner et al., 1987 J. Am. Chem. Soc. 109:3783).

A percent complementarity indicates the percentage of contiguous residues in a first nucleic acid molecule that can form hydrogen bonds (e.g., in Watson-Crick base-pairing) with a second nucleic acid sequence. For example, a first nucleic acid molecule can have 10 nucleotides and a second nucleic acid molecule can have 10 nucleotides, then base pairing of 5, 6, 7, 8, 9, or 10 nucleotides between the first and second nucleic acid molecules, which can or can not form a contiguous double-stranded region, represents 50%, 60%, 70%, 80%, 90%, or 100% complementarity, respectively. Complementarity can be found between two regions of a same nucleic acid molecule, such as, for example, in a hairpin loop or a stem loop structure. In other embodiments, complementarity can be found between two different nucleic acid molecules, such as, for example, in a segmented miRNA mimetic of the invention comprising distinct and separate passenger and guide strands.

In keeping with the usual practice by those of ordinary skill in the art, when the passenger strand and guide strand of the corresponding non-segmented miRNA are aligned on paper, (with the passenger strand arranged from 5' to 3' (left to right) and the guide strand arranged from 3' to 5' (left to right)) such that the each pair of complementary (base-pairing) nucleobases are located at directly opposite positions in the passenger and guide strand, the relative positions of the base-pairing nucleotides are termed "complementary nucleotide positions." It is often helpful to mark the position of the nucleotides in the non-segmented miRNA mimetic and use those positions to mark nicks, gaps, substitutions, or insertions introduced into a corresponding segmented mimetic construct. Typically the first nucleotide position at the 5'-end of the passenger strand of a non-segmented duplex miRNA mimetic is position 1 of passenger strand, the nucleotide immediately adjacent to it is position 2, and so on and so forth. Likewise, the first nucleotide position at the 5'-end of the guide strand of the non-segmented duplex miRNA mimetic is position 1 of the guide strand, the nucleotide immediately adjacent to it is position 2, and so on and so forth.

By "a contiguous stretch of nucleotides" or "a contiguous stretch of nucleotide positions" is meant a continuous series of at least 2 nucleotides or at least two nucleotide positions. For example, a contiguous stretch of nucleotides can refer to an unsegmented or uninterrupted oligonucleotide of 2 to 20 nucleotides in length. When referring to a contiguous stretch of nucleotides, the bonds connecting the nucleotides within the stretch can be phosphodiester bonds or non-phosphodiester linkages. A gap comprising a contiguous stretch of nucleotide positions can refer to a gap occupying, for example, from 1 to 10 or more nucleotide positions.

A segmented miRNA mimetic of the invention provided to a cell is typically designed based on the sequence of a naturally-occurring miRNA in the cell. As such, the naturally-occurring miRNA in the cell is referred to herein as "the corresponding miRNA." A segmented miRNA mimetic of the invention provided to a cell is also understood to target one or more target mRNAs that are also targeted by the corresponding naturally-occurring miRNA. As such, each RNA targeted by the corresponding naturally-occurring miRNA is referred to as "the corresponding miRNA target." It is contemplated that a segmented miRNA molecule introduced to a cell is not necessarily or does not necessarily comprise a nucleic acid sequence that is identical, essentially homologous, or even substantially homologous to a naturally-occurring miRNA, but the segmented miRNA is capable of either becoming or functioning as a naturally-occurring miRNA under appropriate conditions.

The term "discontinuity" as used herein refers to a non-contiguous segment of the nucleotide sequence of the guide strand, passenger strand or both the passenger and guide strands of a segmented micro RNA mimetic. A discontinuity can include one or more nicks, gaps, substitutions or insertions. The discontinuity can comprise, for example, from 0 to 10 (e.g., 0, 1, 2, 3, 4, 5, 6, 7, 8, 9, or 10) or more unoccupied or vacant nucleotide positions in the guide strand, the passenger strand, or both the guide and passenger strands. For example, a nick will comprise 0 unoccupied or vacant nucleotide positions, whereas a gap will comprise one or more (e.g., 1, 2, 3, 4, 5, 6, 7, 8, 9 10 or more) vacant or unoccupied nucleotide positions. Likewise, the discontinuity can comprise, for example, from 0 to 10 (e.g., 0, 1, 2, 3, 4, 5, 6, 7, 8, 9, or 10) or more nucleotide positions that are occupied or replaced by a non-nucleotide moiety in the guide strand, the passenger strand, or both the guide and passenger strands. For example, an insertion will comprise a non-nucleotide moiety that can occupy 0 nucleotide positions, whereas a substitution will comprise a non-nucleotide moiety that occupies one or more (e.g., 1, 2, 3, 4, 5, 6, 7, 8, 9 10 or more) otherwise vacant nucleotide positions.

As used herein, "endogenous" refers to its meaning as is generally accepted in the art. The term generally refers to any material from or produced inside an organism, cell, tissue or system. As used herein, an "endogenous miRNA" is a naturally-occurring miRNA in a cell, tissue, organism, including a mammal, such as, for example, a human. "Exogenous" generally refers to any material introduced from or produced outside an organism, cell, tissue Or system.

The term "expression" refers to its meaning as is generally accepted in the art. The term generally refers to the transcription and/or translation of a particular nucleotide sequence, for example when driven by its promoter.

The term "gap" as used herein refers to a contiguous stretch of one or more (e.g., 1, 2, 3, 4, 5, 6, 7, 8, 9 or 10 or more), internal (as opposed to "terminal") vacant, unoccupied or "unfilled" nucleotide positions in one or both strands of a segmented miRNA mimetic of the invention. The gap can be present in the guide strand, the passenger strand, or in both guide and passenger strands of a segmented microRNA mimetic of the invention.

The term "gene" as used herein, especially in the context of "target gene" for an RNAi agent, refers to the meaning as is generally accepted in the art. The term generally refers to a nucleic acid (e.g., "target DNA" or "target RNA") sequence that comprises partial length or entire length coding sequences necessary for the production of a polypeptide. The target gene can also include a UTR (i.e., untranslated region) or non-coding region of the nucleic acid sequence. A gene or target gene can also encode a functional RNA (fRNA) or non-coding RNA (ncRNA) as are generally known in the art, such as endogenous antisense RNA, small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof, or any other regulatory RNA or precursor thereof. Such non-coding RNAs can serve as target nucleic acid molecules for RNA interference in modulating the activity of fRNA or ncRNA involved in functional or regulatory cellular processes. Aberrant fRNA or ncRNA activity leading to disease can therefore be modulated by the RNAi agents of the invention. RNAi agents targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). A target gene can be a gene derived from a cell, an endogenous gene, a transgene, or exogenous genes such as genes of a pathogen, for example a virus, which is present in the cell after infection thereof. A cell containing a target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, *Science* 300:258-260. In one aspect of the present invention, a segmented miRNA mimetic is capable of exerting regulatory effects on multiple target genes. Also, at least one of these target genes, but typically more than one target genes, can be shared between a segmented miRNA mimetic of the invention and its corresponding endogenous miRNA.

As used herein, "gene silencing" refers to a partial or complete loss-of-function through targeted inhibition of an endogenous miRNA target in a cell. As such, the term is used interchangeably with RNAi, "knockdown," "inhibition," "down-regulation," or "reduction" of expression of a miRNA target gene. Depending on the circumstances and biological problem to be addressed, it can sometimes be preferable to increase expression of one or more related genes, which is termed "up-regulation" herein. Alternatively, it might be desirable to reduce or increase gene expression as much as possible or only to a certain extent.

By "guide strand" of a segmented miRNA of the invention is meant two or more distinct contiguous stretches of nucleotides at least one of which is substantially homologous or identical to the whole or a part of a sequence of a corresponding naturally-occurring miRNA, such as one selected from the miRBase, and for example, such as one selected from SEQ ID NOs: 1-1090 of Table I herein. The nucleotides within each contiguous stretch can be connected by traditional phosphodiester bonds and/or non-phosphodiester connectors. In addition, the guide strand of a segmented miRNA mimetic can comprise two or more distinct stretches of nucleotides that are capable of forming base pairs with the nucleotides or residues at the complementary nucleotide positions of the passenger strand.

As used herein, the term "homologous" (or "homology") refers to its meaning as is generally accepted in the art. The term generally refers to the number of nucleotides of the subject nucleic acid sequence that has been matched to identical nucleotides of a reference nucleic acid sequence, typically by a sequence analysis program or by visual inspection. For example, nucleic acid sequences can be compared using computer programs that align the similar sequences of nucleic acids and therefore define the differences. Exemplary computer programs includes the BLAST program (NCBI) and parameters used therein, as well as the DNAstar system (Madison, Wis.), which can be used to align sequence fragments. Equivalent alignments and assessments can also be obtained through the use of any standard alignment software.

As used herein, the terms "including" (and any form thereof, such as "includes" and "include), "comprising" (and any form thereof, such as "comprise" and "comprises"), "having" (and any form thereof, such as "has" or "have"), or "containing" (and any form thereof, such as "contains" or "contain") are inclusive and open-ended and do not exclude additional, un-recited elements or method steps.

The term "insertion" as used herein refers to a discontinuity wherein one or more non-nucleotide moieties are incorporated into the guide strand and/or passenger strand, while preserving the base pairs in the guide and passenger strands. Examples of such non-nucleotide moieties are provided herein and others are provided as is generally known to those of skill in the art.

The term "internal ends" refers to the ultimate nucleotides of the contiguous stretches of nucleotides on either side of a gap or a nick. Gaps or nicks do not have "terminal ends" for the purpose of this disclosure.

As used herein, the term "internally unpaired nucleotides" refers to nucleotides, which do not form base pairs with nucleotides at the complementary nucleotide positions in the opposite strand according to the standard Waston-Crick base-pairing rules. The term "internally unpaired nucleotides" also refers to nucleotide analogs or non-nucleotide residues that do not form hydrogen bonds or base pairs with the nucleotides, nucleotide analogs, or non-nucleotide residues at the complementary nucleotide positions in the opposite strand.

In certain embodiments, a segmented miRNA of the invention can be isolated. As used herein, an "isolated" oligonucleotide is nucleic acid molecule that exists in a physical form differing from any nucleic acid molecules of identical sequence as found in nature. "Isolated" does not require, although it does not prohibit, that the nucleic acid be physically removed from its native environment. For example, a nucleic acid can be said to be "isolated" when it includes nucleotides and/or internucleotide bonds not found in nature. A nucleic acid can be said to be "isolated" when it exists at a purity not found in nature, where purity can be adjudged with respect to the presence of nucleic acids of other sequences, with respect to the presence of proteins, with respect to the presence of lipids, or with respect to the presence of any other component of a biological cell, or when the nucleic acid lacks sequence that flanks an otherwise identical sequence in an organism's genome, or when the nucleic acid possesses sequence not identically present in nature. In aspects of the invention, a segmented miRNA is isolated by virtue of its having been synthesized in vitro. It will be understood, however, that isolated nucleic acids can be subsequently mixed or pooled together.

As used herein, the term "locked nucleic acid" (LNA) refers to its meaning as is generally accepted in the art. The term generally refers to a structure of the general Formula I:

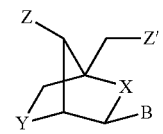

where X and Y are independently selected from the group consisting of —O—, —S—, —N(H)—, —N(R)—, —CH$_2$—, or —CH— (if part of a double bond), —CH$_2$—O—, CH$_2$—S—, CH$_2$—N(H)—, —CH$_2$—N(R)—, —CH$_2$—CH$_2$—, and CH$_2$—CH— (if part of a double bond), —CH═CH—, where R is selected from hydrogen and C$_{1-4}$-alkyl; Z and Z* are independently selected from an internucleotide linkage, a terminal group or a protecting group; B constitutes a natural or non-natural nucleobase; and the asymmetric groups can be found in either orientation.

The 4 chiral centers of Formula I, as shown, are in a fixed configuration. But their configurations are not necessary fixed. Also comprised in the invention are compounds of the generally Formula I, wherein the chiral centers are found in different configurations, such as those represented in Formula II (below). Thus each chiral center in Formula 1 can exist in either R or S configuration. The definition of R (rectus) and S (sininster) are described in the IUPAC 1974 Recommendations, Section E, Fundamental Setereochemistry: The rules can be found in Pure Appl. Chem 45, 13-30 (1976) and In "Nomenclature of Organic Chemistry" pergamon, New York, 1979.

LNA compounds can include an activation group for —OH, —SH, and —NH(R$^H$), respectively. Such activation groups are, for example, selected from optionally substituted O-phosphoramidite, optionally substituted O-phosphortriester, optionally substituted O-phosphordiester, optionally substituted H-phosphonate, and optionally substituted O-phosphonate.

B constitutes a natural or non-natural nucleobase and selected among adenine, cytosine, 5-methylcytosine, isocytosine, pseudoisocytosine, guanine, thymine, uracil, 5-bromouraci, 5-propynyluracil, 5-propyny-6-fluoroluracil, 5-methylthiazoleuracil, 6-aminopurine, 2-aminopurine, inosine, diaminopurine, 7-propyne-7-deazaadenine, 7-propyne-7-deazaguanine, and 2-chloro-6-aminopurine.

Preferably, the Locked Nucleic Acid (LNA) used in a segmented miRNA mimetic of the invention comprises at least one nucleotide comprises a Locked Nucleic Acid (LNA) unit according any of the Formulas II:

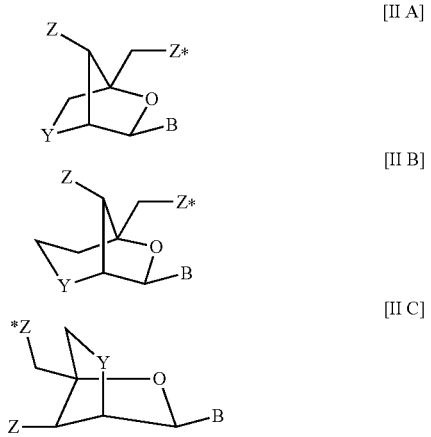

wherein Y is —O—, —S—, —NH—, or N(R$^H$); Z and Z* are independently selected among an internucleotide linkage, a terminal group or a protecting group; and B constitutes a natural or non-natural nucleobase. These exemplary LNA monomers and others, as well as their preparation are described in WO 99/14226 and subsequent applications, WO 00/56746, WO 00/56748, WO 00/66604, WO 00/125248, WO 02/28875, WO 2002/094250 and WO 2003/006475, the disclosure of all of which are incorporated herein by reference.

As used herein, the term "mimetic" refers to its meaning as is generally accepted in the art. The term generally refers to a molecule that is structurally different from the reference molecule (e.g., the corresponding naturally-existing molecule or the corresponding non-segmented mimetic molecule) but is capable of performing one or more or all of the biological, physiological, and/or chemical functions that are within the capabilities of the references molecule. The mimetic and the reference molecule do not have to be functional equivalents but the mimetic should be able to perform one or more functions, and exhibiting at least 5% or more, 10% or more, 20% or more, 30% or more, 40% or more, 50% or more, 60% or more, 70% or more, 80% or more, or 90% or more of the activity of the reference molecule, as measured and compared using assays or parameters that are suitable to represent the shared function(s). As used herein, a segmented miRNA molecule is a miRNA mimetic when the former shares at least one function with its corresponding endogenous miRNA. A miRNA mimetic can be a synthetic RNA duplex, such as a segmented miRNA duplex of the invention, a vector-encoded hairpin molecule, or other suitable structures designed based on a corresponding naturally-occurring endogenous miRNA.

The term, "miRNA" or "microRNA" refers to its meaning as is generally accepted in the art. The term generally refers to an endogenous short RNA molecule, which can be isolated or synthetic, which is found in eukaryotes and is involved in RNA-based gene regulation. A representative set of known endogenous miRNA species is described in the publicly available miRBase sequence database as described in Griffith-Jones et al., Nucleic Acids Research, 2004, 32:D109-D111 and Griffith-Jones et al., Nucleic Acids Research, 2006, 34:D 140-D144, accessible on the World Wide Web at the Wellcome Trust Sanger Institute website. A more selected set of miRNA species are included in Table I herein. Each mature miRNA is partially complementary to one or more messenger RNA (mRNA) molecules, which are also called "miRNA targets," thereby regulating the expression of genes associated with the miRNA targets.

The term "nick" as used herein refers to a break in an internucleotide linkage in one or both strands of a segmented miRNA mimetic of the invention.

The term "non-nucleotide" refers to its meaning as is generally accepted in the art. The term generally refers to any group or compound which can be incorporated into a nucleic acid chain in the place of one or more nucleotide units, such as for example but not limitation abasic moieties, alkyl moieties, polymers such as PEG, peptides, sterols, peptide nucleic acids, and the like.

The term "nucleotide" refers to its meaning as is generally accepted in the art. The term generally refers to compounds that comprise a nucleobase, a sugar, and an internucleoside linkage, e.g., a phosphate group such as a phosphodiester. The base can be a natural bases (standard), modified bases, or a base analog, as are well known in the art. Such bases are generally located at the 1' position of a nucleotide sugar moiety. Additionally, the nucleotides can be unmodified or modified at the sugar, internucleoside linkage, and/or base moiety, (also referred to interchangeably as nucleotide analogs, modified nucleotides, non-natural nucleotides, non-standard nucleotides and others; see, for example, U.S. application Ser. No. 12/064,014).

The term "parenteral," refers to its meaning as is generally accepted in the art. The term generally includes subcutaneous, intravenous, intramuscular, intraarterial, intraabdominal, intraperitoneal, intraarticular, intraocular or retrobulbar, intraaural, intrathecal, intracavitary, intracelial, intraspinal, intrapulmonary or transpulmonary, intrasynovial, and intraurethral injection or infusion techniques.

By "passenger strand" of a segmented miRNA of the invention is meant one or more distinct nucleic acid sequences or contiguous stretches of nucleotides capable of forming base pairs (including traditional base pairs and non-traditional base pairs) to one or more non-overlapping contiguous stretches of nucleotides in the guide strand. The nucleotides within each contiguous stretch can be connected by traditional phosphodiester bonds and/or non-phosphodiester connectors. In addition, the passenger strand of a segmented miRNA can comprise one or more nucleic acid sequences having at least substantial homology, or at least essential homology, or even perfect homology to a RNA sequence that is a target of a corresponding naturally-occurring miRNA, such as one selected from the miRBase, and for example, one selected from Table I herein.

The terms "patient," "subject," "individual" refer to their ordinary meanings as are generally accepted in the art. The terms generally refer to any animal or cells or tissues thereof whether in vitro or in situ, amendable to the methods described herein. They typically refer to an organism, which is a donor or recipient of explanted cells or the cells themselves. They also refer to an organism to which the segmented miRNAs of this disclosure can be administered. In certain non-limiting embodiments, the patient, subject or individual is a mammal or a mammalian cell. In other non-limiting embodiments, the patient, subject or individual is a human or a human cell.

The term "phospholipid" refers to its meaning as is generally accepted in the art. The term generally refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

The term "perfect complementarity" (or "perfect complement") as used herein refers to complete (100%) complementarity within a contiguous region of double-stranded nucleic acid, such as, for example, between a hexamer or heptamer seed sequence of a miRNA and its complementary sequence in a target mRNA. "Perfectly complementary" can also mean that all the contiguous residues of a first nucleic acid sequence form hydrogen bonds with the same number of contiguous residues in a second nucleic acid sequence. For example, 2 or more perfectly complementary nucleic acid strands can have the same number of nucleotides (i.e., have the same length and form one double-stranded region with or without an overhang), or have a different number of nucleotides (e.g., one strand can be shorter but fully contained within a second strand). "Perfect complements" can be formed between modified nucleotides and nucleotide analogs.

The term "perfect homology" (or "perfectly homologous") as used herein refers to complete (100%) homology or "identity" between a reference sequence and a subject nucleic acid sequence. When there is a perfect homology, the reference and the subject sequences are the same.

The term "phosphorothioate" refers to its meaning as is generally accepted in the art. The term generally refers a sulphur substituted internucleotide phosphate linkage, but can also refer to internucleotide linkages selected from the group consisting of: —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —OP(O,S)—S—, —S—P(O)$_2$—S—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—. NR$^H$ CO—NR$^H$—, and/or the internucleotide linkage can be selected form the group consisting of: —O—CO—O—, —O—CO—NR$^H$—, —O—CH$_2$—CO—NR$^H$—, —O—CH$_2$—CH$_2$—NR$^H$—, —CO—NR$^H$—CH$_2$—, —CH$_2$—NR$^H$—CO—, —O—CH$_2$—CH$_2$—S—, —S—CH$_2$CH$_2$O, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C$_{1-4}$-alkyl, Suitably, in some embodiments, sulphur (S) containing internucleotide linkages as provided above can be preferred. Moreover, a segmented miRNA mimetic of the invention can comprise other linkages or mixtures of different linkages—for example, both phosphate or phosphorothioate linkages, or just phosphate linkages, or other linkages as described herein.

The terms "polynucleotide" and "oligonucleotide" refer to their meanings as are generally accepted in the art. The terms generally refers to a chain of nucleotides. "Nucleic acids" or "nucleic acid molecules" are polymers of nucleotides. Thus, "nucleic acids" and "polynucleotides" or "oligonucleotides" are interchangeable herein. One skilled in the art has the general knowledge that nucleic acids are polynucleotides, which can be hydrolyzed into monomeric nucleotides. The monomeric nucleotides can be further hydrolyzed into nucleosides.

The term "protecting group" refers to its meaning as is generally accepted in the art. Protection groups of hydroxy substituents comprises substituted trityl, such as 4,4'-dimethoxytrityloxy (DMT), 4-monomethoxytrityloxy (MMT), and trityloxy, optionally substituted 9-(9-phenyl)xanthenyloxy (pixyl), optionally substituted methoxytetrahydro-pyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), acyloxy such as acetyl or halogen substituted acetyls.

The term "purine" refers to its meaning as is generally accepted in the art. The term generally refers to conventional purine nucleotides, including those with standard purine bases adenine and guanine. In addition, the term "purine" is contemplated to embrace nucleotides with natural non-standard purine bases or acids, such as N$_2$-methylguanine, inosine, 2,6-diaminopurine and the like, as well as chemically modified bases or "universal bases," which can be used to substitute for standard urines herein.

The term "pyrimidine" refers to its meaning as is generally accepted in the art. The term generally refers to conventional pyrimidine nucleotides, including those with standard pyrimidine bases uracil, thymidine and cytosine. In addition, the term pyrimidine is contemplated to embrace nucleotides with natural non-standard pyrimidine bases or acids, such as 5-methyluracil, 2-thio-5-methyluracil, 4-thiouracil, pseudouracil, dihydrouracil, orotate, 5-methylcytosine, or the like, as well as a chemically modified bases or "universal bases," which can be used to substitute for a standard pyrimidine within the nucleic acid molecules of this disclosure.

The term "RNA" refers to its meaning as is generally accepted in the art. The term generally refers to a molecule comprising at least one ribofuranoside residue, such as a ribonucleotide. The term "ribonucleotide" means a nucleotide with a hydroxyl group at the 2' position of a β-D-ribofuranose moiety. The term refers to a double-stranded RNA, a single-stranded RNA, an isolated RNA such as a partially purified RNA, an essentially pure RNA, a synthetic RNA, a recombinantly produced RNA, or an altered RNA that differs from a naturally-occurring RNA by the addition, deletion, substitution and/or alteration of one or more nucleotides therein. Such alterations can include addition of non-nucleotide material, for example, at one or more non-terminal nucleotides of an RNA molecule. As such, nucleotides in the segmented miRNA mimetics of the invention can comprise non-standard nucleotides, such as non-naturally occurring nucleotides, chemically synthesized and/or modified nucleotides, or deoxynucleotides. The altered RNAs are referred to as "RNA analogs" or "analogs of naturally-occurring RNA" containing standard nucleotides (i.e., adenine, cytidine, guanidine, thymidine and uridine), or generally as "modified RNA".

As used herein, the phrase "RNA interference" (also called "RNAi" herein) refers to its meaning as is generally accepted in the art. The term generally refers to the biological process of inhibiting, decreasing, or down-regulating gene expression in a cell, and which is mediated by short interfering nucleic acid molecules (e.g., siRNAs, miRNAs, shRNAs), see for example Zamore and Haley, 2005, *Science* 309:1519-1524; Vaughn and Martienssen, 2005, *Science* 309:1525-1526; Zamore et al., 2000, *Cell* 101:25-33; Bass, 2001, *Nature* 411:428-429; Elbashir et al., 2001, *Nature* 411:494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science* 297:1818-1819;

Volpe et al., 2002, *Science* 297:1833-1837; Jenuwein, 2002, *Science* 297:2215-2218; and Hall et al., 2002, *Science* 297:2232-2237; Hutvagner and Zamore, 2002, *Science* 297: 2056-60; McManus et al., 2002, *RNA* 8:842-850; Reinhart et al., 2002, *Gene & Dev.* 16:1616-1626; and Reinhart & Bartel, 2002, *Science* 297:1831). Additionally, the term "RNA interference" (or "RNAi") is meant to be equivalent to other terms used to describe sequence-specific RNA interference, such as post-transcriptional gene silencing, translational inhibition, transcriptional inhibition, or epigenetics. For example, segmented microRNA mimetics of the invention can be used to epigenetically silence genes at either the post-transcriptional level or the pre-transcriptional level. In a non-limiting example, epigenetic modulation of gene expression by segmented microRNA mimetics of the invention can result from modification of chromatin structure or methylation patterns to alter gene expression (see, for example, Verdel et al., 2004, *Science* 303:672-676; Pal-Bhadra et al., 2004, *Science* 303:669-672; Allshire, 2002, *Science* 297:1818-1819; Volpe et al., 2002, *Science* 297: 1833-1837; Jenuwein, 2002, *Science* 297:2215-2218; and Hall et al., 2002, *Science* 297:2232-2237). In another non-limiting example, modulation of gene expression by segmented microRNA mimetics of the invention can result from cleavage of RNA (either coding or non-coding RNA) via RISC, or via translational inhibition, as is known in the art or modulation can result from transcriptional inhibition (see for example Janowski et al., 2005, *Nature Chemical Biology* 1:216-222).

The term "RNA profile" or "gene expression profile" refers to a set of data regarding the expression pattern for one or more gene or genetic marker in the sample (e.g., a plurality of nucleic acid probes that identify one or more markers). In some embodiments, it can be useful to know whether a cell expresses a particular miRNA endogenously or whether such expression is affected under particular conditions or when it is in a particular disease state. Thus in some embodiments of the invention, methods include assaying a cell or a sample containing a cell for the presence of one or more marker genes or mRNA or other analyte indicative of the expression level of a gene of interest. Consequently in some embodiments, methods include a step of generating an RNA profile for a sample.

As used herein, the term "seed sequence" refers to at least 6 consecutive nucleotides within any of nucleotide positions 1 to 10 of the 5'-end of a naturally-occurring mature miRNA, such as one selected from those listed in miRBase (http://www.mirbase.org/) as of the filing date of the present application, and for example, such as one selected from those listed in Table I, wherein the seed sequence nucleotides of positions 1 to 8 are capitalized. See, e.g., Brennecke et al., 2005, PLOS Biol. 3(3):e85. In a naturally-occurring miRNA, the seed sequence typically determines the target mRNA sequence to which the miRNA can bind and provide gene regulation. As such, multiple naturally-occurring miRNAs can share a seed sequence, or share substantial homology in the seed sequences, and these miRNAs are members of the same miRNA family.

The term "segmented miRNA mimetic" (or "segmented miRNA," interchangeably) as used herein refers to a miRNA mimetic molecule comprising at least one discontinuity in the guide strand that is capable of modulating the expression of a target gene that is also regulated by a corresponding naturally-occurring miRNA, such as one selected from the miRBase as of the filing date of the present application, and for example, such as one selected from SEQ ID NOs: 1-1090 of Table I herein. The discontinuity comprises one or more nicks, gaps, substitutions, or insertions. In one aspect, a segmented miRNA mimetic of the invention will mediate gene silencing via an RNAi mechanism such as RISC mediated cleavage, translational inhibition, or epigenetic silencing as is known in the art. A segmented miRNA of the invention can comprise one or more or all ribonucleotides. Segmented miRNAs of the invention can also comprise nucleotide and non-nucleotide analogs as described herein and as otherwise known in the art.

A segmented miRNA mimetic of the invention is said to be "double-stranded" if the molecule has an overall double-stranded conformation. Each of the "strands" is not necessarily continuous, but rather can comprise one or more distinct contiguous stretches of nucleotides, separated by non-contiguous segments (i.e. gaps, nicks, substitutions, insertions). The strand (including the one or more contiguous stretches of nucleotides) that comprises or comprises essentially of a sequence of a corresponding miRNA target is termed the "passenger strand of the segmented miRNA." The strand (including the one or more contiguous stretches of nucleotides) that comprises or comprises essentially of at least a portion (e.g., a stretch of about 5 to about 8 nucleotides within the seed sequence) of a corresponding endogenous miRNA is termed the "guide strand of the segmented miRNA." Moreover, a guide strand comprising one or more discontinuities (i.e., gaps, nicks, substitutions, insertions) can form a double-stranded RNA complex even if it is hybridized to a passenger strand that also comprises one or more discontinuities (i.e., gaps, nicks, substitutions, insertions). When both strands comprise discontinuities, the discontinuities can, in certain embodiments, be arranged in such relative positions with each other that the segmented miRNA mimetic of the invention maintains a generally double-stranded conformation, thereby allowing its recognition by the cellular RNAi machinery. Linkers can be introduced and various other stabilizing modifications can be applied to confer added thermodynamic stability. In a specific embodiment, linkers or stabilizing modifications are introduced to a molecule comprising structurally overlapping discontinuities, where otherwise the double-stranded molecule would have broken into two double-stranded sections if the contiguous stretches adjacent to the overlapping gaps are not connected.

Each segmented miRNA mimetic of the invention can have a corresponding non-segmented double-stranded miRNA mimetic, where the non-segmented mimetic comprises all of the contiguous stretches of nucleotides of the segmented mimetic, and where the non-segmented mimetic and the segmented mimetic share the same RNA target(s) with their corresponding endogenous miRNA. Essentially, the segmented miRNA mimetic is designed based on the corresponding non-segmented miRNA mimetic by deleting certain internal phosphodiester backbone linkages and/or internal nucleotides (i.e., by placing nicks or gaps) or substituting such nicks or gaps with one or more non-nucleotide moieties.

It is contemplated that multiple segmented miRNAs, having respective multiple corresponding miRNAs, can be applied to a cell. In particular embodiments, two or more segmented miRNAs are introduced to a cell. A combination of multiple segmented miRNAs can act as one or more points of regulation in cellular pathways within the cell, which has aberrant phenotype(s) (i.e., that the cell is a "targeted cell"), and that such combination can have increased efficacy for correcting the aberrant phenotype(s) of the targeted cell. If the targeted cell is mixed with normal cells, it is contemplated that the segmented miRNAs added to the collection of cells, while providing improved efficacy to correct the aberrant phenotypes of the targeted cell, have minimal adverse effect on the normal cells.

The term "siRNA" (also "short interfering RNA" or "small interfering RNA") is given its ordinary meaning as is recognized in the art.

A double-stranded nucleic acid molecule can have strands that are not perfectly complementary, but merely "substantially complementary." By "substantially complementary" it is meant that the nucleic acid sequence of the first strand is at least about 25%, 30%, 35%, 40%, 45%, 50%, 55%, 60%, 65%, 70%, 75%, 80%, 85%, 90%, 95%, 96%, 97%, 98% or 99%© complementary to the nucleic acid sequence of the second strand. In certain embodiments, complementary nucleic acid molecules can have wrongly paired bases—that is, bases that cannot form a traditional Waston-Crick base pair (i.e., forming a hydrogen bond) or other non-traditional types of base pair (i.e., "mismatched" bases, formed or held together by non-traditional forces that are not hydrogen bonds). Non-traditional Waston-Crick base pairs are also understood as "non-canonical base pairs," which is meant any non-Watson Crick base pair, such as mismatches and/or wobble base pairs, including flipped mismatches, single hydrogen bond mismatches, trans-type mismatches, triple base interactions, and quadruple base interactions. Non-limiting examples of such non-canonical base pairs include, but are not limited to, AC reverse Hoogsteen, AC wobble, AU reverse Hoogsteen, GU wobble, AA N7 amino, CC 2-carbonyl-amino(H1)-N3-amino(H2), GA sheared, UC 4-carbonyl-amino, UU imino-carbonyl, AC reverse wobble, AU Hoogsteen, AU reverse Watson Crick, CG reverse Watson Crick, GC N3-amino-amino N3, AA N1-amino symmetric, AA N7-amino symmetric, GA N7-N1 amino-carbonyl, GA+ carbonyl-amino N7-N1, GG N1-carbonyl symmetric, GG N3-amino symmetric, CC carbonyl-amino symmetric, CC N3-amino symmetric, ULT 2-carbonyl-imino symmetric, ULT 4-carbonyl-imino symmetric, AA amino-N3, AA N1-amino, AC amino 2-carbonyl, AC N3-amino, AC N7-amino, AU amino-4-carbonyl, AU N1-imino, AU N3-imino, AU N7-imino, CC carbonyl-amino, GA amino-N1, GA amino-N7, GA carbonyl-amino, GA N3-amino, GC amino-N3, GC carbonyl-amino, GC N3-amino, GC N7-amino, GG amino-N7, GG carbonyl-imino, GG N7-amino, GU amino-2-carbonyl, GU carbonyl-imino, GU imino-2-carbonyl, GU N7-imino, psiU imino-2-carbonyl, UC 4-carbonyl-amino, UC imino-carbonyl, UU imino-4-carbonyl, AC C2-H—N3, GA carbonyl-C2-H, UU imino-4-carbonyl 2 carbonyl-C5-H, AC amino(A) N3(C)-carbonyl, GC imino amino-carbonyl, Gpsi imino-2-carbonyl amino-2-carbonyl, and GU imino amino-2-carbonyl base pairs.

As used herein, the term "substantially homologous" (or "substantial homology") is meant that the subject sequence shares at least 25% (e.g., at least 25%, 30%, 35%, 40%, 45%, 50%, 55%, 60%, 65%, 70%©, 75%, 80%, 85%, 90%, 95%, 96%, 97%, 98% or 99%) homologous nucleotides with the nucleotides of the same nucleotide positions in a reference sequence. By "essentially homologous" (or "essential homology') it is meant that, a first part of a subject sequence having a number of consecutive nucleotides is identical to a first part of a reference sequence having the same number or consecutive nucleotides, whereas the rest of the subject sequence, which does not overlap with the first part of the subject sequence, is substantially homologous to the rest of the reference sequence, which does not overlap with the first part of the reference sequence. For example, as used herein, the term "essentially homologous" with regard to miRNA sequences, can refer to the contiguous stretch from the 5'-terminal of the guide strand of a segmented miRNA mimetic of the invention comprising a sequence that is essentially homologous to a sequence, including the seed sequence, of a corresponding naturally-occurring miRNA. For example, the first contiguous stretch from the 5'-terminal of the guide strand can comprise a 6 to 7-nucleotide stretch within that is perfectly complementary to a 6 to 7-nucleotide stretch of the seed sequence, where the rest of the nucleotides (including nucleotide analogs) in the contiguous stretch can be at least 50% homologous to the rest of the corresponding endogenous mature miRNA sequence. The comparison of sequences and determination of percent homology and/or identity between two sequences can be accomplished using a mathematical algorithm of Karlin and Altschul (1990, PNAS 87:2264-2268), modified as in Karlin and Altschul (1993, PNAS 90:5873-5877) or by visual inspection.

As used herein, the term "substitute non-nucleotide moieties" refers to chemical moieties that are capable of substituting one or more nucleotides in a segmented miRNA mimetic of the invention. The substitute non-nucleotide moieties can allow for non-traditional base-pairing (i.e., not forming traditional hydrogen bonds) between the strands and contribute to the binding free energy. In certain embodiments, the substitute non-nucleotide moieties of the instant disclosure are those that are capable of associating or otherwise interacting with one or more components of the cellular RNAi machinery, including, for example, the PAZ domain, the PIWI domain and/or other Argonaute protein domains associated with the RISC.

The term "substitution" as used herein refers to a discontinuity in which one or more nucleotide(s) of the otherwise continuous nucleotide sequence of the guide strand and/or passenger strand is replaced with one or more non-nucleotide moieties. Examples of such non-nucleotide moieties are provided herein and others are provided as is generally known to those of skill in the art.

The segmented miRNAs of the invention are typically synthetic. The term "synthetic" as used herein generally refers to nucleic acid molecules that are not produced naturally in a cell. In certain aspects, the chemical structure of a synthetic nucleic acid molecule can deviate from a naturally-occurring nucleic acid molecule. On the other hand, a synthesized segmented miRNA can encompass all or part of a naturally-occurring miRNA sequence or a component thereof. Moreover, it is contemplated that, in a specific embodiment, a synthetic segmented miRNA mimetic administered to a cell can subsequently be altered or processed by the cellular components such that its post-processing structure or sequence can be identical to the whole or a part of a naturally-occurring miRNA. The difference between a synthetic miRNA mimetic and its corresponding endogenous miRNA, including miRNA precursors and complements, can comprise missing internal (i.e., at non-terminal positions) phosphordiester bonds, or missing internal nucleotides, altered types of nucleotides, altered internucleotide connectors or linkages, or chemically modified nucleotides. In certain aspects, a synthetic segmented miRNA of the invention is an RNA or an RNA analog.

The phrases "target site," "target sequence," and "target region," as used herein, refer to their meanings as generally accepted in the art. The terms generally refer to a sequence within a target nucleic acid molecule (e.g., target RNA) that is "targeted," e.g., for cleavage mediated by an RNAi molecule that contains a sequence within its guide/antisense region that is partially, substantially, or perfectly complementary to that target sequence. A "target site" for a miRNA mimetic molecule of the present invention refers to a nucleic acid sequence that is partially, substantially, or perfectly complementary to the guide strand of the miRNA mimetic. The target site can be within a coding or a non-coding (i.e., untranslated) region of a target RNA. The target site can be the target site for an endogenous miRNA for which the segmented miRNA molecule is a mimetic, in which case the "target site" can also be referred to as a "miRNA target site" or a "corresponding miRNA target site."

Linkers connecting the terminal ends of a segmented miRNA mimetic of the invention are referred to as "terminal linkers" herein.

The term "therapeutic" refers to its meaning as is generally accepted in the art. The term generally refers to a treatment and/or prophylaxis. A therapeutic effect is obtained by suppression, remission, or eradication of a disease state. In the instant application, the disease state is particularly referred to as one associated with aberrant biological pathways regulated by miRNAs, such as those listed in the miRBase at the time of filing of this application, and especially those listed in Table I herein. The term "treatment" as used herein is meant to include therapeutic treatment as well as prophylactic, or suppressive measures for diseases or disorders. Thus, for example, the term "treatment" includes the administration of an agent prior to or following the onset of a disease or disorder thereby preventing or removing all signs of the disease or disorder. As another example, administration of the agent after clinical manifestation of the disease to combat the symptoms of the diseases is also comprised by the term "treatment."

As used herein, the term "therapeutically effective amount" refers to its meaning as is generally accepted in the art. The term can refer to an amount of a segmented miRNA that is sufficient to result in a decrease in severity of disease symptoms, an increase in frequency or duration of disease symptom-free periods, or a prevention of impairment or disability due to the disease, in the subject (e.g., a mammal or human) to which it is administered. One of ordinary skill in the art would be able to determine such therapeutically effective amounts based on such factors such as the subject's size, the severity of symptoms, and the particular composition or route of administration selected. For example, a therapeutically effective amount of a segmented miRNA of the invention, individually, in combination, or in conjunction with other drugs, can be used or administered at a therapeutically effective amount to a subject or by administering to a particular cells under conditions suitable for treatment, to, for example, decrease tumor size, or otherwise ameliorate symptoms associated with a particular disorder in the subject.

As used herein, "terminals" or "terminal ends" refers to the ultimate ends at the first 5'-nucleotide or the first 3'-nucleotide of a given strand. Substitutions of such terminal ends can be selected independently from hydrogen, azido, halogen, cyano, nitro, hydroxy, Prot-O—, Act-O—, mercapto, Prot-S—. Act-S—, $C_{1-6}$-alkylthio, amino. Prot-N ($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, monothiophosphate, diphosphate, dithiophosphate triphosphate, trithiophosphate. DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N($R^H$)—$CH_2$—, Act-N($R^H$)—$CH_2$—, carboxy methyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl.

Linkers connecting the terminal ends of a segmented miRNA mimetic of the invention are referred to as "terminal linkers" herein.

The term "universal base" refers to its meaning as is generally accepted in the art. The term generally refers to nucleotide base analogs that form base pairs with each of the standard DNA/RNA bases with little discrimination among them, and is recognized by intracellular enzymes. See, e.g., Loakes et al., J. Mol. Bio. 1997, 270:426-435. Non-limiting examples of universal bases include C-phenyl, C-naphthyl and other aromatic derivatives, inosine, azole carbozamides, and nitroazole derivatives such as 3'-nitropyrrole, 4-nitroindole, 5-nitroindole, and 6-nitroindole as known in the art. See, e.g., Loakes, 2001 Nucleic Acids Res. 29:2437.

A "vector" refers to its meaning as is generally accepted in the art. The term generally refers to a replicon, such as a plasmid, phagemid, cosmid, baculovirus, bacmid, bacterial artificial chromosome (BAC), yeast artificial chromosome (YAC), as well as other bacterial, yeast, or viral vectors, to which another nucleic acid segment can be operatively inserted so as to bring about replication or expression of the inserted segment. "Expression vector" refers to a vector comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses).

Any concentration range, percentage range, ratio range, or integer range is to be understood to include the value of any integer within the recited range, and when appropriate, fractions thereof (such as one tenth and one hundredth of an integer), unless otherwise indicated.

Other objects, features and advantages of the present invention will become apparent from the detailed description. It should be understood, however, that the detailed description and the specific examples, while indicating specific embodiments of the invention, are given by way of illustration only, since various changes and modifications within the spirit and scope of the invention will become apparent to those skilled in the art from the detailed description.

A Segmented miRNA of the Invention

The instant disclosure provides a segmented miRNA mimetic molecule (segmented miRNA mimetic) that is double-stranded comprising a passenger strand and a distinct guide strand, wherein at least the guide strand includes one of more discontinuities and wherein the passenger strand and the guide strand each independently comprises, in sum, about 12 to about 26 (e.g., 11, 12, 13, 14, 15, 16, 17, 18, 19, 20, 21, 22, 23, 24, 25, 26, or 27) nucleotides, and the mimetic molecule comprises, in sum, about 10 to about 26 (e.g., 9, 10, 11, 12, 13, 14, 15, 16, 17, 18, 19, 20, 21, 22, 23, 24, 25, 26, or 27) base pairs. In one aspect, a segmented miRNA of the invention comprises 2 or more (e.g., 2, 3, or 4) distinct contiguous stretches of nucleotides in the guide strand. A "contiguous stretch of nucleotides" can comprise as little as 2 nucleotides, according to the present invention.

In another aspect, a segmented miRNA of the invention comprises 2 or more (e.g., from 2, 3, 4, 5, 6, 7, 8, 9, or 10) or more distinct contiguous stretches of nucleotides in each of the passenger strand and the guide strand. The distinct contiguous stretches of nucleotides are arranged such that their complementary sequences located on the opposite strand or within a corresponding miRNA target sequence do not overlap. Within each of the contiguous stretches of nucleotides, the nucleotides are connected by phosphodiester bonds and/or non-phosphodiester connectors. The distinct contiguous stretches of nucleotides in a given strand are arranged from 5'- to 3'-, and the each pair of neighboring stretches can be separated by a nick, gap, substitution, or insertion.

In one embodiment, a first discontinuity in the passenger strand and a second discontinuity in the guide strand of a segmented miRNA mimetic do not overlap provided that RNAi activity against one or more miRNA targets is maintained.

In another embodiment, a first discontinuity in the passenger strand and a second discontinuity in the guide strand of a segmented miRNA mimetic partially overlap provided that RNAi activity against one or more miRNA targets is maintained.

In another embodiment, a first discontinuity in the passenger strand and a second discontinuity in the guide strand of a segmented miRNA mimetic overlap completely provided that RNAi activity against one or more miRNA targets is maintained. For example, overlapping nicks or gaps can result in a miRNA mimetic molecule that is no longer able to associate into duplex form. One of skill in the art will readily appreciate that such designs are to be avoided in order to maintain miRNA medicated RNAi activity.

In one embodiment, a first nick in the passenger strand and a second nick in the guide strand of a segmented miRNA mimetic do not overlap.

In one embodiment, a first gap in the passenger strand and a second gap in the guide strand of a segmented miRNA mimetic do not overlap by at least one complementary nucleotide position.

In one aspect, a segmented miRNA mimetic molecule of the invention can be represented or depicted by Formula III:

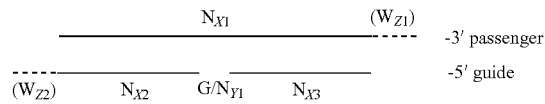

wherein the molecule comprises a passenger strand and a guide strand, where each line shown in the Formula and its adjacent "N" represent a contiguous stretch of nucleotides, each of "X1," "X2" and "X3" represent the number of nucleotide positions in each stretch, "G/N" represents a discontinuity in the guide strand, "Y1" represents a number of nucleotide positions in the discontinuity, and each group of dashed lines " " and its adjacent "(W)" represents a terminal overhang that is optionally present or absent, and each of "Z1" and "Z2" represents the number of overhanging nucleotides.

With reference to Formula III, in one embodiment, X1 is an integer from about 16 to about 26 (e.g., 15, 16, 17, 18, 19, 20, 21, 22, 23, 24, 25, 26, or 27), X2 is an integer from about 2 to about 20 (e.g., 1, 2, 3, 4, 5, 6, 7, 8, 9, 10, 11, 12, 13, 14, 15, 16, 17, 18, 19, 20, or 21). X3 is an integer from about 6 to about 24 (e.g., 5, 6, 7, 8, 9, 10, 11, 12, 13, 14, 15, 16, 17, 18, 19, 20, 21, 22, 23, 24, or 25), Y1 is an integer from 0 to about 10 (e.g., 0, 1, 2, 3, 4, 5, 6, 7, 8, 9, 10, or 11), provided that the sum of X2, X3 and Y1 is an integer from about 16 to about 26 (e.g., 15, 16, 17, 18, 19, 20, 21, 22, 23, 24, 25, 26, or 27). In certain embodiments the discontinuity in the guide strand is a nick. In certain embodiments the discontinuity in the guide strand is a gap. In certain embodiments the discontinuity in the guide strand is a substitution. In certain embodiments the discontinuity in the guide strand is an insertion. In one embodiment, there is no 3'-terminal overhanging nucleotides present (i.e., blunt-ended) in the passenger strand, in the guide strand, or in either strand, i.e., wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In a further embodiment, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strand, wherein Z1 and Z2 are independently about 1 to about 5 (e.g., 1, 2, 3, 4, or 5).

With reference to Formula III, in one embodiment, X1 is an integer from about 16 to about 26 (e.g., 15, 16, 17, 18, 19, 20, 21, 22, 23, 24, 25, 26, or 27), X2 is an integer from about 2 to about 20 (e.g., 1, 2, 3, 4, 5, 6, 7, 8, 9, 10, 11, 12, 13, 14, 15, 16, 17, 18, 19, 20, or 21), X3 is an integer from about 2 to about 24 (e.g., 1, 2, 3, 4, 5, 6, 7, 8, 9, 10, 11, 12, 13, 14, 15, 16, 17, 18, 19, 20, 21, 22, 23, 24, or 25), Y1 is an integer from 0 to about 10 (e.g., 0, 1, 2, 3, 4, 5, 6, 7, 8, 9, 10, or 11), provided that the sum of X2, X3 and Y1 is an integer from about 16 to about 26 (e.g., 15, 16, 17, 18, 19, 20, 21, 22, 23, 24, 25, 26, or 27). In certain embodiments the discontinuity in the guide strand is a nick. In certain embodiments the discontinuity in the guide strand is a gap. In certain embodiments the discontinuity in the guide strand is a substitution. In certain embodiments the discontinuity in the guide strand is an insertion. In one embodiment, there is no Y-terminal overhanging nucleotides present (i.e., blunt-ended) in the passenger strand, in the guide strand, or in either strand, i.e., wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In a further embodiment, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strand, wherein Z1 and Z2 are independently about 1 to about 5 (e.g., 1, 2, 3, 4, or 5).

In another aspect, a segmented miRNA mimetic molecule of the invention can be represented or depicted by Formula IV:

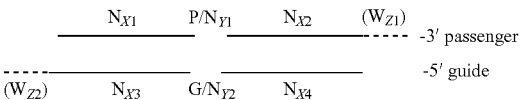

wherein the molecule comprises a passenger strand and a guide strand, where each line in the Formula and its adjacent "N" represent a contiguous stretch of nucleotides, each of "X1," "X2," "X3" and "X4" represents a number of nucleotide positions in each stretch, "P/N" represents a discontinuity in the passenger strand "G/N" represents a discontinuity in the guide strand, "P/N" represents a discontinuity in the passenger strand, each of "Y1" and "Y2" represents a number of nucleotide positions in the discontinuity, and each group of dashed lines " " and its adjacent "(W)" represents a terminal overhang that is optionally present or absent, and each of "Z1" and "Z2" represents the number of overhanging nucleotides.

With reference to Formula IV, in one embodiment, X1 and X2 are integers independently from about 2 to about 24 (e.g., 1, 2, 3, 4, 5, 6, 7, 8, 9, 10, 11, 12, 13, 14, 15, 16, 17, 18, 19, 20, 21, 22, 23, 24 or 25), Y1 is an integer from 0 to about 10 (e.g., 0, 1, 2, 3, 4, 5, 6, 7, 8, 9, 10, or 11), provided that the sum of X1, X2 and Y1 is an integer from about 16 to about 26 (e.g., 15, 16, 17, 18, 19, 20, 21, 22, 23, 24, 25, 26, or 27), X3 is an integer from about 2 to about 20 (e.g., 1, 2, 3, 4, 5, 6, 7, 8, 9, 10, 11, 12, 13, 14, 15, 16, 17, 18, 19, 20, or 21), X4 is an integer from about 2 to about 24 (e.g., 1, 2, 3, 4, 5, 6, 7, 8, 9, 10, 11, 12, 13, 14, 15, 16, 17, 18, 19, 20, 21, 22, 23, 24, or 25), Y2 is an integer from 0 to about 10 (e.g., 0, 1, 2, 3, 4, 5, 6, 7, 8, 9, 10, or 11), provided that the sum of X3, X4 and Y2 is about 16 to about 26 (e.g., 15, 16, 17, 18, 19, 20, 21, 22, 23, 24, 25, 26, or 27). In certain embodiments the discontinuity in the guide and/or passenger strand is a nick. In certain embodiments the discontinuity in the guide and/or passenger strand is a gap. In certain embodiments the discontinuity in the guide and/or passenger strand is a substitution. In certain embodiments the discontinuity in the guide and/or passenger strand is an insertion. In certain embodiments, there is no 3'-terminal overhanging nucleotides present (i.e., blunt-ended) in the passenger strand, in the guide strand, or in either strand, i.e. wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In certain embodiments, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strands, wherein Z1 and Z2 are independently about 1 to about 5 (e.g., 1, 2, 3, 4, or 5).

With reference to Formula IV, in one embodiment, X1 and X2 are integers independently from about 2 to about 24 (e.g., 1, 2, 3, 4, 5, 6, 7, 8, 9, 10, 11, 12, 13, 14, 15, 16, 17, 18, 19, 20, 21, 22, 23, 24 or 25), Y1 is an integer from 0 to about 10 (e.g., 0, 1, 2, 3, 4, 5, 6, 7, 8, 9, 10, or 11), provided that the sum of X1, X2 and Y1 is an integer from about 16 to about 26 (e.g., 15, 16, 17, 18, 19, 20, 21, 22, 23, 24, 25, 26, or 27), X3 is an integer from about 2 to about 20 (e.g., 1, 2, 3, 4, 5, 6, 7, 8, 9, 10, 11, 12, 13, 14, 15, 16, 17, 18, 19, 20, or 21), X4 is an integer from about 6 to about 24 (e.g., 5, 6, 7, 8, 9, 10, 11, 12, 13, 14, 15, 16, 17, 18, 19, 20, 21, 22, 23, 24, or 25), Y2 is an integer from 0 to about 10 (e.g., 0, 1, 2, 3, 4, 5, 6, 7, 8, 9, 10, or 11), provided that the sum of X3, X4 and Y2 is about 16 to about 26 (e.g., 15, 16, 17, 18, 19, 20, 21, 22, 23, 24, 25, 26, or 27). In certain embodiments the discontinuity in the guide and/or passenger strand is a nick. In certain embodiments the discontinuity in the guide and/or passenger strand is a gap. In certain embodiments the discontinuity in the guide and/or passenger strand is a substitution. In certain embodiments the discontinuity in the guide and/or passenger strand is an insertion. In certain embodiments, there is no 3'-terminal overhanging nucleotides present (i.e., blunt-ended) in the passenger strand, in the guide strand, or in either strand, i.e. wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In certain embodiments, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strands, wherein Z1 and Z2 are independently about 1 to about 5 (e.g., 1, 2, 3, 4, or 5).

In yet another aspect, a segmented miRNA mimetic molecule of the invention can be represented or depicted by Formula V:

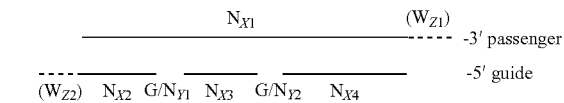

wherein the molecule comprises a passenger strand and a guide strand, where each line in the Formula and its adjacent "N" represent a contiguous stretch of nucleotides, each of "X1," "X2," "X3" and "X4" represents the number of nucleotide positions in each stretch, each "G/N" represents a discontinuity in the guide strand, each of "Y1" and "Y2" represents the number of nucleotide positions in the discontinuity, and each group of dashed lines " " and its adjacent "(W)" represents a terminal overhang that is optionally present or absent, and each of "Z1" and "Z2" represents the number of overhanging nucleotides; wherein X1 is an integer from about 12 to about 26 (e.g., 11, 12, 13, 14, 15, 16, 17, 18, 19, 20, 21, 22, 23, 24, 25, 26, or 27), X2 and X3 are each independently an integer from about 1 to about 16 (e.g., 1, 2, 3, 4, 5, 6, 7, 8, 9, 10, 11, 12, 13, 14, 15, 16, or 17), X4 is an integer from about 6 to about 22 (e.g., 5, 6, 7, 8, 9, 10, 11, 12, 13, 14, 15, 16, 17, 18, 19, 20, 21, 22, or 23), Y1 and Y2 are each independently an integer from 0 to about 10 (e.g., 0, 1, 2, 3, 4, 5, 6, 7, 8, 9, 10, or 11), provided that the sum of X2, X3, X4, Y1 and Y2 is an integer from about 10 to about 26 (e.g., 10, 11, 12, 13, 14, 15, 16, 17, 18, 19, 20, 21, 22, 23, 24, 25, 26, or 27). In certain embodiments the discontinuity in the guide and/or passenger strand is a nick. In certain embodiments the discontinuity in the guide and/or passenger strand is a gap. In certain embodiments the discontinuity in the guide and/or passenger strand is a substitution. In certain embodiments the discontinuity in the guide and/or passenger strand is an insertion. In certain embodiments, there is no 3'-terminal overhanging nucleotides present (i.e., blunt-ended) in the passenger strand, in the guide strand, or in either strand, wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In certain embodiments, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strands, wherein Z1 and Z2 are independently about 1 to about 5 (e.g., 1, 2, 3, 4, or 5).

In a further aspect, a segmented miRNA mimetic molecule of the invention can be represented or depicted by Formula VI:

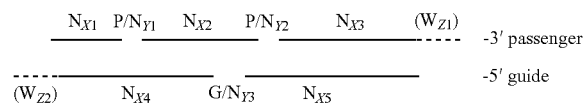

wherein the molecule comprises a passenger strand and a guide strand, where each line in the Formula and its adjacent "N" represent a contiguous stretch of nucleotides, each of "X1," "X2," "X3," "X4" and "X5" represents the number of nucleotide positions in each stretch, "P/N" represents a discontinuity in the passenger strand, "G/N" represents a discontinuity in the guide strand, each "P/N" represents a discontinuity in the passenger strand, each of "Y1," "Y2" and "Y3" represents the number of nucleotide positions in the discontinuity, and each group of dashed lines "-----" and its adjacent "(W)" represents a terminal overhang that is optionally present or absent, and each of "Z1" and "Z2" represents the number of overhanging nucleotides; wherein X1, X2, and X3 are each independently an integer from about 2 to about 22 (e.g., 1, 2, 3, 4, 5, 6, 7, 8, 9, 10, 11, 12, 13, 14, 15, 16, 17, 18, 19, 20, 21, 22, or 23), Y1 and Y2 are each independently an integer from 0 to about 10 (e.g., 0, 1, 2, 3, 4, 5, 6, 7, 8, 9, 10, or 11), provided that the sum of X1, X2, X3, Y1 and Y2 is an integer from about 12 to about 26 (e.g., 11, 12, 13, 14, 15, 16, 17, 18, 19, 20, 21, 22, 23, 24, 25, 26, or 27), X4 is an integer from about 1 to about 20 (e.g., 1, 2, 3, 4, 5, 6, 7, 8, 9, 10, 11, 12, 13, 14, 15, 16, 17, 18, 19, 20, or 21), X5 is an integer from about 6 to about 24 (e.g., 5, 6, 7, 8, 9, 10, 11, 12, 13, 14, 15, 16, 17, 18, 19, 20, 21, 22, 23, 24, or 25), Y3 is an integer from 0 to about 10 (e.g., 0, 1, 2, 3, 4, 5, 6, 7, 8, 9, 10, or 11), provided that the sum of X4, X5 and Y3 is an integer from about 10 to about 26 (e.g., 10, 11, 12, 13, 14, 15, 16, 17, 18, 19, 20, 21, 22, 23, 24, 25, 26, or 27). In certain embodiments the discontinuity in the guide and/or passenger strand is a nick. In certain embodiments the discontinuity in the guide and/or passenger strand is a gap. In certain embodiments the discontinuity in the guide and/or passenger strand is a substitution. In certain embodiments the discontinuity in the guide and/or passenger strand is an insertion. In certain embodiments, there is no 3'-terminal overhanging nucleotides present (i.e., blunt-ended) in the passenger strand, in the guide strand, or in either strand, wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In certain embodiments, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strands, wherein Z1 and Z2 are independently about 1 to about 5 (e.g., 1, 2, 3, 4, or 5).

In a further aspect, a segmented miRNA mimetic molecule of the invention can be represented or depicted by Formula VII:

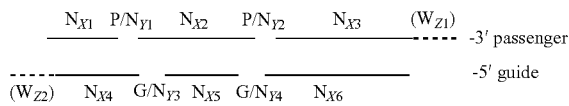

wherein the molecule comprises a passenger strand and a guide strand, where each line in the Formula and its adjacent "N" represent a contiguous stretch of nucleotides, each of "X1," "X2," "X3," "X4," "X5" and "X6" represents the number of nucleotide positions in each stretch, each "P/N" represents a discontinuity in the passenger strand, each "G/N" represents a discontinuity in the guide strand, each of "Y1," "Y2," "Y3" and "Y4" represents the number of nucleotide positions in the discontinuity, and each group of dashed lines " " and its adjacent "(W)" represents a terminal overhang that is optionally present or absent, and each of "Z1" and "Z2" represents the number of overhanging nucleotides; wherein X1, X2, and X3 are each independently an integer from about 2 to about 22 (e.g., 1, 2, 3, 4, 5, 6, 7, 8, 9, 10, 11, 12, 13, 14, 15, 16, 17, 18, 19, 20, 21, 22, or 23), Y1 and Y2 are each independently an integer from 0 to about 10 (e.g., 0, 1, 2, 3, 4, 5, 6, 7, 8, 9, 10, or 11), provided that the sum of X1, X2, X3, Y1 and Y2 is an integer from about 12 to about 26 (e.g., 11, 12, 13, 14, 15, 16, 17, 18, 19, 20, 21, 22, 23, 24, 25, 26, or 27), X4 and X5 are each independently an integer from about 1 to about 16 (e.g., 1, 2, 3, 4, 5, 6, 7, 8, 9, 10, 11, 12, 13, 14, 15, 16, or 17), X6 is an integer from about 7 to about 22 (e.g., 6, 7, 8, 9, 10, 11, 12, 13, 14, 15, 16, 17, 18, 19, 20, 21, 22, or 23), Y3 and Y4 are independently an integer from 0 to about 10 (e.g., 0, 1, 2, 3, 4, 5, 6, 7, 8, 9, 10, or 11), provided that the sum of X4, X5, X6, Y3 and Y4 is about 10 to about 26 (e.g., 10, 11, 12, 13, 14, 15, 16, 17, 18, 19, 20, 21, 22, 23, 24, 25, 26, or 27). In certain embodiments the discontinuity in the guide and/or passenger strand is a nick. In certain embodiments the discontinuity in the guide and/or passenger strand is a gap. In certain embodiments the discontinuity in the guide and/or passenger strand is a substitution. In certain embodiments the discontinuity in the guide and/or passenger strand is an insertion. In certain embodiments, there is no 3'-terminal overhanging nucleotides present (i.e., blunt-ended) in the passenger strand, in the guide strand, or in either strand, wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In certain embodiments, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strands, wherein Z1 and Z2 are independently about 1 to about 5 (e.g., 1, 2, 3, 4, or 5).

In a further aspect, a segmented miRNA mimetic molecule of the invention can be represented or depicted by Formula VIII:

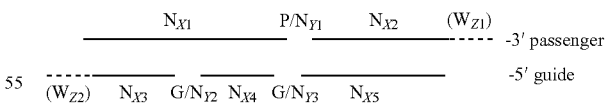

wherein the molecule comprises a passenger strand and a guide strand, where each line in the Formula and its adjacent "N" represent a contiguous stretch of nucleotides, each of "X1," "X2," "X3" and "X4" represents the number of nucleotide positions in each stretch, "P/N" represents a discontinuity in the passenger strand, each "G/N" represents a discontinuity in the guide strand, "P/N" represents a discontinuity in the passenger strand, each of "Y1" and "Y2" represents the number of nucleotide positions in the discontinuity, and each group of dashed lines "-----" and its adjacent "(W)" represents a terminal overhang that is optionally present or absent, and each of "Z1" and "Z2" represents the number of overhanging nucleotides; wherein X1 and X2 are each independently an integer from about 2 to about 24 (e.g., 1, 2, 3, 4, 5, 6, 7, 8, 9, 10, 11, 12, 13, 14, 15, 16, 17, 18, 19, 20, 21, 22, 23, 24 or 25). Y1 is an integer from 0 to about 10 (e.g., 0, 1, 2, 3, 4, 5, 6, 7, 8, 9, 10, or 11), provided that the sum of X1, X2 and Y1 is an integer from about 12 to about 26 (e.g., 11, 12, 13, 14, 15, 16, 17, 18, 19, 20, 21, 22, 23, 24, 25, 26, or 27), X3 and X4 are each independently an integer from about 1 to about 16 (e.g., 1, 2, 3, 4, 5, 6, 7, 8, 9, 10, 11, 12, 13, 14, 15, 16, or 17), X5 is an integer from about 6 to about 24 (e.g., 5, 6, 7, 8, 9, 10, 11, 12, 13, 14, 15, 16, 17, 18, 19, 20, 21, 22, 23, 24, or 25), Y2 and Y3 are each independently an integer from 0 to about 10 (e.g., 0, 1, 2, 3, 4, 5, 6, 7, 8, 9, 10, or 11), provided that the sum of X3, X4, X5, Y2 and Y3 is an integer from about 10 to about 26 (e.g., 10, 11, 12, 13, 14, 15, 16, 17, 18, 19, 20, 21, 22, 23, 24, 25, 26, or 27). In certain embodiments the discontinuity in the guide and/or passenger strand is a nick. In certain embodiments the discontinuity in the guide and/or passenger strand is a gap. In certain embodiments the discontinuity in the guide and/or passenger strand is a substitution. In certain embodiments the discontinuity in the guide and/or passenger strand is an insertion. In certain embodiments, there is no 3'-terminal overhanging nucleotides present (i.e., blunt-ended) in the passenger strand, in the guide strand, or in either strand, wherein Z1, Z2, or both Z1 and Z2 are 0. In another embodiment, there are one or more 3'-terminal overhanging nucleotides present in the passenger strand, wherein Z1 is about 1 to about 5 (e.g., 1, 2, 3, 4, or 5). In certain embodiments, there are one or more 3'-terminal overhanging nucleotides present in the guide strand, wherein Z2 is about 1 to about 5 (e.g., 1, 2, 3, 4, or 5). In yet another embodiment, there are one or more 3'-terminal overhanging nucleotides present in both the passenger strand and the guide strands, wherein Z1 and Z2 are independently about 1 to about 5 (e.g., 1, 2, 3, 4, or 5).

At least one of the 2 or more contiguous stretches of nucleotides in the guide strand of a segmented miRNA mimetic molecule of Formula III, IV, V, VI, VII, or VIII comprises a sequence that is substantially, essentially or perfectly homologous (e.g., at least 25, 30, 35, 40, 45, 50, 55, 60, 65, 70, 75, 80, 85, 90, 95, or 100% homologous) to a nucleotide sequence of a naturally-occurring endogenous miRNA, such as one selected from miRBase as of the filing date of the present invention, and for example, one selected from SEQ ID NOs: 1-1090 of Table I herein. In certain embodiments, the first contiguous stretch of nucleotides from the 5'-end of the guide strand comprises at least 6 (e.g., 6, 7, or 8) consecutive nucleotides that are identical (or perfectly homologous) to a 6, 7, or 8-nucleotide sequence within the seed sequence of a naturally-occurring miRNA, such as one selected from Table I (wherein the seed sequence nucleotides are capitalized). In another embodiment, at least 2 of the 2 or more contiguous stretches of nucleotides in the guide strand of a segmented miRNA mimetic of Formula III-VIII comprise sequences that are substantially, essentially, or perfectly homologous (at least 25, 30, 35, 40, 45, 50, 55, 60, 65, 70, 75, 80, 85, 90, 95, or 100% homologous) to non-overlapping regions of a naturally-occurring endogenous miRNA. In yet another embodiment, all of the contiguous stretches of nucleotides in the guide strand comprise sequences that are substantially, essentially, or perfectly homologous (e.g., at least at least 25, 30, 35, 40, 45, 50, 55, 60, 65, 70, 75, 80, 85, 90, 95, or 100% homologous) to non-overlapping regions of a naturally-occurring endogenous miRNA. Each of the 1 or more contiguous stretches of nucleotides in the passenger strand of a segmented miRNA mimetic molecule of Formula III, IV, V, VI, VII, or VIII comprises a sequence that is substantially or perfectly complementary (e.g., at least 25, 20, 35, 40, 45, 50, 55, 60, 65, 70, 75, 80, 85, 90, 95, or 100% complementary) to a non-overlapping region of a naturally-occurring endogenous miRNA, such as one selected from miRBase as of the filing date of the present invention, and for example, one selected from SEQ ID NOs: 1-1090 of Table I herein.

At least one of the 2 or more contiguous stretches of nucleotides in the guide strand of a segmented miRNA mimetic molecule of Formula III, IV, V, VI, VII, or VIII comprises sequence having 6 or more (e.g., 6, 7, 8, 9, 10, 11, 12, 13, 14, 15, 16, 17, 18, 19, 20, 21, 22, 23, 24, 25, or 26) contiguous nucleotides of a naturally-occurring endogenous miRNA, such as one selected from miRBase as of the filing date of the present invention, and for example, one selected from SEQ ID NOs: 1-1090 of Table I herein. In certain embodiments, the first contiguous stretch of nucleotides from the 5'-end of the guide strand comprises at least 6 (e.g., 6, 7, or 8) consecutive nucleotides of a seed sequence of a naturally-occurring miRNA, such as one selected from Table I (wherein the seed sequence nucleotides are capitalized). In another embodiment, at least 2 of the 2 or more contiguous stretches of nucleotides in the guide strand of a segmented miRNA mimetic of Formula III-VIII comprise sequence having 6 or more (e.g., 6, 7, 8, 9, 10, 11, 12, 13, 14, 15, 16, 17, 18, 19, 20, 21, 22, 23, 24, 25, or 26) contiguous nucleotides non-overlapping regions of a naturally-occurring endogenous miRNA. In yet another embodiment, all of the contiguous stretches of nucleotides in the guide strand comprises sequence having 6 or more (e.g., 6, 7, 8, 9, 10, 11, 12, 13, 14, 15, 16, 17, 18, 19, 20, 21, 22, 23, 24, 25, or 26) contiguous nucleotides to non-overlapping regions of a naturally-occurring endogenous miRNA. Each of the 1 or more contiguous stretches of nucleotides in the passenger strand of a segmented miRNA mimetic molecule of Formula IV, V, VI, VII, or VIII comprises a sequence capable of forming 2 or more (e.g., 2, 3, 4, 5, 6, 7, 8, 9, 10, 11, 12, 13, 14, 15, 16, 17, 18, 19, 20, 21, 22, 23, 24, 25 or 26) base pairs to a non-overlapping region of a naturally-occurring endogenous miRNA, such as one selected from miRBase as of the filing date of the present invention, and for example, one selected from SEQ ID NOs: 1-1090 of Table I herein.

In one aspect, a segmented miRNA mimetic of the invention comprises two separate strands, a guide strand and a separate passenger strand, wherein the strands are not connected to each other at either the 5' or the 3' terminal ends by a linker. Linkers connecting the terminal ends of a segmented miRNA mimetic of the invention are referred to as "terminal linkers" herein. In another aspect, one or both terminal ends of a segmented miRNA mimetic molecule can be connected or linked together by a terminal nucleotide and/or non-nucleotide linker. In certain embodiments, either or both ends of the passenger strand and the guide strand of a segmented miRNA mimetic of the invention can be covalently linked by a terminal nucleotide and/or non-nucleotide linker as described herein and known in the art.

One or more substitutions or insertions can be present in the absence of any terminal linkers, as described above. Alternatively, one or more substitutions or insertions can be present in a given molecule with one or more terminal linkers.

One or more or all of nucleotides of each of the contiguous stretches of nucleotides can be ribonucleotides, modified ribonucleotides, or suitable nucleotide analogs. Incorporation of nucleotide analogs, such as various known sugar, base, and backbone modifications, and LNA monomer units into disrupted strands can significantly enhance serum stability and prolong target knockdown or expression regulatory effects. The segmented miRNA mimetic molecules of the present invention can functionally accommodate and are compatible with various chemical modifications, in various combinations and juxtapositions, and to varying degrees. For example, from one to all (e.g., 1, 2, 3, 4, 5, 6, 7, 8, 9, 10, 11, 12, 13, 14, 15, 16, 17, 18, 19, 20, 21, 22, 23, 24, 25 26, 27, 28, 29, 30, 31, 32, 33, 34, 35, 36, 37, 38, 39, 40, 41, 42, 43, 44, 45, 46, 47, 48, 49, 50, 51, or 52) of the ribonucleotides of the segmented miRNA mimetics of the invention can be modified. The improved properties conferred by the functionally compatible chemical modifications to the sugar, base and/or backbone, or by including suitable nucleotide analog residues, are of particular importance for application of these segmented miRNA mimetic molecules in vivo, for example, for use as a therapeutic agent or as a functional genomic tool.

In certain embodiments, a segmented miRNA mimetic molecule of the present invention can comprise a 3'-terminal overhang in its passenger strand, guide strand, or both the passenger and guide strands. The "overhang" nucleotides are unpaired and single stranded regions located at the terminal ends of an otherwise generally double-stranded nucleic acid molecule. An exemplary segmented miRNA mimetic of the invention can comprise a 3'-terminal overhang of 1 to 5 nucleotides (e.g., 1, 2, 3, 4, or 5 nucleotides) in the passenger strand, the guide strand, or both the passenger and the guide strands. In alternative embodiments, a segmented miRNA mimetic of the present invention can be blunt-ended (i.e., comprising no terminal overhang nucleotides) at either or both terminal ends.

In a further aspect, the segmented miRNA mimetics of the invention, according to any of the embodiments herein, are capable of participating in RNAi against endogenous RNA targets of their corresponding naturally-occurring miRNAs. The inhibition of the miRNA target can be achieved via the standard miRNA-specific interference mechanism. For example, the inhibition of the miRNA target can be by interaction (e.g., base-paring, binding, etc.) with the untranslated mRNA region, with which the corresponding endogenous miRNA interacts, which effectuates the translational regulation of one or more downstream genes. Or, the inhibition of the miRNA target can be achieved via an siRNA-like interference mechanism wherein the binding of the miRNA target by the guide strand of the segmented miRNA mimetic results in the cleavage of the untranslated miRNA target.

Modified Segmented miRNA Mimetics

The introduction of modified nucleotide analogs into segmented miRNA mimetic molecules of the invention provides a tool for overcoming potential limitations of in vivo stability and bioavailability inherent to native RNA molecules (i.e., having standard nucleotides) that are exogenously delivered. In certain embodiments, the use of modified segmented miRNA mimetics of this disclosure can enable achievement of a given therapeutic effect at a lower dose since these molecules can be designed to have an increased melting temperature or half-life in a subject or biological samples (e.g., serum). Furthermore, certain modifications can be used to improve the bioavailability of segmented miRNA mimetics by targeting particular cells or tissues or improving cellular uptake of the segmented miRNA mimetics. Therefore, even if the activity of a segmented miRNA mimetic of this disclosure is somewhat reduced (e.g., by less than about 20%, or 30%, or even 40%) as compared to an unmodified segmented miRNA mimetic of the same structure, the overall activity of the modified segmented miRNA mimetic can be greater than that of its native counterpart due to improved stability or delivery of the molecule. Modified segmented miRNA mimetics can also minimize the possibility of activating an interferon response in, for example, humans.

In certain embodiments, segmented miRNA mimetics of the invention comprise ribonucleotides at about 1 or more (e.g. 1, 2, 3, 4, 5, 6, 7, 8, 9, 10, 11, 12, 13, 14, 15, 16, 17, 18, 19, 20, 21, 22, 23, 24, 25 or 26) of the nucleotide positions in one strand, in each strand, or any combination thereof.

In related embodiments, a segmented miRNA mimetic according to the instant disclosure comprises one or more natural or synthetic non-standard nucleotides. In related embodiments, the non-standard nucleotide is one or more deoxyuridine, L- or D-locked nucleic acid (LNA) molecule (e.g., a 5-methyluridine LNA) or substituted LNA (e.g., having a pyrene), or a universal-binding nucleotide, or a G clamp, or any combination thereof. In certain embodiments, the universal-binding nucleotide can be C-phenyl, C-naphthyl, inosine, azole carboxamide, 1-β-D-ribofuranosyl-4-nitro indole, 1-β-D-ribofuranosyl-5-nitroindole, 1-β-D-ribofuranosyl-6-nitroindole, or 1-β-D-ribofuranosyl-3-nitropyrrole.

Modified nucleotides, which can be present in either or both the passenger and the guide strands of a segmented miRNA mimetic of the invention, comprise modified nucleotide analogs having characteristics similar to natural or standard ribonucleotides. For example, this disclosure features segmented miRNA mimetics comprising nucleotides having a Northern conformation (see, e.g., Northern pseudorotation cycle, Saenger, Springer-Verlag ed., 1984), which are known to potentially impart resistant to nuclease degradation while maintaining the capacity to mediate RNAi, at least when applied to siRNA molecules. Exemplary nucleotides having a Northern configuration include locked nucleic acid (LNA) nucleotides (e.g., 2'-O, 4'-C-methylene-(D-ribofuranosyl) nucleotides), 2'-methoxyethyl (MOE) nucleotides, 2'-methyl-thio-ethyl, 2'-deoxy-2'-fluoro nucleotides, 2'-deoxy-2'-chloro nucleotides, 2'-azido nucleotides, 5-methyluridines, or 2'-O-methyl nucleotides). In any of these embodiments, one or more substituted or modified nucleotides can be a G clamp (e.g., a cytosine analog that forms an additional hydrogen bond to guanine, such as 9-(aminoethoxy)phenoxazine). See, e.g., Lin and Mateucci, 1998 J. Am. Chem. Soc. 720:8531).

In certain embodiments, a segmented miRNA mimetic of the invention comprises an overhang of 1 to 5 nucleotides. The overhang can comprise one or more 2'-O-alkyl modifications or locked nucleic acid (LNAs) as described herein or otherwise known in the art. In certain embodiments, a segmented miRNA mimetic of the invention can comprise one or more 3'-end 2'-O-alkyl or LNA at one or more of the internal terminals. A 2'-O-alkyl or LNA can also be present at positions that are not in the gaps, near the nicks or at the terminal ends of a segmented miRNA mimetic. In any of the embodiments of segmented miRNA mimetics, the 3'-terminal overhangs, if present, can comprise chemically-modified nucleotides that are modified at a nucleic acid sugar, base, or backbone. In any of the embodiments of segmented miRNA mimetics, the 3'-terminal nucleotide overhangs can comprise one or more universal base ribonucleotides. In any of the embodiments of segmented miRNA mimetics, the 3'-terminal nucleotide overhangs can comprise one or more acyclic nucleotides.

In certain embodiments, the 5'-terminal end of the passenger strand or guide strand of a segmented miRNA mimetic of the invention is phosphorylated. In any of the embodiments of segmented miRNA mimetics described herein, the segmented miRNA can further comprise a terminal phosphate group, such as a 5'-phosphate (see Martinez et al., 2002 Cell 110:563; Schwarz et al., 2002 Mole. Cell 70:537) or a 5'3'-diphosphate.

In certain embodiments, a segmented miRNA mimetic comprises one or more (e.g., 1, 2, 3, 4, 5, 6, 7, 8, 9, 10, 11, 12, 13, 14, 15, 16, 17, 18, 19, 20, 21, 22, 23, 24, 25, or 26) 2'-sugar substitutions in one strand or independently each strand, such as a 2'-deoxy, methoxyethyl, 2'-O-methoxyethyl, 2'-halogen (e.g., 2'-fluoro), or the like, or any combination thereof. In still further embodiments, a segmented miRNA mimetic comprises a terminal cap substituent at one or more terminal ends, internal ends, or both, of the passenger strand and/or the guide strands, such as, for example, an alkyl, abasic, deoxy abasic, glyceryl, dinucleotide, acyclic nucleotide, inverted deoxynucleotide moiety, or any combination thereof. In certain embodiments, at least one or more 5'-terminal-end or 5'-internal-end ribonucleotides of the passenger strand have 2'-sugar substitutions. In certain other embodiments, at least one or more 5'-terminal-end or 5'-internal-end ribonucleotides of the guide strand have 2'-sugar substitutions. In certain embodiments, at least one or more 5'-terminal-end or 5'-internal-end ribonucleotides of the passenger strand and the guide strand have 2'-sugar substitutions.

In other embodiments, a segmented miRNA mimetic comprises one or more (e.g., 1, 2, 3, 4, 5, 6, 7, 8, 9, 10, 11, 12, 13, 14, 15, 16, 17, 18, 19, 20, 21, 22, 23, 24, 25, or 26) substitutions in the sugar in one strand or independently each strand, including any combination of ribosyl, 2'-deoxyribosyl, a tetrofuranosyl (e.g., L-α-threofuranosyl), a hexopyranosyl (e.g., ρ-allopyranosyl, β-altropyranosyl and β-glucopyranosyl), a pentopyranosyl (e.g., β-ribopyranosyl, α-lyxopyranosyl, β-xylopyranosyl and α-arabinopyranosyl), a carbocyclic analog, a pyranose, a furanose, a morpholino, or analogs or derivatives thereof.

In yet other embodiments, a segmented miRNA mimetic comprises at least one (e.g., 1, 2, 3, 4, 5, 6, 7, 8, 9, 10, 11, 12, 13, 14, 15, 16, 17, 18, 19, 20, 21, 22, 23, 24, 25, or 26) modified internucleoside linkages in one strand or independently each strand, such as independently a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphonate, phosphoramidate, 3'-amino phosphoramidate, aminoalkylphosphoramidate, thionophosphoramidate, thionoalkylphosphonate, thionoalkylphosphotriester, selenophosphate, boranophosphate linkage, or any combination thereof.

A modified internucleotide linkage, as described herein, can be present in one or more strands of a segmented miRNA mimetic, for example, in the passenger strand, the guide strand, or in both strands. A segmented miRNA mimetic can comprise one or more modified internucleotide linkages at the 3'-terminal end, the 5'-terminal end, or both of the 3'-terminal and 5'-terminal ends of the passenger strand, the guide strand, or both strands. In certain embodiments, a segmented miRNA mimetic of the invention has one modified internucleotide linkage at the 3'-terminal end, such as a phosphorothioate linkage. An exemplary segmented miRNA mimetic comprises about 1, 2, 3, 4, 5, 6, 7, 8, 9, 10 or more phosphorothioate internucleotide linkages in either strand. Another exemplary segmented miRNA mimetic comprises about 1, 2, 3, 4, 5, 6, 7, 8, 9, 10 or more phosphorothioate internucleotide linkages in both strands. A further exemplary segmented miRNA mimetic comprises about 1 to about 5 or more consecutive phosphorothioate internucleotide linkages at for example, the 5'-terminal end of its passenger strand, the 5'-terminal end of its guide strand, both the 5'-terminal ends of both strands, or for example, at one or more of the 5'-internal ends. In yet another exemplary segmented miRNA mimetic, there can be one or more pyrimidine phosphorothioate internucleotide linkages in the passenger strand and/or the guide strand. In a further exemplary segmented miRNA mimetic, there can be one or more purine phosphorothioate internucleotide linkages in the passenger strand and/or the guide strand.

Many exemplary modified nucleotide bases or analogs thereof useful in segmented miRNA mimetics of the instant disclosure include 5-methylcytosine; 5-hydroxymethylcytosine; xanthine; hypoxanthine; 2-aminoadenine; 6-methyl, 2-propyl, or other alkyl derivatives of adenine and guanine; 8-substituted adenines and guanines (e.g., 8-aza, 8-halo, 8-amino, 8-thiol, 8-thioalkyl, 8-hydroxyl, or the like); 7-methyl, 7-deaza, and 3-deaza adenines and guanines; 2-thiouracil; 2-thiothymine; 2-thiocytosine; 5-methyl, 5-propynyl, 5-halo (e.g., 5-bromo or 5-fluoro), 5-trifluoromethyl, or other 5-substituted uracils and cytosines; and 6-azouracil. Further useful nucleotide bases can be found in Kurreck, 2003 Eur. J. Biochem. 270:1628; Herdewijn, 2000 Guide Nucleic Acid Develop. 10:297; Concise Encyclopedia of Polymer Science and Engineering, pp. 858-859, Kroschwitz, J. L, ed. John Wiley & Sons, 1990; U.S. Pat. No. 3,687,808, and similar references, all of which are incorporated by reference herein.

Certain modified nucleotide base moieties are also contemplated. These include 5-substituted pyrimidines; 6-azapyrimidines; and N-2, N-6, or O-6 substituted purines (e.g., 2-aminopropyladenine, 5-propynyluracil and 5-propynylcytosine). Further, for example, 5-methyluridine and 5-methylcytosine substitutions are known to increase nucleic acid duplex stability, which can be combined with 2'-sugar modifications (e.g., 2'-O-methyl or 2'-methoxyethyl) or internucleoside linkages (e.g., phosphorothioate) that provide the desired nuclease resistance to the modified or substituted segmented miRNA mimetics.

In certain embodiments, at least one pyrimidine of a segmented miRNA mimetic of the invention is a locked nucleic acid (LNA) in the form of a bicyclic sugar. In a related embodiment, the LNA comprises a base substitution, such as a 5-methyluridine LNA or 2-thio-5-methyluridine LNA. In certain embodiments, a ribose of the pyrimidine nucleoside or the internucleoside linkage can be optionally modified.

In any of these embodiments, one or more modified nucleotides can be a G clamp (e.g., a cytosine analog that forms an additional hydrogen bond to guanine, such as 9-(aminoethoxy) phenoxazine). See, e.g., Lin and Mateucci, 1998 Nucleic Acids Res. 19:3111).

In addition, the terminal structure of segmented miRNA mimetics of this disclosure can comprise a stem-loop structure in which an end of one strand (e.g., the guide strand) of a segmented miRNA mimetic is connected by a linker nucleic acid, e.g., a linker RNA to an end of the opposite strand (e.g., the passenger strand). When linker segments are employed, there is no particular limitation in the length of the linker as long as it does not hinder pairing of the stem portion. For example, for stable pairing of the stem portion, the linker portion can have a clover-leaf tRNA structure. Even if the linker has a length that would hinder pairing of the stem portion, it is possible, for example, to construct the linker portion to include introns so that the introns are excised during processing of a precursor miRNA mimetic into a mature miRNA mimetic, thereby allowing pairing of the stem portion. In the case of a stem-loop dsRNA, either end (head or tail) of a segmented miRNA mimetic with no loop structure can comprise a low molecular weight RNA, for example, a natural RNA molecule such as a tRNA, rRNA or viral RNA, or an artificial RNA molecule.

A segmented miRNA mimetic of the invention can be constructed such that it takes on an overall circular structure, wherein the entire molecule is about 10 to about 60 nucleotides in length having from about 5 to about 26 base pairs (e.g., about 19 to about 21) wherein the circular oligonucleotide forms a dumbbell shaped structure having about 10 to about 26 base pairs and two loops. In certain embodiments, a circular segmented miRNA mimetic contains two loop motifs, wherein one or both loop portions are biodegradable.

In another aspect of this disclosure, the segmented miRNA mimetic structures of the invention and their potential of allowing more suitable types of chemical modification and allowing modification to a higher extent can be used to reduce interferon activation when a segmented miRNA mimetic is contacted with a biological sample, for example, when it is introduced into a eukaryotic cell. A segmented miRNA mimetic of the invention comprises at least 6 ends, including terminal and internal ends, as compared to its traditional non-segmented duplex miRNA mimetic counterpart, which comprises 4 ends. These ends can conveniently be used for tethering functional chemical groups to enhance, for example, lipophilic and other properties associated with cellular delivery. For instance, it is possible to tether bulky groups like cholesterol to the 5'-ends of each of the contiguous stretches of nucleotides without losing RNAi activity.

Moreover, because the yield of synthesis is usually higher for shorter RNA strands, the cost of large-scale synthesis in connection with therapeutic application can be substantially reduced using the segmented miRNA mimetics of the present invention.

In any of the embodiments described herein, a segmented miRNA mimetic can include multiple types of modifications in combination. For example, a segmented miRNA mimetic having at least one ribothymidine or 2-thioribothymidine can further comprise at least one LNA, 2'-methoxy, 2'-fluoro, 2'-deoxy, phosphorothioate linkage, an inverted base terminal cap, or any combination thereof. In certain exemplary embodiments, a segmented miRNA mimetic can comprise one or more or all uridines (e.g., 1, 2, 3, 4, 5, 6, 7, 8, 9, 10 or more) substituted with 2'-O-methyl uridine and have 1, 2, 3, 4, 5, 6, 7, 8, 9, 10 or more LNA substitutions. In other exemplary embodiments, a segmented miRNA mimetic can comprise from one or more or all uridines substituted with 2'-O-methyl uridine and have up to about 25% phosphorothioate substitutions. In still other exemplary embodiments, a segmented miRNA mimetic can comprise one or more or all uridines (e.g., 1, 2, 3, 4, 5, 6, 7, 8, 9, 10 or more) substituted with 2'-O-methyl uridine and have 1, 2, 3, 4, 5, 6, 7, 8, 9, 10 or more 2'-deoxy-2'-fluoro substitutions.

Within certain aspects, the present disclosure also provides segmented miRNA molecules comprising one or more (e.g., 1, 2, 3, 4, 5, 6, 7, 8, 9, 10 or more) universal base nucleotides. In certain aspects, a segmented miRNA mimetic disclosed herein can include about 1 to about 10 universal base nucleotides, so long as the resulting segmented miRNA mimetic remains capable of modulating one or more of its endogenous miRNA targets.

Suitable modifications can also include one or more suitable conjugates attached to, typically the ends, including the terminal ends and internal ends, of a segmented miRNA mimetic of the invention. The conjugate can be attached via a covalent attachment. In some cases, the conjugate can be linked to the segmented miRNA mimetic via a biodegradable linker, attached the 3'-end, 5' end, or both ends of the passenger strand, the guide strand and/or the internal ends of each of the contiguous stretches of nucleotides. The conjugate molecule can facilitate the delivery of the double-stranded oligonucleotide molecule into a biological system, such as a cell. The conjugate can also be a polyethylene glycol (PEG), human serum albumin, or a ligand for a cellular receptor that can facilitate cellular uptake. However, as explained above, the endogenous miRNA and siRNA paths of biogenesis and machineries are distinct, featuring different components or participants, therefore conjugates or other modifications in this class that are suitable for an exogenously introduced siRNA molecule can still be unsuitable for an exogenously introduced miRNA mimetic molecule such as a segmented miRNA mimetic of the invention.

Substitutions and Insertions

Various non-nucleotide moieties as are provided herein or otherwise known in the art can be used as substitutions and/or insertions in the segmented miRNA mimetics of the invention provided that RNAi activity against one or more miRNA targets is maintained.

In one aspect of the invention, substitutions and/or insertions in the segmented mimetic miRNAs of the invention can comprise one or more alkyl moieties, e.g., any $C_1$-$C_{20}$, and preferably a $C_1$, $C_2$, $C_3$, $C_4$, $C_5$, $C_6$, $C_7$, $C_8$, $C_9$ or $C_{10}$ alkyl moiety. The alkyl moiety can be straight chain, branched, aliphatic or aromatic. The alkyl moiety can be substituted or unsubstituted. In certain embodiments the alkyl moieties are $C_3$ and/or $C_6$.

Segmented mimetic miRNAs of the present invention can comprise substitutions or insertions that incorporate one or more small molecules, lipids or lipophiles, terpenes, phospholipids, antibodies, toxins, cholesterol, a protein binding agent (e.g., a ligand for a cellular receptor that can facilitate cellular uptake), a vitamin, negatively charged polymers and other polymers, for example proteins (e.g., human serum albumin), peptides, hormones, carbohydrates, polyethylene glycols, or polyamines, and those described in, for example, U.S. Patent Publication No. 2005/0196781, and U.S. Patent Publication No. 2006/0293271, the disclosures of which are incorporated herein by reference. Substitutions and insertions can include alkyl chains optionally substituted with a functional group. For example, the alkyl chain can be substituted with a moiety that binds specifically to a target molecule of interest.

Substitutions and insertions of the present invention can further comprise a polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, 1990, *Nucleic Acids Res.* 18:6353; Seela and Kaiser, 1987, *Nucleic Acids Res.* 15:3113; Cload and Schepartz, 1991, *J. Am. Chem. Soc.* 113:6324; Richardson and Schepartz, 1991, *J. Am. Chem. Soc.* 113:5109; Ma et al., 1993, *Nucleic Acids Res.* 27:2585; Ma et al., 1993, *Biochemistry* 32:1751; Durand et al., 1990, *Nucleic Acids Res.* 18:6353; McCurdy et al., 1991, *Nucleosides & Nucleotides* 70:287; Jaschke et al., 1993, *Tetrahedron Lett.* 34:301; Ono et al., 1991, Biochemistry 30:9914; and others. A chemical moiety that provides additional functionality (e.g., specifically binds to a target molecule of interest or facilitates/enhances cellular delivery of the molecule) to the miRNA mimetic can be a part of the substitution or insertion or covalently attached or linked thereto. For example, the additional functional group can impart therapeutic activity to miRNA mimetic of the invention by assisting in transferring the RNAi molecule compounds across cellular membranes, altering the pharmacokinetics, and/or modulating the localization of RNAi molecules of the invention.

Substitutions and insertions of the present invention can aid in delivery and/or localization of RNAi molecules of the invention into a number of cell types originating from different tissues, in the presence or absence of serum (see Sullenger and Cech, U.S. Pat. No. 5,854,038). For example, the conjugate member can be naproxen, nitroindole (or another conjugate that contributes to stacking interactions), folate, ibuprofen, or a C5 pyrimidine linker. The conjugate member can be a glyceride lipid conjugate (e.g., a dialkyl glyceride derivatives), vitamin E conjugates, or thio-cholesterols. The conjugate molecule can alternatively be a peptide that functions, when conjugated to a miRNA mimetic, to facilitate delivery of the molecule into a target cell, or otherwise enhance delivery, stability, or activity of the molecule when contacted with a biological sample. Exemplary peptide conjugate members for use within these aspects of this disclosure, include peptides PN27, PN28, PN29, PN58, PN61, PN73, PN158, PN159, PN173, PN182, PN202, PN204, PN250, PN361, PN365, PN404, PN453, and PN509 as described, for example, in U.S. Patent Application Publication Nos. 2006/0040882 and 2006/0014289, and U.S. Provisional Patent Application No. 60/939,578, which are all incorporated herein by reference.

A substitution or insertion can comprise a moiety that specifically binds to a target molecule. The target molecule can be any molecule of interest. For example, the target molecule can be a ligand-binding domain of a protein, thereby preventing or competing with the interaction of the naturally-occurring ligand with the protein. This is a non-limiting example and those in the art will recognize that other embodiments can be readily generated using techniques generally known in the art (see, e.g., Gold et al, 1995, *Anna. Rev. Biochem.* 64:163; Brody and Gold, 2000, *J. Biotechnol.* 74:5; Sun, 2000, *Curr. Opin. Mol. Ther.* 2:100; Kusser, J., 2000, *Biotechnol.* 74:21; Hermann and Patel, 2000, *Science* 257:820; and Jayasena, 1999, *Clinical Chem.* 45:1628).

The substitution or insertion can provide the ability to administer the segmented miRNA mimetic to specific cell types, such as hepatocytes. For example, the asialoglycoprotein receptor (ASGPr) (Wu and Wu, 1987, *J. Biol. Chem.* 262:4429) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell* 22: 611; Connolly et al., 1982, *J. Biol. Chem.* 257:939). Lee and Lee (1987, *Glycoconjugate J.* 4:317) obtained this high specificity through the use of N-acetyl-D-galactosamine as the carbohydrate moiety, which has higher affinity for the receptor compared to galactose. This "clustering effect" has also been described for the binding and uptake of mannosyl-terminating glycoproteins or glycoconjugates (Ponpiporn et al., 1981, *J. Med. Chem.* 24: 1388). The use of galactose and galactosamine based conjugates to transport exogenous compounds across cell membranes can provide a targeted delivery approach to the treatment of liver disease. The use of bioconjugates can also provide a reduction in the required dose of therapeutic compounds required for treatment. Furthermore, therapeutic bioavailability, pharmacodynamics, and pharmacokinetic parameters can be modulated through the use of bioconjugates of this disclosure.

Terminal Analogs, Modifications, Linkers, and Conjugates

In one embodiment, a miRNA mimetic of the invention comprises one or more terminal nucleotide analogs, non-nucleotide analogs, nucleotide linkers, non-nucleotide linkers, caps, conjugates and the like as are generally known in the art, at the 5'-end, 3'-end, or both 5'- and 3'-ends of the passenger strand, or alternately at the 3'-end of the guide strand.

In certain embodiments, the invention features a nucleic acid linker that covalently attaches on strand to the other. A nucleotide linker can be a nucleic acid aptamer. A non-nucleotide linker can be an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, 1990 Nucleic Acids Res. 18:6353; Seela and Kaiser, 1987 Nucleic Acids Res. 15:3113; Cload and Schepartz, 1991 J. Am. Chem. Soc. 113:6324; Richardson and Schepartz, 1991 J. Am. Chem. Soc. 113:5109; Ma et al., 1993 Nucleic Acids Res. 27:2585; Ma et al., 1993 Biochemistry 32:1751; Durand et al., 1990 Nucleic Acids Res. 18:6353; McCurdy et al., 1991 Nucleosides & Nucleotides 70:287; Jaschke et al., 1993 Tetrahedron Lett. 34:301; Ono et al., 1991 Biochemistry 30:9914; and others.

In another embodiment, a conjugate molecule can be optionally attached to a segmented miRNA mimetic or an analog thereof. For example, such conjugate molecules can be polyethylene glycol, human serum albumin, or a ligand for a cellular receptor that can, for example, mediate cellular uptake. The conjugate molecule can be attached at one or more of the terminal ends and/or one or more of the internal ends. Examples of specific conjugate molecules contemplated by the instant disclosure are described in, for example, U.S. Patent Publication No. 2005/0196781 A1, and U.S. Patent Publication No. 2006/0293271 A1, the disclosures of which are incorporated herein by reference.

In a certain aspect, the invention features conjugates and/or complexes of segmented miRNA mimetics of the invention. Such conjugates and/or complexes can be used to facilitate delivery of one or more segmented miRNA mimetics to a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the design and synthesis of conjugates and complexes for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of segmented miRNA mimetics of the invention into a number of cell types originating from different tissues, in the presence or absence of serum (see Sullenger and Cech, U.S. Pat. No. 5,854,038). Conjugates described herein can be attached to biologically active segmented miRNA mimetics via linkers that are biodegradable, such as biodegradable nucleic acid linker molecules.

A person of skill in the art can screen segmented miRNA mimetics of this disclosure having various conjugates to determine which of the segmented miRNA-conjugate complexes possess improved properties (e.g., pharmacokinetic profile, bioavailability, stability) while maintaining the ability to mediate RNAi in, for example, an animal model as described herein or generally known in the art.

In another aspect, a segmented miRNA mimetic of the invention comprises one or more 5'- and/or a 3'-cap structures, for example at the terminal ends of the passenger strand, guide strand, both strands, or any of the internal ends of the contiguous stretches of nucleotides. In non-limiting examples: a suitable 5'-cap can be one selected from the group comprising inverted abasic residue (moiety); LNA; 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides modified base nucleotide; phosphorodithioate linkage; threo-pentofuranosyl nucleotide; acyclic 3',4'-sero nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In another non-limiting example, a suitable 3'-cap can be selected from a group comprising. LNA; 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties. For more details, see Beaucage and Iyer, 1993, *Tetrahedron* 49:1925, which is incorporated by reference herein.

Making microRNA Mimetics of the Invention

Exemplary molecules of the instant disclosure can be recombinantly produced (e.g., isolated), chemically synthesized, or a combination thereof. Oligonucleotides or individual contiguous stretches of nucleotides (e.g., certain modified oligonucleotides or portions of oligonucleotides lacking ribonucleotides) are synthesized using protocols known in the art, for example, as described in Caruthers et al., 1992 Methods in Enzymol. 211:3; Thompson et al, PCT Publication No. WO 99/54459, Wincott et al., 1995 Nucleic Acids Res. 23:2677; Wincott et al., 1997 Methods Mol. Bio. 74:59; Brennan et al., 1998 Biotechnoh Bioeng. 67:33; and Brennan, U.S. Pat. No. 6,001,311. Synthesis of RNA, including certain segmented miRNA mimetics thereof of this disclosure, can be made using the procedure as described in Usman et al., 1987 J. Am. Chem. Soc. 109: 7845; Scaringe et al., 1990 Nucleic Acids Res. 18:5433; and Wincott et al., 1995 Nucleic Acids Res. 23:2677; Wincott et al., 1997 Methods Mol. Bio. 74:59. In certain embodiments, segmented miRNA mimetics of the present disclosure can be synthesized separately and joined together post-synthetically, for example, by ligation (Moore et al., 1992 Science 256:9923; Draper et al., PCT Publication No. WO 93/23569; Shabarova et al., 1991 Nucleic Acids Res. 19:4247; Bellon et al., 1997 Nucleosides & Nucleotides 16:951; Bellon et aL, 1997 Bioconjugate Chem. 8:204), or by hybridization following synthesis or deprotection. In certain embodiments, a segmented miRNA mimetic of this disclosure can be made as single or multiple transcription products expressed by a polynucleotide vector encoding one or more contiguous stretches of RNAs and directing their expression within host cells. In all of the embodiments herein, the double-stranded portion of a final transcription product to be expressed within the target cell can be, for example, about 10 to about 26 bp, about 12 to about 25 bp, or about 14 to about 22 by long.

Methods for Designing a Segmented miRNA Mimetic

As described herein, a segmented miRNA mimetic can be designed based on a corresponding non-segmented duplex miRNA mimetic molecule, which is in turn designed based on known endogenous miRNA molecules, such as those listed in the miRBase as of the filing date of the present application, and for example, SEQ ID Nos: 1-1090 in Table I. The segmented miRNA mimetic is then characterized as described below and in the Examples herein.

Specifically, any segmented miRNA mimetic of the invention can be designed by introducing one or more discontinuities of the invention (nicks, gaps, substitutions, and/or insertions) into the passenger strand, the guide strand, or both the passenger and the guide strands. The discontinuity can be introduced at the 5'-end of any of position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, and/or position 26 of the guide strand. The discontinuity can be introduced at the 5'-end of any of position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, and/or position 26 of the passenger strand.

In certain embodiments, a method is provided wherein one or more genes, which are known to be regulated by an endogenous miRNA, are selected to indicate the RNAi potency of a segmented miRNA mimetic. The RNAi activity of a given segmented miRNA mimetic can be measured using known methods, such as those described generally in Fire et al., PCT Publication No. WO99/32619. In some embodiments, the instant specification provides methods for selecting more efficacious segmented miRNA mimetic designs by using one or more reporter gene constructs comprising a constitutive promoter, such as a cytomegalovirus (CMV) or phosphoglycerate kinase (PGK) promoter, operably fused to, and capable of altering the expression of one or more reporter genes, such as a luciferase, chloramphenicol (CAT), or β-galactosidase, which, in turn, is operably fused in-frame with a segmented miRNA mimetic.

These reporter gene expression constructs can be co-transfected with one or more segmented miRNA mimetics and the control (corresponding) non-segmented miRNA mimetics. The capacity of a given segmented miRNA mimetic to mediate RNAi of a target mRNA can be determined by comparing the measured reporter gene activity in cells transfected with the segmented miRNA mimetic and the activity in cells transfected with a negative control (i.e., in cells not transfected with the segmented miRNA mimetic) and a positive control (i.e., in cells transfected with the corresponding non-segmented duplex miRNA mimetic). The segmented miRNA mimetics having at least 20% or more, preferably at least 40% or more, or 60% or more, or 80% or more, of the activity of their corresponding non-segmented duplex miRNA mimetics are selected.

Certain embodiments disclosed herein also provide methods for selecting one or more segmented miRNA mimetics based on their predicted stability. A theoretical melting curve can be prepared for each of the segmented miRNA mimetic designs such that those with high theoretical melting curves, and therefore higher duplex stability and corresponding lower cytotoxic effects, would be selected. Alternatively, stability of a segmented miRNA mimetic can be determined empirically and those with higher measured melting temperatures would be selected.

Compositions and Methods of Use

As set forth herein, segmented miRNA mimetics of the invention are miRNA mimetics that are designed to supplement or take the place of corresponding naturally-occurring miRNAs, the reduced or otherwise unsuitably low levels of which have been associated with pathological or diseased conditions. A segmented miRNA mimetic of the invention is therefore preferably capable of participating in the cellular RNAi pathway or otherwise capable of modulating the same or related pathway(s). A segmented miRNA mimetic of the invention can be introduced to a cell, tissue, organism, an in vitro, or an in vivo system to mediate RNAi against an endogenous RNA target of its corresponding naturally-occurring miRNA. As such, a segmented miRNA mimetic can regulate a number of genes, for example, downstream from its RNA target, whose expression levels are associated with or otherwise regulated by the corresponding naturally-occurring miRNA. Because aberrant expression levels of certain naturally-occurring miRNAs have been implicated in various human ailments, including, but are not limited to, hyperproliferative, angiogenic, or inflammatory diseases, states, or adverse conditions, the segmented miRNA mimetics of the present invention can offer valuable therapeutic opportunities. In this context, a segmented miRNA mimetic of this disclosure can regulate (e.g., knockdown or up-regulate) expression of one or more downstream genes of its corresponding endogenous miRNA, such that prevention, alleviation, or reduction of the severity or recurrence of one or more associated disease symptoms can be achieved. Alternatively, for various distinct disease models in which expression of one or more target mRNAs are not necessarily reduced or at a lower-than-normal level as a consequence or sequel of diseases or other adverse conditions, introducing exogenous miRNA mimetics, such as one or more segmented miRNA mimetics of the invention, can nonetheless result in a therapeutic result by affecting the expression levels of genes associated with the disease pathway. The segmented miRNA mimetics of the invention thus are useful reagents, which can be in methods for a variety of therapeutic, diagnostic, target validation, genomic discovery, genetic engineering, and pharmacogenomic applications.

In certain embodiments, aqueous suspensions containing one or more segmented miRNA mimetics of the invention can be prepared in admixture with suitable excipients, such as suspending agents or dispersing or wetting agents. Exemplary suspending agents include sodium carboxymethylcellulose, methylcellulose, hydropropyl-methylcellulose, sodium alginate, polyvinylpyrrolidone, gum tragacanth and gum acacia. Representative dispersing or wetting agents include naturally-occurring phosphatides (e.g., lecithin), condensation products of an alkylene oxide with fatty acids (e.g., polyoxyethylene stearate), condensation products of ethylene oxide with long chain aliphatic alcohols (e.g., heptadecaethyleneoxycetanol), condensation products of ethylene oxide with partial esters derived from fatty acids and hexitol (e.g., polyoxyethylene sorbitol monooleate), or condensation products of ethylene oxide with partial esters derived from fatty acids and hexitol anhydrides (e.g., polyethylene sorbitan monooleate). In certain embodiments, the aqueous suspensions can optionally contain one or more preservatives (e.g., ethyl or w-propyl-p-hydroxybenzoate), one or more coloring agents, one or more flavoring agents, or one or more sweetening agents (e.g., sucrose, saccharin). In additional embodiments, dispersible powders and granules suitable for preparation of an aqueous suspension comprising one or more segmented miRNA mimetics of the invention can be prepared by the addition of water with the segmented miRNA mimetics in admixture with a dispersing or wetting agent, suspending agent and optionally one or more preservative, coloring agent, flavoring agent, or sweetening agent. The present disclosure also includes segmented miRNA mimetic compositions prepared for storage or administration that include a pharmaceutically effective amount of a desired compound in a pharmaceutically acceptable carrier or diluent. Acceptable carriers or diluents for therapeutic use are well known in the pharmaceutical art, and are described, for example, in Remington's Pharmaceutical Sciences, Mack Publishing Co., A. R. Gennaro edit., 21st Edition, 2005. In certain embodiments, pharmaceutical compositions of this disclosure can optionally include preservatives, antioxidants, stabilizers, dyes, flavoring agents, or any combination thereof. Exemplary preservatives include sodium benzoate, esters of p-hydroxybenzoic acid, and sorbic acid.

The segmented miRNA mimetic compositions of the instant disclosure can be effectively employed as pharmaceutically-acceptable formulations. Pharmaceutically-acceptable formulations prevent, alter the occurrence or severity of, or treat (alleviate one or more symptom(s) to a detectable or measurable extent) a disease state or other adverse condition in a subject. A pharmaceutically acceptable formulation includes salts of the above compounds, for example, acid addition salts, such as salts of hydrochloric acid, hydrobromic acid, acetic acid, or benzene sulfonic acid. A pharmaceutical composition or formulation refers to a composition or formulation in a form suitable for administration into a cell, or a subject such as a human (e.g., systemic administration). The formulations of the present disclosure, having an amount of segmented miRNA mimetic sufficient to treat or prevent a disorder associated with target gene expression are, for example, suitable for topical (e.g., creams, ointments, skin patches, eye drops, ear drops) application or administration. Other routes of administration include oral, parenteral, sublingual, bladder washout, vaginal, rectal, enteric, suppository, nasal, and inhalation. The pharmaceutical compositions of the present disclosure are formulated to allow the segmented miRNA mimetic contained therein to be bioavailable upon administration to a subject.

In certain embodiments, a segmented miRNA of this disclosure can be formulated as oily suspensions or emulsions (e.g., oil-in-water) by suspending the segmented miRNA mimetic in, for example, a vegetable oil (e.g., arachis oil, olive oil, sesame oil or coconut oil) or a mineral oil (e.g., liquid paraffin). Suitable emulsifying agents can be naturally-occurring gums (e.g., gum acacia or gum tragacanth), naturally-occurring phosphatides (e.g., soy bean, lecithin, esters or partial esters derived from fatty acids and hexitol), anhydrides (e.g., sorbitan monooleate), or condensation products of partial esters with ethylene oxide (e.g., polyoxyethylene sorbitan monooleate). In certain embodiments, the oily suspensions or emulsions can optionally contain a thickening agent, such as beeswax, hard paraffin or cetyl alcohol. In related embodiments, sweetening agents and flavoring agents can optionally be added to provide palatable oral preparations. In yet other embodiments, these compositions can be preserved by the optionally adding an anti-oxidant, such as ascorbic acid.

In certain embodiments, a segmented miRNA mimetic can be formulated as syrups and elixirs with sweetening agents (e.g., glycerol, propylene glycol, sorbitol, glucose or sucrose). Such formulations can also contain a demulcent, preservative, flavoring, coloring agent, or any combination thereof. In other embodiments, pharmaceutical compositions comprising a segmented miRNA mimetic can be in the form of a sterile, injectable aqueous or oleaginous suspension. The sterile injectable preparation can also be a sterile, injectable solution or suspension in a non-toxic parenterally acceptable diluent or solvent (e.g., as a solution in 1,3-butanediol). Among the exemplary acceptable vehicles and solvents useful in the compositions of this disclosure is water, Ringer's solution, or isotonic sodium chloride solution. In addition, sterile, fixed oils can be employed as a solvent or suspending medium. For this purpose, any bland fixed oil can be employed including synthetic mono- or diglycerides. In addition, fatty acids such as oleic acid find use in the preparation of parenteral formulations.

Within certain embodiments of this disclosure, pharmaceutical compositions and methods are provided that feature the presence or administration of one or more segmented miRNA mimetics, combined, complexed, or conjugated with a polypeptide, optionally formulated with a pharmaceutically-acceptable carrier, such as a diluent, stabilizer, buffer, or the like. The negatively charged segmented miRNA mimetics can be administered to a patient by any standard means, with or without stabilizers, buffers, or the like, to form a composition suitable for treatment. When it is desired to use a liposome delivery mechanism, standard protocols for formation of liposomes can be followed. The compositions of the present disclosure can also be formulated and used as a tablet, capsule or elixir for oral administration, suppository for rectal administration, sterile solution, or suspension for injectable administration, either with or without other compounds known in the art. Thus, a segmented miRNA mimetic of the present disclosure can be administered in any form, such as nasally, transdermally, parenterally, or by local injection.

In accordance with this disclosure herein, a segmented miRNA mimetic (optionally substituted or modified or conjugated), compositions thereof, and methods for inhibiting expression of one or more corresponding target mRNAs in a cell or organism are provided. In certain embodiments, this disclosure provides methods and segmented miRNA mimetic compositions for treating a subject, including a human cell, tissue or individual, having a disease or at risk of developing a disease caused by or associated with the aberrant levels of its corresponding naturally-occurring miRNA. In a certain embodiment, the method includes administering a segmented miRNA mimetic or a pharmaceutical composition containing the segmented miRNA mimetic to a cell or an organism, such as a mammal, such that the level of its corresponding naturally-occurring miRNA within the cell or the organism is increased. Subjects (e.g., mammalian, human) amendable for treatment using the segmented miRNA mimetics (optionally substituted or modified or conjugated), compositions thereof, and methods of the present disclosure include those suffering from one or more disease or condition mediated, at least in part, by an aberrant expression level of its corresponding naturally-occurring miRNA, or which are amenable to treatment by replenishing or increasing the level of RNAi mediated by the corresponding miRNA, including a hyperproliferative (e.g., cancer), angiogenic, metabolic, or inflammatory (e.g., arthritis) disease or disorder or condition.

Compositions and methods disclosed herein are useful in the treatment of a wide variety of target viruses, including retrovirus, such as human immunodeficiency virus (HIV), Hepatitis C Virus, Hepatitis B Virus, Coronavirus, as well as respiratory viruses, including human Respiratory Syncytial Virus, human Metapneumovirus, human Parainfluenza virus Rhinovirus and Influenza virus.

In other examples, the compositions and methods of this disclosure are useful as therapeutic tools to treat or prevent symptoms of, for example, hyperproliferative disorders. Exemplary hyperproliferative disorders include neoplasms, carcinomas, sarcomas, tumors, or cancer. More exemplary hyperproliferative disorders include oral cancer, throat cancer, laryngeal cancer, esophageal cancer, pharyngeal cancer, nasopharyngeal cancer, oropharyngeal cancer, gastrointestinal tract cancer, gastrointestinal stromal tumors (GIST), small intestine cancer, colon cancer, rectal cancer, colorectal cancer, anal cancer, pancreatic cancer, breast cancer, cervical cancer, uterine cancer, vulvar cancer, vaginal cancer, urinary tract cancer, bladder cancer, kidney cancer, adrenocortical cancer, islet cell carcinoma, gallbladder cancer, stomach cancer, prostate cancer, ovarian cancer, endometrial cancer, trophoblastic tumor, testicular cancer, penial cancer, bone cancer, osteosarcoma, liver cancer, extrahepatic bile duct cancer, skin cancer, basal cell carcinoma (BCC), lung cancer, small cell lung cancer, non-small cell lung cancer (NSCLC), brain cancer, melanoma, Kaposi's sarcoma, eye cancer, head and neck cancer, squamous cell carcinoma of head and neck, tymoma, thymic carcinoma, thyroid cancer, parathyroid cancer, Hippel-Lindau syndrome, leukemia, acute myeloid leukemia, chronic myelogenous leukemia, acute lymphoblastic leukemia, hairy cell leukemia, lymphoma, non-Hodgkin's lymphoma, Burkitt's lymphoma, T-cell lymphoma, multiple myeloma, malignant pleural mesothelioma, Barrett's adenocarcinoma, Wilm's tumor, or the like. In other examples, the compositions and methods of this disclosure are useful as therapeutic tools to regulate expression of one or more target gene to treat or prevent symptoms of, for example, inflammatory disorders. Exemplary inflammatory disorders include diabetes mellitus, rheumatoid arthritis, pannus growth in inflamed synovial lining, collagen-induced arthritis, spondylarthritis, ankylosing spondylitis, multiple sclerosis, encephalomyelitis, inflammatory bowel disease, Chron's disease, psoriasis or psoriatic arthritis, myasthenia gravis, systemic lupus erythematosis, graft-versus-host disease, atherosclerosis, and allergies.

Other exemplary disorders that can be treated with segmented miRNA mimetics, compositions and methods of the instant disclosure include metabolic disorders, cardiac disease, pulmonary disease, neovascularization, ischemic disorders, age-related macular degeneration, diabetic retinopathy, glomerulonephritis, diabetes, asthma, chronic obstructive pulmonary disease, chronic bronchitis, lymphangiogenesis, and atherosclerosis.

Within additional aspects, combination formulations and methods are provided comprising an effective amount of one or more segmented miRNA mimetics in combination with one or more secondary or adjunctive active agents that are formulated together or administered coordinately with the segmented miRNA mimetics of the invention to control one or more target gene-associated disease or condition as described herein. Useful adjunctive therapeutic agents in these combinatorial formulations and coordinate treatment methods include, for example, enzymatic nucleic acid molecules, allosteric nucleic acid molecules, guide, decoy, or aptamer nucleic acid molecules, antibodies such as monoclonal antibodies, small molecules and other organic or inorganic compounds including metals, salts and ions, and other drugs and active agents indicated for treating one or more target gene-associated disease or condition, including chemotherapeutic agents used to treat cancer, steroids, non-steroidal anti-inflammatory drugs (NSAIDs), or the like. Exemplary chemotherapeutic agents include alkylating agents (e.g., cisplatin, oxaliplatin, carboplatin, busulfan, nitrosoureas, nitrogen mustards, uramustine, temozolomide), antimetabolites (e.g., aminopterin, methotrexate, mercaptopurine, fluorouracil, cytarabine), taxanes (e.g., paclitaxel, docetaxel), anthracyclines (e.g., doxorubicin, daunorubicin, epirubicin, idaruicin, mitoxantrone, valrubicin), bleomycin, mytomycin, actinomycin, hydroxyurea, topoisomerase inhibitors (e.g., camptothecin, topotecan, irinotecan, etoposide, teniposide), monoclonal antibodies (e.g., alemtuzumab, bevacizumab, cetuximab, gemtuzumab, panitumumab, rituximab, tositumomab, trastuzumab), vinca alkaloids (e.g., vincristine, vinblastine, vindesine, vinorelbine), cyclophosphamide, prednisone, leucovorin, oxaliplatin. To practice the coordinate administration methods of this disclosure, a segmented miRNA mimetic is administered simultaneously or sequentially in a coordinated treatment protocol with one or more secondary or adjunctive therapeutic agents described herein or known in the art. The coordinate administration can be done in either order, and there can be a time period while only one or both (or all) active therapeutic agents, individually or collectively, exert their biological activities. A distinguishing aspect of all such coordinate treatment methods is that the segmented miRNA mimetic present in a composition elicits some favorable clinical response, which can or can not be in conjunction with a secondary clinical response provided by the secondary therapeutic agent. For example, the coordinate administration of a segmented miRNA mimetic with a secondary therapeutic agent as contemplated herein can yield an enhanced (e.g., synergistic) therapeutic response beyond the therapeutic response elicited by either or both the purified segmented miRNA mimetic and the secondary therapeutic agent alone.

In another embodiment, a segmented miRNA mimetic of this disclosure can include a conjugate member on one or more of the nucleotides, at the terminal positions or the internal positions. The conjugate member can be, for example, a lipophile, a terpene, a protein binding agent, a vitamin, a carbohydrate, or a peptide. For example, the conjugate member can be naproxen, nitroindole (or another conjugate that contributes to stacking interactions), folate, ibuprofen, or a C5 pyrimidine linker. In other embodiments, the conjugate member is a glyceride lipid conjugate (e.g., a dialkyl glyceride derivatives), vitamin E conjugates, or thio-cholesterols. Additional conjugate members include peptides that function, when conjugated to a modified segmented miRNA mimetic, to facilitate delivery of the mimetic into a target cell, or otherwise enhance delivery, stability, or activity of the mimetic when contacted with a biological sample. Exemplary peptide conjugate members for use within these aspects of this disclosure, include peptides PN27, PN28, PN29, PN58, PN61, PN73, PN158, PN159, PN173, PN182, PN202, PN204, PN250, PN361, PN365, PN404, PN453, and PN509 are described, for example, in U.S. Patent Application Publication Nos. 2006/0040882 and 2006/0014289, and U.S. Provisional Patent Application No. 60/939,578, which are all incorporated herein by reference. In certain embodiments, when peptide conjugate partners are used to enhance delivery of one or more segmented miRNA mimetics of this disclosure, the resulting formulations and methods will often exhibit further reduction of an interferon response in target cells as compared to a segmented miRNA mimetic delivered in combination with alternate delivery vehicles, such as lipid delivery vehicles (e.g., Lipofectamine™). In still another embodiment, a segmented miRNA mimetic of the invention can be conjugated to a polypeptide and admixed with one or more non-cationic lipids or a combination of a non-cationic lipid and a cationic lipid to form a composition that enhances intracellular delivery of the segmented miRNA mimetic as compared to delivery resulting from contacting the target cells with a naked segmented miRNA mimetic without the lipids. In more detailed aspects of this disclosure, the mixture, complex or conjugate comprising a segmented miRNA mimetic and a polypeptide can be optionally combined with (e.g., admixed or complexed with) a cationic lipid, such as Lipofectin™. To produce these compositions comprised of a polypeptide, a segmented miRNA mimetic and a cationic lipid, the segmented miRNA mimetic and the polypeptide can be mixed together first in a suitable medium such as a cell culture medium, after which the cationic lipid is added to the mixture to form an segmented miRNA mimetic/delivery peptide/cationic lipid composition. Optionally, the peptide and cationic lipid can be mixed together first in a suitable medium such as a cell culture medium, followed by the addition of the segmented miRNA mimetic to form the segmented miRNA mimetic/delivery peptide/cationic lipid composition.

This disclosure also features the use of segmented miRNA mimetic compositions comprising surface-modified liposomes containing poly(ethylene glycol) lipids (PEG-modified, or long-circulating liposomes or stealth liposomes). These formulations can offer increased accumulation of drugs in target tissues (Lasic et al., 1995 Chem. Rev., 95:2601; Ishiwata et al., 1995 Chem. Pharm. Bull. 43:1005). Such liposomes have been shown to accumulate selectively in tumors, presumably by extravasation and capture in the neovascularized target tissues (Lasic et al., 1995 Science 267:1215; Oku et al., 1995 Biochim. Biophys. Acta 1238:86). The long-circulating liposomes enhance the pharmacokinetics and pharmacodynamics of nucleic acid molecules as compared to conventional cationic liposomes, which are known to accumulate in tissues of the mononuclear phagocytic system (MPS) (Liu et al., 1995 J. Biol. Chem.

42:24864; Choi et al., PCT Publication No. WO 96/10391; Ansell et al., PCT Publication No. WO 96/10390; Holland et al., PCT Publication No. WO 96/10392). Long-circulating liposomes can also provide additional protection from nuclease degradation as compared to cationic liposomes in theory due to avoiding accumulation in metabolically aggressive MPS tissues, such as the liver and spleen. In a certain embodiment, this disclosure provides compositions suitable for administering segmented miRNA mimetics of this disclosure to specific cell types, such as hepatocytes. For example, the asialoglycoprotein receptor (ASGPr) (Wu and Wu, 1987 J. Biol. Chem. 262:4429) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, 1980 Cell 22: 611; Connolly et al., 1982 J. Biol. Chem. 257:939). Lee and Lee (1987 Glycoconjugate J. 4:317) obtained this high specificity through the use of N-acetyl-D-galactosamine as the carbohydrate moiety, which has higher affinity for the receptor compared to galactose. This "clustering effect" has also been described for the binding and uptake of mannosyl-terminating glycoproteins or glycoconjugates (Ponpipom et al., 1981 J. Med. Chem. 24: 1388). The use of galactose and galactosamine based conjugates to transport exogenous compounds across cell membranes can provide a targeted delivery approach to the treatment of liver disease. The use of bioconjugates can also provide a reduction in the required dose of therapeutic compounds required for treatment. Furthermore, therapeutic bioavailability, pharmacodynamics, and phaimacokinetic parameters can be modulated through the use of bioconjugates of this disclosure.

The present disclosure also features a method for preparing segmented miRNA mimetic nanoparticles. A first solution containing melamine derivatives is dissolved in an organic solvent such as dimethyl sulfoxide, or dimethyl formamide to which an acid such as HCl has been added. The concentration of HCl would be about 3.3 moles of HCl for every mole of the melamine derivative. The first solution is then mixed with a second solution, which includes a nucleic acid dissolved or suspended in a polar or hydrophilic solvent (e.g., an aqueous buffer solution containing, for instance, ethylenediaminetraacetic acid (EDTA), or tris(hydroxymethyl) aminomethane (TRIS), or combinations thereof. The mixture forms a first emulsion. The mixing can be done using any standard technique such as, for example, sonication, vortexing, or in a micro fluidizer. The resultant nucleic acid particles can be purified and the organic solvent removed using size-exclusion chromatography or dialysis or both. The complexed nucleic acid nanoparticles can then be mixed with an aqueous solution containing either polyarginine or a Gln-Asn polymer, or both, in an aqueous solution. A preferred molecular weight of each polymer is about 5000 to about 15,000 Daltons. This forms a solution containing nanoparticles of nucleic acid complexed with the melamine derivative and the polyarginine and the Gln-Asn polymers. The mixing steps are carried out in a manner that minimizes shearing of the nucleic acid while producing nanoparticles on average smaller than about 200 nanometers in diameter. It is believed that the polyarginine complexes with the negative charge of the phosphate groups within the minor groove of the nucleic acid, and the polyarginine wraps around the trimeric nucleic acid complex. At either terminus of the polyarginine other moieties, such as the TAT polypeptide, mannose or galactose, can be covalently bound to the polymer to direct binding of the nucleic acid complex to specific tissues, such as to the liver when galactose is used. While not being bound to theory, it is believed that the Gln-Asn polymer complexes with the nucleic acid complex within the major groove of the nucleic acid through hydrogen bonding with the bases of the nucleic acid. The polyarginine and the Gln-Asn polymer should be present at a concentration of 2 moles per every mole of nucleic acid having 20 base pairs. The concentration should be increased proportionally for a nucleic acid having more than 20 base pairs. For example, if the nucleic acid has 25 base pairs, the concentration of the polymers should be 2.5-3 moles per mole of double-stranded nucleic acid. The resultant nanoparticles can be purified by standard means such as size exclusion chromatography followed by dialysis. The purified complexed nanoparticles can then be lyophilized using techniques well known in the art. In certain embodiments of the present disclosure provides nanoparticles less than 100 nanometers (nm) comprising a segmented miRNA mimetic.

A pharmaceutically effective dose is that dose required to prevent, inhibit the occurrence, or treat (alleviate a symptom to some extent, preferably all of the symptoms) a disease state. The pharmaceutically effective dose depends on the type of disease, the composition used, the route of administration, the type of subject being treated, the physical characteristics of the specific subject under consideration for treatment, concurrent medication, and other factors that those skilled in the medical arts will recognize. For example, an amount between 0.1 mg/kg and 100 mg/kg body weight/day of active ingredients can be administered depending on the potency of a segmented miRNA mimetic of this disclosure.

Dosage levels in the order of about 0.1 mg to about 140 mg per kilogram of body weight per day can be useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy. Following administration of a segmented miRNA mimetic composition according to the formulations and methods of this disclosure, test subjects will exhibit about a 10% up to about a 99% reduction in one or more symptoms associated with the disease or disorder being treated, as compared to placebo-treated or other suitable control subjects.

Nucleic acid molecules and polypeptides can be administered to cells or organisms by a variety of methods known to those of skill in the art, including administration of formulations that comprise a miRNA mimetic and/or a polypeptide alone, or formulations that further comprise one or more additional components, such as a pharmaceutically acceptable carrier, diluent, excipient, adjuvant, emulsifier, buffer, stabilizer, preservative, or the like. In certain embodiments, a segmented miRNA mimetic of the invention, and/or the polypeptide can be encapsulated in liposomes, administered by iontophoresis, or incorporated into other vehicles, such as hydrogels, cyclodextrins, biodegradable nanocapsules, bioadhesive microspheres, or proteinaceous vectors (see, e.g., PCT Publication No. WO 00/53722). Alternatively, a nucleic acid/peptide/vehicle combination can be locally delivered by direct injection or by use of an infusion pump. Direct injection of the nucleic acid molecules of this disclosure, whether subcutaneous, intramuscular, or intradermal, can take place using standard needle and syringe methodologies, or by needle-free technologies, such as those described in Conroy et al, 1999 Clin. Cancer Res. 5:2330; and PCT Publication No. WO 99/31262.

A segmented miRNA mimetic of the invention can also be administered in the form of suppositories, for example, for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

Further methods for delivery of nucleic acid molecules, such as a segmented miRNA mimetic of this invention, have been described in, for example, Boado et al., 1998 J. Pharm. ScL, 87:1308; Tyler et al., 1999 FEBS Lett. 421:2m; Pardridge et al., 1995 Proc. Nat'l Acad. ScL USA 92:5592; Boado, 1995 Adv. Drug Delivery Rev. 15:73; Aldrian-Herrada et al. 1998 Nucleic Acids Res. 26:4910; Tyler et al., 1999 Proc. Nat'l Acad. Sci. USA 96:7053; Akhtar et al., 1992 Trends Cell Bio. 2:139; "Delivery Strategies for Guide Oligonucleotide Therapeutics," ed. Akhtar, 1995, Maurer et al., 1999 Mol Membr. Biol. 16:129; Lee et al., 2000 ACS Symp. Ser., 752:184. In addition to in vivo and therapeutic applications, a skilled person in the art will appreciate that the segmented miRNA mimetics of the present disclosure are useful in a wide variety of in vitro applications, such as in scientific and commercial research (e.g., elucidation of physiological pathways, drug discovery and development), and medical and veterinary diagnostics.

All U.S. patents, U.S. patent publications, U.S. patent applications, foreign patents, foreign patent applications, non-patent publications, figures, and websites referred to in this specification are expressly incorporated herein by reference, in their entirety.

Table I lists certain endogenous mammalian and viral miRNA sequences, wherein the seed sequences, confirmed or projected, are capitalized. All miRNA sequences in Table I are derived from humans and are shown in 5' to 3' orientation. Other miRNA sequences of the present invention can be found in the miRBase, the content of which is incorporated by reference herein.

TABLE I

| miRNA name | miRBase number | Sequence | SEQ ID NO |
| --- | --- | --- | --- |
| hsa-let-7a | MIMAT0000062 | UGAGGUAGuagguuguauaguu | 1 |
| hsa-let-7a* | MIMAT0004481 | CUAUACAAucuacugucuuuc | 2 |
| hsa-let-7a-2* | MIMAT0010195 | CUGUACAGccuccuagcuuucc | 3 |
| hsa-let-7b | MIMAT0000063 | UGAGGUAGuagguugugugguu | 4 |
| hsa-let-7b* | MIMAT0004482 | CUAUACAAccuacugccuuccc | 5 |
| hsa-let-7c | MIMAT0000064 | UGAGGUAGuagguuguaugguu | 6 |
| hsa-let-7c* | MIMAT0004483 | UAGAGUUAcacccugggaguua | 7 |
| hsa-let-7d | MIMAT0000065 | AGAGGUAGuagguugcauaguu | 8 |
| hsa-let-7d* | MIMAT0004484 | CUAUACGAccugcugccuuucu | 9 |
| hsa-let-7e | MIMAT0000066 | UGAGGUAGgagguuguauaguu | 10 |
| hsa-let-7e* | MIMAT0004485 | CUAUACGGccuccuagcuuucc | 11 |
| hsa-let-7f | MIMAT0000067 | UGAGGUAGuagauuguauaguu | 12 |
| hsa-let-7f-1* | MIMAT0004486 | CUAUACAAucuauugccuuccc | 13 |
| hsa-let-7f-2* | MIMAT0004487 | CUAUACAGucuacugucuuucc | 14 |
| hsa-miR-15a | MIMAT0000068 | UAGCAGCAcauaaugguuugug | 15 |
| hsa-miR-15a* | MIMAT0004488 | CAGGCCAUauugugcugccuca | 16 |
| hsa-miR-16 | MIMAT0000069 | UAGCAGCAcguaaauauuggcg | 17 |
| hsa-miR-16-1* | MIMAT0004489 | CCAGUAUUaacugugcugcuga | 18 |
| hsa-miR-17 | MIMAT0000070 | CAAAGUGCuuacagugcagguag | 19 |
| hsa-miR-17* | MIMAT0000071 | ACUGCAGUgaaggcacuuguag | 20 |
| hsa-miR-18a | MIMAT0000072 | UAAGGUGCaucuagugcagauag | 21 |

TABLE I-continued

| miRNA name | miRBase number | Sequence | SEQ ID NO |
|---|---|---|---|
| hsa-miR-18a* | MIMAT0002891 | ACUGCCCUaagugcuccuucugg | 22 |
| hsa-miR-19a* | MIMAT0004490 | AGUUUUGCauaguugcacuaca | 23 |
| hsa-miR-19a | MIMAT0000073 | UGUGCAAAucuaugcaaaacuga | 24 |
| hsa-miR-19b-1* | MIMAT0004491 | AGUUUUGCagguuugcauccagc | 25 |
| hsa-miR-19b | MIMAT0000074 | UGUGCAAAuccaugcaaaacuga | 26 |
| hsa-miR-19b-2* | MIMAT0004492 | AGUUUUGCagguuugcauuuca | 27 |
| hsa-miR-20a | MIMAT0000075 | UAAAGUGCuuauagugcagguag | 28 |
| hsa-miR-20a* | MIMAT0004493 | ACUGCAUUaugagcacuuaaag | 29 |
| hsa-miR-21 | MIMAT0000076 | UAGCUUAUcagacugauguuga | 30 |
| hsa-miR-21* | MIMAT0004494 | CAACACCAgucgaugggcugu | 31 |
| hsa-miR-22* | MIMAT0004495 | AGUUCUUCaguggcaagcuuua | 32 |
| hsa-miR-22 | MIMAT0000077 | AAGCUGCCaguugaagaacugu | 33 |
| hsa-miR-23a* | MIMAT0004496 | GGGGUUCCuagggaugggauuu | 34 |
| hsa-miR-23a | MIMAT0000078 | AUCACAUUgccagggauuucc | 35 |
| hsa-miR-24-1* | MIMAT0000079 | UGCCUACUgagcugauaucagu | 36 |
| hsa-miR-24 | MIMAT0000080 | UGGCUCAGuucagcaggaacag | 37 |
| hsa-miR-24-2* | MIMAT0004497 | UGCCUACUgagcugaaacacag | 38 |
| hsa-miR-25* | MIMAT0004498 | AGGCGGAGacuugggcaauug | 39 |
| hsa-miR-25 | MIMAT0000081 | CAUUGCACuugucucggucuga | 40 |
| hsa-miR-26a | MIMAT0000082 | UUCAAGUAauccaggauaggcu | 41 |
| hsa-miR-26a-1* | MIMAT0004499 | CCUAUUCUugguuacuugcacg | 42 |
| hsa-miR-26b | MIMAT0000083 | UUCAAGUAauucaggauaggu | 43 |
| hsa-miR-26b* | MIMAT0004500 | CCUGUUCUccauuacuuggcuc | 44 |
| hsa-miR-27a* | MIMAT0004501 | AGGGCUUAgcugcuugugagca | 45 |
| hsa-miR-27a | MIMAT0000084 | UUCACAGUggcuaaguuccgc | 46 |
| hsa-miR-28-5p | MIMAT0000085 | AAGGAGCUcacagucuauugag | 47 |
| hsa-miR-28-3p | MIMAT0004502 | CACUAGAUugugagcuccugga | 48 |
| hsa-miR-29a* | MIMAT0004503 | ACUGAUUUcuuuugguguucag | 49 |
| hsa-miR-29a | MIMAT0000086 | UAGCACCAucugaaaucgguua | 50 |
| hsa-miR-30a | MIMAT0000087 | UGUAAACAuccucgacuggaag | 51 |
| hsa-miR-30a* | MIMAT0000088 | CUUUCAGUcggauguuugcagc | 52 |
| hsa-miR-31 | MIMAT0000089 | AGGCAAGAugcuggcauagcu | 53 |
| hsa-miR-31* | MIMAT0004504 | UGCUAUGCcaacauauugccau | 54 |
| hsa-miR-32 | MIMAT0000090 | UAUUGCACauuacuaaguugca | 55 |
| hsa-miR-32* | MIMAT0004505 | CAAUUUAGugugugugauauuu | 56 |
| hsa-miR-33a | MIMAT0000091 | GUGCAUUGuaguugcauugca | 57 |
| hsa-miR-33a* | MIMAT0004506 | CAAUGUUUccacagugcaucac | 58 |
| hsa-miR-92a-1* | MIMAT0004507 | AGGUUGGGaucgguugcaaugcu | 59 |

TABLE I-continued

| miRNA name | miRBase number | Sequence | SEQ ID NO |
|---|---|---|---|
| hsa-miR-92a | MIMAT0000092 | UAUUGCACuugucccggccugu | 60 |
| hsa-miR-92a-2* | MIMAT0004508 | GGGUGGGGauuuguugcauuac | 61 |
| hsa-miR-93 | MIMAT0000093 | CAAAGUGCuguucgugcagguag | 62 |
| hsa-miR-93* | MIMAT0004509 | ACUGCUGAgcuagcacuucccg | 63 |
| hsa-miR-95 | MIMAT0000094 | UUCAACGGguauuuauugagca | 64 |
| hsa-miR-96 | MIMAT0000095 | UUUGGCACuagcacauuuugcu | 65 |
| hsa-miR-96* | MIMAT0004510 | AAUCAUGUgcagugccaauaug | 66 |
| hsa-miR-98 | MIMAT0000096 | UGAGGUAGuaaguuguauuguu | 67 |
| hsa-miR-99a | MIMAT0000097 | AACCCGUAgauccgaucuugug | 68 |
| hsa-miR-99a* | MIMAT0004511 | CAAGCUCGcuucuaugggucug | 69 |
| hsa-miR-100 | MIMAT0000098 | AACCCGUAgauccgaacuugug | 70 |
| hsa-miR-100* | MIMAT0004512 | CAAGCUUGuaucuauaggguaug | 71 |
| hsa-miR-101* | MIMAT0004513 | CAGUUAUCacagugcugaugcu | 72 |
| hsa-miR-101 | MIMAT0000099 | UACAGUACugugauaacugaa | 73 |
| hsa-miR-29b-1* | MIMAT0004514 | GCUGGUUUcauauggugguuuaga | 74 |
| hsa-miR-29b | MIMAT0000100 | UAGCACCAuuugaaaucagugu | 75 |
| hsa-miR-29b-2* | MIMAT0004515 | CUGGUUUCacauggugggcuuag | 76 |
| hsa-miR-103-2* | MIMAT0009196 | AGCUUCUUuacagugcugccuug | 77 |
| hsa-miR-103 | MIMAT0000101 | AGCAGCAUuguacagggcuauga | 78 |
| hsa-miR-105 | MIMAT0000102 | UCAAAUGCucagacuccugugu | 79 |
| hsa-miR-105* | MIMAT0004516 | ACGGAUGUuugagcaugugcua | 80 |
| hsa-miR-106a | MIMAT0000103 | AAAAGUGCuuacagugcagguag | 81 |
| hsa-miR-106a* | MIMAT0004517 | CUGCAAUGuaagcacuucuuac | 82 |
| hsa-miR-107 | MIMAT0000104 | AGCAGCAUuguacagggcuauca | 83 |
| hsa-miR-16-2* | MIMAT0004518 | CCAAUAUUacugugcugcuuua | 84 |
| hsa-miR-192 | MIMAT0000222 | CUGACCUAugaauugacagcc | 85 |
| hsa-miR-192* | MIMAT0004543 | CUGCCAAUuccauaggucacag | 86 |
| hsa-miR-196a | MIMAT0000226 | UAGGUAGUuucauguuguuggg | 87 |
| hsa-miR-197 | MIMAT0000227 | UUCACCACcuucuccacccagc | 88 |
| hsa-miR-198 | MIMAT0000228 | GGUCCAGAggggagauagguuc | 89 |
| hsa-miR-199a-5p | MIMAT0000231 | CCCAGUGUucagacuaccuguuc | 90 |
| hsa-miR-199a-3p | MIMAT0000232 | ACAGUAGUcugcacauugguua | 91 |
| hsa-miR-208a | MIMAT0000241 | AUAAGACGagcaaaaagcuugu | 92 |
| hsa-miR-129-5p | MIMAT0000242 | CUUUUUGCggucugggcuugc | 93 |
| hsa-miR-129* | MIMAT0004548 | AAGCCCUUaccccaaaaaguau | 94 |
| hsa-miR-148a* | MIMAT0004549 | AAAGUUCUgagacacuccgacu | 95 |
| hsa-miR-148a | MIMAT0000243 | UCAGUGCAcuacagaacuuugu | 96 |
| hsa-miR-30c | MIMAT0000244 | UGUAAACAuccuacacucucagc | 97 |
| hsa-miR-30c-2* | MIMAT0004550 | CUGGGAGAaggcuguuuacucu | 98 |

TABLE I-continued

| miRNA name | miRBase number | Sequence | SEQ ID NO |
|---|---|---|---|
| hsa-miR-30d | MIMAT0000245 | UGUAAACAuccccgacuggaag | 99 |
| hsa-miR-30d* | MIMAT0004551 | CUUUCAGUcagauguuugcugc | 100 |
| hsa-miR-139-5p | MIMAT0000250 | UCUACAGUgcacgugucuccag | 101 |
| hsa-miR-139-3p | MIMAT0004552 | GGAGACGCggcccuguggagu | 102 |
| hsa-miR-147 | MIMAT0000251 | GUGUGUGGaaaugcuucugc | 103 |
| hsa-miR-7 | MIMAT0000252 | UGGAAGACuagugauuuuguugu | 104 |
| hsa-miR-7-1* | MIMAT0004553 | CAACAAAUcacagucugccaua | 105 |
| hsa-miR-7-2* | MIMAT0004554 | CAACAAAUcccagucuaccuaa | 106 |
| hsa-miR-10a | MIMAT0000253 | UACCCUGUagauccgaauuugug | 107 |
| hsa-miR-10a* | MIMAT0004555 | CAAAUUCGuaucuaggggaaua | 108 |
| hsa-miR-10b | MIMAT0000254 | UACCCUGUagaaccgaauuugug | 109 |
| hsa-miR-10b* | MIMAT0004556 | ACAGAUUCgauucuaggggaau | 110 |
| hsa-miR-34a | MIMAT0000255 | UGGCAGUGucuuagcugguugu | 111 |
| hsa-miR-34a* | MIMAT0004557 | CAAUCAGCaaguauacugcccu | 112 |
| hsa-miR-181a | MIMAT0000256 | AACAUUCAacgcugucggugagu | 113 |
| hsa-miR-181a-2* | MIMAT0004558 | ACCACUGAccguugacuguacc | 114 |
| hsa-miR-181b | MIMAT0000257 | AACAUUCAuugcugucgguggu | 115 |
| hsa-miR-181c | MIMAT0000258 | AACAUUCAaccgucggugagu | 116 |
| hsa-miR-181c* | MIMAT0004559 | AACCAUCGaccguugaguggac | 117 |
| hsa-miR-182 | MIMAT0000259 | UUUGGCAAugguaaaacucacacu | 118 |
| hsa-miR-182* | MIMAT0000260 | UGGUUCUAgacuugccaacua | 119 |
| hsa-miR-183 | MIMAT0000261 | UAUGGCACuaguagaauucacu | 120 |
| hsa-miR-183* | MIMAT0004560 | GUGAAUUAccgaagggccauaa | 121 |
| hsa-miR-187* | MIMAT0004561 | GGCUACAAacacaggacccgggc | 122 |
| hsa-miR-187 | MIMAT0000262 | UCGUGUCUuguguugcagccg | 123 |
| hsa-miR-196a* | MIMAT0004562 | CGGCAACAagaaacugccugag | 124 |
| hsa-miR-199b-5p | MIMAT0000263 | CCCAGUGUuuagacuaucuguuc | 125 |
| hsa-miR-199b-3p | MIMAT0004563 | ACAGUAGUcugcacauugguua | 91 |
| hsa-miR-203 | MIMAT0000264 | GUGAAAUGuuuaggaccacuag | 126 |
| hsa-miR-204 | MIMAT0000265 | UUCCCUUUgucauccuaugccu | 127 |
| hsa-miR-205 | MIMAT0000266 | UCCUUCAUuccaccggagucug | 128 |
| hsa-miR-205* | MIMAT0009197 | GAUUUCAGuggagugaaguuc | 129 |
| hsa-miR-210 | MIMAT0000267 | CUGUGCGUgugacagcggcuga | 130 |
| hsa-miR-211 | MIMAT0000268 | UUCCCUUUgucauccuucgccu | 131 |
| hsa-miR-212 | MIMAT0000269 | UAACAGUCccagucacggcc | 132 |
| hsa-miR-181a* | MIMAT0000270 | ACCAUCGAccguugauuguacc | 133 |
| hsa-miR-214* | MIMAT0004564 | UGCCUGUCuacacuugcugugc | 134 |
| hsa-miR-214 | MIMAT0000271 | ACAGCAGGcacagacaggcagu | 135 |

TABLE I-continued

| miRNA name | miRBase number | Sequence | SEQ ID NO |
|---|---|---|---|
| hsa-miR-215 | MIMAT0000272 | AUGACCUAugaauugacagac | 136 |
| hsa-miR-216a | MIMAT0000273 | UAAUCUCAgcuggcaacuguga | 137 |
| hsa-miR-217 | MIMAT0000274 | UACUGCAUcaggaacugauugga | 138 |
| hsa-miR-218 | MIMAT0000275 | UUGUGCUUgaucuaaccaugu | 139 |
| hsa-miR-218-1* | MIMAT0004565 | AUGGUUCCgucaagcaccaugg | 140 |
| hsa-miR-218-2* | MIMAT0004566 | CAUGGUUCUgucaagcaccgcg | 141 |
| hsa-miR-219-5p | MIMAT0000276 | UGAUUGUCcaaacgcaauucu | 142 |
| hsa-miR-219-1-3p | MIMAT0004567 | AGAGUUGAgucuggacgucccg | 143 |
| hsa-miR-220a | MIMAT0000277 | CCACACCGuaucugacacuuu | 144 |
| hsa-miR-221* | MIMAT0004568 | ACCUGGCAuacaauguagauuu | 145 |
| hsa-miR-221 | MIMAT0000278 | AGCUACAUugucugcugggUuuc | 146 |
| hsa-miR-222* | MIMAT0004569 | CUCAGUAGccaguguagauccu | 147 |
| hsa-miR-222 | MIMAT0000279 | AGCUACAUcuggcuacugggu | 148 |
| hsa-miR-223* | MIMAT0004570 | CGUGUAUUugacaagcugaguu | 149 |
| hsa-miR-223 | MIMAT0000280 | UGUCAGUUugucaaauacccca | 150 |
| hsa-miR-224 | MIMAT0000281 | CAAGUCACuagugguuccguu | 151 |
| hsa-miR-224* | MIMAT0009198 | AAAAUGGUgcccuagugacuaca | 152 |
| hsa-miR-200b* | MIMAT0004571 | CAUCUUACugggcagcauuaga | 153 |
| hsa-miR-200b | MIMAT0000318 | UAAUACUGccugguaaugauga | 154 |
| hsa-let-7g | MIMAT0000414 | UGAGGUAGuaguuuguacaguu | 155 |
| hsa-let-7g* | MIMAT0004584 | CUGUACAGgccacugccuugc | 156 |
| hsa-let-7i | MIMAT0000415 | UGAGGUAGuaguuugugcuguu | 157 |
| hsa-let-7i* | MIMAT0004585 | CUGCGCAAgcuacugccuugcu | 158 |
| hsa-miR-1 | MIMAT0000416 | UGGAAUGUaaagaaguauguau | 159 |
| hsa-miR-15b | MIMAT0000417 | UAGCAGCAcaucaugguuuaca | 160 |
| hsa-miR-15b* | MIMAT0004586 | CGAAUCAUuauuugcugcucua | 161 |
| hsa-miR-23b* | MIMAT0004587 | UGGGUUCCuggcaugcugauuu | 162 |
| hsa-miR-23b | MIMAT0000418 | AUCACAUUgccagggauuacc | 163 |
| hsa-miR-27b* | MIMAT0004588 | AGAGCUUAgcugauuggugaac | 164 |
| hsa-miR-27b | MIMAT0000419 | UUCACAGUggcuaaguucugc | 165 |
| hsa-miR-30b | MIMAT0000420 | UGUAAACAuccuacacucagcu | 166 |
| hsa-miR-30b* | MIMAT0004589 | CUGGGAGGuggauauuuacuuc | 167 |
| hsa-miR-122 | MIMAT0000421 | UGGAGUGUgacaaugguguuug | 168 |
| hsa-miR-122* | MIMAT0004590 | AACGCCAUuaucacacuaaaua | 169 |
| hsa-miR-124* | MIMAT0004591 | CGUGUUCAcagcggaccuugau | 170 |
| hsa-miR-124 | MIMAT0000422 | UAAGGCACgcggugaaugcc | 171 |
| hsa-miR-125b | MIMAT0000423 | UCCCUGAGacccuaacuuguga | 172 |
| hsa-miR-125b-1* | MIMAT0004592 | ACGGGUUAggcucuuggggagcu | 173 |
| hsa-miR-128 | MIMAT0000424 | UCACAGUGaaccggucucuuu | 174 |

TABLE I-continued

| miRNA name | miRBase number | Sequence | SEQ ID NO |
|---|---|---|---|
| hsa-miR-130a* | MIMAT0004593 | UUCACAUUgugcuacugucugc | 175 |
| hsa-miR-130a | MIMAT0000425 | CAGUGCAAuguuaaaagggcau | 176 |
| hsa-miR-132* | MIMAT0004594 | ACCGUGGCuuucgauuguuacu | 177 |
| hsa-miR-132 | MIMAT0000426 | UAACAGUCuacagccauggucg | 178 |
| hsa-miR-133a | MIMAT0000427 | UUUGGUCCccuucaaccagcug | 179 |
| hsa-miR-135a | MIMAT0000428 | UAUGGCUUuuuauuccuauguga | 180 |
| hsa-miR-135a* | MIMAT0004595 | UAUAGGGAuuggagccguggcg | 181 |
| hsa-miR-137 | MIMAT0000429 | UUAUUGCUuaagaauacgcguag | 182 |
| hsa-miR-138 | MIMAT0000430 | AGCUGGUGuugugaaucaggccg | 183 |
| hsa-miR-138-2* | MIMAT0004596 | GCUAUUUCacgacaccagogguu | 184 |
| hsa-miR-140-5p | MIMAT0000431 | CAGUGGUUuuacccuauggua | 185 |
| hsa-miR-140-3p | MIMAT0004597 | UACCACAGgguagaaccacgg | 186 |
| hsa-miR-141* | MIMAT0004598 | CAUCUUCCaguacaguguugga | 187 |
| hsa-miR-141 | MIMAT0000432 | UAACACUGucugguaaagaugg | 188 |
| hsa-miR-142-5p | MIMAT0000433 | CAUAAAGUagaaagcacuacu | 189 |
| hsa-miR-142-3p | MIMAT0000434 | UGUAGUGUuuccuacuuuaugga | 190 |
| hsa-miR-143* | MIMAT0004599 | GGUGCAGUgcugcaucucuggu | 191 |
| hsa-miR-143 | MIMAT0000435 | UGAGAUGAagcacuguagcuc | 192 |
| hsa-miR-144* | MIMAT0004600 | GGAUAUCAucauauacuguaag | 193 |
| hsa-miR-144 | MIMAT0000436 | UACAGUAUagaugauguacu | 194 |
| hsa-miR-145 | MIMAT0000437 | GUCCAGUUuucccaggaauccccu | 195 |
| hsa-miR-145* | MIMAT0004601 | GGAUUCCUggaaauacuguucu | 196 |
| hsa-miR-152 | MIMAT0000438 | UCAGUGCAugacagaacuugg | 197 |
| hsa-miR-153 | MIMAT0000439 | UUGCAUAGucacaaaagugauc | 198 |
| hsa-miR-191 | MIMAT0000440 | CAACGGAAucccaaaagcagcug | 199 |
| hsa-miR-191* | MIMAT0001618 | GCUGCGCUuggauuucgucccc | 200 |
| hsa-miR-9 | MIMAT0000441 | UCUUUGGUuaucuagcuguauga | 201 |
| hsa-miR-9* | MIMAT0000442 | AUAAAGCUaaauaaccgaaagu | 202 |
| hsa-miR-125a-5p | MIMAT0000443 | UCCCUGAGacccuuuaaccuguga | 203 |
| hsa-miR-125a-3p | MIMAT0004602 | ACAGGUGAgguucuugggagcc | 204 |
| hsa-miR-125b-2* | MIMAT0004603 | UCACAAGUcaggcucuugggac | 205 |
| hsa-miR-126* | MIMAT0000444 | CAUUAUUAcuuuugguacgcg | 206 |
| hsa-miR-126 | MIMAT0000445 | UCGUACCGugaguaauaaugcg | 207 |
| hsa-miR-127-5p | MIMAT0004604 | CUGAAGCUcagagggcucugau | 208 |
| hsa-miR-127-3p | MIMAT0000446 | UCGGAUCCgucugagcuuggcu | 209 |
| hsa-miR-129-3p | MIMAT0004605 | AAGCCCUUaccccaaaaagcau | 210 |
| hsa-miR-134 | MIMAT0000447 | UGUGACUGguugaccagagggg | 211 |
| hsa-miR-136 | MIMAT0000448 | ACUCCAUUuguuuugaugaugga | 212 |

TABLE I-continued

| miRNA name | miRBase number | Sequence | SEQ ID NO |
|---|---|---|---|
| hsa-miR-136* | MIMAT0004606 | CAUCAUCGucucaaaugagucu | 213 |
| hsa-miR-138-1* | MIMAT0004607 | GCUACUUCacaacaccagggcc | 214 |
| hsa-miR-146a | MIMAT0000449 | UGAGAACUgaauuccaugggu | 215 |
| hsa-miR-146a* | MIMAT0004608 | CCUCUGAAauucaguucuucag | 216 |
| hsa-miR-149 | MIMAT0000450 | UCUGGCUCcgugucuucacuccc | 217 |
| hsa-miR-149* | MIMAT0004609 | AGGGAGGGacggggcugugc | 218 |
| hsa-miR-150 | MIMAT0000451 | UCUCCCAAcccuuguaccagug | 219 |
| hsa-miR-150* | MIMAT0004610 | CUGGUACAggccuggggggacag | 220 |
| hsa-miR-154 | MIMAT0000452 | UAGGUUAUccguguugccuucg | 221 |
| hsa-miR-154* | MIMAT0000453 | AAUCAUACacgguugaccuauu | 222 |
| hsa-miR-184 | MIMAT0000454 | UGGACGGAgaacugauaagggu | 223 |
| hsa-miR-185 | MIMAT0000455 | UGGAGAGAaaggcaguuccuga | 224 |
| hsa-miR-185* | MIMAT0004611 | AGGGGCUGGcuuuccucugguc | 225 |
| hsa-miR-186 | MIMAT0000456 | CAAAGAAUucuccuuuugggcu | 226 |
| hsa-miR-186* | MIMAT0004612 | GCCCAAAGgugaauuuuuggg | 227 |
| hsa-miR-188-5p | MIMAT0000457 | CAUCCCUUgcauggugaggg | 228 |
| hsa-miR-188-3p | MIMAT0004613 | CUCCCACAugcagggguugca | 229 |
| hsa-miR-190 | MIMAT0000458 | UGAUAUGUuugauauauuaggu | 230 |
| hsa-miR-193a-5p | MIMAT0004614 | UGGGUCUUugcgggcgagauga | 231 |
| hsa-miR-193a-3p | MIMAT0000459 | AACUGGCCuacaaaguccagu | 232 |
| hsa-miR-194 | MIMAT0000460 | UGUAACAGcaacuccaugugga | 233 |
| hsa-miR-195 | MIMAT0000461 | UAGCAGCAcagaaauauuggc | 234 |
| hsa-miR-195* | MIMAT0004615 | CCAAUAUUggcugugcugcucc | 235 |
| hsa-miR-206 | MIMAT0000462 | UGGAAUGUaaggaagugugugg | 236 |
| hsa-miR-320a | MIMAT0000510 | AAAAGCUGgguugagagggcga | 237 |
| hsa-miR-200c* | MIMAT0004657 | CGUCUUACccagcaguguuugg | 238 |
| hsa-miR-200c | MIMAT0000617 | UAAUACUGccggguaaugaugga | 239 |
| hsa-miR-155 | MIMAT0000646 | UUAAUGCUaaucgugauaggggu | 240 |
| hsa-miR-155* | MIMAT0004658 | CUCCUACAuauuagcauuaaca | 241 |
| hsa-miR-194* | MIMAT0004671 | CCAGUGGGgcugcuguuaucug | 242 |
| hsa-miR-106b | MIMAT0000680 | UAAAGUGCugacagugcagau | 243 |
| hsa-miR-106b* | MIMAT0004672 | CCGCACUGugggguacuugcugc | 244 |
| hsa-miR-29c* | MIMAT0004673 | UGACCGAUuucuccuggguguuc | 245 |
| hsa-miR-29c | MIMAT0000681 | UAGCACCAuuugaaaucgguua | 246 |
| hsa-miR-30c-1* | MIMAT0004674 | CUGGGAGAgggguuguuuacuccc | 247 |
| hsa-miR-200a* | MIMAT0001620 | CAUCUUACcggacagugcugga | 248 |
| hsa-miR-200a | MIMAT0000682 | UAACACUGucugguaacgaugu | 249 |
| hsa-miR-302a* | MIMAT0000683 | ACUUAAACgugggaugauacuugcu | 250 |
| hsa-miR-302a | MIMAT0000684 | UAAGUGCUuccauguuuugguga | 251 |

TABLE I-continued

| miRNA name | miRBase number | Sequence | SEQ ID NO |
|---|---|---|---|
| hsa-miR-219-2-3p | MIMAT0004675 | AGAAUUGUggcuggacaucugu | 252 |
| hsa-miR-34b* | MIMAT0000685 | UAGGCAGUgucauuagcugauug | 253 |
| hsa-miR-34b | MIMAT0004676 | CAAUCACUaacuccacugccau | 254 |
| hsa-miR-34c-5p | MIMAT0000686 | AGGCAGUGuaguuagcugauugc | 255 |
| hsa-miR-34c-3p | MIMAT0004677 | AAUCACUAaccacacggccagg | 256 |
| hsa-miR-299-5p | MIMAT0002890 | UGGUUUACcaucccacauacau | 257 |
| hsa-miR-299-3p | MIMAT0000687 | UAUGUGGGaugguaaaccgcuu | 258 |
| hsa-miR-301a | MIMAT0000688 | CAGUGCAAuaguauugucaaagc | 259 |
| hsa-miR-99b | MIMAT0000689 | CACCCGUAgaaccgaccuugcg | 260 |
| hsa-miR-99b* | MIMAT0004678 | CAAGCUCGugucuguggguccg | 261 |
| hsa-miR-296-5p | MIMAT0000690 | AGGGCCCCcccucaauccugu | 262 |
| hsa-miR-296-3p | MIMAT0004679 | GAGGGUUGGgguggaggcucucc | 263 |
| hsa-miR-130b* | MIMAT0004680 | ACUCUUUCccuguugcacuac | 264 |
| hsa-miR-130b | MIMAT0000691 | CAGUGCAAugaugaaagggcau | 265 |
| hsa-miR-30e | MIMAT0000692 | UGUAAACAuccuugacuggaag | 266 |
| hsa-miR-30e* | MIMAT0000693 | CUUUCAGUcggauguuuacagc | 267 |
| hsa-miR-26a-2* | MIMAT0004681 | CCUAUUCUugauuacuuguuuc | 268 |
| hsa-miR-361-5p | MIMAT0000703 | UUAUCAGAaucuccaggggauc | 269 |
| hsa-miR-361-3p | MIMAT0004682 | UCCCCCAGgugugauucugauuu | 270 |
| hsa-miR-362-5p | MIMAT0000705 | AAUCCUUGgaaccuagguaugagu | 271 |
| hsa-miR-362-3p | MIMAT0004683 | AACACACCuauucaaggauuca | 272 |
| hsa-miR-363* | MIMAT0003385 | CGGGUGGAucacgaugcaauuu | 273 |
| hsa-miR-363 | MIMAT0000707 | AAUUGCACgguauccaucugua | 274 |
| hsa-miR-365 | MIMAT0000710 | UAAUGCCCuaaaaauccuuau | 275 |
| hsa-miR-365* | MIMAT0009199 | AGGGACUUucaggggcagcugu | 276 |
| hsa-miR-302b* | MIMAT0000714 | ACUUUAACauggaagugcuuuc | 277 |
| hsa-miR-302b | MIMAT0000715 | UAAGUGCUuccauguuuuaguag | 278 |
| hsa-miR-302c* | MIMAT0000716 | UUUAACAUgggggguaccugcug | 279 |
| hsa-miR-302c | MIMAT0000717 | UAAGUGCUuccauguuucagugg | 280 |
| hsa-miR-302d* | MIMAT0004685 | ACUUUAACauggaggcacuugc | 281 |
| hsa-miR-302d | MIMAT0000718 | UAAGUGCUuccauguuugagugu | 282 |
| hsa-miR-367* | MIMAT0004686 | ACUGUUGCuaauaugcaacucu | 283 |
| hsa-miR-367 | MIMAT0000719 | AAUUGCACuuuagcaaugguga | 284 |
| hsa-miR-376c | MIMAT0000720 | AACAUAGAggaaauuccacgu | 285 |
| hsa-miR-369-5p | MIMAT0001621 | AGAUCGACcguguuauauucgc | 286 |
| hsa-miR-369-3p | MIMAT0000721 | AAUAAUACaugguugaucuuu | 287 |
| hsa-miR-370 | MIMAT0000722 | GCCUGCUGggguggaaccuggu | 288 |
| hsa-miR-371-5p | MIMAT0004687 | ACUCAAACuguggggggcacu | 289 |

TABLE I-continued

| miRNA name | miRBase number | Sequence | SEQ ID NO |
|---|---|---|---|
| hsa-miR-371-3p | MIMAT0000723 | AAGUGCCGccaucuuuugagugu | 290 |
| hsa-miR-372 | MIMAT0000724 | AAAGUGCUgcgacauuugagcgu | 291 |
| hsa-miR-373* | MIMAT0000725 | ACUCAAAAuggggggcgcuuucc | 292 |
| hsa-miR-373 | MIMAT0000726 | GAAGUGCUucgauuuuggggugu | 293 |
| hsa-miR-374a | MIMAT0000727 | UUAUAAUAcaaccugauaagug | 294 |
| hsa-miR-374a* | MIMAT0004688 | CUUAUCAGauuguauuguaauu | 295 |
| hsa-miR-375 | MIMAT0000728 | UUUGUUCGuucggcucgcguga | 296 |
| hsa-miR-376a* | MIMAT0003386 | GUAGAUUCuccuucuaugagua | 297 |
| hsa-miR-376a | MIMAT0000729 | AUCAUAGAggaaaaauccacgu | 298 |
| hsa-miR-377* | MIMAT0004689 | AGAGGUUGcccuuggugaauuc | 299 |
| hsa-miR-377 | MIMAT0000730 | AUCACACAaaggcaacuuuugu | 300 |
| hsa-miR-378* | MIMAT0000731 | CUCCUGACuccagguccugugu | 301 |
| hsa-miR-378 | MIMAT0000732 | ACUGGACUuggagucagaagg | 302 |
| hsa-miR-379 | MIMAT0000733 | UGGUAGACuauggaacguagg | 303 |
| hsa-miR-379* | MIMAT0004690 | UAUGUAACaugguccacuaacu | 304 |
| hsa-miR-380* | MIMAT0000734 | UGGUUGACcauagaacaugcgc | 305 |
| hsa-miR-380 | MIMAT0000735 | UAUGUAAUaugguccacaucuu | 306 |
| hsa-miR-381 | MIMAT0000736 | UAUACAAGggcaagcucucugu | 307 |
| hsa-miR-382 | MIMAT0000737 | GAAGUUGUucgugguggauucg | 308 |
| hsa-miR-383 | MIMAT0000738 | AGAUCAGAaggugauuguggcu | 309 |
| hsa-miR-340 | MIMAT0004692 | UUAUAAAGcaaugagacugauu | 310 |
| hsa-miR-340* | MIMAT0000750 | UCCGUCUCaguuacuuuauagc | 311 |
| hsa-miR-330-5p | MIMAT0004693 | UCUCUGGGccugugucuuaggc | 312 |
| hsa-miR-330-3p | MIMAT0000751 | GCAAAGCAcacggccugcagaga | 313 |
| hsa-miR-328 | MIMAT0000752 | CUGGCCCUcucugcccuuccgu | 314 |
| hsa-miR-342-5p | MIMAT0004694 | AGGGGUGCuaucugugauuga | 315 |
| hsa-miR-342-3p | MIMAT0000753 | UCUCACACagaaaucgcacccgu | 316 |
| hsa-miR-337-5p | MIMAT0004695 | GAACGGCUucauacaggaguu | 317 |
| hsa-miR-337-3p | MIMAT0000754 | CUCCUAUAugaugccuuucuuc | 318 |
| hsa-miR-323-5p | MIMAT0004696 | AGGUGGUCcguggcgcguucgc | 319 |
| hsa-miR-323-3p | MIMAT0000755 | CACAUUACacggucgaccucu | 320 |
| hsa-miR-326 | MIMAT0000756 | CCUCUGGGcccuuccuccag | 321 |
| hsa-miR-151-5p | MIMAT0004697 | UCGAGGAGcucacagucuagu | 322 |
| hsa-miR-151-3p | MIMAT0000757 | CUAGACUGaagcuccuugagg | 323 |
| hsa-miR-135b | MIMAT0000758 | UAUGGCUUuucauuccuauguga | 324 |
| hsa-miR-135b* | MIMAT0004698 | AUGUAGGGcuaaaagccauggg | 325 |
| hsa-miR-148b* | MIMAT0004699 | AAGUUCUGuuuauacacucaggc | 326 |
| hsa-miR-148b | MIMAT0000759 | UCAGUGCAucacagaacuuugu | 327 |
| hsa-miR-331-5p | MIMAT0004700 | CUAGGUAUgguccccagggaucc | 328 |

TABLE I-continued

| miRNA name | miRBase number | Sequence | SEQ ID NO |
|---|---|---|---|
| hsa-miR-331-3p | MIMAT0000760 | GCCCCUGGgccuauccuagaa | 329 |
| hsa-miR-324-5p | MIMAT0000761 | CGCAUCCCcuagggcauuggugu | 330 |
| hsa-miR-324-3p | MIMAT0000762 | ACUGCCCCaggugcugcugg | 331 |
| hsa-miR-338-5p | MIMAT0004701 | AACAAUAUccuggugcugagug | 332 |
| hsa-miR-338-3p | MIMAT0000763 | UCCAGCAUcagugauuuuguug | 333 |
| hsa-miR-339-5p | MIMAT0000764 | UCCCUGUCcuccaggagcucacg | 334 |
| hsa-miR-339-3p | MIMAT0004702 | UGAGCGCCucgacgacagagccg | 335 |
| hsa-miR-335 | MIMAT0000765 | UCAAGAGCaauaacgaaaaauau | 336 |
| hsa-miR-335* | MIMAT0004703 | UUUUUCAUuauugcuccugacc | 337 |
| hsa-miR-133b | MIMAT0000770 | UUUGGUCCccuucaaccagcua | 338 |
| hsa-miR-325 | MIMAT0000771 | CCUAGUAGguguccaguaagugu | 339 |
| hsa-miR-345 | MIMAT0000772 | GCUGACUCcuaguccagggcuc | 340 |
| hsa-miR-346 | MIMAT0000773 | UGUCUGCCcgcaugccugccucu | 341 |
| hsa-miR-384 | MIMAT0001075 | AUUCCUAGaaauuguucaua | 342 |
| hsa-miR-196b | MIMAT0001080 | UAGGUAGUuuccuguuguuggg | 343 |
| hsa-miR-196b* | MIMAT0009201 | UCGACAGCacgacacugccuuc | 344 |
| hsa-miR-422a | MIMAT0001339 | ACUGGACUuaggglucagaaggc | 345 |
| hsa-miR-423-5p | MIMAT0004748 | UGAGGGGCagagagcgagacuuu | 346 |
| hsa-miR-423-3p | MIMAT0001340 | AGCUCGGUcugaggccccucagu | 347 |
| hsa-miR-424 | MIMAT0001341 | CAGCAGCAauucauguuuugaa | 348 |
| hsa-miR-424* | MIMAT0004749 | CAAAACGUgaggcgcugcuau | 349 |
| hsa-miR-425 | MIMAT0003393 | AAUGACACgaucacucccguuga | 350 |
| hsa-miR-425* | MIMAT0001343 | AUCGGGAAugucguguccgccc | 351 |
| hsa-miR-18b | MIMAT0001412 | UAAGGUGCaucuagugcaguuag | 352 |
| hsa-miR-18b* | MIMAT0004751 | UGCCCUAAaugccccuucggc | 353 |
| hsa-miR-20b | MIMAT0001413 | CAAAGUGCucauagugcagguag | 354 |
| hsa-miR-20b* | MIMAT0004752 | ACUGUAGUaugggcacuuccag | 355 |
| hsa-miR-448 | MIMAT0001532 | UUGCAUAUguaggaugucccau | 356 |
| hsa-miR-429 | MIMAT0001536 | UAAUACUGucugguaaaaccgu | 357 |
| hsa-miR-449a | MIMAT0001541 | UGGCAGUGuauuguuagcugguu | 358 |
| hsa-miR-450a | MIMAT0001545 | UUUUGCGAuguguuccuaauau | 359 |
| hsa-miR-431 | MIMAT0001625 | UGUCUUGCaggccgucaugca | 360 |
| hsa-miR-431* | MIMAT0004757 | CAGGUCGUcuugcagggcuucu | 361 |
| hsa-miR-433 | MIMAT0001627 | AUCAUGAUgggcuccucggugu | 362 |
| hsa-miR-329 | MIMAT0001629 | AACACACCugguuaaccucuuu | 363 |
| hsa-miR-451 | MIMAT0001631 | AAACCGUUaccauuacugaguu | 364 |
| hsa-miR-452 | MIMAT0001635 | AACUGUUUgcagaggaaacuga | 365 |
| hsa-miR-452* | MIMAT0001636 | CUCAUCUGcaaagaaguaagug | 366 |

TABLE I-continued

| miRNA name | miRBase number | Sequence | SEQ ID NO |
|---|---|---|---|
| hsa-miR-409-5p | MIMAT0001638 | AGGUUACCcgagcaacuuugcau | 367 |
| hsa-miR-409-3p | MIMAT0001639 | GAAUGUUGcucggugaaccccu | 368 |
| hsa-miR-412 | MIMAT0002170 | ACUUCACCugguccacuagccgu | 369 |
| hsa-miR-410 | MIMAT0002171 | AAUAUAACacagauggccugu | 370 |
| hsa-miR-376b | MIMAT0002172 | AUCAUAGAggaaaauccauguu | 371 |
| hsa-miR-483-5p | MIMAT0004761 | AAGACGGGaggaaagaagggag | 372 |
| hsa-miR-483-3p | MIMAT0002173 | UCACUCCUcuccucccgucuu | 373 |
| hsa-miR-484 | MIMAT0002174 | UCAGGCUCagucccucccgau | 374 |
| hsa-miR-485-5p | MIMAT0002175 | AGAGGCUGgccgugaugaauuc | 375 |
| hsa-miR-485-3p | MIMAT0002176 | GUCAUACAcggcucuccucucu | 376 |
| hsa-miR-486-5p | MIMAT0002177 | UCCUGUACugagcugccccgag | 377 |
| hsa-miR-486-3p | MIMAT0004762 | CGGGGCAGcucaguacaggau | 378 |
| hsa-miR-487a | MIMAT0002178 | AAUCAUACagggacauccaguu | 379 |
| hsa-miR-488* | MIMAT0002804 | CCCAGAUAauggcacucucaa | 380 |
| hsa-miR-488 | MIMAT0004763 | UUGAAAGGcuauuucuugguc | 381 |
| hsa-miR-489 | MIMAT0002805 | GUGACAUCacauauacggcagc | 382 |
| hsa-miR-490-5p | MIMAT0004764 | CCAUGGAUcuccaggugggu | 383 |
| hsa-miR-490-3p | MIMAT0002806 | CAACCUGGaggacuccaugcug | 384 |
| hsa-miR-491-5p | MIMAT0002807 | AGUGGGGAacccuuccaugagg | 385 |
| hsa-miR-491-3p | MIMAT0004765 | CUUAUGCAagauucccuucuac | 386 |
| hsa-miR-511 | MIMAT0002808 | GUGUCUUUugcucugcaguca | 387 |
| hsa-miR-146b-5p | MIMAT0002809 | UGAGAACUgaauuccauaggcu | 388 |
| hsa-miR-146b-3p | MIMAT0004766 | UGCCCUGUggacucaguucugg | 389 |
| hsa-miR-202* | MIMAT0002810 | UUCCUAUGcauauacuucuuug | 390 |
| hsa-miR-202 | MIMAT0002811 | AGAGGUAUagggcaugggaa | 391 |
| hsa-miR-492 | MIMAT0002812 | AGGACCUGcgggacaagauucuu | 392 |
| hsa-miR-493* | MIMAT0002813 | UUGUACAUgguaggcuuucauu | 393 |
| hsa-miR-493 | MIMAT0003161 | UGAAGGUCuacugugugccagg | 394 |
| hsa-miR-432 | MIMAT0002814 | UCUUGGAGuaggucauugggugg | 395 |
| hsa-miR-432* | MIMAT0002815 | CUGGAUGGcuccuccaugucu | 396 |
| hsa-miR-494 | MIMAT0002816 | UGAAACAUacacgggaaaccuc | 397 |
| hsa-miR-495 | MIMAT0002817 | AAACAAACauggugcacuucuu | 398 |
| hsa-miR-496 | MIMAT0002818 | UGAGUAUUacauggccaaucuc | 399 |
| hsa-miR-193b* | MIMAT0004767 | CGGGGUUUugagggcgagauga | 400 |
| hsa-miR-193b | MIMAT0002819 | AACUGGCCucaaagucccgcu | 401 |
| hsa-miR-497 | MIMAT0002820 | CAGCAGCAcacugugguuugu | 402 |
| hsa-miR-497* | MIMAT0004768 | CAAACCACacugugguguuaga | 403 |
| hsa-miR-181d | MIMAT0002821 | AACAUUCAuuguugucgguggu | 404 |
| hsa-miR-512-5p | MIMAT0002822 | CACUCAGCcuugagggcacuuuc | 405 |

TABLE I-continued

| miRNA name | miRBase number | Sequence | SEQ ID NO |
|---|---|---|---|
| hsa-miR-512-3p | MIMAT0002823 | AAGUGCUGucauagcugagguc | 406 |
| hsa-miR-498 | MIMAT0002824 | UUUCAAGCcaggggcguuuuuc | 407 |
| hsa-miR-520e | MIMAT0002825 | AAAGUGCUuccuuuuugaggg | 408 |
| hsa-miR-515-5p | MIMAT0002826 | UUCUCCAAaagaaagcacuuucug | 409 |
| hsa-miR-515-3p | MIMAT0002827 | GAGUGCCUucuuuuggagcguu | 410 |
| hsa-miR-519e* | MIMAT0002828 | UUCUCCAAaagggagcacuuuc | 411 |
| hsa-miR-519e | MIMAT0002829 | AAGUGCCUccuuuuagaguguu | 412 |
| hsa-miR-520f | MIMAT0002830 | AAGUGCUUccuuuuagagggu | 413 |
| hsa-miR-519c-5p | MIMAT0002831 | CUCUAGAGggaagcgcuuucug | 414 |
| hsa-miR-519c-3p | MIMAT0002832 | AAAGUGCAucuuuuuagaggau | 415 |
| hsa-miR-520a-5p | MIMAT0002833 | CUCCAGAGggaaguacuuucu | 416 |
| hsa-miR-520a-3p | MIMAT0002834 | AAAGUGCUucccuuuggacugu | 417 |
| hsa-miR-526b | MIMAT0002835 | CUCUUGAGggaagcacuuucugu | 418 |
| hsa-miR-526b* | MIMAT0002836 | GAAAGUGCuuccuuuuagaggc | 419 |
| hsa-miR-519b-5p | MIMAT0005454 | CUCUAGAGggaagcgcuuucug | 414 |
| hsa-miR-519b-3p | MIMAT0002837 | AAAGUGCAuccuuuuagagguu | 420 |
| hsa-miR-525-5p | MIMAT0002838 | CUCCAGAGggaugcacuuucu | 421 |
| hsa-miR-525-3p | MIMAT0002839 | GAAGGCGCuucccuuuagagcg | 422 |
| hsa-miR-523* | MIMAT0005449 | CUCUAGAGggaagcgcuuucug | 414 |
| hsa-miR-523 | MIMAT0002840 | GAACGCGCuucccuauagagggu | 423 |
| hsa-miR-5I8f* | MIMAT0002841 | CUCUAGAGggaagcacuuucuc | 424 |
| hsa-miR-518f | MIMAT0002842 | GAAAGCGCuucucuuuagagg | 425 |
| hsa-miR-520b | MIMAT0002843 | AAAGUGCUuccuuuuagaggg | 426 |
| hsa-miR-518b | MIMAT0002844 | CAAAGCGCuccccuuuagaggu | 427 |
| hsa-miR-526a | MIMAT0002845 | CUCUAGAGggaagcacuuucug | 428 |
| hsa-miR-520c-5p | MIMAT0005455 | CUCUAGAGggaagcacuuucug | 428 |
| hsa-miR-520c-3p | MIMAT0002846 | AAAGUGCUuccuuuuagagggu | 429 |
| hsa-miR-518c* | MIMAT0002847 | UCUCUGGAgagaagcacuuucug | 430 |
| hsa-miR-518c | MIMAT0002848 | CAAAGCGCuucucuuuagagugu | 431 |
| hsa-miR-524-5p | MIMAT0002849 | CUACAAAGggaagcacuuucuc | 432 |
| hsa-miR-524-3p | MIMAT0002850 | GAAGGCGCuucccuuuggagu | 433 |
| hsa-miR-517* | MIMAT0002851 | CCUCUAGAuggaagcacugucu | 434 |
| hsa-miR-517a | MIMAT0002852 | AUCGUGCAucccuuuagagugu | 435 |
| hsa-miR-519d | MIMAT0002853 | CAAAGUGCcucccuuuagagug | 436 |
| hsa-miR-521 | MIMAT0002854 | AACGCACUucccuuuagagugu | 437 |
| hsa-miR-520d-5p | MIMAT0002855 | CUACAAAGggaagcccuuuc | 438 |
| hsa-miR-520d-3p | MIMAT0002856 | AAAGUGCUucucuuuggugggu | 439 |
| hsa-miR-517b | MIMAT0002857 | UCGUGCAUcccuuuagaguguu | 440 |

TABLE I-continued

| miRNA name | miRBase number | Sequence | SEQ ID NO |
|---|---|---|---|
| hsa-miR-520g | MIMAT0002858 | ACAAAGUGcuucccuuuagagugu | 441 |
| hsa-miR-516b | MIMAT0002859 | AUCUGGAGguaagaagcacuuu | 442 |
| hsa-miR-516b* | MIMAT0002860 | UGCUUCCUuucagagggu | 443 |
| hsa-miR-518e* | MIMAT0005450 | CUCUAGAGggaagcgcuuucug | 414 |
| hsa-miR-518e | MIMAT0002861 | AAAGCGCUucccuucagagug | 444 |
| hsa-miR-518a-5p | MIMAT0005457 | CUGCAAAGggaagcccuuuc | 445 |
| hsa-miR-518a-3p | MIMAT0002863 | GAAAGCGCuucccuuugcugga | 446 |
| hsa-miR-518d-5p | MIMAT0005456 | CUCUAGAGggaagcacuuucg | 428 |
| hsa-miR-518d-3p | MIMAT0002864 | CAAAGCGCuucccuuuggagc | 447 |
| hsa-miR-517c | MIMAT0002866 | AUCGUGCAuccuuuuagagugu | 448 |
| hsa-miR-520h | MIMAT0002867 | ACAAAGUGcuucccuuuagagu | 449 |
| hsa-miR-522* | MIMAT0005451 | CUCUAGAGggaagcgcuuucug | 414 |
| hsa-miR-522 | MIMAT0002868 | AAAAUGGUucccuuuagagugu | 450 |
| hsa-miR-519a* | MIMAT0005452 | CUCUAGAGggaagcgcuuucug | 414 |
| hsa-miR-519a | MIMAT0002869 | AAAGUGCAuccuuuuagagugu | 451 |
| hsa-miR-527 | MIMAT0002862 | CUGCAAAGggaagcccuuuc | 445 |
| hsa-miR-516a-5p | MIMAT0004770 | UUCUCGAGgaaagaagcacuuuc | 452 |
| hsa-miR-516a-3p | MIMAT0006778 | UGCUUCCUuucagagggu | 443 |
| hsa-miR-499-5p | MIMAT0002870 | UUAAGACUugcagugauguuu | 453 |
| hsa-miR-499-3p | MIMAT0004772 | AACAUCAcagcaagucugugcu | 454 |
| hsa-miR-500 | MIMAT0004773 | UAAUCCUUgcuaccugggugaga | 455 |
| hsa-miR-500* | MIMAT0002871 | AUGCACCUgggcaaggauucug | 456 |
| hsa-miR-501-5p | MIMAT0002872 | AAUCCUUUgucccuggguga | 457 |
| hsa-miR-501-3p | MIMAT0004774 | AAUGCACCcgggcaaggauucu | 458 |
| hsa-miR-502-5p | MIMAT0002873 | AUCCUUGCuaucuggguga | 459 |
| hsa-miR-502-3p | MIMAT0004775 | AAUGCACCugggcaaggauuca | 460 |
| hsa-miR-503 | MIMAT0002874 | UAGCAGCGggaacaguucugcag | 461 |
| hsa-miR-504 | MIMAT0002875 | AGACCCUGgucugcacucuauc | 462 |
| hsa-miR-505* | MIMAT0004776 | GGGAGCCAggaaguauugaugu | 463 |
| hsa-miR-505 | MIMAT0002876 | CGUCAACAcuugcugguuuccu | 464 |
| hsa-miR-513a-5p | MIMAT0002877 | UUCACAGGgaggugucau | 465 |
| hsa-miR-513a-3p | MIMAT0004777 | UAAAUUUCaccuuucugagaagg | 466 |
| hsa-miR-506 | MIMAT0002878 | UAAGGCACccuucugaguaga | 467 |
| hsa-miR-507 | MIMAT0002879 | UUUUGCACcuuuuggagugaa | 468 |
| hsa-miR-508-5p | MIMAT0004778 | UACUCCAGagggcgucacucaug | 469 |
| hsa-miR-508-3p | MIMAT0002880 | UGAUUGUAgccuuuggaguaga | 470 |
| hsa-miR-509-5p | MIMAT0004779 | UACUGCAGacaguggcaauca | 471 |
| hsa-miR-509-3p | MIMAT0002881 | UGAUUGGUacgucugggguag | 472 |
| hsa-miR-510 | MIMAT0002882 | UACUCAGGagaguggcaaucac | 473 |

TABLE I-continued

| miRNA name | miRBase number | Sequence | SEQ ID NO |
|---|---|---|---|
| hsa-miR-514 | MIMAT0002883 | AUUGACACuucugugaguaga | 474 |
| hsa-miR-532-5p | MIMAT0002888 | CAUGCCUUgaguguaggaccgu | 475 |
| hsa-miR-532-3p | MIMAT0004780 | CCUCCCACacccaaggcuugca | 476 |
| hsa-miR-455-5p | MIMAT0003150 | UAUGUGCCuuuggacuacaucg | 477 |
| hsa-miR-455-3p | MIMAT0004784 | GCAGUCCAugggcauauacac | 478 |
| hsa-miR-539 | MIMAT0003163 | GGAGAAAUuauccuuggugugu | 479 |
| hsa-miR-544 | MIMAT0003164 | AUUCUGCAuuuuuagcaaguuc | 480 |
| hsa-miR-545* | MIMAT0004785 | UCAGUAAAuguuuauuagauga | 481 |
| hsa-miR-545 | MIMAT0003165 | UCAGCAAAcauuuauugugugc | 482 |
| hsa-miR-487b | MIMAT0003180 | AAUCGUACagggucauccacuu | 483 |
| hsa-miR-551a | MIMAT0003214 | GCGACCCAcucuugguuucca | 484 |
| hsa-miR-552 | MIMAT0003215 | AACAGGUGacugguuagacaa | 485 |
| hsa-miR-553 | MIMAT0003216 | AAAACGGUgagauuuuguuuu | 486 |
| hsa-miR-554 | MIMAT0003217 | GCUAGUCCugacucagccagu | 487 |
| hsa-miR-92b* | MIMAT0004792 | AGGGACGGgacgcggugcagug | 488 |
| hsa-miR-92b | MIMAT0003218 | UAUUGCACucgucccggccucc | 489 |
| hsa-miR-555 | MIMAT0003219 | AGGGUAAGcugaaccucugau | 490 |
| hsa-miR-556-5p | MIMAT0003220 | GAUGAGCUcauuguaauaugag | 491 |
| hsa-miR-556-3p | MIMAT0004793 | AUAUUACCauuagcucaucuuu | 492 |
| hsa-miR-557 | MIMAT0003221 | GUUUGCACgggugggccuugucu | 493 |
| hsa-miR-558 | MIMAT0003222 | UGAGCUGCuguaccaaaau | 494 |
| hsa-miR-559 | MIMAT0003223 | UAAAGUAAauaugcaccaaaa | 495 |
| hsa-miR-561 | MIMAT0003225 | CAAAGUUUaagauccuugaagu | 496 |
| hsa-miR-562 | MIMAT0003226 | AAAGUAGCuguaccauuugc | 497 |
| hsa-miR-563 | MIMAT0003227 | AGGUUGACauacguuuccc | 498 |
| hsa-miR-564 | MIMAT0003228 | AGGCACGGuaucagcaggc | 499 |
| hsa-miR-566 | MIMAT0003230 | GGGCGCCUgugaucccaac | 500 |
| hsa-miR-567 | MIMAT0003231 | AGUAUGUUcuuccaggacagaac | 501 |
| hsa-miR-568 | MIMAT0003232 | AUGUAUAAauguauacacac | 502 |
| hsa-miR-551b* | MIMAT0004794 | GAAAUCAAgcgugagugagacc | 503 |
| hsa-miR-551b | MIMAT0003233 | GCGACCCAuacuugguuucag | 504 |
| hsa-miR-569 | MIMAT0003234 | AGUUAAUGaauccuggaaagu | 505 |
| hsa-miR-570 | MIMAT0003235 | CGAAAACAgcaauuaccuuugc | 506 |
| hsa-miR-571 | MIMAT0003236 | UGAGUUGGccaucugagugag | 507 |
| hsa-miR-572 | MIMAT0003237 | GUCCGCUCggcgguggccca | 508 |
| hsa-miR-573 | MIMAT0003238 | CUGAAGUGauguguaacugaucag | 509 |
| hsa-miR-574-5p | MIMAT0004795 | UGAGUGUGuguguguaauguau | 510 |
| hsa-miR-574-3p | MIMAT0003239 | CACGCUCAugcacacacccaca | 511 |

TABLE I-continued

| miRNA name | miRBase number | Sequence | SEQ ID NO |
|---|---|---|---|
| hsa-miR-575 | MIMAT0003240 | GAGCCAGUuagacaggagc | 512 |
| hsa-miR-576-5p | MIMAT0003241 | AUUCUAAUuucuccacgucuuu | 513 |
| hsa-miR-576-3p | MIMAT0004796 | AAGAUGUGgaaaaauuggaauc | 514 |
| hsa-miR-577 | MIMAT0003242 | UAGAUAAAauauuggguaccug | 515 |
| hsa-miR-578 | MIMAT0003243 | CUUCUUGUgcucuaggauugu | 516 |
| hsa-miR-579 | MIMAT0003244 | UUCAUUUGguauaaaccgcgauu | 517 |
| hsa-miR-580 | MIMAT0003245 | UUGAGAAUgaugaaucauuagg | 518 |
| hsa-miR-581 | MIMAT0003246 | UCUUGUGUucucuagaucagu | 519 |
| hsa-miR-582-5p | MIMAT0003247 | UUACAGUUguucaaccaguuacu | 520 |
| hsa-miR-582-3p | MIMAT0004797 | UAACUGGUugaacaacugaacc | 521 |
| hsa-miR-583 | MIMAT0003248 | CAAAGAGGaaggucccauuac | 522 |
| hsa-miR-584 | MIMAT0003249 | UUAUGGUUugccugggacugag | 523 |
| hsa-miR-585 | MIMAT0003250 | UGGGCGUAucuguaugcua | 524 |
| hsa-miR-548a-3p | MIMAT0003251 | CAAAACUGgcaauuacuuuugc | 525 |
| hsa-miR-586 | MIMAT0003252 | UAUGCAUUguauuuuuaggucc | 526 |
| hsa-miR-587 | MIMAT0003253 | UUUCCAUAggugaugagucac | 527 |
| hsa-miR-548b-5p | MIMAT0004798 | AAAAGUAAuugugguuuuggcc | 528 |
| hsa-miR-548b-3p | MIMAT0003254 | CAAGAACCucaguugcuuuugu | 529 |
| hsa-miR-588 | MIMAT0003255 | UUGGCCACaauggguuagaac | 530 |
| hsa-miR-589 | MIMAT0004799 | UGAGAACCacgucugcucugag | 531 |
| hsa-miR-589* | MIMAT0003256 | UCAGAACAaaugccgguucccaga | 532 |
| hsa-miR-550 | MIMAT0004800 | AGUGCCUGagggaguaagagccc | 533 |
| hsa-miR-550* | MIMAT0003257 | UGUCUUACucccucaggcacau | 534 |
| hsa-miR-590-5p | MIMAT0003258 | GAGCUUAUucauaaaagugcag | 535 |
| hsa-miR-590-3p | MIMAT0004801 | UAAUUUUAuguauaagcuagu | 536 |
| hsa-miR-591 | MIMAT0003259 | AGACCAUGgguucucauugu | 537 |
| hsa-miR-592 | MIMAT0003260 | UUGUGUCAauaugcgaugaugu | 538 |
| hsa-miR-593* | MIMAT0003261 | AGGCACCAgccaggcauugcucagc | 539 |
| hsa-miR-593 | MIMAT0004802 | UGUCUCUGcuggggguuucu | 540 |
| hsa-miR-595 | MIMAT0003263 | GAAGUGUGccgugguugucu | 541 |
| hsa-miR-596 | MIMAT0003264 | AAGCCUGCccggcuccucggg | 547 |
| hsa-miR-597 | MIMAT0003265 | UGUGUCACucgaugaccacucu | 543 |
| hsa-miR-598 | MIMAT0003266 | UACGUCAUcguugucaucguca | 544 |
| hsa-miR-599 | MIMAT0003267 | GUUGUGUCacuuuaucaaac | 545 |
| hsa-miR-548a-5p | MIMAT0004803 | AAAAGUAAuugcgaguuuuacc | 546 |
| hsa-miR-600 | MIMAT0003268 | ACUUACAGacaagagccuugcuc | 547 |
| hsa-miR-601 | MIMAT0003269 | UGGUCUAGgauuguuggaggag | 548 |
| hsa-miR-602 | MIMAT0003270 | GACACGGGcgacagcugcgcccc | 549 |
| hsa-miR-603 | MIMAT0003271 | CACACACUgcaauuacuuuugc | 550 |

TABLE I-continued

| miRNA name | miRBase number | Sequence | SEQ ID NO |
|---|---|---|---|
| hsa-miR-604 | MIMAT0003272 | AGGCUGCGgaauucaggac | 551 |
| hsa-miR-605 | MIMAT0003273 | UAAAUCCCauggugccuucuccu | 552 |
| hsa-miR-606 | MIMAT0003274 | AAACUACUgaaaaucaaagau | 553 |
| hsa-miR-607 | MIMAT0003275 | GUUCAAAUccagaucuauaac | 554 |
| hsa-miR-608 | MIMAT0003276 | AGGGGUGGuguugggacagcuccgu | 555 |
| hsa-miR-609 | MIMAT0003277 | AGGGUGUUucucucaucucu | 556 |
| hsa-miR-610 | MIMAT0003278 | UGAGCUAAaugugugcuggga | 557 |
| hsa-miR-611 | MIMAT0003279 | GCGAGGACcccucggggucugac | 558 |
| hsa-miR-612 | MIMAT0003280 | GCUGGGCAgggcuucugagcuccuu | 559 |
| hsa-miR-613 | MIMAT0003281 | AGGAAUGUuccuucuuugcc | 560 |
| hsa-miR-614 | MIMAT0003282 | GAACGCCUguucuugccaggugg | 561 |
| hsa-miR-615-5p | MIMAT0004804 | GGGGGUCCccggugcucggauc | 562 |
| hsa-miR-615-3p | MIMAT0003283 | UCCGAGCCugggucucccucuu | 563 |
| hsa-miR-616* | MIMAT0003284 | ACUCAAAAcccuucagugacuu | 564 |
| hsa-miR-616 | MIMAT0004805 | AGUCAUUGgagggguuugagcag | 565 |
| hsa-miR-548c-5p | MIMAT0004806 | AAAAGUAAuugcgguuuuugcc | 566 |
| hsa-miR-548c-3p | MIMAT0003285 | CAAAAAUCucaauuacuuuugc | 567 |
| hsa-miR-617 | MIMAT0003286 | AGACUUCCcauuugaaggugc | 568 |
| hsa-miR-618 | MIMAT0003287 | AAACUCUAcuuguccuucugagu | 569 |
| hsa-miR-619 | MIMAT0003288 | GACCUGGAcauguuugugcccagu | 570 |
| hsa-miR-620 | MIMAT0003289 | AUGGAGAUagauauagaaau | 571 |
| hsa-miR-621 | MIMAT0003290 | GGCUAGCAacagcgcuuaccu | 572 |
| hsa-miR-622 | MIMAT0003291 | ACAGUCUGcugagguuggagc | 573 |
| hsa-miR-623 | MIMAT0003292 | AUCCCUUGcaggggcuguugggu | 574 |
| hsa-miR-624* | MIMAT0003293 | UAGUACCAguaccuugugquuca | 575 |
| hsa-miR-624 | MIMAT0004807 | CACAAGGUauugguauuaccu | 576 |
| hsa-miR-625 | MIMAT0003294 | AGGGGGAAaguucuauagucc | 577 |
| hsa-miR-625* | MIMAT0004808 | GACUAUAGaacuuccccuca | 578 |
| hsa-miR-626 | MIMAT0003295 | AGCUGUCUgaaaaugucuu | 579 |
| hsa-miR-627 | MIMAT0003296 | GUGAGUCUcuaagaaaagagga | 580 |
| hsa-miR-628-5p | MIMAT0004809 | AUGCUGACauauuuacuagagg | 581 |
| hsa-miR-628-3p | MIMAT0003297 | UCUAGUAAgaguggcagucga | 582 |
| hsa-miR-629 | MIMAT0004810 | UGGGUUUAcguugggagaacu | 583 |
| hsa-miR-629* | MIMAT0003298 | GUUCUCCCaacguaagcccagc | 584 |
| hsa-miR-630 | MIMAT0003299 | AGUAUUCUguaccagggaaggu | 585 |
| hsa-miR-631 | MIMAT0003300 | AGACCUGGcccagaccucagc | 586 |
| hsa-miR-33b | MIMAT0003301 | GUGCAUUGcuguuuccauugc | 587 |
| hsa-miR-33b* | MIMAT0004811 | CAGUGCCUcggcagugcagccc | 588 |

TABLE I-continued

| miRNA name | miRBase number | Sequence | SEQ ID NO |
|---|---|---|---|
| hsa-miR-632 | MIMAT0003302 | GUGUCUGCuuccuguggga | 589 |
| hsa-miR-633 | MIMAT0003303 | CUAAUAGUaucuaccacaauaaa | 590 |
| hsa-miR-634 | MIMAT0003304 | AACCAGCAccccaacuuuggac | 591 |
| hsa-miR-635 | MIMAT0003305 | ACUUGGGCacugaaacaaugucc | 592 |
| hsa-miR-636 | MIMAT0003306 | UGUGCUUGcucgucccgcccgca | 593 |
| hsa-miR-637 | MIMAT0003307 | ACUGGGGGcuuucgggcucugcgu | 594 |
| hsa-miR-638 | MIMAT0003308 | AGGGAUCGcgggcggguggcggccu | 595 |
| hsa-miR-639 | MIMAT0003309 | AUCGCUGCgguugcgagcgcugu | 596 |
| hsa-miR-640 | MIMAT0003310 | AUGAUCCAggaaccugccucu | 597 |
| hsa-miR-641 | MIMAT0003311 | AAAGACAUaagauagagucaccuc | 598 |
| hsa-miR-642 | MIMAT0003312 | GUCCCUCUccaaauguqucuug | 599 |
| hsa-miR-643 | MIMAT0003313 | ACUUGUAUgcuagcucagguag | 600 |
| hsa-miR-644 | MIMAT0003314 | AGUGUGGCuuucuuagagc | 601 |
| hsa-miR-645 | MIMAT0003315 | UCUAGGCUgguacugcuga | 602 |
| hsa-miR-646 | MIMAT0003316 | AAGCAGCUgccucugaggc | 603 |
| hsa-miR-647 | MIMAT0003317 | GUGGCUGCacucacuuccuuc | 604 |
| hsa-miR-648 | MIMAT0003318 | AAGUGUGCagggcacuggu | 605 |
| hsa-miR-649 | MIMAT0003319 | AAACCUGUguuguucaagaguc | 606 |
| hsa-miR-650 | MIMAT0003320 | AGGAGGCAgcgcucucaggac | 607 |
| hsa-miR-651 | MIMAT0003321 | UUUAGGAUaagcuugacuuuug | 608 |
| hsa-miR-652 | MIMAT0003322 | AAUGGCGCcacuagggUuGug | 609 |
| hsa-miR-548d-5p | MIMAT0004812 | AAAAGUAAuugugguuuuugcc | 610 |
| hsa-miR-548d-3p | MIMAT0003323 | CAAAAACCacaguuucuuuugc | 611 |
| hsa-miR-661 | MIMAT0003324 | UGCCUGGGucucuggccugcgcgu | 612 |
| hsa-miR-662 | MIMAT0003325 | UCCCACGUuguggcccagcag | 613 |
| hsa-miR-663 | MIMAT0003326 | AGGCGGGGcgccgcgagaccgc | 614 |
| hsa-miR-449b | MIMAT0003327 | AGGCAGUGuauuguuagcuggc | 615 |
| hsa-miR-449b* | MIMAT0009203 | CAGCCACAacuacccugccacu | 616 |
| hsa-miR-653 | MIMAT0003328 | GUGUUGAAacaaucucuacug | 617 |
| hsa-miR-411 | MIMAT0003329 | UAGUAGACcguauagcguacg | 618 |
| hsa-miR-411* | MIMAT0004813 | UAUGUAACacgguccacuaacc | 619 |
| hsa-miR-654-5p | MIMAT0003330 | UGGUGGGCcgcagaacaugugc | 620 |
| hsa-miR-654-3p | MIMAT0004814 | UAUGUCUGcugaccaucaccuu | 621 |
| hsa-miR-655 | MIMAT0003331 | AUAAUACAuggUuaaccucuuu | 622 |
| hsa-miR-656 | MIMAT0003332 | AAUAUUAUacagucaaccucu | 623 |
| hsa-miR-549 | MIMAT0003333 | UGACAACUauggaugagcucu | 624 |
| hsa-miR-657 | MIMAT0003335 | GGCAGGUUcucacccucucuagg | 625 |
| hsa-miR-658 | MIMAT0003336 | GGCGGAGGgaaguaggUCCguuggu | 626 |
| hsa-miR-659 | MIMAT0003337 | CUUGGUUCaggagggUCCcca | 627 |

TABLE I-continued

| miRNA name | miRBase number | Sequence | SEQ ID NO |
|---|---|---|---|
| hsa-miR-660 | MIMAT0003338 | UACCCAUUgcauaucggaguug | 628 |
| hsa-miR-421 | MIMAT0003339 | AUCAACAGacauuaauugggcgc | 629 |
| hsa-miR-542-5p | MIMAT0003340 | UCGGGGAUcaucaugucacgaga | 630 |
| hsa-miR-542-3p | MIMAT0003389 | UGUGACAGauugauaacugaaa | 631 |
| hsa-miR-758 | MIMAT0003879 | UUUGUGACcugguccacuaacc | 632 |
| hsa-miR-1264 | MIMAT0005791 | CAAGUCUUauuugagcaccuguu | 633 |
| hsa-miR-671-5p | MIMAT0003880 | AGGAAGCCcuggaggggcuggag | 634 |
| hsa-miR-671-3p | MIMAT0004819 | UCCGGUUCucagggcuccacc | 635 |
| hsa-miR-668 | MIMAT0003881 | UGUCACUCggcucggcccacuac | 636 |
| hsa-miR-767-5p | MIMAT0003882 | UGCACCAUgguugucugagcaug | 637 |
| hsa-miR-767-3p | MIMAT0003883 | UCUGCUCAuaccccaugguuucu | 638 |
| hsa-miR-1224-5p | MIMAT0005458 | GUGAGGACucgggaggugg | 639 |
| hsa-miR-1224-3p | MIMAT0005459 | CCCCACCUccucucuccucag | 640 |
| hsa-miR-320b | MIMAT0005792 | AAAAGCUGgguugagagggcaa | 641 |
| hsa-miR-320c | MIMAT0005793 | AAAAGCUGgguugagagggu | 642 |
| hsa-miR-1296 | MIMAT0005794 | UUAGGGCCcuggcuccaucucc | 643 |
| hsa-miR-1468 | MIMAT0006789 | CUCCGUUUgccuguuucgcug | 644 |
| hsa-miR-1323 | MIMAT0005795 | UCAAAACUgaggggcauuuucu | 645 |
| hsa-miR-1271 | MIMAT0005796 | CUUGGCACcuagcaagcacuca | 646 |
| hsa-miR-1301 | MIMAT0005797 | UUGCAGCUGccugggagugacuuc | 647 |
| hsa-miR-454* | MIMAT0003884 | ACCCUAUCaauauugucucugc | 648 |
| hsa-miR-454 | MIMAT0003885 | UAGUGCAAauauugcuuauaggu | 649 |
| hsa-miR-1185 | MIMAT0005798 | AGAGGAUAcccuuuguauguu | 650 |
| hsa-miR-449c | MIMAT0010251 | UAGGCAGUguauugcuagcggcugu | 651 |
| hsa-miR-449c* | MIMAT0013771 | UUGCUAGUugcacuccucucugu | 652 |
| hsa-miR-1283 | MIMAT0005799 | UCUACAAAggaaagcgcuuucu | 653 |
| hsa-miR-769-5p | MIMAT0003886 | UGAGACCUcuggguucugagcu | 654 |
| hsa-miR-769-3p | MIMAT0003887 | CUGGGAUCccggggucuugguu | 655 |
| hsa-miR-766 | MIMAT0003888 | ACUCCAGCcccacagccucagc | 656 |
| hsa-miR-762 | MIMAT0010313 | GGGGCUGGggccggggccgagc | 657 |
| hsa-miR-802 | MIMAT0004185 | CAGUAACAaagauucauccuugu | 658 |
| hsa-miR-670 | MIMAT0010357 | GUCCCUGAguguaugugguog | 659 |
| hsa-miR-1298 | MIMAT0005800 | UUCAUUCGgcuguccagauga | 660 |
| hsa-miR-2113 | MIMAT0009206 | AUUUGUGCuuggcucugucac | 661 |
| hsa-miR-761 | MIMAT0010364 | GCAGCAGGgugaaacugacaca | 662 |
| hsa-miR-764 | MIMAT0010367 | GCAGGUGCucacuugucccuccu | 663 |
| hsa-miR-759 | MIMAT0010497 | GCAGAGUGcaaacaauuuugac | 664 |
| hsa-miR-765 | MIMAT0003945 | UGGAGGAGaaggaaggugaug | 665 |

TABLE I-continued

| miRNA name | miRBase number | Sequence | SEQ ID NO |
|---|---|---|---|
| hsa-miR-770-5p | MIMAT0003948 | UCCAGUACcacgugucagggcca | 666 |
| hsa-miR-675 | MIMAT0004284 | UGGUGCGGagagggcccacagug | 667 |
| hsa-miR-675* | MIMAT0006790 | CUGUAUGCccucaccgcuca | 668 |
| hsa-miR-298 | MIMAT0004901 | AGCAGAAGcagggagguucuccca | 669 |
| hsa-miR-891a | MIMAT0004902 | UGCAACGAaccugagccacuga | 670 |
| hsa-miR-300 | MIMAT0004903 | UAUACAAGggcagacucucucu | 671 |
| hsa-miR-886-5p | MIMAT0004905 | CGGGUCGGaguuagcucaagcgg | 672 |
| hsa-miR-886-3p | MIMAT0004906 | CGCGGGUGcuuacugacccuu | 673 |
| hsa-miR-892a | MIMAT0004907 | CACUGUGUccuuucugcguag | 674 |
| hsa-miR-220b | MIMAT0004908 | CCACCACCgugucugacacuu | 675 |
| hsa-miR-450b-5p | MIMAT0004909 | UUUUGCAAauguuccugaaua | 676 |
| hsa-miR-450b-3p | MIMAT0004910 | UUGGGAUCauuuuccauccaua | 677 |
| hsa-miR-874 | MIMAT0004911 | CUGCCCUGgcccgagggaccga | 678 |
| hsa-miR-890 | MIMAT0004912 | UACUUGGAaaggcaucaguug | 679 |
| hsa-miR-891b | MIMAT0004913 | UGCAACUUaccugagcauuga | 680 |
| hsa-miR-220c | MIMAT0004915 | ACACAGGGcguuugugaagacu | 681 |
| hsa-miR-888 | MIMAT0004916 | UACUCAAAaagcugucaguca | 682 |
| hsa-miR-888* | MIMAT0004917 | GACUGACAccucuuugggugaa | 683 |
| hsa-miR-892b | MIMAT0004918 | CACUGGCUccuuucuggguaga | 684 |
| hsa-miR-541* | MIMAT0004919 | AAAGGAUUcugcugucggucccacu | 685 |
| hsa-miR-541 | MIMAT0004920 | UGGUGGGCacagaaucuggacu | 686 |
| hsa-miR-889 | MIMAT0004921 | UUAAUAUCggacaaccauugu | 687 |
| hsa-miR-875-5p | MIMAT0004922 | UAUACCUCaguuuuaucaggug | 688 |
| hsa-miR-875-3p | MIMAT0004923 | CCUGGAAAcacugagguugug | 689 |
| hsa-miR-876-5p | MIMAT0004924 | UGGAUUUCuuugugaaucacca | 690 |
| hsa-miR-876-3p | MIMAT0004925 | UGGUGGUUuacaaaguaauuca | 691 |
| hsa-miR-708 | MIMAT0004926 | AAGGAGCUuacaaucuagcuggg | 692 |
| hsa-miR-708* | MIMAT0004927 | CAACUAGAcugugagcuucuag | 693 |
| hsa-miR-147b | MIMAT0004928 | GUGUGCGGaaaugcuucugcua | 694 |
| hsa-miR-190b | MIMAT0004929 | UGAUAUGUuugauauugggguu | 695 |
| hsa-miR-744 | MIMAT0004945 | UGCGGGGCuagggcuaacagca | 696 |
| hsa-miR-744* | MIMAT0004946 | CUGUUGCCacuaaccucaaccu | 697 |
| hsa-miR-885-5p | MIMAT0004947 | UCCAUUACacuacccugcucu | 698 |
| hsa-miR-885-3p | MIMAT0004948 | AGGCAGCGggguguagugaua | 699 |
| hsa-miR-877 | MIMAT0004949 | GUAGAGGAgauggcgcaggg | 700 |
| hsa-miR-877* | MIMAT0004950 | UCCUCUUCucccucccag | 701 |
| hsa-miR-887 | MIMAT0004951 | GUGAACGGgcgccaucccgagg | 702 |
| hsa-miR-665 | MIMAT0004952 | ACCAGGAGgcugagggcccu | 703 |
| hsa-miR-873 | MIMAT0004953 | GCAGGAACuugugagucuccu | 704 |

TABLE I-continued

| miRNA name | miRBase number | Sequence | SEQ ID NO |
|---|---|---|---|
| hsa-miR-543 | MIMAT0004954 | AAACAUUCgcggugcacuucuu | 705 |
| hsa-miR-374b | MIMAT0004955 | AUAUAAUAcaaccugcuaagug | 706 |
| hsa-miR-374b* | MIMAT0004956 | CUUAGCAGuuguauuaucauu | 707 |
| hsa-miR-760 | MIMAT0004957 | CGGCUCUGggucugugggga | 708 |
| hsa-miR-301b | MIMAT0004958 | CAGUGCAAugauauugucaaagc | 709 |
| hsa-miR-216b | MIMAT0004959 | AAAUCUCUgcaggcaaauguga | 710 |
| hsa-miR-208b | MIMAT0004960 | AUAAGACGaacaaaagguuugu | 711 |
| hsa-miR-920 | MIMAT0004970 | GGGGAGCUguggaagcagua | 712 |
| hsa-miR-921 | MIMAT0004971 | CUAGUGAGggacagaaccaggauuc | 713 |
| hsa-miR-922 | MIMAT0004972 | GCAGCAGAgaauaggacuacguc | 714 |
| hsa-miR-924 | MIMAT0004974 | AGAGUCUUgugaugucuugc | 715 |
| hsa-miR-509-3-5p | MIMAT0004975 | UACUGCAGacguggcaaucaug | 716 |
| hsa-miR-933 | MIMAT0004976 | UGUGCGCAgggagaccucuccc | 717 |
| hsa-miR-934 | MIMAT0004977 | UGUCUACUacuggagacacugg | 718 |
| hsa-miR-935 | MIMAT0004978 | CCAGUUACcgcuuccgcuaccgc | 719 |
| hsa-miR-936 | MIMAT0004979 | ACAGUAGAgggaggaaucgcag | 720 |
| hsa-miR-937 | MIMAT0004980 | AUCCGCGCucugacucucugcc | 721 |
| hsa-miR-938 | MIMAT0004981 | UGCCCUUAaaggugaacccagu | 722 |
| hsa-miR-939 | MIMAT0004982 | UGGGGAGCugaggcucugggggug | 723 |
| hsa-miR-940 | MIMAT0004983 | AAGGCAGGgccccgcuccc | 724 |
| hsa-miR-941 | MIMAT0004984 | CACCCGGCugugugcacaugugc | 725 |
| hsa-miR-942 | MIMAT0004985 | UCUUCUCUguuuuggccaugug | 726 |
| hsa-miR-943 | MIMAT0004986 | CUGACUGUugccguccuccag | 727 |
| hsa-miR-944 | MIMAT0004987 | AAAUUAUUguacaucggaugag | 728 |
| hsa-miR-297 | MIMAT0004450 | AUGUAUGUgugcaugugcaug | 729 |
| hsa-miR-1178 | MIMAT0005823 | UUGCUCACuguucuucccuag | 730 |
| hsa-miR-1179 | MIMAT0005824 | AAGCAUUCuuucauugguugg | 731 |
| hsa-miR-1180 | MIMAT0005825 | UUUCCGGCucgcguggguugu | 732 |
| hsa-miR-1181 | MIMAT0005826 | CCGUCGCCgccacccgagccg | 733 |
| hsa-miR-1182 | MIMAT0005827 | GAGGGUCUugggagggaugugac | 734 |
| hsa-miR-1183 | MIMAT0005828 | CACUGUAGgugauggugagaguggca | 735 |
| hsa-miR-1184 | MIMAT0005829 | CCUGCAGCgacuugauggcuucc | 736 |
| hsa-miR-1225-5p | MIMAT0005572 | GUGGGUACggcccaguggggg | 737 |
| hsa-miR-1225-3p | MIMAT0005573 | UGAGCCCCugugccgcccccag | 738 |
| hsa-miR-1226* | MIMAT0005576 | GUGAGGGCaugcaggccuggaugggg | 739 |
| hsa-miR-1226 | MIMAT0005577 | UCACCAGCccuguguucccuag | 740 |
| hsa-miR-1227 | MIMAT0005580 | CGUGCCACccuuuucccag | 741 |
| hsa-miR-1228* | MIMAT0005582 | GUGGGCGGgggcaggugugug | 742 |

TABLE I-continued

| miRNA name | miRBase number | Sequence | SEQ ID NO |
|---|---|---|---|
| hsa-miR-1228 | MIMAT0005583 | UCACACCUgccucgcccccc | 743 |
| hsa-miR-1229 | MIMAT0005584 | CUCUCACCacugcccucccacag | 744 |
| hsa-miR-1231 | MIMAT0005586 | GUGUCUGGgcggacagcugc | 745 |
| hsa-miR-1233 | MIMAT0005588 | UGAGCCCUguccucccgcag | 746 |
| hsa-miR-1234 | MIMAT0005589 | UCGGCCUGaccacccaccccac | 747 |
| hsa-miR-1236 | MIMAT0005591 | CCUCUUCCccuugucucuccag | 748 |
| hsa-miR-1237 | MIMAT0005592 | UCCUUCUGcuccgucccccag | 749 |
| hsa-miR-1238 | MIMAT0005593 | CUUCCUCGucugucugcccc | 750 |
| hsa-miR-1200 | MIMAT0005863 | CUCCUGAGccauucugagccuc | 751 |
| hsa-miR-1201 | MIMAT0005864 | AGCCUGAUuaaacacaugcucuga | 752 |
| hsa-miR-1202 | MIMAT0005865 | GUGCCAGCugcaguggggag | 753 |
| hsa-miR-1203 | MIMAT0005866 | CCCGGAGCcaggaugcagcuc | 754 |
| hsa-miR-663b | MIMAT0005867 | GGUGGCCCggccgugccugagg | 755 |
| hsa-miR-1204 | MIMAT0005868 | UCGUGGCCuggucuccauuau | 756 |
| hsa-miR-1205 | MIMAT0005869 | UCUGCAGGguuugcuuugag | 757 |
| hsa-miR-1206 | MIMAT0005870 | UGUUCAUGuagauguuuaagc | 758 |
| hsa-miR-1207-5p | MIMAT0005871 | UGGCAGGGaggcugggagggg | 759 |
| hsa-miR-1207-3p | MIMAT0005872 | UCAGCUGGcccucauuuc | 760 |
| hsa-miR-1208 | MIMAT0005873 | UCACUGUUcagacaggcgga | 761 |
| hsa-miR-548e | MIMAT0005874 | AAAAACUGagacuacuuuugca | 762 |
| hsa-miR-548j | MIMAT0005875 | AAAAGUAAuuacgucuuuggu | 763 |
| hsa-miR-1285 | MIMAT0005876 | UCUGGGCAacaaagugagaccu | 764 |
| hsa-miR-1286 | MIMAT0005877 | UGCAGGACcaagaugagcccu | 765 |
| hsa-miR-1287 | MIMAT0005878 | UGCUGGAUcagugguucgaguc | 766 |
| hsa-miR-1289 | MIMAT0005879 | UGGAGUCCaggaaucugcauuuu | 767 |
| hsa-miR-1290 | MIMAT0005880 | UGGAUUUUuggaucaggga | 768 |
| hsa-miR-1291 | MIMAT0005881 | UGGCCCUGacugaagaccagcagu | 769 |
| hsa-miR-548k | MIMAT0005882 | AAAAGUACuugcgaauuuugcu | 770 |
| hsa-miR-1293 | MIMAT0005883 | UGGGUGGUcuggaaauuuguac | 771 |
| hsa-miR-1294 | MIMAT0005884 | UGUGAGGUuggcauuguugucu | 772 |
| hsa-miR-1295 | MIMAT0005885 | UUAGGCCGcagaucuggguga | 773 |
| hsa-miR-1297 | MIMAT0005886 | UUCAAGUAauucaggug | 774 |
| hsa-miR-1299 | MIMAT0005887 | UUCUGGAAuucugugugaggga | 775 |
| hsa-miR-548l | MIMAT0005889 | AAAAGUAUuugcgguuuuguc | 776 |
| hsa-miR-1302 | MIMAT0005890 | UUGGGACAuacuuaugcuaaa | 777 |
| hsa-miR-1303 | MIMAT0005891 | UUUAGAGAcggggucuugcucu | 778 |
| hsa-miR-1304 | MIMAT0005892 | UUUGAGGCuacagugagaugug | 779 |
| hsa-miR-1305 | MIMAT0005893 | UUUUCAACucuaagggagaga | 780 |
| hsa-miR-1243 | MIMAT0005894 | AACUGGAUcaauuauaggagug | 781 |

TABLE I-continued

| miRNA name | miRBase number | Sequence | SEQ ID NO |
|---|---|---|---|
| hsa-miR-548f | MIMAT0005895 | AAAAACUGuaauuacuuuu | 782 |
| hsa-miR-1244 | MIMAT0005896 | AAGUAGUUgguuuguaugagauggu u | 783 |
| hsa-miR-1245 | MIMAT0005897 | AAGUGAUCuaaaggccuacau | 784 |
| hsa-miR-1246 | MIMAT0005898 | AAUGGAUUuuuggagcagg | 785 |
| hsa-miR-1247 | MIMAT0005899 | ACCCGUCCcguucguccccgga | 786 |
| hsa-miR-1248 | MIMAT0005900 | ACCUUCUUguauaagcacugugcuaaa | 787 |
| hsa-miR-1249 | MIMAT0005901 | ACGCCCUUcccccccuucuuca | 788 |
| hsa-miR-1250 | MIMAT0005902 | ACGGUGCUggaugugggccuuu | 789 |
| hsa-miR-1251 | MIMAT0005903 | ACUCUAGCugccaaaggcgcu | 790 |
| hsa-miR-1253 | MIMAT0005904 | AGAGAAGAagaucagccugca | 791 |
| hsa-miR-1254 | MIMAT0005905 | AGCCUGGAagcuggagccugcagu | 792 |
| hsa-miR-1255a | MIMAT0005906 | AGGAUGAGcaaagaaaguagauu | 793 |
| hsa-miR-1256 | MIMAT0005907 | AGGCAUUGacuucucacuagcu | 794 |
| hsa-miR-1257 | MIMAT0005908 | AGUGAAUGaugggu ucugacc | 795 |
| hsa-miR-1258 | MIMAT0005909 | AGUUAGGAuuaggucguggaa | 796 |
| hsa-miR-1259 | MIMAT0005910 | AUAUAUGAugacuuagcuuuu | 797 |
| hsa-miR-1260 | MIMAT0005911 | AUCCCACCucugccacca | 798 |
| hsa-miR-548g | MIMAT0005912 | AAAACUGUaauuacuuuuguac | 799 |
| hsa-miR-1261 | MIMAT0005913 | AUGGAUAAggcuuuggcuu | 800 |
| hsa-miR-1262 | MIMAT0005914 | AUGGGUGAauuuguagaaggau | 801 |
| hsa-miR-1263 | MIMAT0005915 | AUGGUACCcuggcauacugagu | 802 |
| hsa-miR-548n | MIMAT0005916 | CAAAAGUAauguggauuuugu | 803 |
| hsa-miR-548m | MIMAT0005917 | CAAAGGUAuuugugguuuuug | 804 |
| hsa-miR-1265 | MIMAT0005918 | CAGGAUGUggucaaguguuguu | 805 |
| hsa-miR-548o | MIMAT0005919 | CCAAAACUGcaguuacuuuugc | 806 |
| hsa-miR-1266 | MIMAT0005920 | CCUCAGGGcuguagaacaggacu | 807 |
| hsa-miR-1267 | MIMAT0005921 | CCUGUUGAaguguaaucccca | 808 |
| hsa-miR-1268 | MIMAT0005922 | CGGGCGUGguggugggg | 809 |
| hsa-miR-1269 | MIMAT0005923 | CUGGACUGagccgugcuacugg | 810 |
| hsa-miR-1270 | MIMAT0005924 | CUGGAGAUauggaagagcugugu | 811 |
| hsa-miR-1272 | MIMAT0005925 | GAUGAUGAuggcagcaaauucugaaa | 812 |
| hsa-miR-1273 | MIMAT0005926 | GGGCGACAaagcaagacucuuucuu | 813 |
| hsa-miR-1274a | MIMAT0005927 | GUCCCUGUucaggcgcca | 814 |
| hsa-miR-548h | MIMAT0005928 | AAAAGUAAucgcgguuuuuguc | 815 |
| hsa-miR-1275 | MIMAT0005929 | GUGGGGGAgaggcuguc | 816 |
| hsa-miR-1276 | MIMAT0005930 | UAAAGAGCccuguggagaca | 817 |
| hsa-miR-302e | MIMAT0005931 | UAAGUGCUuccaugcuu | 818 |
| hsa-miR-302f | MIMAT0005932 | UAAUUGCUuccauguuu | 819 |

TABLE I-continued

| miRNA name | miRBase number | Sequence | SEQ ID NO |
|---|---|---|---|
| hsa-miR-1277 | MIMAT0005933 | UACGUAGAuauauaugauuuu | 820 |
| hsa-miR-548p | MIMAT0005934 | UAGCAAAAacugcaguuacuuu | 821 |
| hsa-miR-548i | MIMAT0005935 | AAAAGUAAuugcggauuuugcc | 822 |
| hsa-miR-1278 | MIMAT0005936 | UAGUACUGugcauaucaucuau | 823 |
| hsa-miR-1279 | MIMAT0005937 | UCAUAUUGcuucuuucu | 824 |
| hsa-miR-1274b | MIMAT0005938 | UCCCUGUUcgggcgcca | 825 |
| hsa-miR-1281 | MIMAT0005939 | UCGCCUCCuccucuccc | 826 |
| hsa-miR-1282 | MIMAT0005940 | UCGUUUGCcuuuuucugcuu | 827 |
| hsa-miR-1284 | MIMAT0005941 | UCUAUACAgacccuggcuuuuc | 828 |
| hsa-miR-1288 | MIMAT0005942 | UGGACUGCccugaucuggaga | 829 |
| hsa-miR-1292 | MIMAT0005943 | UGGGAACGgguuccggcagacgcug | 830 |
| hsa-miR-1252 | MIMAT0005944 | AGAAGGAAauugaauucauuua | 831 |
| hsa-miR-1255b | MIMAT0005945 | CGGAUGAGcaaagaaaguggguu | 832 |
| hsa-miR-1280 | MIMAT0005946 | UCCCACCGcugccaccc | 833 |
| hsa-miR-1308 | MIMAT0005947 | GCAUGGGUgguucaguag | 834 |
| hsa-miR-664* | MIMAT0005948 | ACUGGCUAgggaaaaugauuggau | 835 |
| hsa-miR-664 | MIMAT0005949 | UAUUCAUUuauccccagccuaca | 836 |
| hsa-miR-1306 | MIMAT0005950 | ACGUUGGCucugguggug | 837 |
| hsa-miR-1307 | MIMAT0005951 | ACUCGGCGuggcgucggucgug | 838 |
| hsa-miR-513b | MIMAT0005788 | UUCACAAGgaggugucauuuau | 839 |
| hsa-miR-513c | MIMAT0005789 | UUCUCAAGgaggugucguuuau | 840 |
| hsa-miR-1321 | MIMAT0005952 | CAGGGAGGugaaugugau | 841 |
| hsa-miR-1322 | MIMAT0005953 | GAUGAUGCugcugaugcug | 842 |
| hsa-miR-720 | MIMAT0005954 | UCUCGCUGgggccucca | 843 |
| hsa-miR-1197 | MIMAT0005955 | UAGGACACauggucuacuucu | 844 |
| hsa-miR-1324 | MIMAT0005956 | CCAGACAGaauucuaugcacuuuc | 845 |
| hsa-miR-1469 | MIMAT0007347 | CUCGGCGCggggcgcgggcucc | 846 |
| hsa-miR-1470 | MIMAT0007348 | GCCCUCCGcccgugcacccccg | 847 |
| hsa-miR-1471 | MIMAT0007349 | GCCCGCGUgugggagccaggugu | 848 |
| hsa-miR-1537 | MIMAT0007399 | AAAACCGUcuaguuacaguugu | 849 |
| hsa-miR-1538 | MIMAT0007400 | CGGCCCGGGcugcugcuguuccu | 850 |
| hsa-miR-1539 | MIMAT0007401 | UCCUGCGCgucccagaugccc | 851 |
| hsa-miR-103-as | MIMAT0007402 | UCAUAGCCcuguacaaugcugcu | 852 |
| hsa-miR-320d | MIMAT0006764 | AAAAGCUGgguugagagga | 853 |
| hsa-miR-1825 | MIMAT0006765 | UCCAGUGCccuccucucc | 854 |
| hsa-miR-1826 | MIMAT0006766 | AUUGAUCAucgacacuucgaacgcaau | 855 |
| hsa-miR-1827 | MIMAT0006767 | UGAGGCAGualauuo-aau | 856 |
| hsa-miR-1908 | MIMAT0007881 | CGGCGGGAcgcgcauugguc | 857 |
| hsa-miR-1909* | MIMAT0007882 | UGAGUGCCgaugccugcccug | 858 |

TABLE I-continued

| miRNA name | miRBase number | Sequence | SEQ ID NO |
|---|---|---|---|
| hsa-miR-1909 | MIMAT0007883 | CGCAGGGGccggGugcucaccg | 859 |
| hsa-miR-1910 | MIMAT0007884 | CCAGUCCUgugccugccgccu | 860 |
| hsa-miR-1911 | MIMAT0007885 | UGAGUACCgccaugucuauggg | 861 |
| hsa-miR-1911* | MIMAT0007886 | CACCAGGCauguggucucc | 862 |
| hsa-miR-1912 | MIMAT0007887 | UACCCAGAgcaugcagugugaa | 863 |
| hsa-miR-1913 | MIMAT0007888 | UCUGCCCCcuccgcugcugcca | 864 |
| hsa-miR-1914 | MIMAT0007889 | CCCUGUGCccggcccacuucug | 865 |
| hsa-miR-1914* | MIMAT0007890 | GGAGGGGUcccgcacugggagg | 866 |
| hsa-miR-1915* | MIMAT0007891 | ACCUUGCCuugcugcccgggcc | 867 |
| hsa-miR-1915 | MIMAT0007892 | CCCCAGGGCgacgcggcggg | 868 |
| hsa-miR-1972 | MIMAT0009447 | UCAGGCCAggcacaguggcuca | 869 |
| hsa-miR-1973 | MIMAT0009448 | ACCGUGCAaagguagcaua | 870 |
| hsa-miR-1975 | MIMAT0009450 | CCCCCACAaccgcgcuugacuagcu | 871 |
| hsa-miR-1976 | MIMAT0009451 | CCUCCUGCccuccuugcugu | 872 |
| hsa-miR-1979 | MIMAT0009454 | CUCCCACUgcuucacuugacua | 873 |
| hsa-miR-2052 | MIMAT0009977 | UGUUUUGAuaacaguaaugu | 874 |
| hsa-miR-2053 | MIMAT0009978 | GUGUUAAUuaaaccucuauuuac | 875 |
| hsa-miR-2054 | MIMAT0009979 | CUGUAAUAuaaauuuaauuuauu | 876 |
| hsa-miR-2110 | MIMAT0010133 | UUGGGGAAacggccgcugagug | 877 |
| hsa-miR-2114 | MIMAT0011156 | UAGUCCCUuccuugaagcgguc | 878 |
| hsa-miR-2114* | MIMAT0011157 | CGAGCCUCaagcaagggacuu | 879 |
| hsa-miR-2115 | MIMAT0011158 | AGCUUCCAugacuccugaugga | 880 |
| hsa-miR-2115* | MIMAT0011159 | CAUCAGAAuucauggaggcuag | 881 |
| hsa-miR-2116 | MIMAT0011160 | GGUUCUUAgcauaggaggucu | 882 |
| hsa-miR-2116* | MIMAT0011161 | CCUCCCAUgccaagaacuccc | 883 |
| hsa-miR-2117 | MIMAT0011162 | UGUUCUCUuugccaaggacag | 884 |
| hsa-miR-548q | MIMAT0011163 | GCUGGUGCaaaaguaauggcgg | 885 |
| hsa-miR-2276 | MIMAT0011775 | UCUGCAAGugucagaggcgagg | 886 |
| hsa-miR-2277 | MIMAT0011777 | UGACAGCGcccugccuggcuc | 887 |
| hsa-miR-2278 | MIMAT0011778 | GAGAGCAGuguguguugccugg | 888 |
| hsa-miR-711 | MIMAT0012734 | GGGACCCAgggagagacguaag | 889 |
| hsa-miR-718 | MIMAT0012735 | CUUCCGCCcgccgggcgucg | 890 |
| hsa-miR-2861 | MIMAT0013802 | GGGGCCUGgcgguggggcgg | 891 |
| hsa-miR-2909 | MIMAT0013863 | GUUAGGGCcaacaucucuugg | 892 |
| hsa-miR-3115 | MIMAT0014977 | AUAUGGGUuuacuaguuagu | 893 |
| hsa-miR-3116 | MIMAT0014978 | UGCCUGGAacauaguagggacu | 894 |
| hsa-miR-3117 | MIMAT0014979 | AUAGGACUcauauaaugccag | 895 |
| hsa-miR-3118 | MIMAT0014980 | UGUGACUGcauuaugaaaauucu | 896 |

TABLE I-continued

| miRNA name | miRBase number | Sequence | SEQ ID NO |
|---|---|---|---|
| hsa-miR-3119 | MIMAT0014981 | UGGCUUUUaacuuugauggc | 897 |
| hsa-miR-3120 | MIMAT0014982 | CACAGCAAguguagacaggca | 898 |
| hsa-miR-3121 | MIMAT0014983 | UAAAUAGAguaggcaaaggaca | 899 |
| hsa-miR-3122 | MIMAT0014984 | GUUGGGACaagaggacggucuu | 900 |
| hsa-miR-3123 | MIMAT0014985 | CAGAGAAUuguuuaauc | 901 |
| hsa-miR-3124 | MIMAT0014986 | UUCGCGGGcgaaggcaaaguc | 902 |
| hsa-miR-548s | MIMAT0014987 | AUGGCCAAaacugcaguuauuuu | 903 |
| hsa-miR-3125 | MIMAT0014988 | UAGAGGAAgcugugagaga | 904 |
| hsa-miR-3126-5p | MIMAT0014989 | UGAGGGACagaugccagaagca | 905 |
| hsa-miR-3126-3p | MIMAT0015377 | CAUCUGGCauccgucacacaga | 906 |
| hsa-miR-3127 | MIMAT0014990 | AUCAGGGCuuguggaaugagaag | 907 |
| hsa-miR-3128 | MIMAT0014991 | UCUGGCAAguaaaaaaacucucau | 908 |
| hsa-miR-3129 | MIMAT0014992 | GCAGUAGUguagagauugauuu | 909 |
| hsa-miR-3130-5p | MIMAT0014995 | UACCCAGUcuccggugcagcc | 910 |
| hsa-miR-3130-3p | MIMAT0014994 | GCUGCACCggagacugggua | 911 |
| hsa-miR-3131 | MIMAT0014996 | UCGAGGACugguggaagggccuu | 912 |
| hsa-miR-3132 | MIMAT0014997 | UGGGUAGAgaaggagcucagagga | 913 |
| hsa-miR-3133 | MIMAT0014998 | UAAAGAACucuuaaaacccaau | 914 |
| hsa-miR-378b | MIMAT0014999 | ACUGGACUuggaggcagaa | 915 |
| hsa-miR-3134 | MIMAT0015000 | UGAUGGAUaaaagacuacauauu | 916 |
| hsa-miR-3135 | MIMAT0015001 | UGCCUAGGcugagacugcagug | 917 |
| hsa-miR-466 | MIMAT0015002 | AUACACAUacacgcaacacacau | 918 |
| hsa-miR-3136 | MIMAT0015003 | CUGACUGAauaggguagggucauu | 919 |
| hsa-miR-544b | MIMAT0015004 | ACCUGAGGuugugcauuucuaa | 920 |
| hsa-miR-3137 | MIMAT0015005 | UCUGUAGCcugggagcaauggggu | 921 |
| hsa-miR-3138 | MIMAT0015006 | UGUGGACAgugagguaaagggagu | 922 |
| hsa-miR-3139 | MIMAT0015007 | UAGGAGCUcaacagaugccuguu | 923 |
| hsa-miR-3140 | MIMAT0015008 | AGCUUUUGggaauucaaguagu | 924 |
| hsa-miR-548t | MIMAT0015009 | CAAAAGUGaucgugguuuuug | 925 |
| hsa-miR-3141 | MIMAT0015010 | GAGGGCGGguggaggagc-a | 926 |
| hsa-miR-3142 | MIMAT0015011 | AAGGCCUUucugaaccuucaga | 927 |
| hsa-miR-3143 | MIMAT0015012 | AUAACAUUguaaagcgcuucuuucg | 928 |
| hsa-miR-548u | MIMAT0015013 | CAAAGACUgcaauuacuuuugcg | 929 |
| hsa-miR-3144-5p | MIMAT0015014 | AGGGGACCaaagagauauauag | 930 |
| hsa-miR-3144-3p | MIMAT0015015 | AUAUACCUguucggucucuuua | 931 |
| hsa-miR-3145 | MIMAT0015016 | AGAUAUUUgaguguuuggaauug | 932 |
| hsa-miR-1273c | MIMAT0015017 | GGCGACAAaacgagacccuguc | 933 |
| hsa-miR-3146 | MIMAT0015018 | CAUGCUAGgauagaaagaaugg | 934 |
| hsa-miR-3147 | MIMAT0015019 | GGUUGGGCagugaggagggguguga | 935 |

TABLE I-continued

| miRNA name | miRBase number | Sequence | SEQ ID NO |
|---|---|---|---|
| hsa-miR-548v | MIMAT0015020 | AGCUACAGuuacuuuugcacca | 936 |
| hsa-miR-3148 | MIMAT0015021 | UGGAAAAAacuggugugugcuu | 937 |
| hsa-miR-3149 | MIMAT0015022 | UUUGUAUGgauaugugugugu au | 938 |
| hsa-miR-3150 | MIMAT0015023 | CUGGGGAGauccucaagguugg | 939 |
| hsa-miR-3151 | MIMAT0015024 | GGUGGGGCaaugggaucaggu | 940 |
| hsa-miR-3152 | MIMAT0015025 | UGUGUUAGaauaggggcaauaa | 941 |
| hsa-miR-3153 | MIMAT0015026 | GGGGAAAGcgaguagggacauuu | 942 |
| hsa-miR-3074 | MIMAT0015027 | GAUAUCAGcucaguaggcaccg | 943 |
| hsa-miR-3154 | MIMAT0015028 | CAGAAGGGaguuggga gcaga | 944 |
| hsa-miR-3155 | MIMAT0015029 | CCAGGCUCugcagugggaacu | 945 |
| hsa-miR-3156 | MIMAT0015030 | AAAGAUCUggaagugggagaca | 946 |
| hsa-miR-3157 | MIMAT0015031 | UUCAGCCAggcuagugcagucu | 947 |
| hsa-miR-3158 | MIMAT0015032 | AAGGGCUUccucucugcaggac | 948 |
| hsa-miR-3159 | MIMAT0015033 | UAGGAUUAcaagucucggccac | 949 |
| hsa-miR-3160 | MIMAT0015034 | AGAGCUGAgacuagaaagccca | 950 |
| hsa-miR-3161 | MIMAT0015035 | CUGAUAAGaacagaggcccagau | 951 |
| hsa-miR-3162 | MIMAT0015036 | UUAGGGAGuagaagggugggaag | 952 |
| hsa-miR-3163 | MIMAT0015037 | UAUAAAAUgagggcaguaagac | 953 |
| hsa-miR-3164 | MIMAT0015038 | UGUGACUUuaagggaaauggcg | 954 |
| hsa-miR-3165 | MIMAT0015039 | AGGUGGAUgcaaugugaccuca | 955 |
| hsa-miR-3166 | MIMAT0015040 | CGCAGACAaugccuacuggccua | 956 |
| hsa-miR-1260b | MIMAT0015041 | AUCCCACCacugccaccau | 957 |
| hsa-miR-3167 | MIMAT0015042 | AGGAUUUCagaaauacuggugu | 958 |
| hsa-miR-3168 | MIMAT0015043 | GAGUUCUAcagucagac | 959 |
| hsa-miR-3169 | MIMAT0015044 | UAGGACUGugcuuggcacauag | 960 |
| hsa-miR-3170 | MIMAT0015045 | CUGGGGUUcugagacagacagu | 961 |
| hsa-miR-3171 | MIMAT0015046 | AGAUGUAUggaaucuguauauauc | 962 |
| hsa-miR-3172 | MIMAT0015047 | UGGGGUUUugcaguccuua | 963 |
| hsa-miR-3173 | MIMAT0015048 | AAAGGAGGaaauaggcaggcca | 964 |
| hsa-miR-1193 | MIMAT0015049 | GGGAUGGUagaccggugacgugc | 965 |
| hsa-miR-323b-5p | MIMAT0001630 | AGGUUGUCcguggugaguucgca | 966 |
| hsa-miR-323b-3p | MIMAT0015050 | CCCAAUACacggucgaccucuu | 967 |
| hsa-miR-3174 | MIMAT0015051 | UAGUGAGUuagagaugcagagcc | 968 |
| hsa-miR-3175 | MIMAT0015052 | CGGGGAGAgaacgcagugacgu | 969 |
| hsa-miR-3176 | MIMAT0015053 | ACUGGCCUgggacuaccgg | 970 |
| hsa-miR-3177 | MIMAT0015054 | UGCACGGCacuggggacacgu | 971 |
| hsa-miR-3178 | MIMAT0015055 | GGGGCGCGgccggaucg | 972 |
| hsa-miR-3179 | MIMAT0015056 | AGAAGGGGugaaauuuaaacgu | 973 |

TABLE I-continued

| miRNA name | miRBase number | Sequence | SEQ ID NO |
|---|---|---|---|
| hsa-miR-3180-5p | MIMAT0015057 | CUUCCAGAcgcuccgccccacgucg | 974 |
| hsa-miR-3180-3p | MIMAT0015058 | UGGGGCGGagcuuccggaggcc | 975 |
| hsa-miR-548w | MIMAT0015060 | AAAAGUAAcugcgguuuuugccu | 976 |
| hsa-miR-3181 | MIMAT0015061 | AUCGGGCCcucggcgccgg | 977 |
| hsa-miR-3182 | MIMAT0015062 | GCUUCUGUaguguaguc | 978 |
| hsa-miR-3183 | MIMAT0015063 | GCCUCUCUcggagucgcucgga | 979 |
| hsa-miR-3184 | MIMAT0015064 | UGAGGGGCcucagaccgagcuuuu | 980 |
| hsa-miR-3185 | MIMAT0015065 | AGAAGAAGcggucggucugcgg | 981 |
| hsa-miR-3065-5p | MIMAT0015066 | UCAACAAAaucacugaugcugga | 982 |
| hsa-miR-3065-3p | MIMAT0015378 | UCAGCACCaggauauuguuggag | 983 |
| hsa-miR-3186-5p | MIMAT0015067 | CAGGCGUCugucuacguggcuu | 984 |
| hsa-miR-3186-3p | MIMAT0015068 | UCACGCGGagagauggcuuug | 985 |
| hsa-miR-3187 | MIMAT0015069 | UUGGCCAUggggcugcgcgg | 986 |
| hsa-miR-3188 | MIMAT0015070 | AGAGGCUUugugcggauacgggg | 987 |
| hsa-miR-3189 | MIMAT0015071 | CCCUUGGGucugauggggaug | 988 |
| hsa-miR-320e | MIMAT0015072 | AAAGCUGGguugagaagg | 989 |
| hsa-miR-3190-5p | MIMAT0015073 | UGUGGAAGguagacggccagaga | 990 |
| hsa-miR-3190-3p | MIMAT0015074 | UGGAAGGUagacggccagagag | 991 |
| hsa-miR-3191 | MIMAT0015075 | UGGGGACGuagcuggccagacag | 992 |
| hsa-miR-3192 | MIMAT0015076 | UCUGGGAGguuguagcaguggaa | 993 |
| hsa-miR-3193 | MIMAT0015077 | UCCUGCGUaggaucugaggagu | 994 |
| hsa-miR-3194 | MIMAT0015078 | GGCCAGCCaccaggagggcug | 995 |
| hsa-miR-3195 | MIMAT0015079 | CGCGCCGGgcccgggguu | 996 |
| hsa-miR-3196 | MIMAT0015080 | CGGGGCGGcaggggccuc | 997 |
| hsa-miR-548x | MIMAT0015081 | UAAAAACUgcaauuacuuuca | 998 |
| hsa-miR-3197 | MIMAT0015082 | GGAGGCGCaggcucggaaaggcg | 999 |
| hsa-miR-3198 | MIMAT0015083 | GUGGAGUCcuggggaauggaga | 1000 |
| hsa-miR-3199 | MIMAT0015084 | AGGGACUGccuuaggagaaaguu | 1001 |
| hsa-miR-3200 | MIMAT0015085 | CACCUUGCgcuacucaggucug | 1002 |
| hsa-miR-3201 | MIMAT0015086 | GGGAUAUGaagaaaaau | 1003 |
| hsa-miR-514b-5p | MIMAT0015087 | UUCUCAAGagggaggcaaucau | 1004 |
| hsa-miR-514b-3p | MIMAT0015088 | AUUGACACcucugugagugga | 1005 |
| hsa-miR-3202 | MIMAT0015089 | UGGAAGGGagaagagcuuuaau | 1006 |
| hsa-miR-1273d | MIMAT0015090 | GAACCCAUgagguugaggcugcagu | 1007 |
| hsa-miR-4295 | MIMAT0016844 | CAGUGCAAuguuuuccuu | 1008 |
| hsa-miR-4296 | MIMAT0016845 | AUGUGGGCucaggcuca | 1009 |
| hsa-miR-4297 | MIMAT0016846 | UGCCUUCCugucugug | 1010 |
| hsa-miR-378c | MIMAT0016847 | ACUGGACUuggagucagaagagugg | 1011 |
| hsa-miR-4293 | MIMAT0016848 | CAGCCUGAcaggaacag | 1012 |

TABLE I-continued

| miRNA name | miRBase number | Sequence | SEQ ID NO |
|---|---|---|---|
| hsa-miR-4294 | MIMAT0016849 | GGGAGUCUacagcaggg | 1013 |
| hsa-miR-4301 | MIMAT0016850 | UCCCACUAcuucacuuguga | 1014 |
| hsa-miR-4299 | MIMAT0016851 | GCUGGUGAcaugagaggc | 1015 |
| hsa-miR-4298 | MIMAT0016852 | CUGGGACAggaggaggaggcag | 1016 |
| hsa-miR-4300 | MIMAT0016853 | UGGGAGCUggacuacuuc | 1017 |
| hsa-miR-4304 | MIMAT0016854 | CCGGCAUGuccagggca | 1018 |
| hsa-miR-4302 | MIMAT0016855 | CCAGUGUGgcucagcgag | 1019 |
| hsa-miR-4303 | MIMAT0016856 | UUCUGAGCugaggacag | 1020 |
| hsa-miR-4305 | MIMAT0016857 | CCUAGACAccuccaguuc | 1021 |
| hsa-miR-4306 | MIMAT0016858 | UGGAGAGAaaggcagua | 1022 |
| hsa-miR-4309 | MIMAT0016859 | CUGGAGUCuaggauucca | 1023 |
| hsa-miR-4307 | MIMAT0016860 | AAUGUUUUuccuguuucc | 1024 |
| hsa-miR-4308 | MIMAT0016861 | UCCCUGGAguuucuucuu | 1025 |
| hsa-miR-4310 | MIMAT0016862 | GCAGCAUUcauguccc | 1026 |
| hsa-miR-4311 | MIMAT0016863 | GAAAGAGAgcugagugug | 1027 |
| hsa-miR-4312 | MIMAT0016864 | GGCCUUGUuccugucccca | 1028 |
| hsa-miR-4313 | MIMAT0016865 | AGCCCCCUggcccaaaccc | 1029 |
| hsa-miR-4315 | MIMAT0016866 | CCGCUUUCugagcuggac | 1030 |
| hsa-miR-4316 | MIMAT0016867 | GGUGAGGCuagcuggug | 1031 |
| hsa-miR-4314 | MIMAT0016868 | CUCUGGGAaaugggacag | 1032 |
| hsa-miR-4318 | MIMAT0016869 | CACUGUGGguacaugcu | 1033 |
| hsa-miR-4319 | MIMAT0016870 | UCCCUGAGcaaagccac | 1034 |
| hsa-miR-4320 | MIMAT0016871 | GGGAUUCUguagcuuccu | 1035 |
| hsa-miR-4317 | MIMAT0016872 | ACAUUGCCagggaguuu | 1036 |
| hsa-miR-4322 | MIMAT0016873 | CUGUGGGCucagcgcgugggg | 1037 |
| hsa-miR-4321 | MIMAT0016874 | UUAGCGGUggaccgcccugcg | 1038 |
| hsa-miR-4323 | MIMAT0016875 | CAGCCCCAcagccucaga | 1039 |
| hsa-miR-4324 | MIMAT0016876 | CCCUGAGAcccuaaccuuaa | 1040 |
| hsa-miR-4256 | MIMAT0016877 | AUCUGACCugaugaaggu | 1041 |
| hsa-miR-4257 | MIMAT0016878 | CCAGAGGUggggacugag | 1042 |
| hsa-miR-4258 | MIMAT0016879 | CCCCGCCAccgccuugg | 1043 |
| hsa-miR-4259 | MIMAT0016880 | CAGUUGGGucuaggggucagga | 1044 |
| hsa-miR-4260 | MIMAT0016881 | CUUGGGGCauggaguccca | 1045 |
| hsa-miR-4253 | MIMAT0016882 | AGGGCAUGuccaggggu | 1046 |
| hsa-miR-4251 | MIMAT0016883 | CCUGAGAAaagggccaa | 1047 |
| hsa-miR-4254 | MIMAT0016884 | GCCUGGAGcuacuccaccaucuc | 1048 |
| hsa-miR-4255 | MIMAT0016885 | CAGUGUUCagagaugga | 1049 |
| hsa-miR-4252 | MIMAT0016886 | GGCCACUGagucagcacca | 1050 |

TABLE I-continued

| miRNA name | miRBase number | Sequence | SEQ ID NO |
|---|---|---|---|
| hsa-miR-4325 | MIMAT0016887 | UUGCACUUgucucaguga | 1051 |
| hsa-miR-4326 | MIMAT0016888 | UGUUCCUCugucucccagac | 1052 |
| hsa-miR-4327 | MIMAT0016889 | GGCUUGCAuggggacugg | 1053 |
| hsa-miR-4261 | MIMAT0016890 | AGGAAACAgggaccca | 1054 |
| hsa-miR-4265 | MIMAT0016891 | CUGUGGGCucagcucuggg | 1055 |
| hsa-miR-4266 | MIMAT0016892 | CUAGGAGGccuuggcc | 1056 |
| hsa-miR-4267 | MIMAT0016893 | UCCAGCUCgguggcac | 1057 |
| hsa-miR-4262 | MIMAT0016894 | GACAUUCAgacuaccug | 1058 |
| hsa-miR-2355 | MIMAT0016895 | AUCCCCAGauacaauggacaa | 1059 |
| hsa-miR-4268 | MIMAT0016896 | GGCUCCUCcucucaggaugug | 1060 |
| hsa-miR-4269 | MIMAT0016897 | GCAGGCACagacagcccuggc | 1061 |
| hsa-miR-4263 | MIMAT0016898 | AUUCUAAGugccuuggcc | 1062 |
| hsa-miR-4264 | MIMAT0016899 | ACUCAGUCauggucauu | 1063 |
| hsa-miR-4270 | MIMAT0016900 | UCAGGGAGucaggggagggc | 1064 |
| hsa-miR-4271 | MIMAT0016901 | GGGGGAAGaaaaggugggg | 1065 |
| hsa-miR-4272 | MIMAT0016902 | CAUUCAACuagugauugu | 1066 |
| hsa-miR-4273 | MIMAT0016903 | GUGUUCUCugauggacag | 1067 |
| hsa-miR-4276 | MIMAT0016904 | CUCAGUGAcucaugugc | 1068 |
| hsa-miR-4275 | MIMAT0016905 | CCAAUUACcacuucuuu | 1069 |
| hsa-miR-4274 | MIMAT0016906 | CAGCAGUCccuccccug | 1070 |
| hsa-miR-4281 | MIMAT0016907 | GGGUCCCGgggagggggg | 1071 |
| hsa-miR-4277 | MIMAT0016908 | GCAGUUCUgagcacaguacac | 1072 |
| hsa-miR-4279 | MIMAT0016909 | CUCUCCUCccggcuuc | 1073 |
| hsa-miR-4278 | MIMAT0016910 | CUAGGGGGuuugcccuug | 1074 |
| hsa-miR-4280 | MIMAT0016911 | GAGUGUAGuucugagcagagc | 1075 |
| hsa-miR-4282 | MIMAT0016912 | UAAAAUUUgcauccagga | 1076 |
| hsa-miR-4285 | MIMAT0016913 | GCGGCGAGuccgacucau | 1077 |
| hsa-miR-4283 | MIMAT0016914 | UGGGGCUCagcgaguuu | 1078 |
| hsa-miR-4284 | MIMAT0016915 | GGGCUCACaucaccccau | 1079 |
| hsa-miR-4286 | MIMAT0016916 | ACCCCACUccugguacc | 1080 |
| hsa-miR-4287 | MIMAT0016917 | UCUCCCUUgagggcacuuu | 1081 |
| hsa-miR-4288 | MIMAT0016918 | UUGUCUGCuaaguuucc | 1082 |
| hsa-miR-4292 | MIMAT0016919 | CCCCUGGGccggccuugg | 1083 |
| hsa-miR-4289 | MIMAT0016920 | GCAUUGUGcagggcuauca | 1084 |
| hsa-miR-4290 | MIMAT0016921 | UGCCCUCCuuucuucccuc | 1085 |
| hsa-miR-4291 | MIMAT0016922 | UUCAGCAGgaacagcu | 1086 |
| hsa-miR-4329 | MIMAT0016923 | CCUGAGACccuaguccac | 1087 |
| hsa-miR-4330 | MIMAT0016924 | CCUCAGAUcagagccuugc | 1088 |

TABLE I-continued

| miRNA name | miRBase number | Sequence | SEQ ID NO |
|---|---|---|---|
| hsa-miR-500b | MIMAT0016925 | AAUCCUUGcuaccugggu | 1089 |
| hsa-miR-4328 | MIMAT0016926 | CCAGUUUUcccaggauu | 1090 |

EXAMPLES

Example 1

Segmented miRNA Mimetics

MicroRNAs (miRNAs) are a class of ~22 nt noncoding RNAs that play important roles in regulating gene expression in plants and animals. MicroRNAs are usually produced by a process in which a RNA pol II transcript is cut by Drosha to produce a precursor hairpin, which is cut by Dicer in the cytoplasm to produce a two stranded duplex that is incorporated into Argonaute (Ago) proteins. After elimination of the passenger strand by cleavage or helicase activity, the guide strand can then bind to complementary target RNAs. Studies have found that the most prevalent aspect of miRNA target recognition is complementary binding to a target 3' UTR by the miRNA seed region (positions 2 through 8 at the 5' end of the guide strand), leading to downregulation at mRNA and protein levels.

Agog mediated cleavage of the passenger strand has been found to be important for assembly of siRNAs and some miRNAs and a nicked passenger strand was found to rescue the activity of an siRNA containing a phosphorothioate bond that prevented passenger strand cleavage by Ago. This concept has been applied to the design of siRNAs (Bramsen et al., 2007 supra), where passenger segmentation was found to maintain siRNA activity (while eliminating passenger strand activity), while guide segmentation was found to eliminate the desired siRNA activity.

Applicant has surprisingly found that, as opposed to siRNA, segmentation is well tolerated in the guide strand of microRNA. Applicant demonstrates herein that this segmentation provides for the alternative design of various miRNA mimetics that include nicks and gaps, as well as substitutions and insertions that can confer additional properties toward therapeutic use.

Materials and Methods

Oligonucleotides used to obtain data in this Example were synthesized at Sigma-Aldrich or Merck & Co. using standard methodologies. Annealing was accomplished by mixing single stranded RNA at 10 uM in 10 mM TrisHCl/50 mM NaCl and heating at 95° C. for 2 minutes before slowly cooling to 37° C. over the course of 1 hour.

The RNA oligonucleotides synthesized are shown in the following Table II.

TABLE II

| Name | Sequence | SEQ ID NO. |
|---|---|---|
| G | UUAAGGCACGCGGUGAAUGCCA | 1091 |
| P | GCAUUCACCGCGUGCCUUAAAU | 1092 |
| G10 | UUAAGGCACG | 1093 |
| G.10 | CGGUGAAUGCCA | 1094 |
| G.9 | GGUGAAUGCCA | 1095 |
| P10 | GCAUUCACCG | 1096 |
| P.10 | CGUGCCUUAAAU | 1097 |
| G10i | UUAAGGCACG-iB | 1098 |
| G10Cy3 | UUAAGGCACG-Cy3 | 1099 |
| 58-mer | GCGUUCACCGCGGACCUUGAUU UAAAUGUCCAUACAAUUAAGGC ACGCGGUGAAUGCC | 1100 |
| 48-mer | GCGUUCACCGCGGACCUUGAUU UAAAUGUCCAUACAAUUAAGGC ACGCGGUGAAUGCC | 1101 |
| 10-mer | GGUGAAUGCC | 1102 |

Sequences in the table above are shown in 5' to 3' orientation. "iB" denotes an inverted abasic, while "Cy3" denotes a Cy3 fluorescent dye molecule.

Figure 14B:
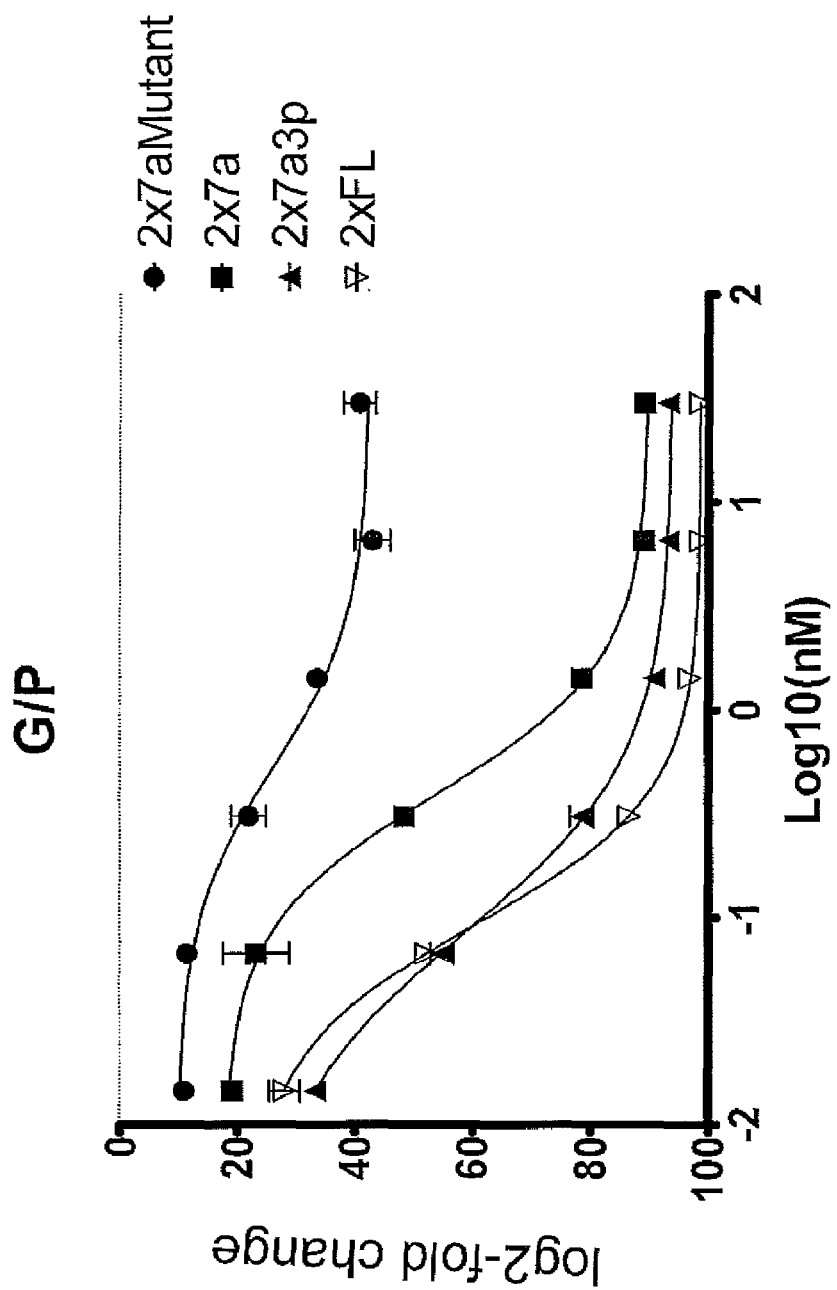
Figure 14C:
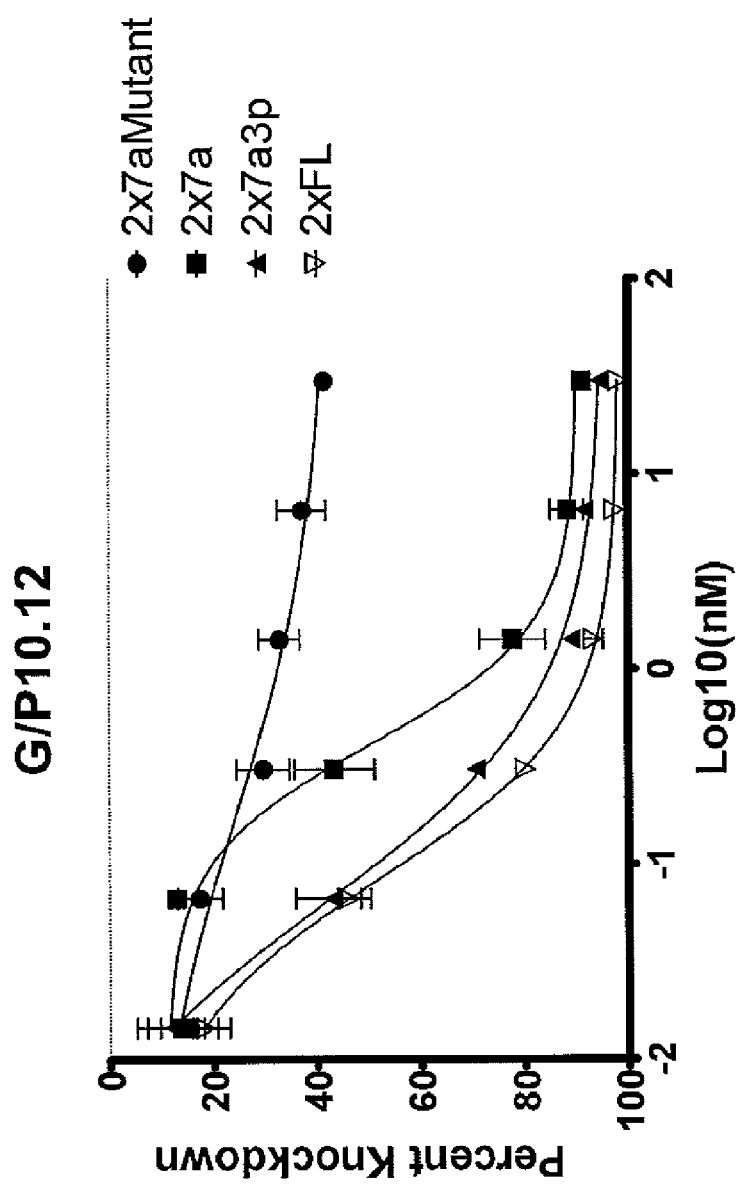
Figure 14D:
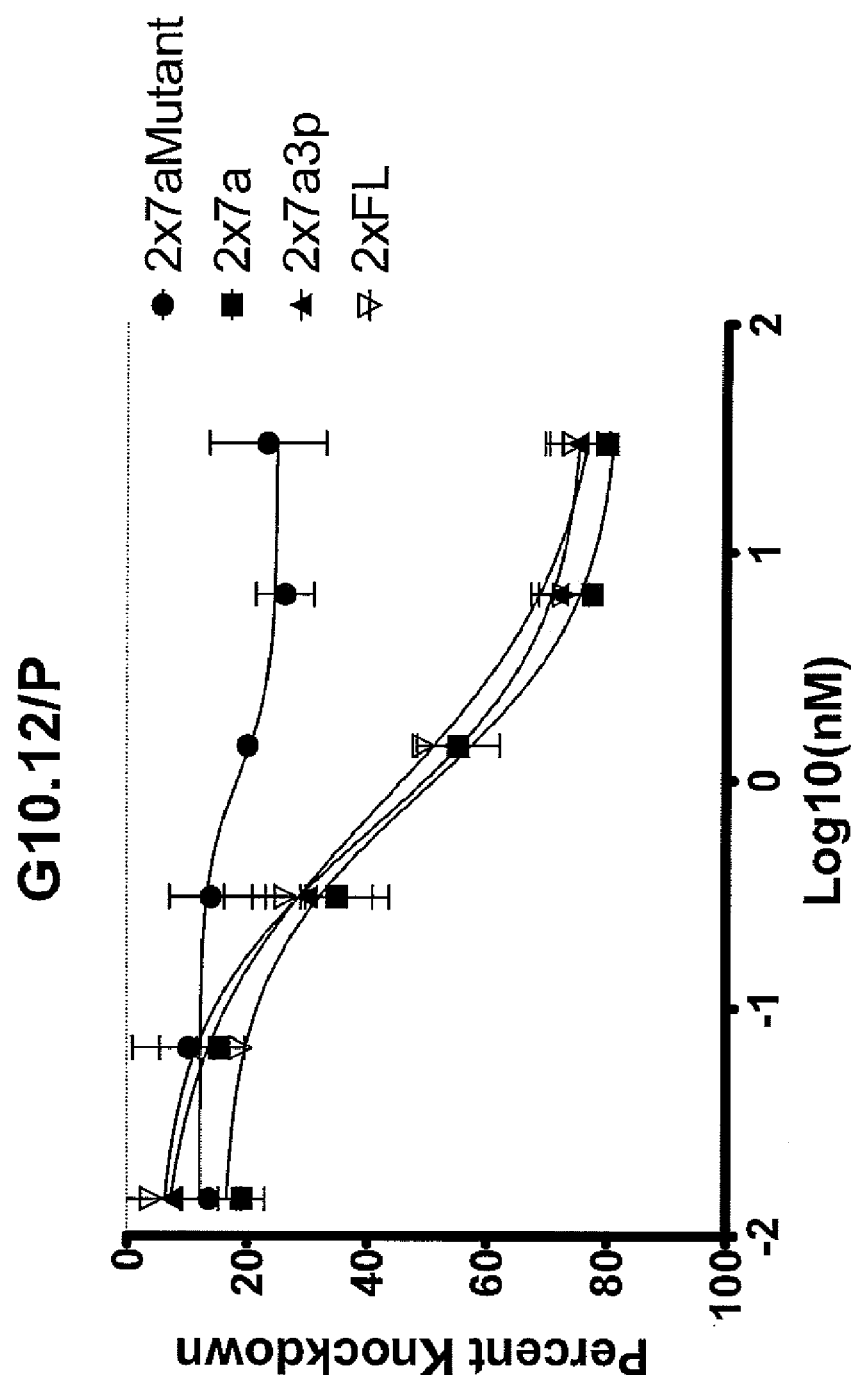

HCT-116 cells were cultured in McCoy's 5A Medium (Mediatech Inc.) supplemented with 10% fetal bovine serum and 1% penicillin-streptomycin, plated in 96-well culture plates at a density of 25,000 cells/well 24 hours prior to transfection, and then transfected using Opti-MEM I Reduced Serum Media (Gibco) and Lipofectamine 2000 (Invitrogen) with a final concentration of our miRNAs ranging from 30 nM down to 0.01 nM along a 12-point titration curve. Twenty-four hours after transfection, cells were washed with phosphate-buffered saline and processed using the TaqMan® Gene Expression Cells-to-CTT™ Kit (Applied Biosystems/Ambion) to extract RNA, synthesize cDNA, and perform RT-qPCR using CD164-specific probes (Applied Biosystems) on an ABI Prism 7900HT Sequence Detector. Reverse transcription conditions were as follows: 60 minutes at 37° C. followed by 5 minutes at 95° C. RT-qPCR conditions were as follows: 2 minutes at 50° C., 10 minutes at 95° C., followed by 40 cycles of 15 seconds at 95° C. and 1 minute at 60° C. GUSB mRNA levels were used for data normalization.

miRNAs were co-transfected with siCHECK2 vectors (Genscript) containing cloned target inserts, as shown in FIG. 14, consisting of a tandem repeat of a seed match to miR-124 (2×7a), a seed match containing additional 3' complementarity to positions 13-17 of miR-124 (2×7a3p), or a full-length match to miR-124 (2×FL). A seed match with a two-base mutation (2×7aMutant) was used as a control. Twenty-four hours after transfection, transfection medium was replaced with fresh growth medium. Forty-eight hours after transfection, cells were lysed and both firefly and Renilla luciferase activity were measured using the Dual-Glo™ Luciferase Assay System (Promega) on a Wallac EnVision 2103 Multilabel Reader (PerkinElmer).

HCT-116 cells were transfected with 10 nM miRNA duplex as described previously (Jackson et al 2006). RNA was extracted using RNeasy (Qiagen), amplified using the Ovation protocol (Nugen), and profiled on custom Affymetrix arrays (Rosetta Custom Human 1.0, Affymetrix). Array signals were analyzed with Affymetrix GeneChip Operating Software and Affymetrix Power Tools. UTR hexamer analysis was carried out as described previously (Jackson et al 2006).

Results

Structural variants of a miR-124 duplex were tested, wherein a nick was introduced 10 nucleotides from the 5' end of either the guide (or miRNA) or passenger (or miRNA*) strand (FIG. 12A). Duplexes were transfected into cells and changes in the mRNA levels of miR-124 target CD164 were measured. Division of the passenger strand (G/P10.10) had little effect on miR-124 activity (FIG. 12B), leading to a slight increase in EC50 (0.12 nM to 0.29 nM). Division of the guide strand (G10.10/P) still allowed for miR-124 activity (EC50 of 0.22 nM), indicating that a continuous guide strand is not required for miRNA RISC activity. The addition of a one base gap between the guide halves, or capping of the junction with a Cy3 dye or an inverted abasic residue, still gave miR-124 activity, indicating that this activity was not a result of ligation of the guide halves. Toleration of guide strand segmentation is not a property only of the miR-124 sequence, as division of the guide strand in a miR-34 duplex still allowed for miR-34a activity (FIG. 9).

Figure 13A:
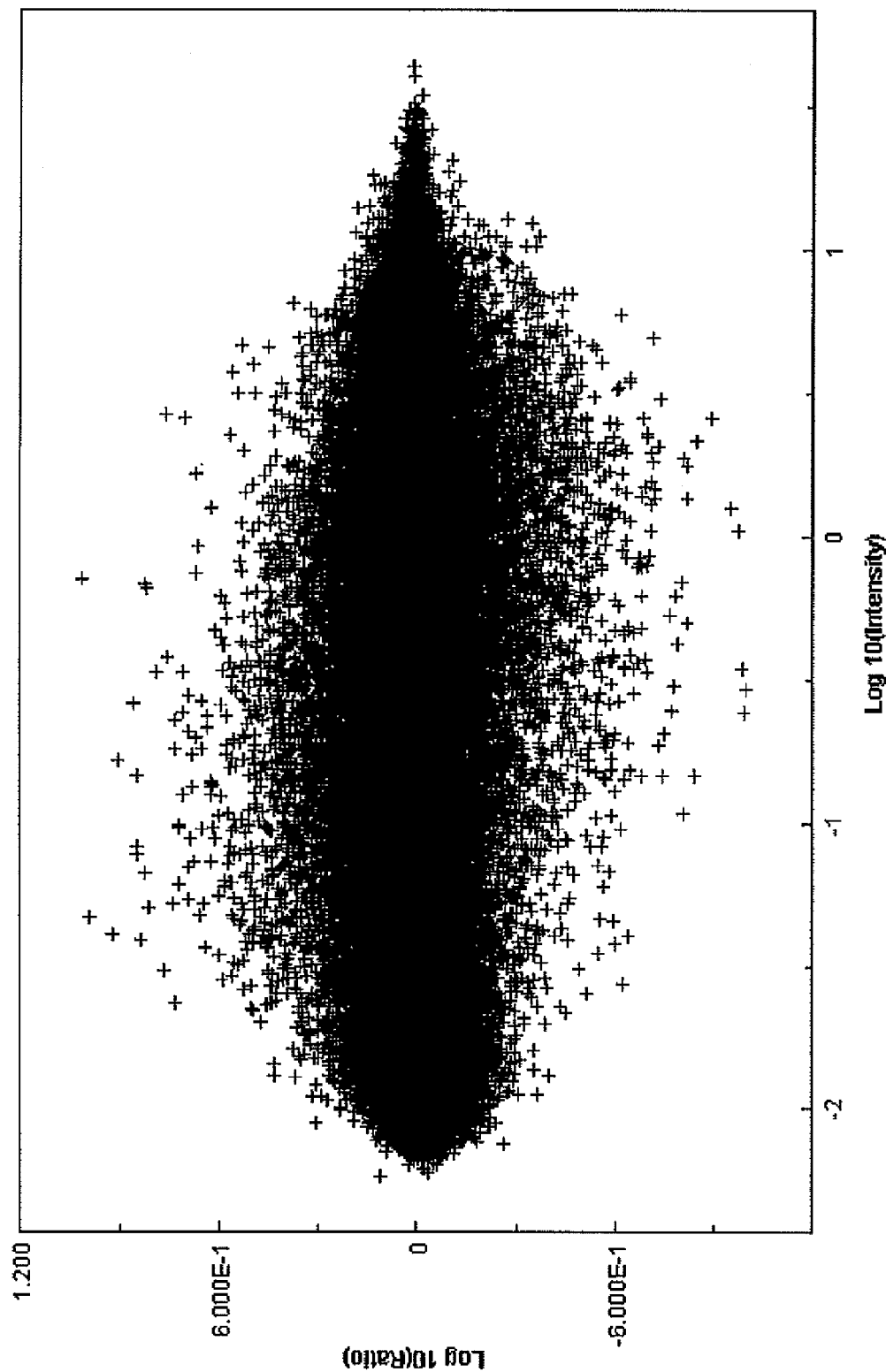
FIGS. 13A and 13B provide a microarray analysis showing seed-based activity from a segmented guide strand.
Figure 13B:
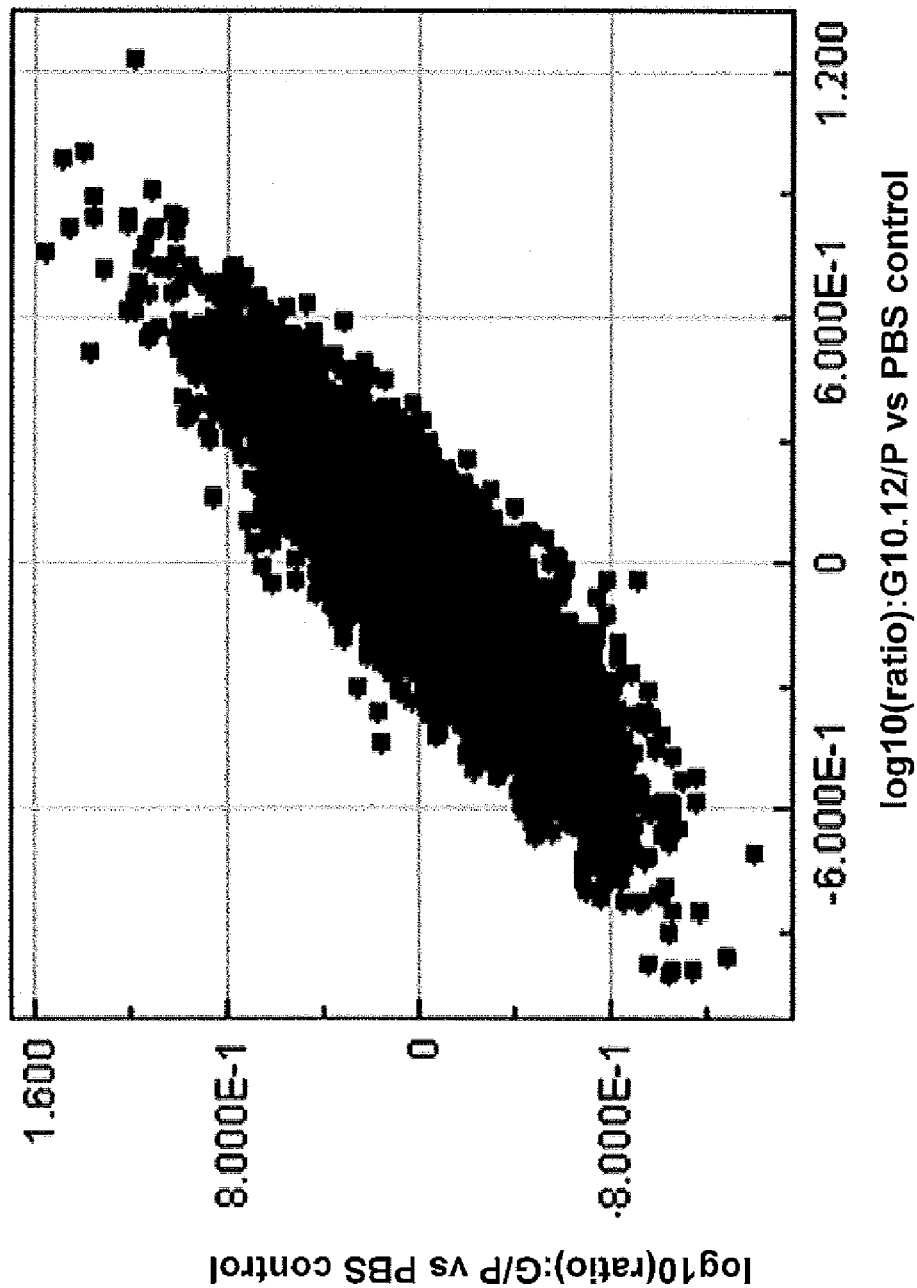

Microarrays were used to profile cells transfected with a miR-124 duplex containing the divided guide strand (FIG. 13A) to further confirm the targeting activity of a segmented microRNA duplex, in this instance at a genome-wide level. Analysis of the 3' UTR sequences of the downregulated genes shows that the most significantly enriched hexamer is GCCTTA, which corresponds to the seed sequence of miR-124. Profiling of the effects of the segmented miR-124 duplex G10.10/P showed correlation (r=0.90) with profiling of the effects of the fully intact duplex (G/P), consistent with the preservation of the bulk of miR-124 targeting (FIG. 13B).

Figure 16:
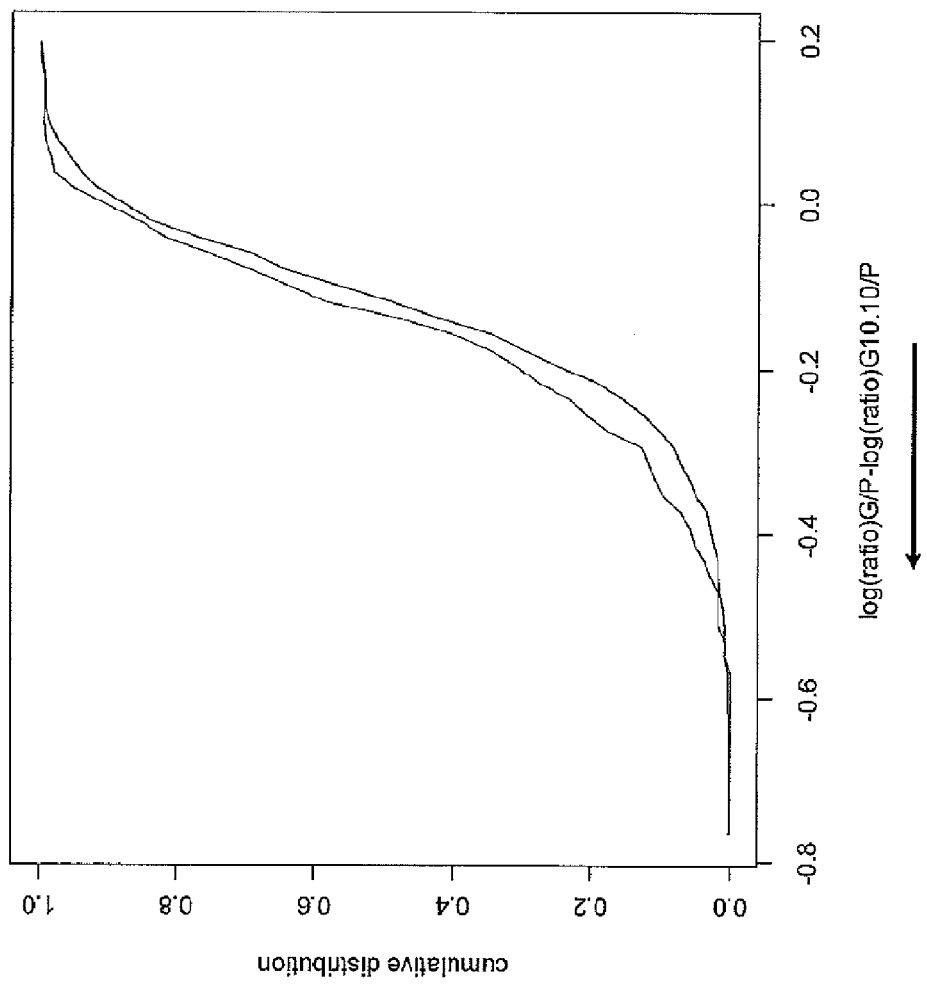

Previous work analyzing microarray profiles has shown that although the preponderance of miRNA targeting is due to seed sequence activity, a much smaller degree of downregulation can be attributed to other contributing factors, among them the supplementary binding of positions 13-16 of the miRNA. Microarray profiling of miR-124 targets containing supplementary 3' binding was analyzed, and a shift following guide strand segmentation was detected that was indicative of a loss of supplementary 3' binding activity in the divided miRNA (FIG. 16).

The effects of segmented miRNAs on luciferase reporter vectors were tested, using miRNAs whose 3' UTRs had been engineered (FIG. 14A) to contain miRNA-complementary sites that constituted a full-length match (2×FL), a seed sequence match (2×7a), or a seed sequence plus supplementary 3' match (2×7a3p). For an intact duplex (G/P), the repressive activity of miR-124 on luciferase activity was highest for 2×FL and followed the order 2×FL~2×7a3p>2×7a. (FIG. 14B) Similar behavior was seen with a segmented passenger strand (G/P10.10, FIG. 14C). However, when the guide strand was divided (G10.10/P, FIG. 14D), the activities of the 2×FL and 2×7a3p reporters became equivalent to that of 2×7a, showing that the discontinuity at position 10 of the guide strand prevents productive 3' binding, while permitting seed-based activity from the 5' half.

Figure 15A:
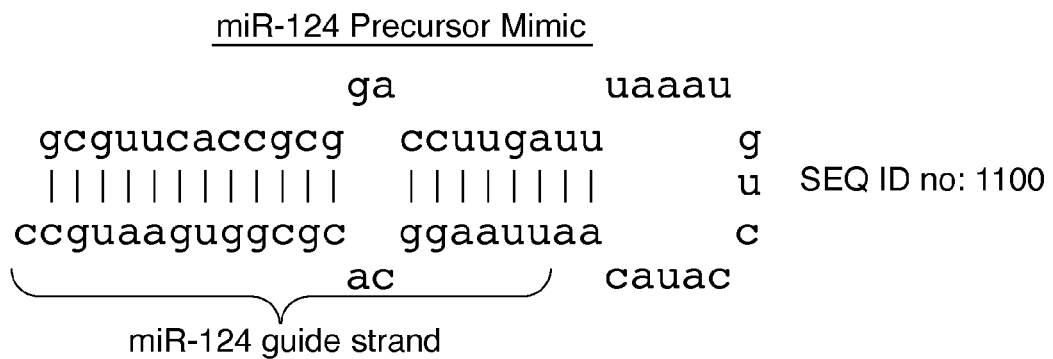
FIGS. 15A and 15B illustrates RNAi activity mediated by a segmented miR-124 precursor. A 58-mer miR-124 precursor was designed and transfected into HCT-116 cells at varying concentrations.
Figure 15B:
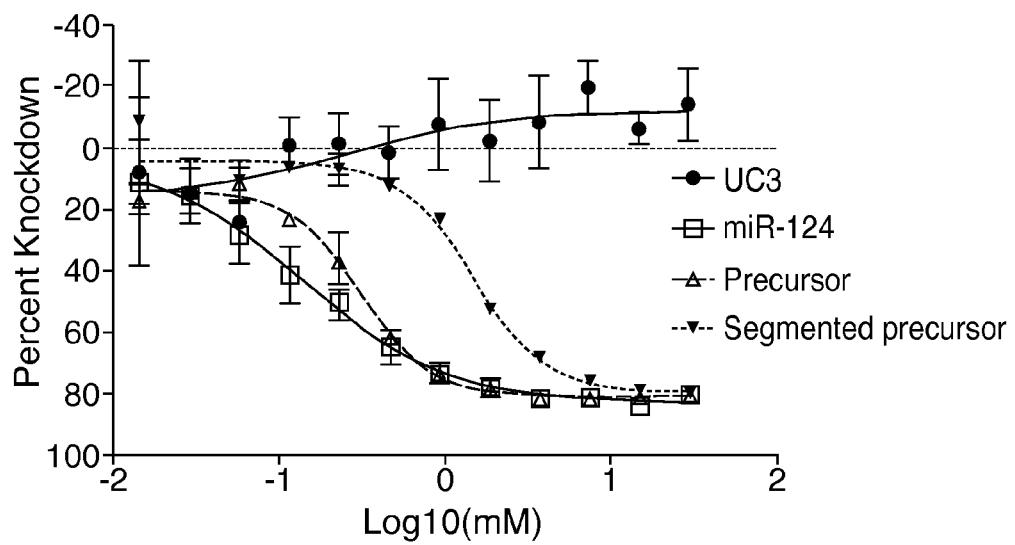

Activity of a segmented guide strand was tested in the context of a hairpin sequence that was designed to emulate the natural miR-124 hairpin. Appreciable activity was observed following guide strand division (FIG. 15B), indicating that processing of a hairpin into an Ago-recognizable duplex can occur in spite of a break in the guide strand.

Example 2

Segmented miRNA Mimetics Targeted to CD164

MicroRNAs can down-regulate gene expression by inhibiting translation of their target transcripts and/or mediating the degradation of these transcripts. This Example demonstrates that certain of the segmented miRNA mimetic constructs according to the present disclosure designed based on the corresponding naturally-occurring miRNAs are capable of doing the same. This example also indicates that segmented miRNA mimetics can comprise one or more locked nucleic acids (named "(L)", underlined nucleotides are locked nucleic acid residues in Table III, IV, V and VI). Nicks are marked within the sequence as "(nick)." Gaps are marked within the sequence as "( € )" with each box indicating a one nucleotide gap.

Synthetic duplex mimetic of miR-124 and segmented miR-124 mimetic constructs (sequences shown in Table III, passenger strand shown on top and guide strand on bottom) and a non-targeting control "Universal Control (UC)" duplex were transfected into HCT116 DICER$^{ex5}$, a human colorectal cancer cell line with hypomorphic DICER function (Cummins, J. M., et al., PNAS 103:3687-3692, 2006). The transfections were carried out using Lipofectamine RNAiMax (Invitrogen) per the manufacturer's instructions. RNA was isolated at 24 hours post-transfection using the RNeasy Kit (Qiagen) according to the manufacturer's instructions. The transcript abundance of the target gene, CD164, was measured by Taqman Real-time PCR and Biomek NX (Biomek FX Dual-96).

Passenger strand sequences in Table III are shown in 5' to 3' orientation and guide strand sequences are in 3' to 5' orientation.

TABLE III

| Name | Sequence | SEQ ID NOs. P | G |
|---|---|---|---|
| miR-124/124(p)/124(g) | (passenger) GCAUUCACCGCGUGCCUUAAAU<br>ACCGUAAGUGGCGCACGGAAUU (guide) | 1092 | 1091 |
| (124p)10(L).10(L)/<br>(1242) | (passenger) GC<u>A</u>UUCACCG(nick)CGUG<u>C</u>CUUAAAU<br>ACCGUAAGUGGCGCACGGAAUU (guide) | 1107/<br>1108 | 1091 |

TABLE III-continued

| Name | Sequence | SEQ ID NOs. P | G |
|---|---|---|---|
| (124p)10.10/ (124g) | (passenger) GCAUUCACCG(nick)CGUGCCUUAAAU ACCGUAAGUGGCGCACGGAAUU (guide) | 1096/ 1097 | 1091 |
| (124p)12(L).8(L)/ (124g) | (passenger) GCAUUCACCGCG(nick)UGCCUUAAAU ACCGUAAGUGGCGCACGGAAUU (guide) | 1105/ 1106 | 1091 |
| (124p)10(L).8(L)/ (124g) | (passenger) GCAUUCACCG(££)UGCCUUAAAU ACCGUAAGUGGCGCACGGAAUU (guide) | 1107/ 1109 | 1091 |
| (124p)/ (124g)10(L).10(L) | (passenger) GCAUUCACCGCGUGCCUUAAAU ACCGUAAGUGG(nick)CGCACGGAAUU (guide) | 1092 | 1103/ 1104 |
| (124p)/ (124g)10.10 | (passenger) GCAUUCACCGCGUGCCUUAAAU ACCGUAAGUGG(nick)CGCACGGAAUU (guide) | 1092 | 1093/ 1094 |
| (124p)/ (124g)10(L).9(L) | (passenger) GCAUUCACCGCGUGCCUUAAAU ACCGUAAGUGG(£)GCACGGAAUU (guide) | 1092 | 1103/ 1110 |
| (124p)/ (124g)10(L).8(L) | (passenger) GCAUUCACCGCGUGCCUUAAAU ACCGUAAGUG(££)GCACGGAAUU (guide) | 1092 | 1103/ 1112 |
| (124p)/ (124g)10(L).7(L) | (passenger) GCAUUCACCGCGUGCCUUAAAU ACCGUAAGU(£££)GCACGGAAUU (guide) | 1092 | 1103 |
| (124p)/ (124g)10(L).7 | (passenger) GCAUUCACCGCGUGCCUUAAAU ACCGUAAGU(£££)GCACGGAAUU (guide) | 1092 | 1093 |
| (124p)/ (124g)11(L).9(L) | (passenger) GCAUUCACCGCGUGCCUUAAAU ACCGUAAGUGG(nick)CGCACGGAAUU (guide) | 1092 | 1111/ 1110 |
| (124p)/ (124g)11(L).8(L) | (passenger) GCAUUCACCGCGUGCCUUAAAU ACCGUAAGUG(£)CGCACGGAAUU (guide) | 1092 | 1111/ 1112 |
| (124p)/ (124g)11(L).7(L) | (passenger) GCAUUCACCGCGUGCCUUAAAU ACCGUAAGU(££)CGCACGGAAUU (guide) | 1092 | 1111 |
| (124p)/ (124g)12(L).8(L) | (passenger) GCAUUCACCGCGUGCCUUAAAU ACCGUAAGUG(nick)GCGCACGGAAUU (guide) | 1092 | 1113/ 1112 |
| (124p)/ (124g)12(L).7(L) | (passenger) GCAUUCACCGCGUGCCUUAAAU ACCGUAAGU(£)GCGCACGGAAUU (guide) | 1092 | 1113 |
| (124p)/ (124g)13(L).7(L) | (passenger) GCAUUCACCGCGUGCCUUAAAU ACCGUAAGU(nick)GGCGCACGGAAUU (guide) | 1092 | 1114 |

Results of the activities are shown in FIG. 7. In brief, most of the constructs tested demonstrated a capacity of knocking down CD164, a known target to the naturally-occurring endogenous miR-124. Constructs comprising nicks in one or both strands of the segmented miRNA mimetic demonstrated at least 25% of knockdown (e.g., 30%, 40%, 50%, 60%, 70%, 80%, 90%, 100% or more) achieved by the non-segmented miR-24 positive control.

Example 3

Segmented miRNA Mimetics Targeted to VAMP3

Segmented miRNA mimetics can be designed to include a discontinuity comprising a nick or gap in one or both strands of any miRNA sequence of the invention in which target specific silencing activity is maintained. In the following example, nicks and gaps were introduced into miR-124 miRNA mimetics and downstream target silencing was confirmed.

Synthetic duplex mimetic of miR-124 and segmented miR-124 mimetic constructs (sequences shown in Table IV) and a non-targeting control "Universal Control (UC)" duplex were transfected into HCT116 DICERex5, a human colorectal cancer cell line with hypomorphic DICER function (Cummins, J. M., et al., PNAS 103:3687-3692, 2006). The transfections were carried out using Lipofectamine RNAiMax (Invitrogen) per the manufacturer's instructions. RNA was isolated at 24 hours post-transfection using the RNeasy Kit (Qiagen) according to the manufacturer's instructions. The transcript abundance of the target gene, VAMP3, was measured by Taqman Real-time PCR and Biomek NX (Biomek FX Dual-96).

Passenger strand sequences in Table IV are shown in 5' to 3' orientation and guide strand sequences are in 3' to 5' orientation.

TABLE IV

| Name | Sequence | SEQ ID NO(s). P | G |
|---|---|---|---|
| miR-124/ (124g(124g) | (passenger) GCAUUCACCGCGUGCCUUAAAU ACCGUAAGUGGCGCACGGAAUU (guide) | 1092 | 1091 |
| (124p)10(L).10(L)/ (124g) | (passenger) GCAUUCACCG(nick)CGUGCCUUAAAU ACCGUAAGUGGCGCACGGAAUU (guide) | 1107/ 1108 | 1091 |
| (124p)/ (124g)10(L).10(L) | (passenger) GCAUUCACCGCGUGCCUUAAAU ACCGUAAGUGGC(nick)GCACGGAAUU (guide) | 1092 | 1103/ 1104 |
| (124p)/ (124g)11(L).9(L) | (passenger) GCAUUCACCGCGUGCCUUAAAU ACCGUAAGUGG(nick)CGCACGGAAUU (guide) | 1092 | 1111/ 1110 |
| (124p)10(L).10(L)/ (124g)10(L).10(L) | (passenger) GCAUUCACCG(nick)CGUGCCUUAAAU ACCGUAAGUGGC(nick)GCACGGAAUU (guide) | 1107/ 1108 | 1103/ 1104 |
| (124p)10(L).10(L)/ (124a)10.10 | (passenger) GCAUUCACCG(nick)CGUGCCUUAAAU ACCGUAAGUGGC(nick)GCACGGAAUU (guide) | 1107/ 1108 | 1093/ 1094 |
| (124p)10.10/ (124g)10(L).10(L) | (passenger) GCAUUCACCG(nick)CGUGCCUUAAAU ACCGUAAGUGGC(nick)GCACGGAAUU (guide) | 1096/ 1097 | 1103/ 1104 |
| (124p)10.10/ (124g)10.10 | (passenger) GCAUUCACCG(nick)CGUGCCUUAAAU ACCGUAAGUGGC(nick)GCACGGAAUU (guide) | 1096/ 1097 | 1093/ 1094 |
| (124p)10(L).10(L)/ (124g)11(L).9(L) | (passenger) GCAUUCACCG(nick)CGUGCCUUAAAU ACCGUAAGUGG(nick)CGCACGGAAUU (guide) | 1107/ 1108 | 1111/ 1110 |
| (124p)10.10/ (124g)11(L).9(L) | (passenger) GCAUUCACCG(nick)CGUGCCUUAAAU ACCGUAAGUGG(nick)CGCACGGAAUU (guide) | 1096/ 1097 | 1111/ 1110 |
| (124p)10(L).10(L)/ (124g)12(L).8(L) | (passenger) GCAUUCACCG(nick)CGUGCCUUAAAU ACCGUAAGUG(nick)GCGCACGGAAUU (guide) | 1107/ 1108 | 1113/ 1112 |
| (124p)10.10/ (124g)12(L).8(L) | (passenger) GCAUUCACCG(nick)CGUGCCUUAAAU ACCGUAAGUG(nick)GCGCACGGAAUU (guide) | 1096/ 1097 | 1113/ 1112 |
| (124p)10(L).10(L)/ (124g)13(L).7(L) | (passenger) GCAUUCACCG(nick)CGUGCCUUAAAU ACCGUAAGU(nick)GGCGCACGGAAUU (guide) | 1107/ 1108 | 1114 |
| (124p)10.10/ (124g)13(L).7(L) | (passenger) GCAUUCACCG(nick)CGUGCCUUAAAU ACCGUAAGU(nick)GGCGCACGGAAUU (guide) | 1096/ 1097 | 1114 |
| (124p)12(L).8(L)/ (124g)10(L).10(L) | (passenger) GCAUUCACCGCG(nick)UGCCUUAAAU ACCGUAAGUGGC(nick)GCACGGAAUU (guide) | 1105/ 1106 | 1103/ 1104 |
| (124p)12(L).8(L)/ (124g)10.10 | (passenger) GCAUUCACCGCG(nick)UGCCUUAAAU ACCGUAAGUGGC(nick)GCACGGAAUU (guide) | 1105/ 1106 | 1103/ 1104 |
| (124p)12(L).8(L)/ (124g)11(L).9(L) | (passenger) GCAUUCACCGCG(nick)UGCCUUAAAU ACCGUAAGUGG(nick)CGCACGGAAUU (guide) | 1105/ 1106 | 1111/ 1110 |
| (124p)12(L).8(L)/ (124g)12(L).8(L) | (passenger) GCAUUCACCGCG(nick)UGCCUUAAAU ACCGUAAGUG(nick)GCGCACGGAAUU (guide) | 1105/ 1106 | 1113/ 1112 |
| (124p)12(L).8(L)/ (124g)13(L).7(L) | (passenger) GCAUUCACCGCG(nick)UGCCUUAAAU ACCGUAAGU(nick)GGCGCACGGAAUU (guide) | 1105/ 1106 | 1114 |

Results of this example are shown in FIG. 8. A number of the segmented miRNA mimetic constructs of this example, each strand comprising two distinct contiguous stretches of nucleotides, achieved at least 20%, at least 25%, at least 30%, at least 40%, at least 50%, at least 60%, at least 70%, at least 80%, at least 90%, or at least 100% of the knockdown effect as compared to the non-segmented duplex miR-124 mimetic.

Example 4

Segmented miRNA Mimetics of miR-124 Versus miR-34

Segmented miRNA mimetics can be designed to include a discontinuity comprising a nick or gap in any miRNA sequence of the invention in which the target specificity is maintained. In the following example, nicks and gaps were introduced into miR-124 and miR-34 miRNA mimetics and downstream target specificity determined.

Synthetic duplex mimetic of miR-124 and segmented miR-124 constructs (sequences shown in Table V) and a non-targeting control "Universal Control (UC)" duplex were transfected into HCT116 DICER[ex6], a human colorectal cancer cell line with hypomorphic DICER function (Cummins, J. M., et al., PNAS 103:3687-3692, 2006). The transfections were carried out using Lipofectamine RNAiMax (Invitrogen) per the manufacturer's instructions. RNA was isolated at 24 hours post-transfection using the RNeasy Kit (Qiagen) according to the manufacturer's instructions. The transcript abundance of the target gene, CD164, was measured by Taqman Real-time PCR and Biomek NX (Biomek FX Dual-96). The knockdown effect achieved by segmented miRNA-124 was also compared with the knockdown, or the lack thereof, achieved by segmented miRNA-34 and a duplex miR-34 mimetic, which are known to not target CD164.

Synthetic duplex mimetic of miR-34 and segmented miR-34 constructs (sequences shown in Table V) and a non-targeting control "Universal Control (UC)" duplex were transfected into HCT116 DICER$^{ex5}$, a human colorectal cancer cell line with hypomorphic DICER function (Cummins, J. M., et al., PNAS 103:3687-3692, 2006). The transfections were carried out using Lipofectamine RNAiMax (Invitrogen) per the manufacturer's instructions. RNA was isolated at 24 hours post-transfection using the RNeasy Kit (Qiagen) according to the manufacturer's instructions. The transcript abundance of the target gene, TK1, was measured by Taqman Real-time PCR and Biomek NX (Biomek EX Dual-96). The knockdown effect achieved by segmented miRNA-34 was also compared with the knockdown, or the lack thereof, achieved by segmented miRNA-124 and a duplex miR-124 mimetic, which are known to not target TK1.

The nucleotides that were changed to effectuate the mismatches are indicated in lower case letters in the sequences. Passenger strand sequences in Table V are shown in 5' to 3' orientation and guide strand sequences are in 3' to 5' orientation.

TABLE V

| Name | Sequence | SEQ ID NO(s). P | G |
|---|---|---|---|
| miR-124/ (124p)/(124g) | (passenger) GCAUUCACCGCGUGCCUUAAAU ACCGUAAGUGGCGCACGGAAUU (guide) | 1092 | 1091 |
| miR-124 (blunt end) | (passenger) GCAUUCACCGCGUGCCUUAAAU CGUAAGUGGCGCACGGAAUU (guide) | 1092 | 1115 |
| miR-124 (shorter guide) | (passenger) GCAUUCACCGCGUGCCUUAAAU UAAGUGGCGCACGGAAUU (guide) | 1092 | 1116 |
| (124p)/ (124g)10(L).10(L) | (passenger) GCAUUCACCGCGUGCCUUAAAU ACCGUAAGUGGC(nick)GCACGGAAUU (guide) | 1092 | 1103/ 1104 |
| (124p)/ (124g)10.10 | (passenger) GCAUUCACCGCGUGCCUUAAAU ACCGUAAGUGGC(nick)GCACGGAAUU (guide) | 1092 | 1093/ 1094 |
| (124p)10.10/ (124g) | (passenger) GCAUUCACCG(nick)CGUGCCUUAAAU ACCGUAAGUGGCGCACGGAAUU (guide) | 1096/ 1097 | 1091 |
| (124p)/ (124g)10.10 | (passenger) GCAUUCACCGCGUGCCUUAAAU ACCGUAAGUGGC(nick)GCACGGAAUU (guide) | 1092 | 1093/ 1094 |
| (124p)/ (124g)11.9 | (passenger) GCAUUCACCGCGUGCCUUAAAU ACCGUAAGUGG(nick)CGCACGGAAUU (guide) | 1092 | 1117/ 1118 |
| (124p)/(124g) 10.10m (mismatch) | (passenger) GCAUcUACCG(nick)CGUGCCUUAAAU ACCGUAgaUGGC(nick)GCACGGAAUU (guide) | 1119/ 1097 | 1093/ 1120 |
| (124p)/(124g)10 m3.10 (mismatch) | (passenger) GCAUUCACCG(nick)CGUcgCUUAAAU ACCGUAAGUGGC(nick)GCAgcGAAUU (guide) | 1096/ 1121 | 1122/ 1094 |
| m5.10(124p)/(124g) 10 (mismatch) | (passenger) GCAUUCACCG(nick)CGUGCCUauAAU ACCGUAAGUGG(nick)CGCACGGAuaU (guide) | 1096/ 1123 | 1124/ 1118 |
| (124p)/ (124g)10.9 | (passenger) GCAUUCACCGCGUGCCUUAAAU ACCGUAAGUG(£)CGCACGGAAUU (guide) | 1092 | 1117/ 1125 |
| (124p)/(124g)10 m3.9 (mismatch) | (passenger) GCAUUCACCGCGUcgCUUAAAU ACCGUAAGU(£)GCGCAgcGAAUU (guide) | 1126 | 1127 |
| (124p)/(124g)10 m5.9 (mismatch) | (passenger) GCAUUCACCG(nick)CGUGCCUauAAU ACCGUAAGUG(nick)GCGCACGGAuaU (guide) | 1096/ 1128/ 1112 | 1128/ 1112 |
| miR-34a/ (34p)/(34g) | (passenger) CACGAGCUAAGACACUGCUAAU UGGUGCUCGAUUCUGUGACGGU (guide) | 1093 | 1094 |
| (34p)/ (34a)10.10 | (passenger) CACGAGCUAAGACACUGCUAAU UGGUGCUCGAUU(nick)CUGUGACGGU (guide) | 1093 | 1129/ 1130 |
| (34p)/ (34g)11.9 | (passenger) CACGAGCUAAGACACUGCUAAU UGGUGCUCGAU(nick)UCUGUGACGGU (guide) | 1093 | 1131/ 1132 |
| (34p)/ (34g)10.9 | (passenger) CACGAGCUAAGACACUGCUAAU UGGUGCUCGAU(£)CUGUGACGGU (guide) | 1093 | 1129/ 1132 |

Figure 9A:
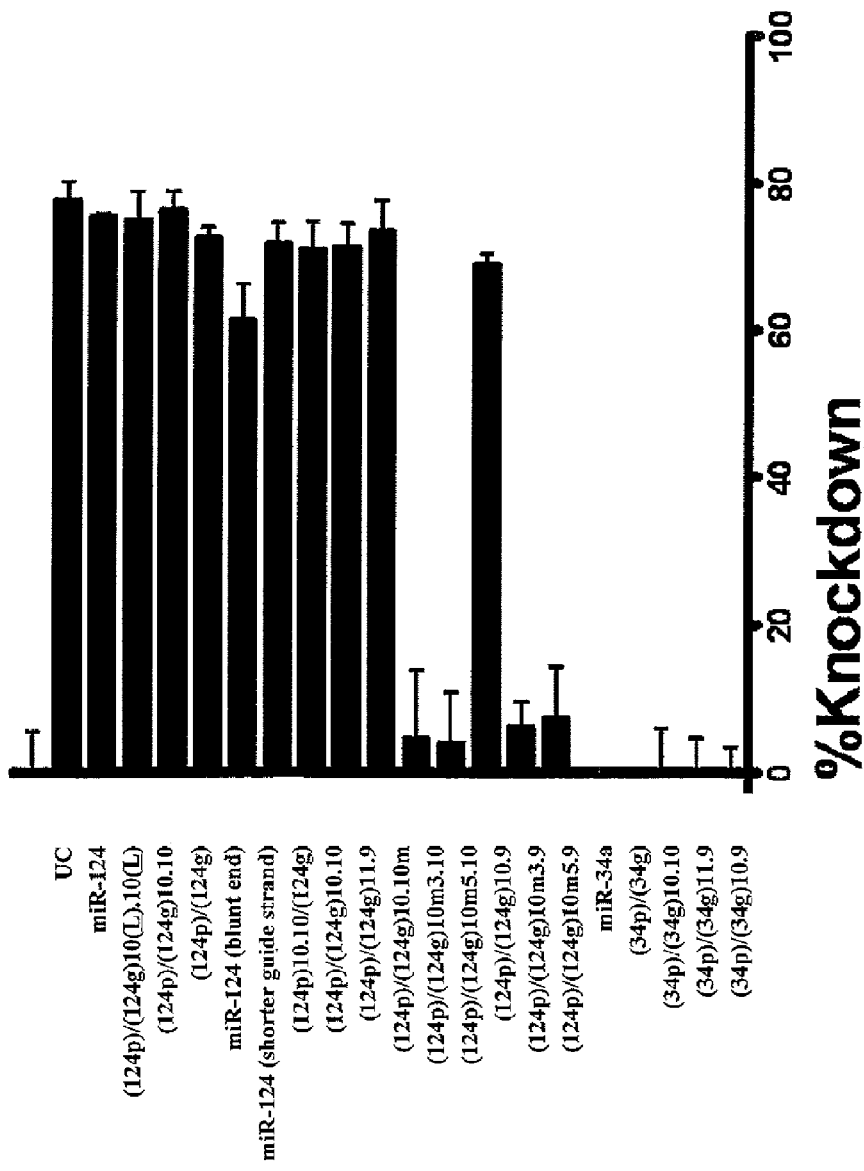
FIG. 9A illustrates RNAi activity of various segmented miR-124 mimetics (i.e., of Table V) against CD164. Levels of knockdown achieved by the segmented miR-124 constructs and by the corresponding non-segmented miR-124 mimetic, comprising the endogenous mature miR-124 sequence as its guide strand, were determined. Knockdown or inhibition, or the lack thereof, by segmented miR-34 constructs, which were designed based on human miR-34, is presented as a negative control.
Figure 9B:
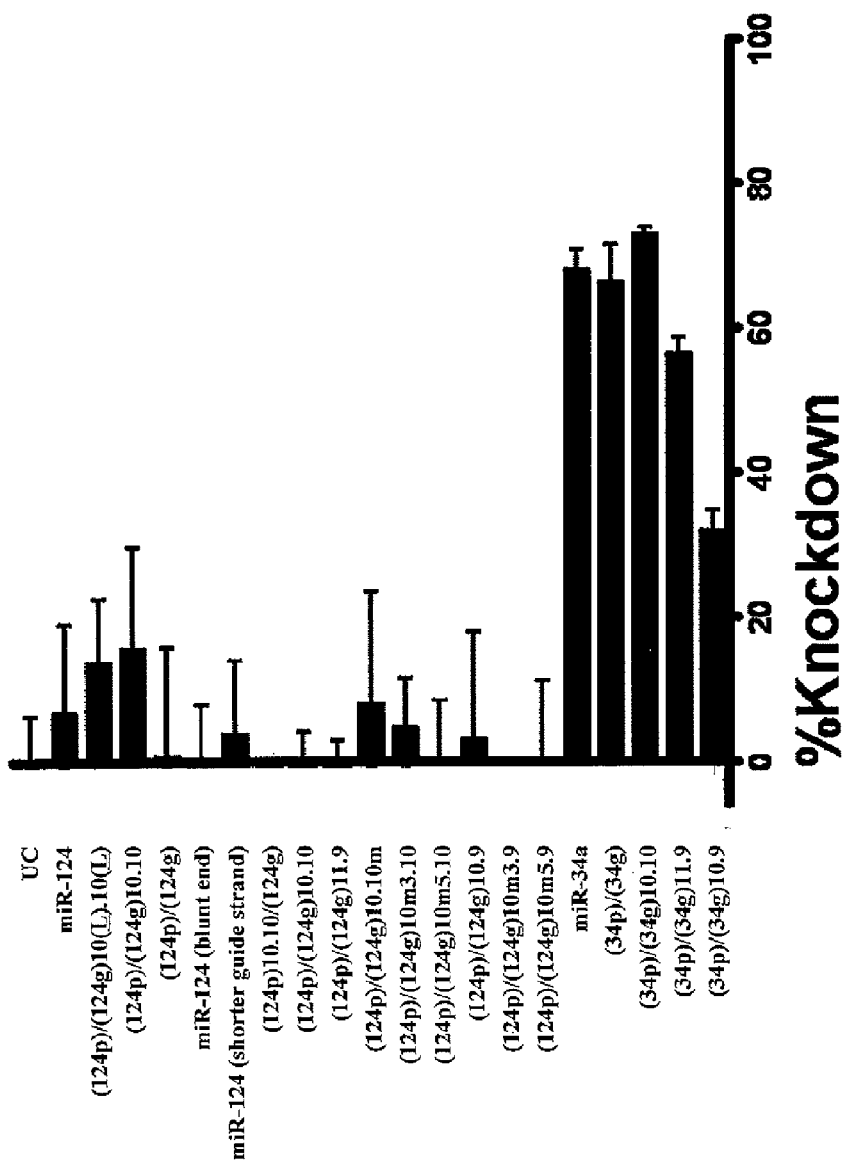
FIG. 9B illustrates RNAi activity against an endogenous miR-34 target, TK1, of various segmented miRNA mimetics derived from miR-34 ("segmented miR-34") (i.e., molecules of Table V). Levels of knockdown achieved by the segmented miR-34 constructs and by the corresponding non-segmented miR-34 mimetic, comprising the endogenous mature miR-34 sequence as its guide strand, were determined. Knockdown or inhibition, or the lack thereof, by segmented miR-124 constructs, is presented as a negative control.

The results are presented in FIGS. 9A and 9B. Certain segmented miRNA mimetic constructs of this example, achieved at least 20%, at least 25%, at least 30%, at least 40%, at least 50%, at least 60%, at least 70%, at least 80%, at least 90%, or at least 100% of the knockdown effect as compared to their respective non-segmented duplex mimetics.

Example 5

Segmented miRNA Mimetics Comprising Abasic Insertions

Segmented miRNA mimetics can be designed to include a discontinuity comprising a nick or gap, in which one or more non-nucleotide moieties of the invention are inserted into the terminal portions of sequence adjacent to the nick or gap. In the following example, abasic moieties were used to cap the internal ends of nucleotide positions in the guide strand of a segmented miRNA mimetic. Likewise, insertions with other non-nucleotide moieties described herein or otherwise known in the art can be similarly performed by one of general skill following the methodologies herein.

Synthetic duplex mimetic of miR-124 and segmented miR-124 mimetic constructs (sequences shown in Table VI), comprising one or more inverted abasic modifications at the internal ends, and a non-targeting control "Universal Control (UC)" duplex were transfected into HCT116 DICER$^{ex5}$, a human colorectal cancer cell line with hypomorphic DICER function (Cummins. J. M., et al., PNAS 103:3687-3692, 2006). The transfections were carried out using Lipofectamine RNAiMax (Invitrogen) per the manufacturer's instructions. RNA was isolated at 24 hours post-transfection using the RNeasy Kit (Qiagen) according to the manufacturer's instructions. The transcript abundance of the target genes, CD164 and VAMP3, was measured by Taqman Real-time PCR and Biomek NX (Biomek FX Dual-96).

The position of the inverted abasic group is indicated as "(i)" in both the names and the sequences of the following table. Passenger strand sequences in Table VI are shown in 5' to 3' orientation and guide strand sequences are in 3' to 5' orientation.

TABLE VI

| Name | Sequence | SEQ ID NO(s). P | G |
|---|---|---|---|
| miR-124 | (passenger) GCAUUCACCGCGUGCCUUAAAU<br>ACCGUAAGUGGCGCACGGAAUU (guide) | 1092 | 1091 |
| (124p)/(124g)<br>7(i).13(i) | (passenger) GCAUUCACCGCGUGCCUUAAAU<br>ACCGUAAGUGGCGCA(i)(nick)(i)CGGAAUU (guide) | 1092 | 1133 |
| (124p)/(124g)<br>8(i).12(i) | (passenger) GCAUUCACCGCGUGCCUUAAAU<br>ACCGUAAGUGGCGC(i)(nick)(i)ACGGAAUU (guide) | 1092 | 1134 |
| (124p)/(124g)<br>9(i).11(i) | (passenger) GCAUUCACCGCGUGCCUUAAAU<br>ACCGUAAGUGGCG(i)(nick)(i)CACGGAAUU (guide) | 1092 | 1135 |
| (124p)/(124g)<br>10(i).10(i) | (passenger) GCAUUCACCGCGUGCCUUAAAU<br>ACCGUAAGUGGC(i)(nick)(i)GCACGGAAUU (guide) | 1092 | 1136/<br>1137 |
| (124p)/(124g)<br>11(i).9(i) | (passenger) GCAUUCACCGCGUGCCUUAAAU<br>ACCGUAAGUGG(i)(nick)(i)CGCACGGAAUU (guide) | 1092 | 1138/<br>1139 |
| (124p)/(124g)<br>12(i).8(i) | (passenger) GCAUUCACCGCGUGCCUUAAAU<br>ACCGUAAGUG(i)(nick)(i)GCGCACGGAAUU (guide) | 1092 | 1140/<br>1141 |
| (124p)/(124g)<br>13(i).7(i) | (passenger) GCAUUCACCGCGUGCCUUAAAU<br>ACCGUAAGU(i)(nick)(i)GGCGCACGGAAUU (guide) | 1092 | 1142 |
| (124p)/(124g)<br>7(i).13 | (passenger) GCAUUCACCGCGUGCCUUAAAU<br>ACCGUAAGUGGCGCA(nick)(i)CGGAAUU (guide) | 1092 | 1143 |
| (124p)/(124g)<br>8(i).12 | (passenger) GCAUUCACCGCGUGCCUUAAAU<br>ACCGUAAGUGGCGC(nick)(i)ACGGAAUU (guide) | 1092 | 1144 |
| (124p)/(124g)<br>9(i).11 | (passenger) GCAUUCACCGCGUGCCUUAAAU<br>ACCGUAAGUGGCG(nick)(i)CACGGAAUU (guide) | 1092 | 1145 |
| (124p)/(124a)<br>10(i).10 | (passenger) GCAUUCACCGCGUGCCUUAAAU<br>ACCGUAAGUGGC(nick)(i)GCACGGAAUU (guide) | 1092 | 1136/<br>1094 |
| (124p)/(124g)<br>11(i).9 | (passenger) GCAUUCACCGCGUGCCUUAAAU<br>ACCGUAAGUGG(nick)(i)CGCACGGAAUU (guide) | 1092 | 1138/<br>1118 |
| (124p)/(124g)<br>12(i).8 | (passenger) GCAUUCACCGCGUGCCUUAAAU<br>ACCGUAAGUG(nick)(i)GCGCACGGAAUU (guide) | 1092 | 1140/<br>1125 |
| (124p)/(124g)<br>13(i).7 | (passenger) GCAUUCACCGCGUGCCUUAAAU<br>ACCGUAAGU(nick)(i)GGCGCACGGAAUU (guide) | 1092 | 1142 |
| (124p)/(124g)<br>7.13(i) | (passenger) GCAUUCACCGCGUGCCUUAAAU<br>ACCGUAAGUGGCGCA(i)(nick)CGGAAUU (guide) | 1092 | 1133 |

TABLE VI-continued

| Name | Sequence | SEQ ID NO(s). P | SEQ ID NO(s). G |
|---|---|---|---|
| (124p)/(124g) 8.12(i) | (passenger) GCAUUCACCGCGUGCCUUAAAU ACCGUAAGUGGCGC(i)(nick)ACGGAAUU (guide) | 1092 | 1134 |
| (124p)/(124g) 9.11(i) | (passenger) GCAUUCACCGCGUGCCUUAAAU ACCGUAAGUGGCG(i)(nick)CACGGAAUU (guide) | 1092 | 1135 |
| (124p)/(124g) 10.10(i) | (passenger) GCAUUCACCGCGUGCCUUAAAU ACCGUAAGUGGC(i)(nick)GCACGGAAUU (guide) | 1092 | 1093/ 1137 |
| (124p)/(124g) 11.9(i) | (passenger) GCAUUCACCGCGUGCCUUAAAU ACCGUAAGUGG(i)(nick)CGCACGGAAUU (guide) | 1092 | 1117/ 1139 |
| (124p)/(124g) 12.8(i) | (passenger) GCAUUCACCGCGUGCCUUAAAU ACCGUAAGUG(i)(nick)GCGCACGGAAUU (guide) | 1092 | 1146/ 1141 |
| (124p)/(124g) 13.7(i) | (passenger) GCAUUCACCGCGUGCCUUAAAU ACCGUAAGU(i)(nick)GGCGCACGGAAUU (guide) | 1092 | 1147 |

Figure 10A:
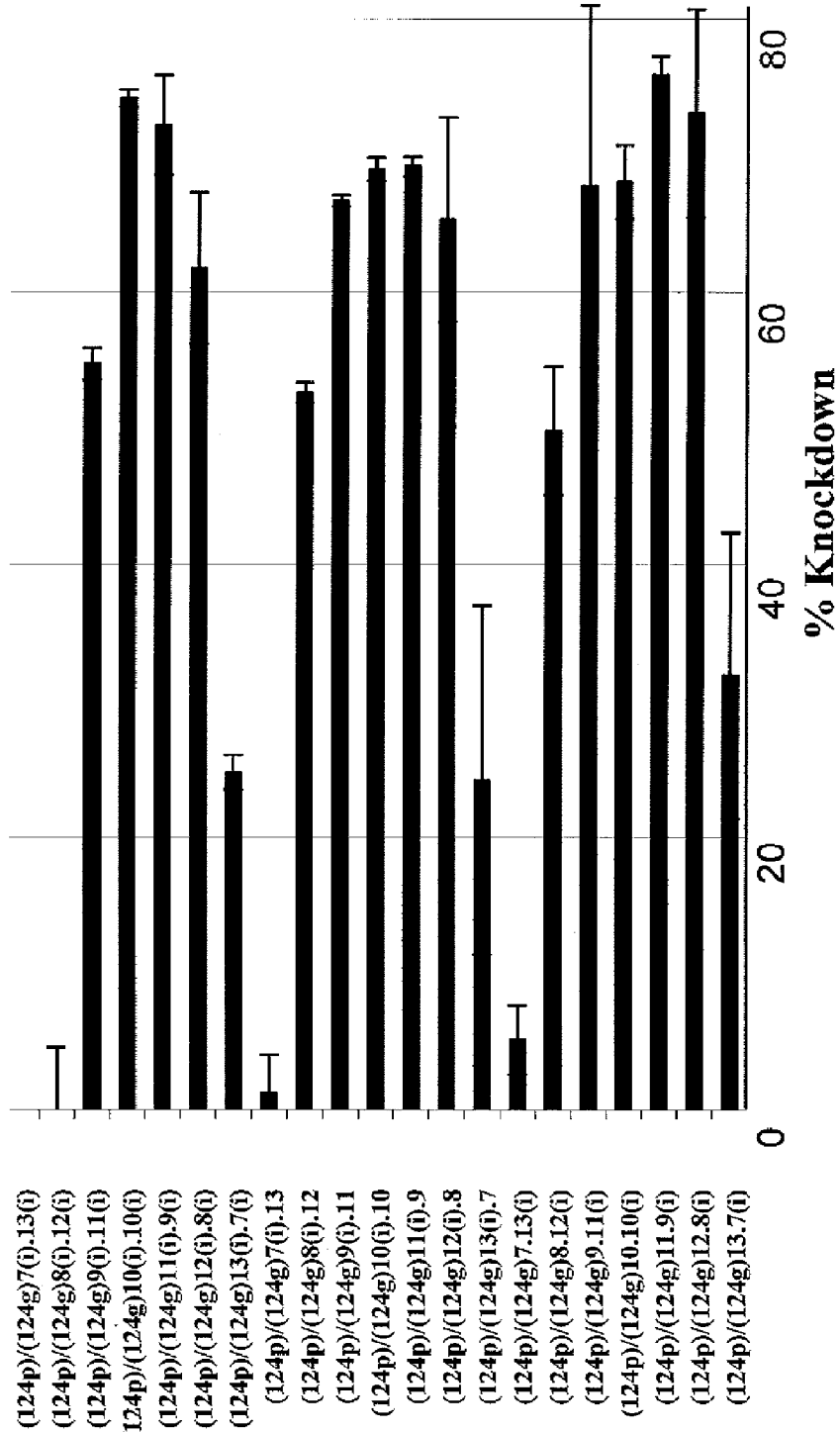
FIG. 10A illustrates RNAi-mediated activity against CD164 by segmented miR-124 constructs comprising one or more inverted abasic modified internal ends (i.e., molecules of Table VI).
Figure 10B:
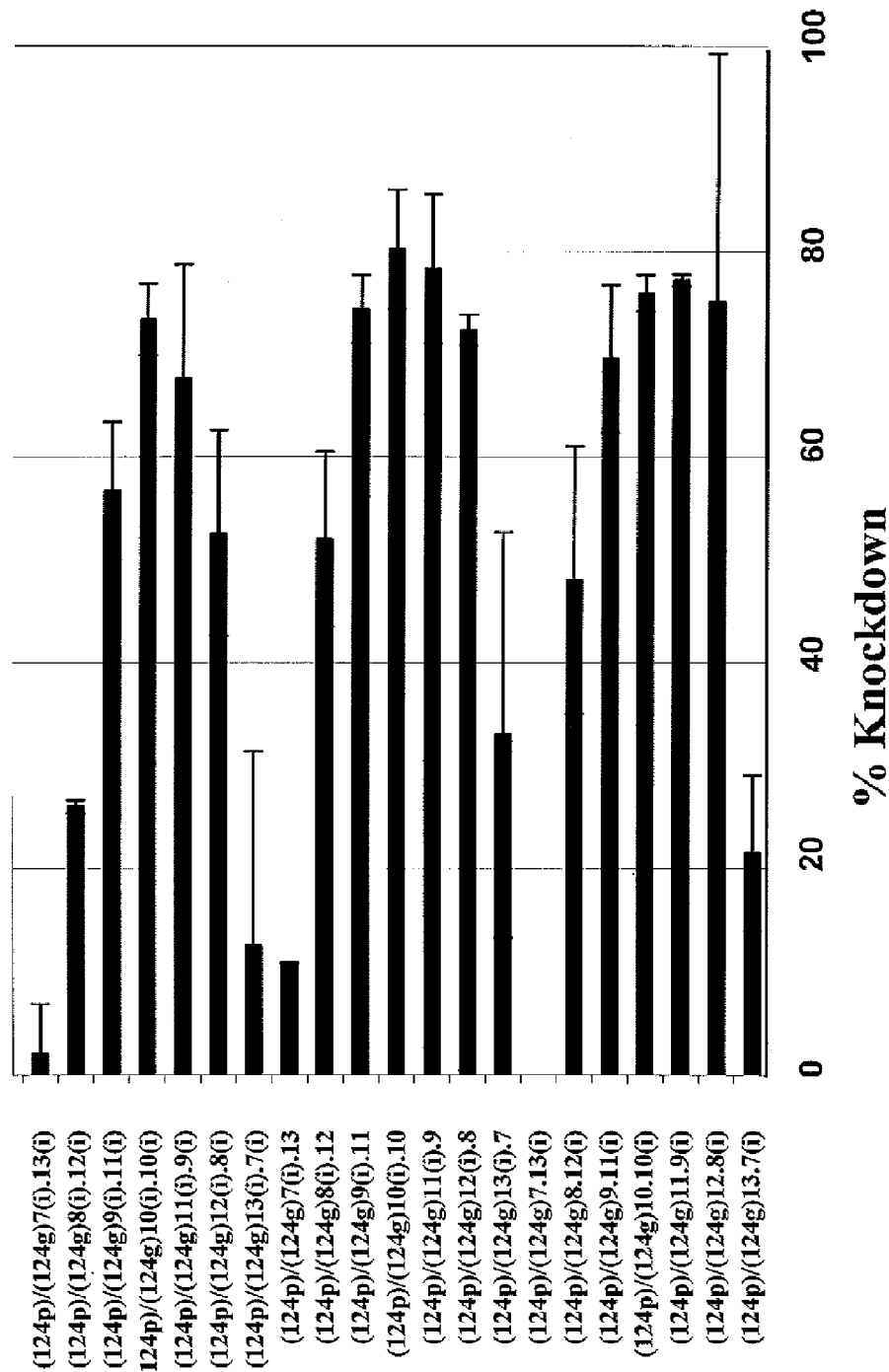
FIG. 10B illustrates RNAi-mediated activity against VAMP3 by segmented miR-124 constructs comprising one or more inverted abasic modified internal ends.

The results of this example are indicated in FIGS. 10A and 10B. As can be seen from this example, modifying the internal ends with one or more deoxyabasic moieties or modifications can impart further improvement of activity to the segmented miRNA mimetics of the invention.

Example 6

Segmented miRNA Mimetics Comprising Abasic Substitutions

Segmented miRNA mimetics can be designed to include a discontinuity comprising one or more non-nucleotide substitutions of the invention that occupy deleted sequence portions. In the following example, abasic linkers were used to substitute deleted nucleotide positions in both the guide and passenger strands of a miRNA mimetic. Likewise, substitution with other non-nucleotide linking moieties described herein or otherwise known in the art can be similarly performed by one of general skill following the methodologies herein.

Synthetic duplex mimetic of miR-124 and segmented miR-124 mimetic constructs (sequences shown in Table VII), comprising one or more abasic substitutions and a non-targeting control "Universal Control (UC)" duplex were transfected into HCT116 DICER$^{ex5}$, a human colorectal cancer cell line with hypomorphic DICER function (Cummins, J. M., et al., PNAS 103:3687-3692 (2006). The transfections were carried out using Lipofectamine RNAiMax (Invitrogen) per the manufacturer's instructions. RNA was isolated at 24 hours post-transfection using the RNeasy Kit (Qiagen) according to the manufacturer's instructions. The transcript abundance of the target genes, CD164 and VAMP3, was measured by Taqman Real-time PCR and Biomek NX (Biomek FX Dual-96).

The positions of the abasic linker is indicated as "(ab)" in both the names and the sequences of the following table. Passenger strand sequences in Table VII are shown in 5' to 3' orientation and guide strand sequences are in 3' to 5' orientation.

TABLE VII

| Name | Sequence | SEQ ID NO(s). P | SEQ ID NO(s). G |
|---|---|---|---|
| miR-124 | (passenger) GCAUUCACCGCGUGCCUUAAAU ACCGUAAGUGGCGCACGGAAUU (guide) | 1092 | 1091 |
| (124p)8(ab)$_2$11/ (124g)9(ab)$_2$12 | (passenger) GCAUUCAC(ab)(ab)CGUGCCUUAAAU ACCGUAAGUGG(ab)(ab)CACGGAAUU (guide) | 1148 | 1149 |
| (124p)7(ab)$_3$11/ (124g)9(ab)$_3$13 | (passenger) GCAUUCA(ab)(ab)(ab)CGUGCCUUAAAU ACCGUAAGUG(ab)(ab)(ab)CACGGAAUU (guide) | 1150 | 1151 |
| (124p)/6(ab)$_4$11/ (124g)9(ab)$_4$14 | (passenger) GCAUUC(ab)(ab)(ab)(ab)CGUGCCUUAAAU ACCGUAAGU(ab)(ab)(ab)(ab)CACGGAAUU (guide) | 1152 | 1153 |
| (124p)/5(ab)$_5$11/ (124g)9(ab)$_5$15 | (passenger) GCAUU(ab)(ab)(ab)(ab)(ab)CGUGCCUUAAAU ACCGUAAG(ab)(ab)(ab)(ab)(ab)CACGGAAUU (guide) | 1154 | 1155 |
| (124p)/7(ab)$_2$10/ (124g)10(ab)$_2$13 | (passenger) GCAUUCA(ab)(ab)GCGUGCCUUAAAU ACCGUAAGUG(ab)(ab)GCACGGAAUU (guide) | 1148 | 1156 |
| (124p)/6(ab)$_3$10/ (124g)10(ab)$_3$14 | (passenger) GCAUUC(ab)(ab)(ab)GCGUGCCUUAAAU ACCGUAAGU(ab)(ab)(ab)GCACGGAAUU (guide) | 1157 | 1158 |

TABLE VII-continued

| Name | Sequence | SEQ ID NO(s). P | G |
|---|---|---|---|
| (124p)/5(ab)₄10/ (124g)10(ab)₄15 | (passenger) GCAUU(ab)(ab)(ab)(ab)GCGUGCCUUAAAU ACCGUAAG(ab)(ab)(ab)(ab)GCACGGAAUU (guide) | 1159 | 1160 |
| (124p)/4(ab)₅10/ (124g)10(ab)₅16 | (passenger) GCAU(ab)(ab)(ab)(ab)(ab)GCGUGCCUUAAAU ACCGUAA(ab)(ab)(ab)(ab)(ab)GCACGGAAUU (guide) | 1161 | 1162 |
| (124p)/(124g) 8(ab)₂11 | (passenger) GCAUUCACCGCGUGCCUUAAAU ACCGUAAGUGGC(ab)(ab)ACGGAAUU (guide) | 1092 | 1163 |
| (124p)/(124g) 8(ab)₃12 | (passenger) GCAUUCACCGCGUGCCUUAAAU ACCGUAAGUGG(ab)(ab)(ab)ACGGAAUU (guide) | 1092 | 1164 |
| (124p)/(124g) 8(ab)₄13 | (passenger) GCAUUCACCGCGUGCCUUAAAU ACCGUAAGUG(ab)(ab)(ab)(ab)ACGGAAUU (guide) | 1092 | 1165 |
| (124p) 9(ab)11/ (124g) | (passenger) GCAUUCACC(ab)CGUGCCUUAAAU ACCGUAAGUGGCGCACGGAAUU (guide) | 1166 | 1091 |
| (124p) 8(ab)₂11/ (124g) | (passenger) GCAUUCAC(ab)(ab)CGUGCCUUAAAU ACCGUAAGUGGCGCACGGAAUU (guide) | 1148 | 1091 |
| (124p) 7(ab)₃11/ (124g) | (passenger) GCAUUCA(ab)(ab)(ab)CGUGCCUUAAAU ACCGUAAGUGGCGCACGGAAUU (guide) | 1150 | 1091 |
| (124p) 6(ab)₄11/ (124g) | (passenger) GCAUUC(ab)(ab)(ab)(ab)CGUGCCUUAAAU ACCGUAAGUGGCGCACGGAAUU (guide) | 1152 | 1091 |
| (124p) 5(ab)₅11/ (124g) | (passenger) GCAUU(ab)(ab)(ab)(ab)(ab)CGUGCCUUAAAU ACCGUAAGUGGCGCACGGAAUU (guide) | 1154 | 1091 |
| (124p) 4(ab)₆11/ (124g) | (passenger) GCAU(ab)(ab)(ab)(ab)(ab)(ab)CGUGCCUAAAUU ACCGUAAGUGGCGCACGGAAUU (guide) | 1167 | 1091 |
| (124p) 8(ab)10/ (124g) | (passenger) GCAUUCAC(ab)GCGUGCCUUAAAU ACCGUAAGUGGCGCACGGAAUU (guide) | 1168 | 1091 |
| (124p) 7(ab)₂10/ (124g) | (passenger) GCAUUCA(ab)(ab)GCGUGCCUUAAAU ACCGUAAGUGGCGCACGGAAUU (guide) | 1169 | 1091 |
| (124p) 6(ab)₃10/ (124g) | (passenger) GCAUUC(ab)(ab)(ab)GCGUGCCUUAAAU ACCGUAAGUGGCGCACGGAAUU (guide) | 1170 | 1091 |
| (124p) 5(ab)₄10/ (124g) | (passenger) GCAUU(ab)(ab)(ab)(ab)GCGUGCCUUAAAU ACCGUAAGUGGCGCACGGAAUU (guide) | 1171 | 1091 |
| (124p) 4(ab)₅10/ (124g) | (passenger) GCAU(ab)(ab)(ab)(ab)(ab)GCGUGCCUUAAAU ACCGUAAGUGGCGCACGGAAUU (guide) | 1172 | 1091 |
| (124p) 3(ab)₆10/ (124g) | (passenger) GCA(ab)(ab)(ab)(ab)(ab)(ab)GCGUGCCUUAAAU ACCGUAAGUGGCGCACGGAAUU (guide) | 1173 | 1091 |
| (124p)/(124g) 10(ab)₂13 | (passenger) GCAUUCACCGCGUGCCUUAAAU ACCGUAAGUG(ab)(ab)GCACGGAAUU (guide) | 1092 | 1156 |
| (124p)/(124g) 10(ab)₃14 | (passenger) GCAUUCACCGCGUGCCUUAAAU ACCGUAAGU(ab)(ab)(ab)GCACGGAAUU (guide) | 1092 | 1158 |
| (124p)/(124g) 10(ab)₄15 | (passenger) GCAUUCACCGCGUGCCUUAAAU ACCGUAAG(ab)(ab)(ab)(ab)GCACGGAAUU (guide) | 1092 | 1160 |
| (124p)/(124g) 10(ab)₅16 | (passenger) GCAUUCACCGCGUGCCUUAAAU ACCGUAA(ab)(ab)(ab)(ab)(ab)GCACGGAAUU (guide) | 1092 | 1162 |
| (124p)/(124g) 11(ab)₂14 | (passenger) GCAUUCACCGCGUGCCUUAAAU ACCGUAAGU(ab)(ab)CGCACGGAAUU (guide) | 1092 | 1174 |
| (124p)/(124g) 11(ab)₃15 | (passenger) GCAUUCACCGCGUGCCUUAAAU ACCGUAAG(ab)(ab)(ab)CGCACGGAAUU (guide) | 1092 | 1175 |
| (124p)/(124g) 11(ab)₄16 | (passenger) GCAUUCACCGCGUGCCUUAAAU ACCGUAA(ab)(ab)(ab)(ab)CGCACGGAAUU (guide) | 1092 | 1176 |
| (124p)/(124g) 11(ab)₅17 | (passenger) GCAUUCACCGCGUGCCUUAAAU ACCGUA(ab)(ab)(ab)(ab)(ab)CGCACGGAAUU (guide) | 1092 | 1177 |

Figure 11A:
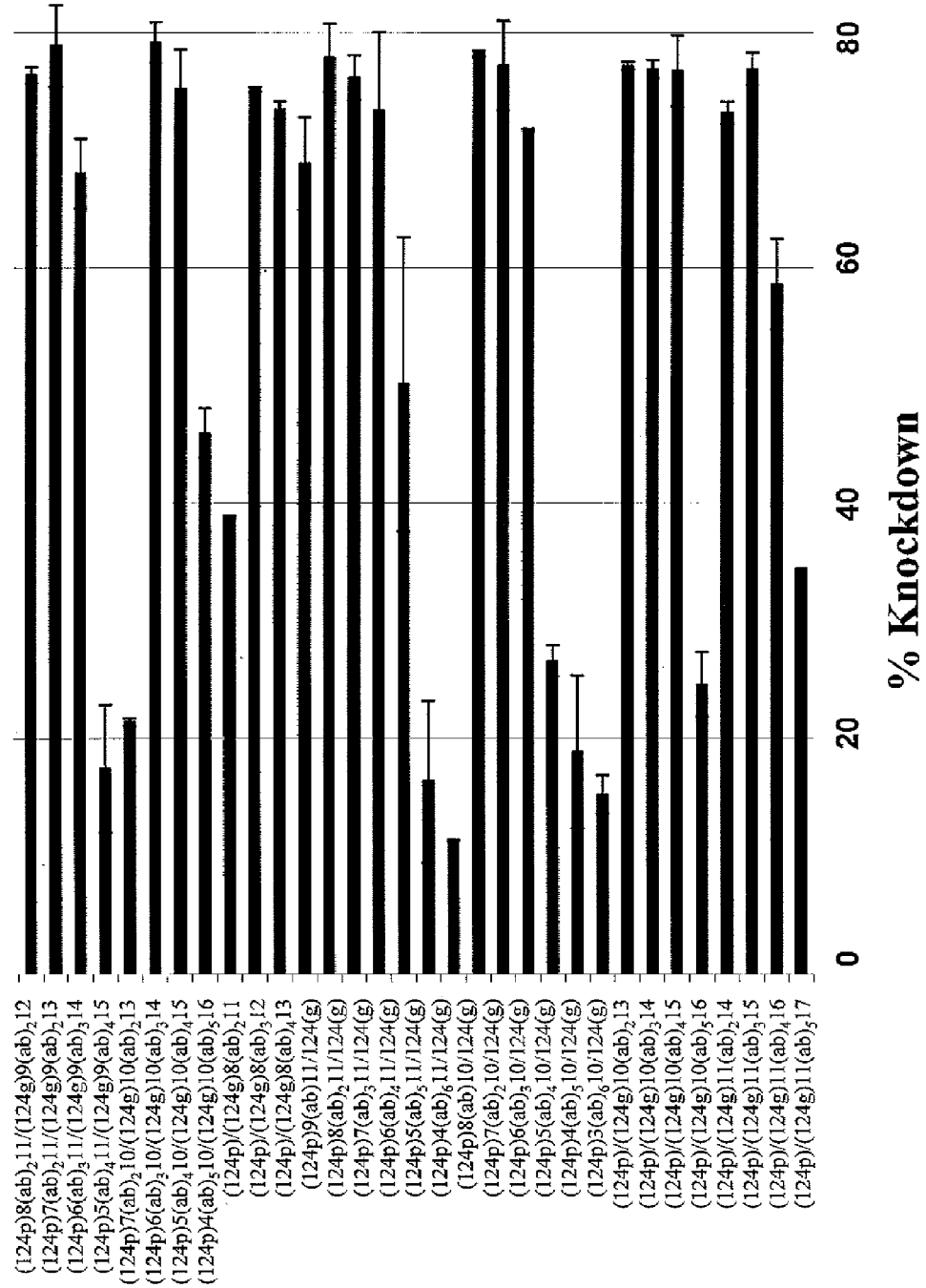
FIG. 11A illustrates RNAi-mediated activity against CD164 by segmented miRNA-124 constructs comprising abasic substitutions (i.e., molecules of Table VII).
Figure 11B:
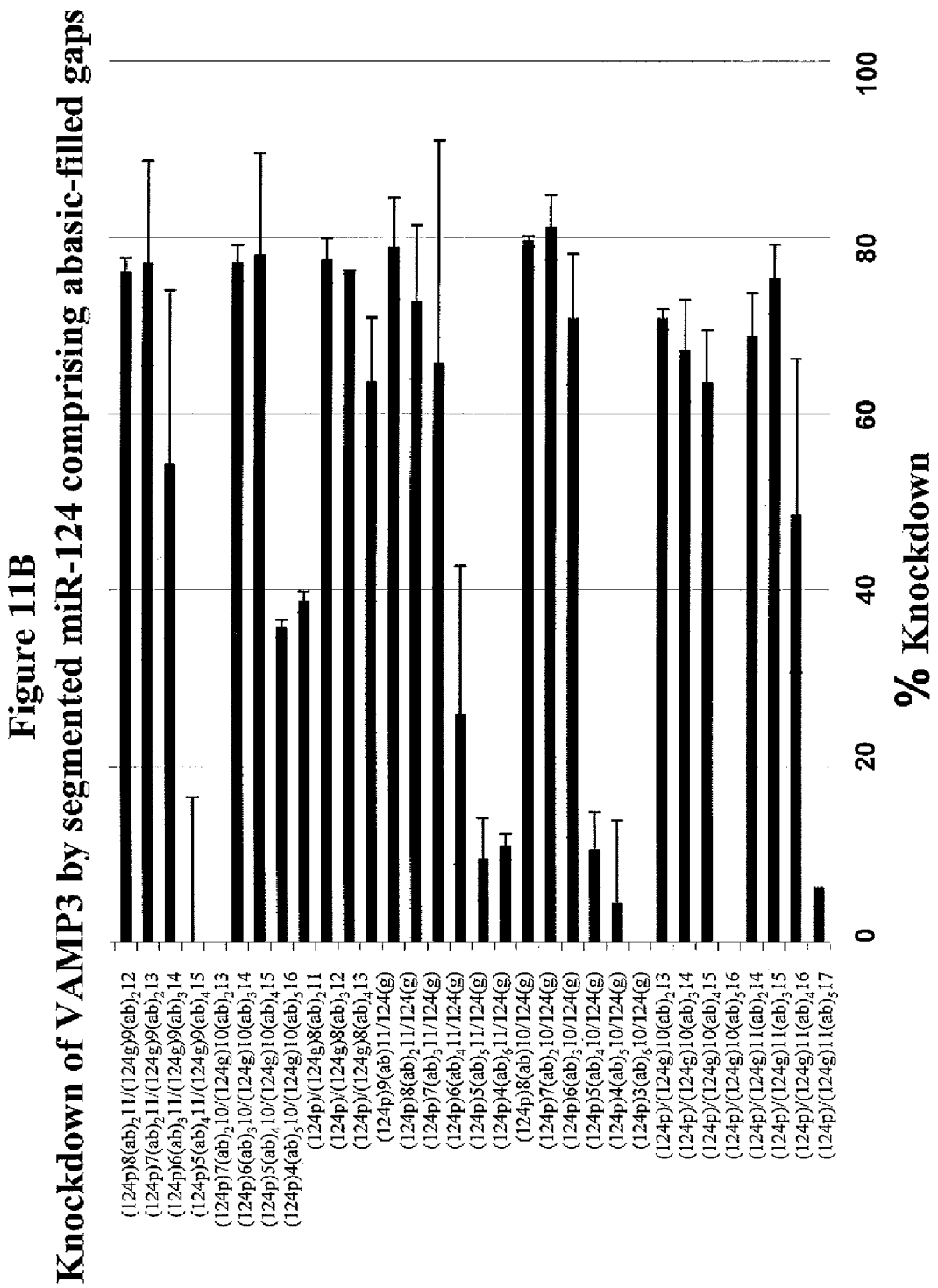
FIG. 11B illustrates RNAi-mediated activity against VAMP3 by segmented miR-124 constructs comprising abasic substitutions.

The results of this example are indicated in FIGS. 11A and 11B. As can be seen from this example, abasic substitutions can impart further advantageous properties to the segmented miRNA mimetics of the invention.

Example 7

Segmented miRNA Mimetics with Multiple Nucleotide Position Deletions and Substitutions Segmented miRNA mimetics can be designed to include a discontinuity comprising one or more non-nucleotide substitutions of the invention that occupy deleted sequence portions of 1 or more nucleotide positions. In the following example, alkyl linkers were used to substitute deleted nucleotide positions in both the guide and passenger strands of a miRNA mimetic. Likewise, substitution with other non-nucleotide linking moieties described herein or otherwise known in the art can be similarly performed by one of general skill following the methodologies herein.

Oligonucleotides comprising C3 and C6 linkers were synthesized using protocols well known in the art (solid phase synthesis) using commercially available phosphoramidites, then purified by reversed phase solid phase extraction (SPE). The C3 ($C_{33}H_{43}N_2O_5P$) and C6 ($C_{36}H_{49}N_2O_5P$) phosphoramidites were purchased from ChemGenes.

Briefly, the single strand oligonucleotides were synthesized using phosphoramidite chemistry on an automated solid-phase synthesizer, using procedures as are generally known in the art (see for example U.S. application Ser. No. 12/064,014). A synthesis column was packed with solid support derivatized with the first nucleoside residue (natural or chemically modified). Synthesis was initiated by detritylation of the acid labile 5'-O-dimethoxytrityl group to release the 5'-hydroxyl. A suitably protected phosphoramidite and a suitable activator in acetonitrile were delivered simultaneously to the synthesis column resulting in coupling of the amidite to the 5'-hydroxyl. The column was then washed with a solvent, such as acetonitrile. An oxidizing solution, such as an iodine solution was pumped through the column to oxidize the phosphite triester linkage P(III) to its phosphotriester P(V) analog. Unreacted 5'-hydroxyl groups were capped using reagents such as acetic anhydride in the presence of 2,6-lutidine and N-methylimidazole. The elongation cycle was resumed with the detritylation step for the next phosphoramidite incorporation. This process was repeated until the desired sequence was synthesized. The synthesis concluded with the final 5'-terminus protecting group (trityl or 5'-O-dimethoxytrityl).

Upon completion of the synthesis, the solid-support and associated oligonucleotide were dried under argon pressure or vacuum. Aqueous base was added and the mixture was heated to effect cleavage of the succinyl linkage, removal of the cyanoethyl phosphate protecting group, and deprotection of the exocyclic amine protection.

The following process was performed on single strands that do not contain ribonucleotides. After treating the solid support with the aqueous base, the mixture was filtered to separate the solid support from the deprotected crude synthesis material. The solid support was then rinsed with DMSO, which is combined with the filtrate. The resultant basic solution allows for retention of the 5'-O-dimethoxytrityl group to remain on the 5' terminal position (trityl-on).

For single strands that contain ribonucleotides, the following process was performed. After treating the solid support with the aqueous base, the mixture was filtered to separate the solid support from the deprotected crude synthesis material. The solid support was then rinsed with dimethylsulfoxide (DMSO), which was combined with the filtrate. Fluoride reagent, such as triethylamine trihydrofluoride, was added to the mixture, and the solution was heated. The reaction was quenched with suitable buffer to provide a solution of crude single strand with the 5'-O-dimethoxytrityl group on the final 5' terminal position.

The trityl-on solution of each crude single strand was purified using chromatographic purification, such as SPE RPC purification. The hydrophobic nature of the trityl group permits stronger retention of the desired full-length oligo than the non-tritylated truncated failure sequences. The failure sequences were selectively washed from the resin with a suitable solvent, such as low percent acetonitrile. Retained oligonucleotides were then detritylated on-column with trifluoroacetic acid to remove the acid-labile trityl group. Residual acid was washed from the column, a salt exchange was performed, and a final desalting of the material commenced. The full-length oligo was recovered in a purified form with an aqueous-organic solvent. The final product was then analyzed for purity (HPLC), identity (Maldi-TOF MS), and yield (UV A260). The oligos were dried via lyophilization or vacuum condensation.

Synthetic duplex mimetic of miR-124 and segmented miR-124 mimetic constructs (sequences shown in Table VIII), from which bases have been deleted, and a non-targeting control "Universal Control (UC3)" duplex were transfected into HCT-116 cells (wild-type) and cultured in McCoy's 5A Medium (Mediatech Inc.) supplemented with 10% fetal bovine serum and 1% penicillin-streptomycin. These cells were plated in 96-well culture plates at a density of 6000 cells/well 24 hours prior to transfection. Transfection was carried out using Opti-MEM I Reduced Serum Media (Gibco) and Lipofectamine RNAiMax (Invitrogen) with a final concentration of our miRNAs at 10 nM. Twenty-four hours after transfection, cells were washed with phosphate-buffered saline and processed using the TaqMan® Gene Expression Cells-to-CT™ Kit (Applied Biosystems/Ambion) to extract RNA, synthesize cDNA, and perform RT-qPCR using gene-specific probes (Applied Biosystems) on an ABI Prism 7900HT Sequence Detector.

Reverse transcription conditions were as follows: 60 minutes at 37° C. followed by 5 minutes at 95° C. RT-qPCR conditions were as follows: 2 minutes at 50° C., 10 minutes at 95° C., followed by 40 cycles of 15 seconds at 95° C. and 1 minute at 60° C. GUSB mRNA levels were used for data normalization. Knockdown of miR-124 targets was calculated as the two-fold change in target cDNA measured in experimentally-treated cells relative to the target cDNA measured in non-targeting control-treated cells.

The positions of deleted bases are indicated as "( € )" in both the names and the sequences of the following table. C3 and C6 linkers are identified as "(c3)" and "(c6)", respectively. Passenger strand sequences in Table VIII are shown in 5' to 3' orientation and guide strand sequences are in 3' to 5' orientation.

TABLE VIII

| Name | Sequence | SEQ ID NO(s). P | SEQ ID NO(s). G |
|---|---|---|---|
| miR-124 (iP/G) | (passenger) GCAUUCACCGCGUGCCUUAAAU ACCGUAAGUGGCGCACGGAAUU (guide) | 1092 | 1091 |
| iP9-10del/G11-12del | (passenger) GCAUUCAC(£)(£)CGUGCCUUAAAU ACCGUAAGUG(£)(£)GCACGGAAUU (guide) | 1097 | 1093 |
| iP8-10del/G11-13del | (passenger) GCAUUCA(£)(£)(£)CGUGCCUUAAAU ACCGUAAGU(£)(£)(£)GCACGGAAUU (guide) | 1097 | 1093 |
| iP7-10del/G11-14del | (passenger) GCAUUC(£)(£)(£)(£)CGUGCCUUAAAU ACCGUAAG(£)(£)(£)(£)GCACGGAAUU (guide) | 1097 | 1093 |
| iP7-11del/G10-14del | (passenger) GCAUUC(£)(£)(£)(£)(£)GUGCCUUAAAU ACCGUAAG(£)(£)(£)(£)(£)CACGGAAUU (guide) | 1178 | n/a |
| iP7-12del/G9-14del | (passenger) GCAUUC(£)(£)(£)(£)(£)(£)UGCCUUAAAU ACCGUAAG(£)(£)(£)(£)(£)(£)ACGGAAUU (guide) | 1109 | n/a |
| iP9-10_1x_c3/G11-12_1x_c3 | (passenger) GCAUUCAC(£)(£)(c3)CGUGCCUUAAAU ACCGUAAGUG(£)(£)(c3)GCACGGAAUU (guide) | 1179 | 1180 |
| iP8-10_1x_c3/G11-13_1x_c3 | (passenger) GCAUUCA(£)(£)(£)(c3)CGUGCCUUAAAU ACCGUAAGU(£)(£)(£)(c3)GCACGGAAUU (guide) | 1181 | 1182 |
| iP7-10_1x_c3/G11-14_1x_c3 | (passenger) GCAUUC(£)(£)(£)(£)(c3)CGUGCCUUAAAU ACCGUAAG(£)(£)(£)(£)(c3)GCACGGAAUU (guide) | 1183 | 1184 |
| iP7-11_1x_c3/G10-14_1x_c3 | (passenger) GCAUUC(£)(£)(£)(£)(£)(c3)GUGCCUUAAAU ACCGUAAG(£)(£)(£)(£)(£)(c3)CACGGAAUU (guide) | 1185 | 1186 |
| iP7-12_1x_c3/G9-14_1x_c3 | (passenger) GCAUUC(£)(£)(£)(£)(£)(£)(c3)UGCCUUAAAU ACCGUAAG(£)(£)(£)(£)(£)(£)(c3)ACGGAAUU (guide) | 1187 | 1188 |
| iP9-10_1x_c3/G11-12_1x_c6 | (passenger) GCAUUCAC(£)(£)(c3)CGUGCCUUAAAU ACCGUAAGUG(£)(£)(c6)GCACGGAAUU (guide) | 1179 | 1189 |
| iP8-10_1x_c3/G11-13_1x_c6 | (passenger) GCAUUCA(£)(£)(£)(c3)CGUGCCUUAAAU ACCGUAAGU(£)(£)(£)(c6)GCACGGAAUU (guide) | 1181 | 1190 |
| iP7-10_1x_c3/G11-14_1x_c6 | (passenger) GCAUUC(£)(£)(£)(£)(c3)CGUGCCUUAAAU ACCGUAAG(£)(£)(£)(£)(c6)GCACGGAAUU (guide) | 1183 | 1191 |
| iP7-11_1x_c3/G10-14_1x_c6 | (passenger) GCAUUC(£)(£)(£)(£)(£)(c3)GUGCCUUAAAU ACCGUAAG(£)(£)(£)(£)(£)(c6)CACGGAAUU (guide) | 1185 | 1192 |
| iP7-12_1x_c3/G9-14_1x_c6 | (passenger) GCAUUC(£)(£)(£)(£)(£)(£)(c3)UGCCUUAAAU ACCGUAAG(£)(£)(£)(£)(£)(£)(c6)ACGGAAUU (guide) | 1187 | 1193 |

Figure 17A:
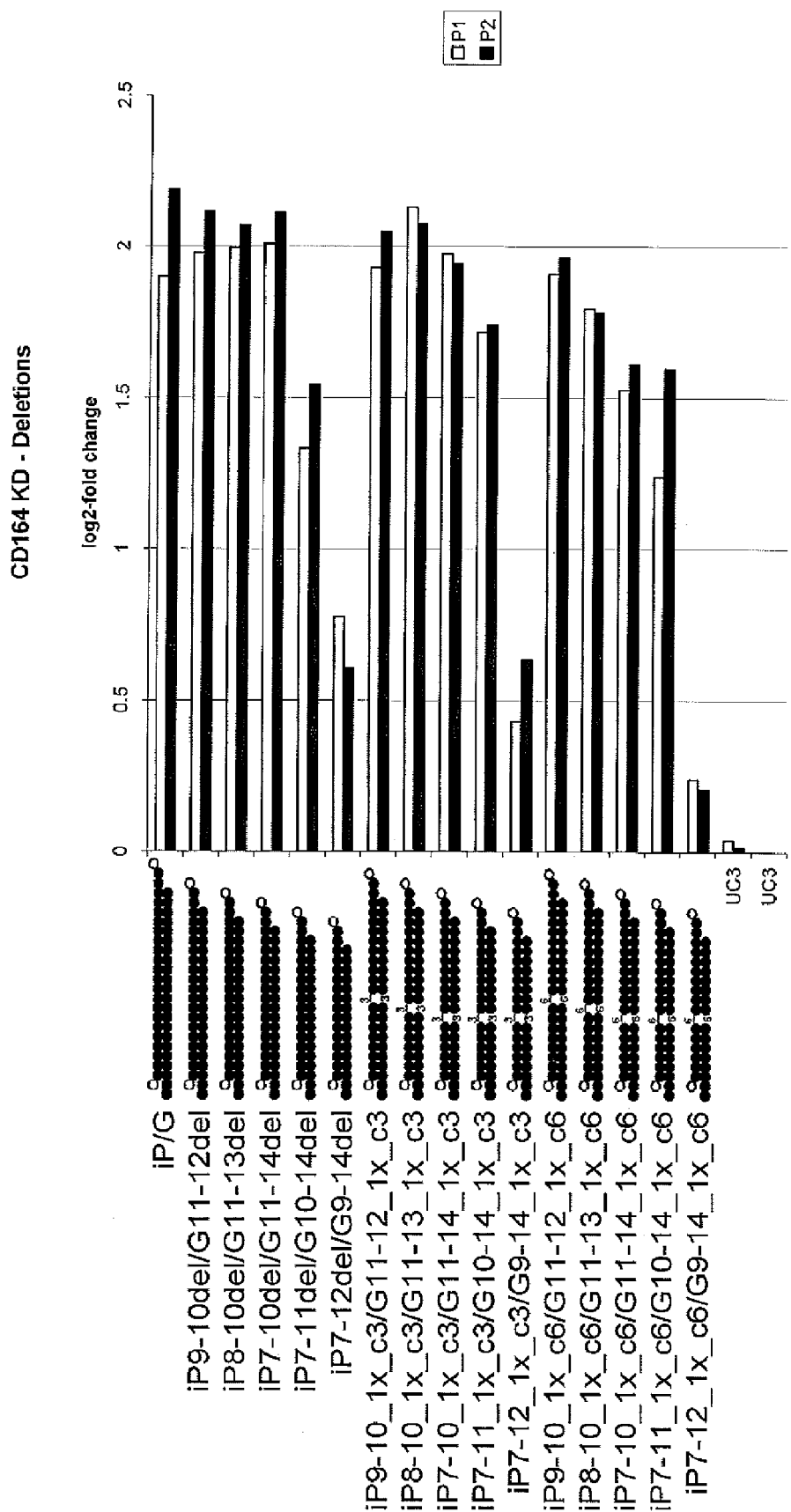
Figure 17B:
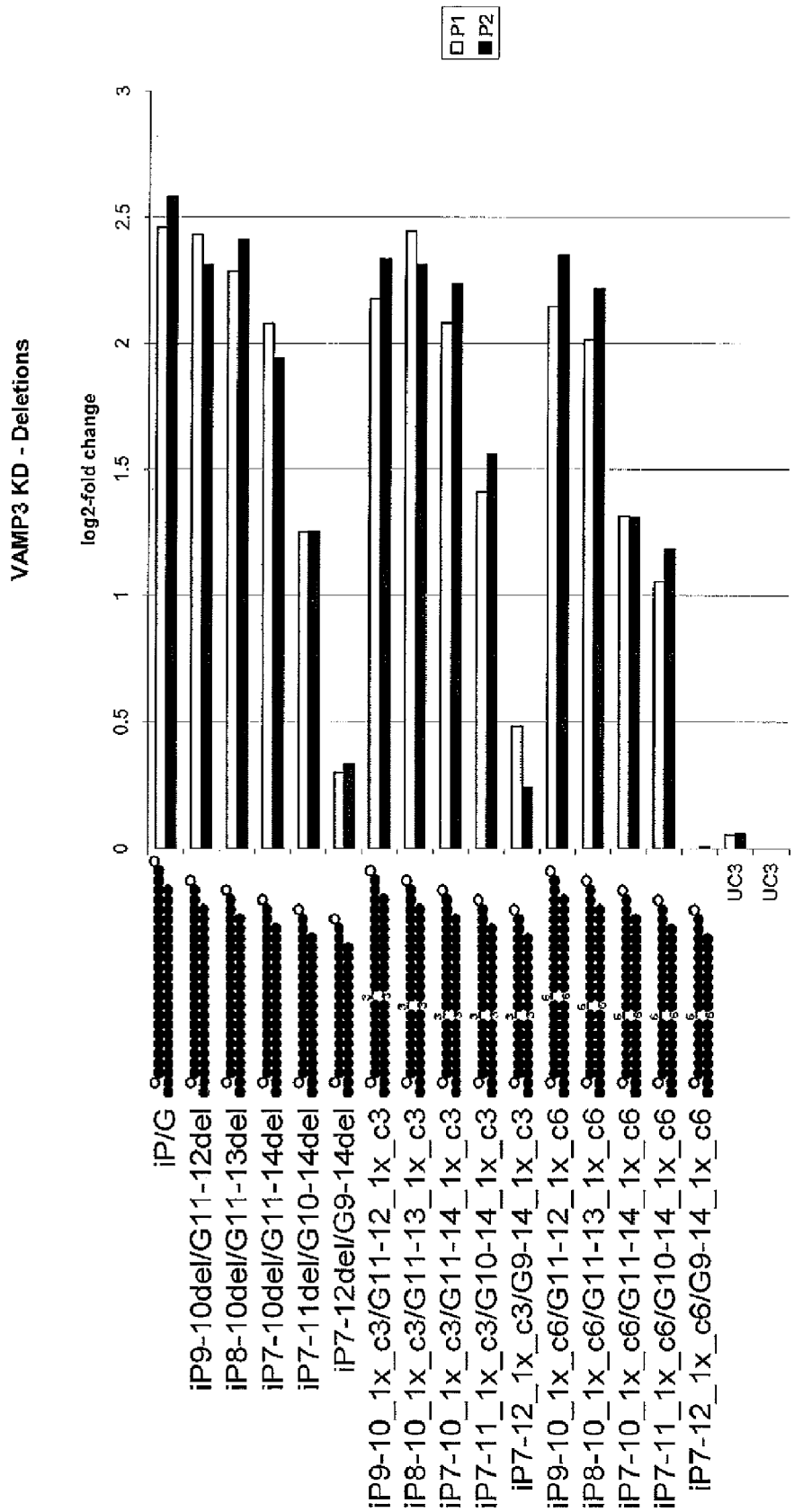
FIG. 17B illustrates knockdown of VAMP3 expression by these segmented microRNAs.

The results of this example are shown in FIGS. 17A and 17B. A number of the segmented miRNA mimetic constructs of this example achieved a significant knockdown effect as compared to the non-segmented duplex miR-124.

Example 8

Segmented miRNA Mimetics Comprising Small Substitutions

Segmented miRNA mimetics can be designed to include a discontinuity comprising non-nucleotide substitutions of the invention that occupy deleted nucleotide positions. In the following example, C3 alkyl linkers were used to substitute deleted nucleotide positions in both the guide and passenger strand of a miRNA mimetic. Likewise, substitution with other non-nucleotide linking moieties described herein or otherwise known in the art can be similarly performed by one of general skill following the methodologies herein.

Synthetic duplex mimetic of miR-124 and segmented miR-124 mimetic constructs (sequences shown in Table IX), comprising C3 substitutions, and a non-targeting control "Universal Control (UC3)" duplex were transfected into HCT-116 cells (wild-type) and cultured in McCoy's 5A Medium (Mediatech Inc.) supplemented with 10% fetal bovine serum and 1% penicillin-streptomycin. These cells were plated in 96-well culture plates at a density of 6000 cells/well 24 hours prior to transfection. Transfection was carried out using Opti-MEM I Reduced Serum Media (Gibco) and Lipofectamine RNAiMax (Invitrogen) with a final concentration of our miRNAs at 10 nM. Twenty-four hours after transfection, cells were washed with phosphate-buffered saline and processed using the TaqMan® Gene Expression Cells-to-CT™ Kit (Applied Biosystems/Ambion) to extract RNA, synthesize cDNA, and perform RT-qPCR using gene-specific probes (Applied Biosystems) on an ABI Prism 7900HT Sequence Detector.

Reverse transcription conditions were as follows: 60 minutes at 37° C. followed by 5 minutes at 95° C. RT-qPCR conditions were as follows: 2 minutes at 50° C., 10 minutes at 95° C., followed by 40 cycles of 15 seconds at 95° C. and 1 minute at 60° C. GUSB mRNA levels were used for data normalization. Knockdown of miR-124 targets was calculated as the two-fold change in target cDNA measured in experimentally-treated cells relative to the target cDNA measured in non-targeting control-treated cells.

The positions of c3 substitutions are shown in both the names and the sequences of the following table. C3 linkers are identified as "(c3)". Passenger strand sequences in Table IX are shown in 5' to 3' orientation and guide strand sequences are in 3' to 5' orientation.

TABLE IX

| Name | Sequence | SEQ ID NO(s). P | G |
|---|---|---|---|
| miR-124 (iP/G) | (passenger) GCAUUCACCGCGUGCCUUAAAU<br>ACCGUAAGUGGCGCACGGAAUU (guide) | 1092 | 1091 |
| iP22-22c3/G | (passenger) GCAUUCACCGCGUGCCUUAAA(c3)<br>ACCGUAAGUGGCGCACGGAAUU (guide) | 1194 | 1091 |
| iP21-21c3/G | (passenger) GCAUUCACCGCGUGCCUUAA(c3)U<br>ACCGUAAGUGGCGCACGGAAUU (guide) | 1195 | 1091 |
| iP20-20c3/G1-1c3 | (passenger) GCAUUCACCGCGUGCCUUA(c3)AU<br>ACCGUAAGUGGCGCACGGAAU(c3) (guide) | 1196 | 1216 |
| iP19-19c3/G2-2c3 | (passenger) GCAUUCACCGCGUGCCUU(c3)AAU<br>ACCGUAAGUGGCGCACGGAA(c3)U (guide) | 1197 | 1217 |
| iP18-18c3/G3-3c3 | (passenger) GCAUUCACCGCGUGCCU(c3)AAAU<br>ACCGUAAGUGGCGCACGGA(c3)UU (guide) | 1198 | 1218 |
| iP17-17c3/G4-4c3 | (passenger) GCAUUCACCGCGUGCC(c3)UAAAU<br>ACCGUAAGUGGCGCACGG(c3)AUU (guide) | 1199 | 1219 |
| iP16-16c3/G5-5c3 | (passenger) GCAUUCACCGCGUGC(c3)UUAAAU<br>ACCGUAAGUGGCGCACG(c3)AAUU (guide) | 1200 | 1220 |
| iP15-15c3/G6-6c3 | (passenger) GCAUUCACCGCGUG(c3)CUUAAAU<br>ACCGUAAGUGGCGCAC(c3)GAAUU (guide) | 1201 | 1221 |
| iP14-14c3/G7-7c3 | (passenger) GCAUUCACCGCGU(c3)CCUUAAAU<br>ACCGUAAGUGGCGCA(c3)GGAAUU (guide) | 1202 | 1222 |
| iP13-13c3/G8-8c3 | (passenger) GCAUUCACCGCG(c3)GCCUUAAAU<br>ACCGUAAGUGGCGC(c3)CGGAAUU (guide) | 1203 | 1223 |
| iP12-12c3/G9-9c3 | (passenger) GCAUUCACCGC(c3)UGCCUUAAAU<br>ACCGUAAGUGGCG(c3)ACGGAAUU (guide) | 1204 | 1224 |
| iP11-11c31G-10-10c3 | (passenger) GCAUUCACCG(c3)GUGCCUUAAAU<br>ACCGUAAGUGGC(c3)CACGGAAUU (guide) | 1205 | 1225 |
| 1P10-10c3/G11-11c3 | (passenger) GCAUUCACC(c3)CGUGCCUUAAAU<br>ACCGUAAGUGG(c3)GCACGGAAUU (guide) | 1206 | 1226 |
| iP9-9c3/G12-12c3 | (passenger) GCAUUCAC(c3)GCGUGCCUUAAAU<br>ACCGUAAGUG(c3)CGCACGGAAUU (guide) | 1207 | 1227 |
| iP8-8c3/G-13-13c3 | (passenger) GCAUUCA(c3)CGCGUGCCUUAAAU<br>ACCGUAAGU(c3)GCGCACGGAAUU (guide) | 1208 | 1228 |
| iP7-7c3/G14-14c3 | (passenger) GCAUUC(c3)CCGCGUGCCUUAAAU<br>ACCGUAAG(c3)GGCGCACGGAAUU (guide) | 1209 | 1229 |
| iP6-6e3/G15-15c3 | (passenger) GCAUU(c3)ACCGCGUGCCUUAAAU<br>ACCGUAA(c3)UGGCGCACGGAAUU (guide) | 1210 | 1230 |
| iP5-5c3/G16-16c3 | (passenger) GCAU(c3)CACCGCGUGCCUUAAAU<br>ACCGUA(c3)GUGGCGCACGGAAUU (guide) | 1211 | 1231 |
| iP4-4c3/G17-17c3 | (passenger) GCA(c3)UCACCGCGUGCCUUAAAU<br>ACCGU(c3)AGUGGCGCACGGAAUU (guide) | 1212 | 1232 |
| iP3-3c3/G18-18c3 | (passenger) GC(c3)UUCACCGCGUGCCUUAAAU<br>ACCG(c3)AAGUGGCGCACGGAAUU (guide) | 1213 | 1233 |
| iP2-2c3/G19-19c3 | (passenger) G(c3)AUUCACCGCGUGCCUUAAAU<br>ACC(c3)UAAGUGGCGCACGGAAUU (guide) | 1214 | 1234 |
| iP1-1c3/G20-20c3 | (passenger) (c3)CAUUCACCGCGUGCCUUAAAU<br>AC(c3)GUAAGUGGCGCACGGAAUU (guide) | 1215 | 1235 |

TABLE IX-continued

| Name | Sequence | SEQ ID NO(s). P | G |
|---|---|---|---|
| iP/G21-21c3 | (passenger) GCAUUCACCGCGUGCCUUAAAU<br>A(c3)CGUAAGUGGCGCACGGAAUU (guide) | 1092 | 1236 |

Figure 18A:
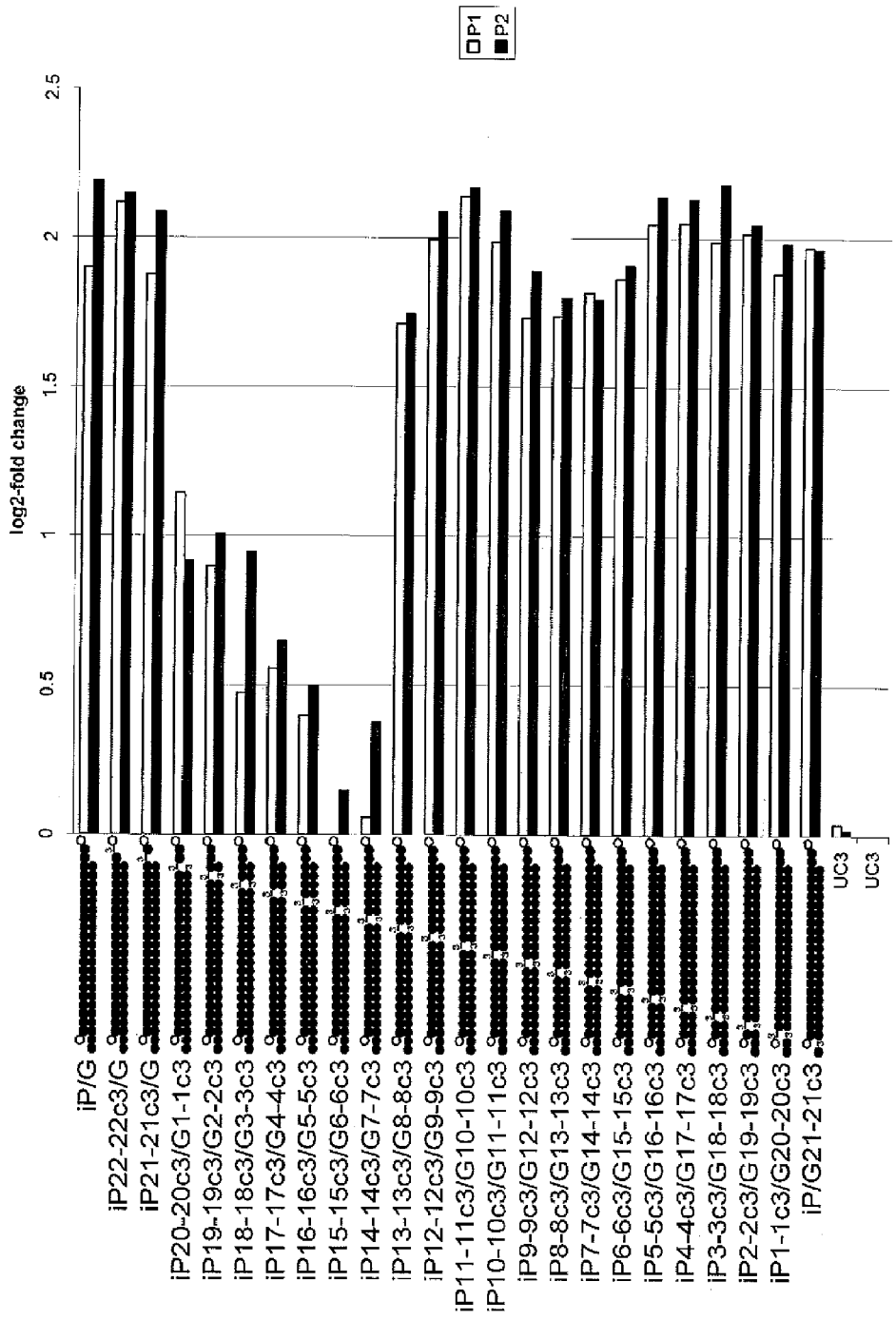
Figure 18B:
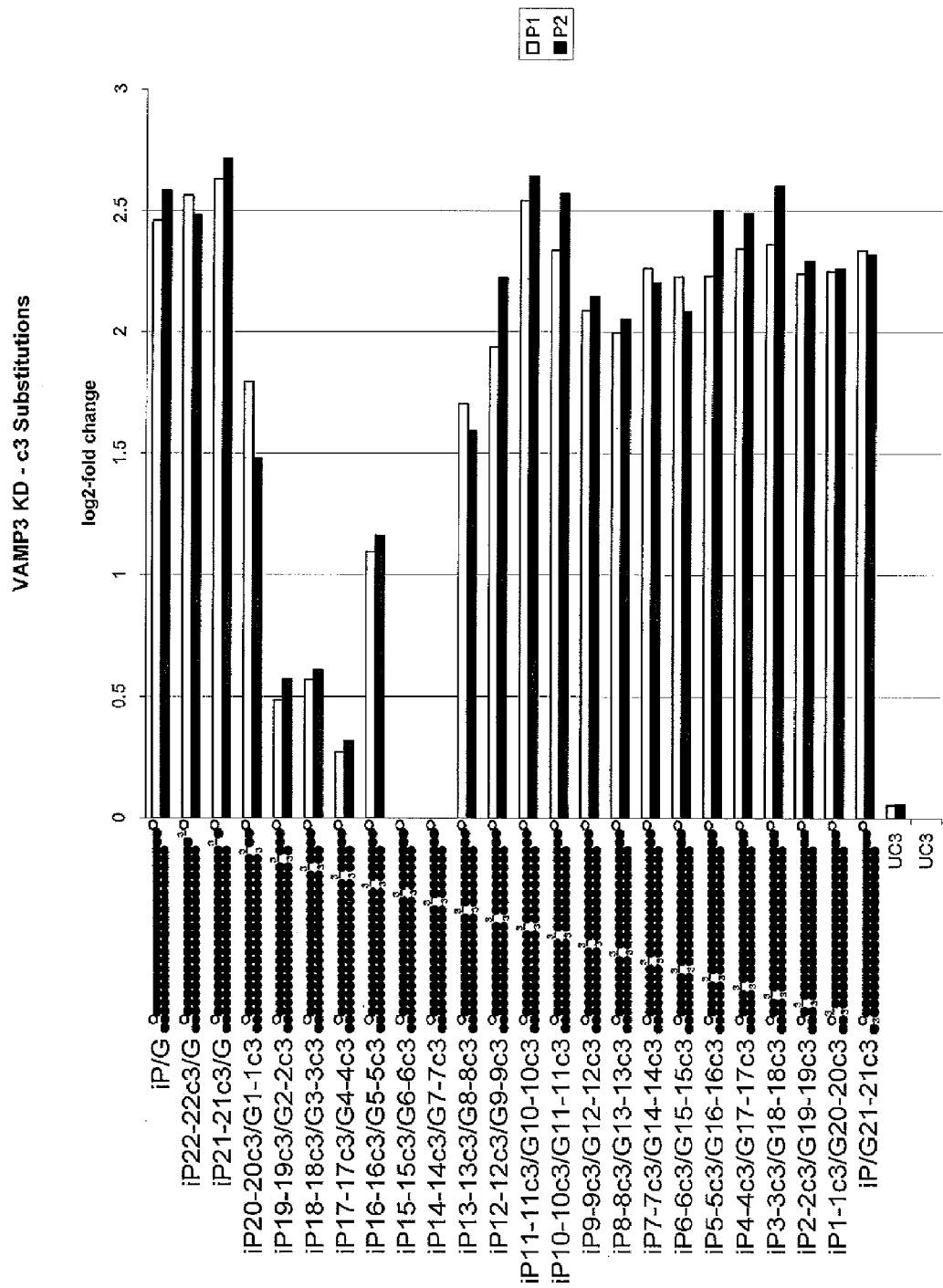
FIG. 18B illustrates knockdown of VAMP3 expression by these segmented microRNAs.

The results of this example are shown in FIGS. 18A and 18B. A number of the segmented miRNA mimetics of this example showed improved knockdown in comparison to the non-segmented duplex miR-124.

Example 9

Segmented miRNA Mimetics Comprising Larger Substitutions

Segmented miRNA mimetics can be designed to include a discontinuity comprising non-nucleotide substitutions of the invention that occupy deleted nucleotide positions. In the following example, C6 alkyl linkers were used to substitute deleted nucleotide positions in both the guide and passenger strand of a miRNA mimetic. Likewise, substitution with other larger non-nucleotide linking moieties described herein or otherwise known in the art can be similarly performed by one of general skill following the methodologies herein.

Synthetic duplex mimetic of miR-124 and segmented miR-124 mimetic constructs (sequences shown in Table X), comprising c6 substitutions, and a non-targeting control "Universal Control (UC3)" duplex were transfected into HCT-116 cells (wild-type) and cultured in McCoy's 5A Medium (Mediatech Inc.) supplemented with 10% fetal bovine serum and 1% penicillin-streptomycin. These cells were plated in 96-well culture plates at a density of 6000 cells/well 24 hours prior to transfection. Transfection was carried out using Opti-MEM I Reduced Serum Media (Gibco) and Lipofectamine RNAiMax (Invitrogen) with a final concentration of our miRNAs at 10 nM. Twenty-four hours after transfection, cells were washed with phosphate-buffered saline and processed using the TaqMan® Gene Expression Cells-to-CT™ Kit (Applied Biosystems/Ambion) to extract RNA, synthesize cDNA, and perform RT-qPCR using gene-specific probes (Applied Biosystems) on an ABI Prism 7900HT Sequence Detector.

Reverse transcription conditions were as follows: 60 minutes at 37° C. followed by 5 minutes at 95° C. RT-qPCR conditions were as follows: 2 minutes at 50° C., 10 minutes at 95° C., followed by 40 cycles of 15 seconds at 95° C. and 1 minute at 60° C. GUSB mRNA levels were used for data normalization. Knockdown of miR-124 targets was calculated as the two-fold change in target cDNA measured in experimentally-treated cells relative to the target cDNA measured in non-targeting control-treated cells.

The positions of c6 substitutions are shown in both the names and the sequences of the following table. C6 linkers are identified as "(c6)". Passenger strand sequences in Table X are shown in 5' to 3' orientation and guide strand sequences are in 3' to 5' orientation.

TABLE X

| Name | Sequence | SEQ ID NO(s). P | G |
|---|---|---|---|
| miR-124 (iP/G) | (passenger) GCAUUCACCGCGUGCCUUAAAU<br>ACCGUAAGUGGCGCACGGAAUU (guide) | 1092 | 1091 |
| iP22-22c61G | (passenger) GCAUUCACCGCGUGCCUUAAA(c6)<br>ACCGUAAGUGGCGCACGGAAUU (guide) | 1237 | 1091 |
| iP21-21c6/G | (passenaer) GCAUUCACCGCGUGCCUUAA(c6)U<br>ACCGUAAGUGGCGCACGGAAUU (guide) | 1238 | 1091 |
| iP20-20c6/G1-1c6 | (passenger) GCAUUCACCGCGUGCCUUA(c6)AU<br>ACCGUAAGUGGCGCACGGAAU(c6) (guide) | 1239 | 1259 |
| iP19-19c6/G2-2c6 | (passenger) GCAUUCACCGCGUGCCUU(c6)AAU<br>ACCGUAAGUGGCGCACGGAA(c6)U (guide) | 1240 | 1260 |
| iP18-18c6/G3-3c6 | (passenger) GCAUUCACCGCGUGCCU(c6)AAAU<br>ACCGUAAGUGGCGCACGGA(c6)UU (guide) | 1241 | 1261 |
| iP17-17c6/G4-4c6 | (passenger) GCAUUCACCGCGUGCC(c6)UAAAU<br>ACCGUAAGUGGCGCACGG(c6)AUU (guide) | 1242 | 1262 |
| iP16-16c6/G5-5c6 | (passenger) GCAUUCACCGCGUGC(c6)UUAAAU<br>ACCGUAAGUGGCGCACG(c6)AAUU (guide) | 1243 | 1263 |
| iP15-15c6/G6-6c6 | (passenger) GCAUUCACCGCGUG(c6)CUUAAAU<br>ACCGUAAGUGGCGCAC(c6)GAAUU (guide) | 1244 | 1264 |

TABLE X-continued

| Name | Sequence | SEQ ID NO(s). P | SEQ ID NO(s). G |
|---|---|---|---|
| iP14-14c6/G7-7c6 | (passenger) GCAUUCACCGCGU(c6)CCUUAAAU ACCGUAAGUGGCGCA(c6)GGAAUU (guide) | 1245 | 1265 |
| iP13-13c6/G8-8c6 | (passenger) GCAUUCACCGCG(c6)GCGAUAAAU ACCGUAAGUGGCGC(c6)CGGAAUU (guide) | 1246 | 1266 |
| iP12-12c6/G9-9c6 | (passenger) GCAUUCACCGC(c6)UGCCUUAAAU ACCGUAAGUGGCG(c6)ACGGAAUU (guide) | 1247 | 1267 |
| iP11-11c6/G10-10c6 | (passenger) GCAUUCACCG(c6)GUGCCUUAAAU ACCGUAAGUGGC(c6)CACGGAAUU (guide) | 1248 | 1268 |
| 1P10-10c6/G11-11c6 | (passenger) GCAUCACC(c6)CGUGCCUUAAAUU ACCGUAAGUGG(c6)GCACGGAAUU (guide) | 1249 | 1269 |
| iP9-9c6/G12-12c6 | (passenger) GCAUUCAC(c6)GCGUGCCUUAAAU ACCGUAAGUG(c6)CGCACGGAAUU (guide) | 1250 | 1270 |
| iP8-8c6/G13-13c6 | (passenger) GCAUUCA(c6)CGCGUGCCUUAAAU ACCGUAAGU(c6)GCGCACGGAAUU (guide) | 1251 | 1271 |
| iP7-7c6/G14-14c6 | (passenger) GCAUUC(c6)CCGCGUGCCUUAAAU ACCGUAAG(c6)GGCGCACGGAAUU (guide) | 1252 | 1272 |
| iP6-6c6/G15-15c6 | (passenger) GCAUU(c6)ACCGCGUGCCUUAAAU ACCGUAA(c6)UGGCGCACGGAAUU (guide) | 1253 | 1273 |
| iP5-5c6/G16-16c6 | (passenger) GCAU(c6)CACCGCGUGCCUUAAAU ACCGUA(c6)GUGGCGCACGGAAUU (guide) | 1254 | 1274 |
| iP4-4c6/G17-17c6 | (passenger) GCA(c6)UCACCGCGUGCCUUAAAU ACCGU(c6)AGUGGCGCACGGAAUU (guide) | 1255 | 1275 |
| iP3-3c6/G18-18c6 | (passenger) GC(c6)UUCACCGCGUGCCUUAAAU ACCG(c6)AAGUGGCGCACGGAAUU (guide) | 1256 | 1276 |
| iP2-2c6/G19-19c6 | (passenger) G(c6)AUUCACCGCGUGCCUUAAAU ACC(c6)UAAGUGGCGCACGGAAUU (guide) | 1257 | 1277 |
| iP1-1c6/G20-20c6 | (passenger) (c6)CAUUCACCGCGUGCCUUAAAU AC(c6)GUAAGUGGCGCACGGAAUU (guide) | 1258 | 1278 |
| iP/G21-21c6 | (passenger) GCAUUCACCGCGUGCCUUAAAUU A(c6)CGUAAGUGGCGCACGGAAUU (guide) | 1092 | 1279 |

Figure 19A:
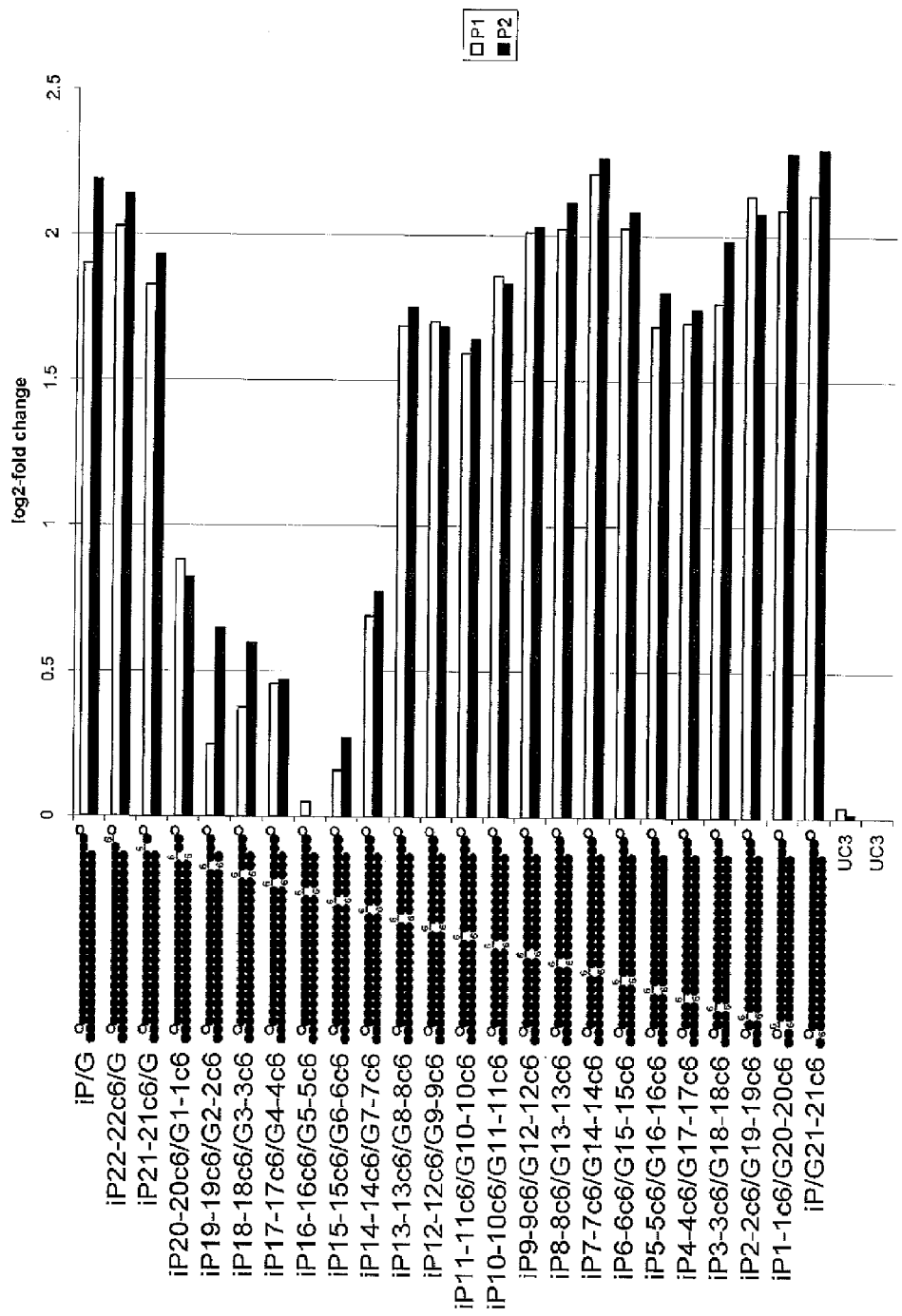
Figure 19B:
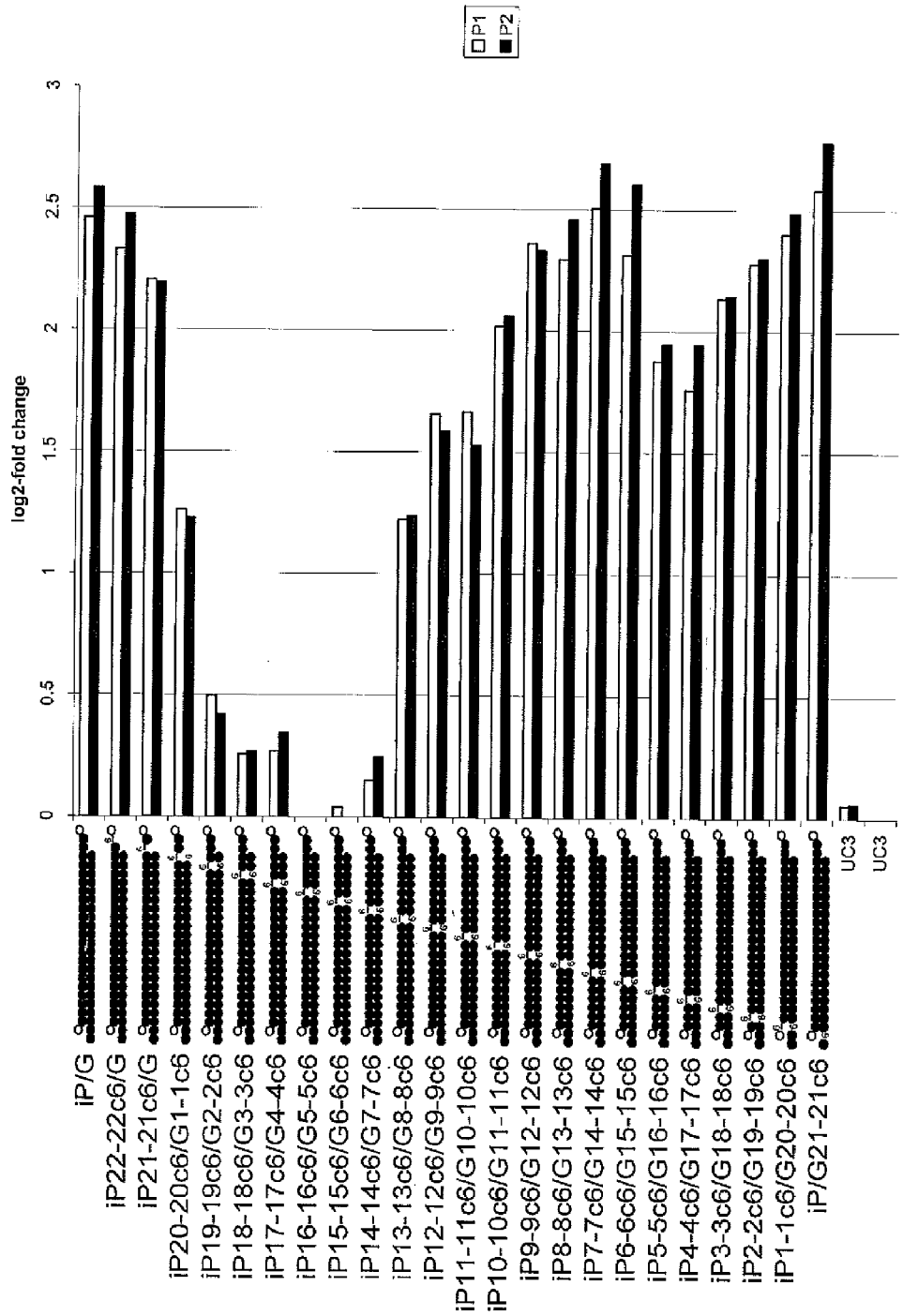
FIG. 19B illustrates knockdown of VAMP3 expression by these segmented microRNAs.

The results of this example are indicated in FIGS. 19A and 19B. A number of the segmented miRNA mimetics of this example showed increased knockdown in comparison to the non-segmented duplex miR-124.

Example 10

Segmented miRNA Mimetics Comprising Non-Nucleotide Insertions

Segmented miRNA mimetics can be designed to include a discontinuity comprising non-nucleotide insertions of the invention. In the following example, both small (C3) and larger (C6) alkyl moieties were used to connect segmented positions in both the guide and passenger strand of a miRNA mimetic. Likewise, insertions with other non-nucleotide linking moieties described herein or otherwise known in the art can be similarly performed by one of general skill following the methodologies herein.

Synthetic duplex mimetic of miR-124 and segmented miR-124 mimetic constructs (sequences shown in Table XI), comprising c3 and c6 insertions, and a non-targeting control "Universal Control (UC3)" duplex were transfected into HCT-116 cells (wild-type) and cultured in McCoy's 5A Medium (Mediatech Inc.) supplemented with 10% fetal bovine serum and 1% penicillin-streptomycin. These cells were plated in 96-well culture plates at a density of 6000 cells/well 24 hours prior to transfection. Transfection was carried out using Opti-MEM I Reduced Serum Media (Gibco) and Lipofectamine RNAiMax (Invitrogen) with a final concentration of our miRNAs at 10 nM. Twenty-four hours after transfection, cells were washed with phosphate-buffered saline and processed using the TaqMan® Gene Expression Cells-to-CT™ Kit (Applied Biosystems/Ambion) to extract RNA, synthesize cDNA, and perform RT-qPCR using gene-specific probes (Applied Biosystems) on an ABI Prism 7900HT Sequence Detector.

Reverse transcription conditions were as follows: 60 minutes at 37° C. followed by 5 minutes at 95° C. RT-qPCR conditions were as follows: 2 minutes at 50° C., 10 minutes at 95° C., followed by 40 cycles of 15 seconds at 95° C. and 1 minute at 60° C. GUSB mRNA levels were used for data normalization. Knockdown of miR-124 targets was calculated as the two-fold change in target cDNA measured in experimentally-treated cells relative to the target cDNA measured in non-targeting control-treated cells.

The positions of c3 and c6 insertions are shown in both the names and the sequences of the following table. C3 and C6 linkers are identified as "(c3)" and "(c6)", respectively. Passenger strand sequences in Table XI are shown in 5' to 3' orientation and guide strand sequences are in 3' to 5' orientation.

TABLE XI

| Name | Sequence | SEQ ID NO(s). P | G |
|---|---|---|---|
| miR-124 (iP/G) | (passenger) GCAUUCACCGCGUGCCUUAAAU ACCGUAAGUGGCGCACGGAAUU (guide) | 1092 | 1091 |
| iP/G1insertc6 | (passenger) GCAUUCACCGCGUGCCUUAAAU ACCGUAAGUGGCGCACGGAAU(c6)U (guide) | 1092 | 1280 |
| iP/G2insertc6 | (passenger) GCAUUCACCGCGUGCCUUAAAU ACCGUAAGUGGCGCACGGAA(c6)UU (guide) | 1092 | 1281 |
| iP/G3insertc6 | (passenger) GCAUUCACCGCGUGCCUUAAAU ACCGUAAGUGGCGCACGGA(c6)AUU (guide) | 1092 | 1282 |
| iP/G4insertc6 | (Passenger) GCAUUCACCGCGUGCCUAAAU ACCGUAAGUGGCGCACGG(c6)AAUU (guide) | 1092 | 1283 |
| iP/G5insertc6 | (passenger) GCAUUCACCGCGUGCCUUAAAU ACCGUAAGUGGCGCACG(c6)GAAUU (guide) | 1092 | 1284 |
| iP/G6insertc6 | (passenger) GCAUUCACCGCGUGCCUUAAAU ACCGUAAGUGGCGCAC(c6)GGAAUU (guide) | 1092 | 1285 |
| iP/G7insertc6 | (passenger) GCAUUCACCGCGUGCCUUAAAU ACCGUAAGUGGCGCA(c6)CGGAAUU (guide) | 1092 | 1286 |
| iP/G8insertc6 | (passenger) GCAUUCACCGCGUGCCUUAAAU ACCGUAAGUGGCGC(c6)ACGGAAUIT (guide) | 1092 | 1287 |
| iP/G9insertc6 | (passenger) GCAUUCACCGCGUGCCUUAAAU ACCGUAAGUGGCG(c6)CACGGAAUU (guide) | 1092 | 1288 |
| iP/G10insertc6 | (passenger) GCAUUCACCGCGUGCCUUAAAU ACCGUAAGUGGC(c6)GCACGGAAUU (guide) | 1092 | 1289 |
| iP/G11insertc6 | (passenger) GCAUUCACCGCGUGCCUUAAAU ACCGUAAGUGG(c6)CGCACGGAAUU (guide) | 1092 | 1290 |
| iP/G12insertc6 | (passenger) GCAUUCACCGCGUGCCUUAAAU ACCGUAAGUG(c6)GCGCACGGAAUU (guide) | 1092 | 1291 |
| iP/G13insertc6 | (passenger) GCAUUCACCGCGUGCCUUAAAU ACCGUAAGU(c6)GGCGCACGGAAUU (guide) | 1092 | 1292 |
| iP/G14insertc6 | (Passenger) GCAUUCACCGCGUGCCUAAAU ACCGUAAG(c6)UGGCGCACGGAAUU (guide) | 1092 | 1293 |
| iP/G15insertc6 | (passenger) GCAUUCACCGCGUGCCUUAAAU ACCGUAA(c6)GUGGCGCACGGAAUU (guide) | 1092 | 1294 |
| iP/G16insertc6 | (passenger) GCAUUCACCGCGUGCCUUAAAU ACCGUA(c6)AGUGGCGCACGGAAUU (guide) | 1092 | 1295 |
| iP/G17insertc6 | (passenger) GCAUUCACCGCGUGCCUUAAAU ACCGU(c6)AAGUGGCGCACGGAAUU (guide) | 1092 | 1296 |
| iP/G18insertc6 | (passenger) GCAUUCACCGCGUGCCUUAAAU ACCG(c6)UAAGUGGCGCACGGAAUU (guide) | 1092 | 1297 |
| iP/G19insertc6 | (passenger) GCAUUCACCGCGUGCCUUAAAU ACC(c6)GUAAGUGGCGCACGGAAUU (guide) | 1092 | 1298 |
| iP/G20insertc6 | (passenger) GCAUUCACCGCGUGCCUUAAAU AC(c6)CGUAAGUGGCGCACGGAAUU (guide) | 1092 | 1299 |
| iP/G21insertc6 | (passenger) GCAUUCACCGCGUGCCUUAAAU A(c6)CCGUAAGUGGCGCACGGAAUU (guide) | 1092 | 1300 |
| iP10insertc6/G | (passenger) GCAUUCACCG(c6)CGUGCCUU AAAUACCGUAAGUGGCGCACGGAAUU (guide) | 1301 | 1091 |

TABLE XI-continued

| Name | Sequence | SEQ ID NO(s). P | G |
|---|---|---|---|
| iP9insertc6/G | (passenger) GCAUUCACC(c6)GCGUGCCUU AAAUACCGUAAGUGGCGCACGGAAUU (guide) | 1302 | 1091 |
| iP8insertc6/G | (passenger) GCAUUCAC(c6)CGCGUGCCUU AAAUACCGUAAGUGGCGCACGGAAUU (guide) | 1303 | 1091 |
| iP7insertc6/G | (passenger) GCAUUCA(c6)CCGCGUGCCUU AAAUACCGUAAGUGGCGCACGGAAUU (guide) | 1304 | 1091 |
| iP6insertc6/G | (passenger) GCAUUC(c6)ACCGCGUGCCUU AAAUACCGUAAGUGGCGCACGGAAUU (guide) | 1305 | 1091 |
| iP10insertc6/ G10insertc6 | (passenger) GCAUUCACCG(c6)CGUGCCUUAA AUACCGUAAGUGGC(c6)GCACGGAAUU (guide) | 1301 | 1289 |
| iP9insertc6/ G11insertc6 | (passenger) GCAUUCAC(c6)CGCGUGCCUUAA AUACCGUAAGUG(c6)GCGCACGGAAUU (guide) | 1302 | 1290 |
| iP8insertc6/ G12insertc6 | (passenger) GCAUUCA(c6)CCGCGUGCCUUAA AUACCGUAAGU(c6)GGCGCACGGAAUU (guide) | 1303 | 1291 |
| iP7insertc6/ G13insertc6 | (passenger) GCAUUC(c6)ACCGCGUGCCUUAA AUACCGUAAG(c6)UGGCGCACGGAAUU (guide) | 1304 | 1292 |
| iP6insertc6/ G14insertc6 | (passenger) GCAUU(c6)CACCGCGUGCCUUAA AUACCGUAA(c6)GUGGCGCACGGAAUU (guide) | 1305 | 1293 |
| iP10insertc3/ G10insertc3 | (passenger) GCAUUCACCG(c3)CGUGCCUUAA AUACCGUAAGUGGC(c3)GCACGGAAUU (guide) | 1306 | 1307 |

Figure 20A:
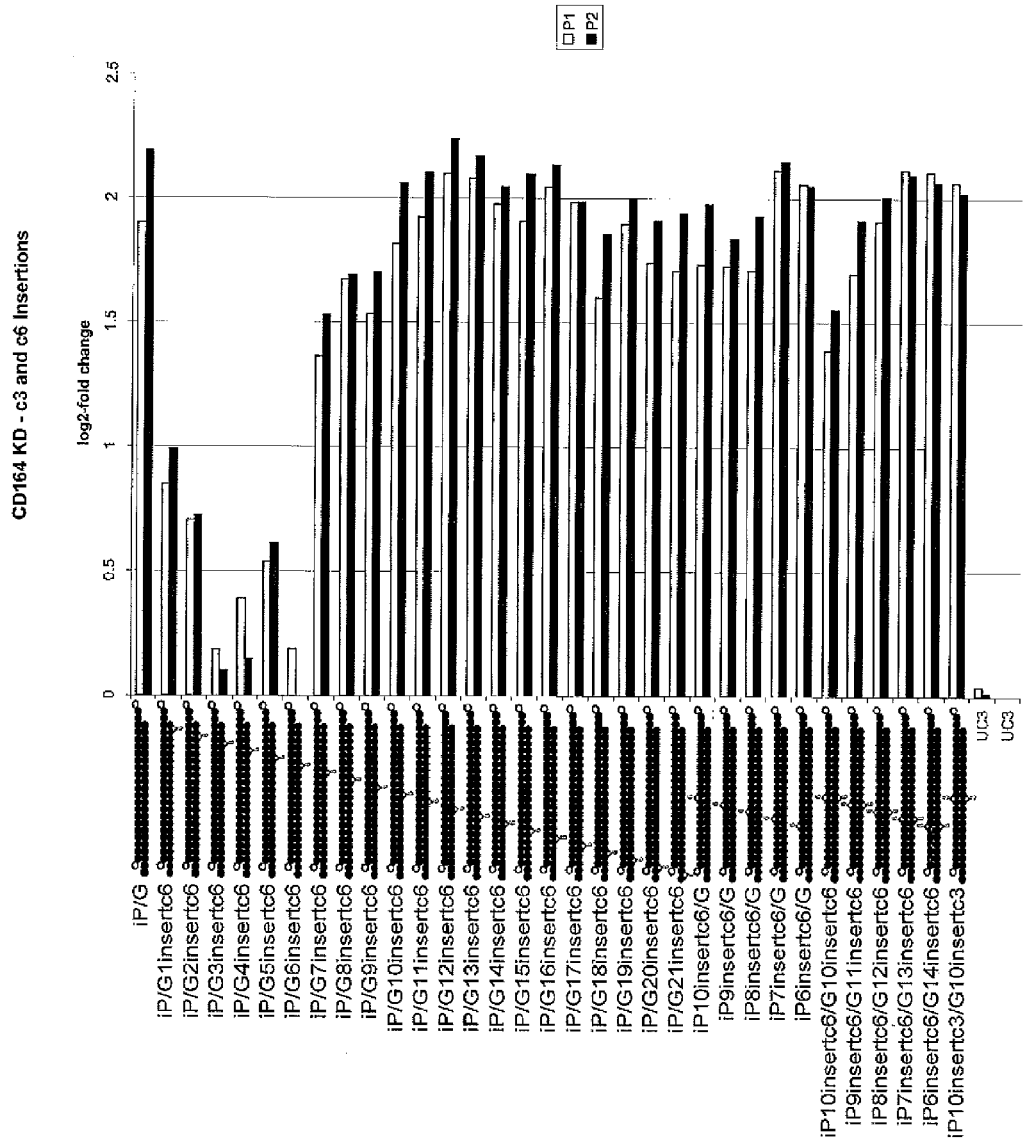
Figure 20B:
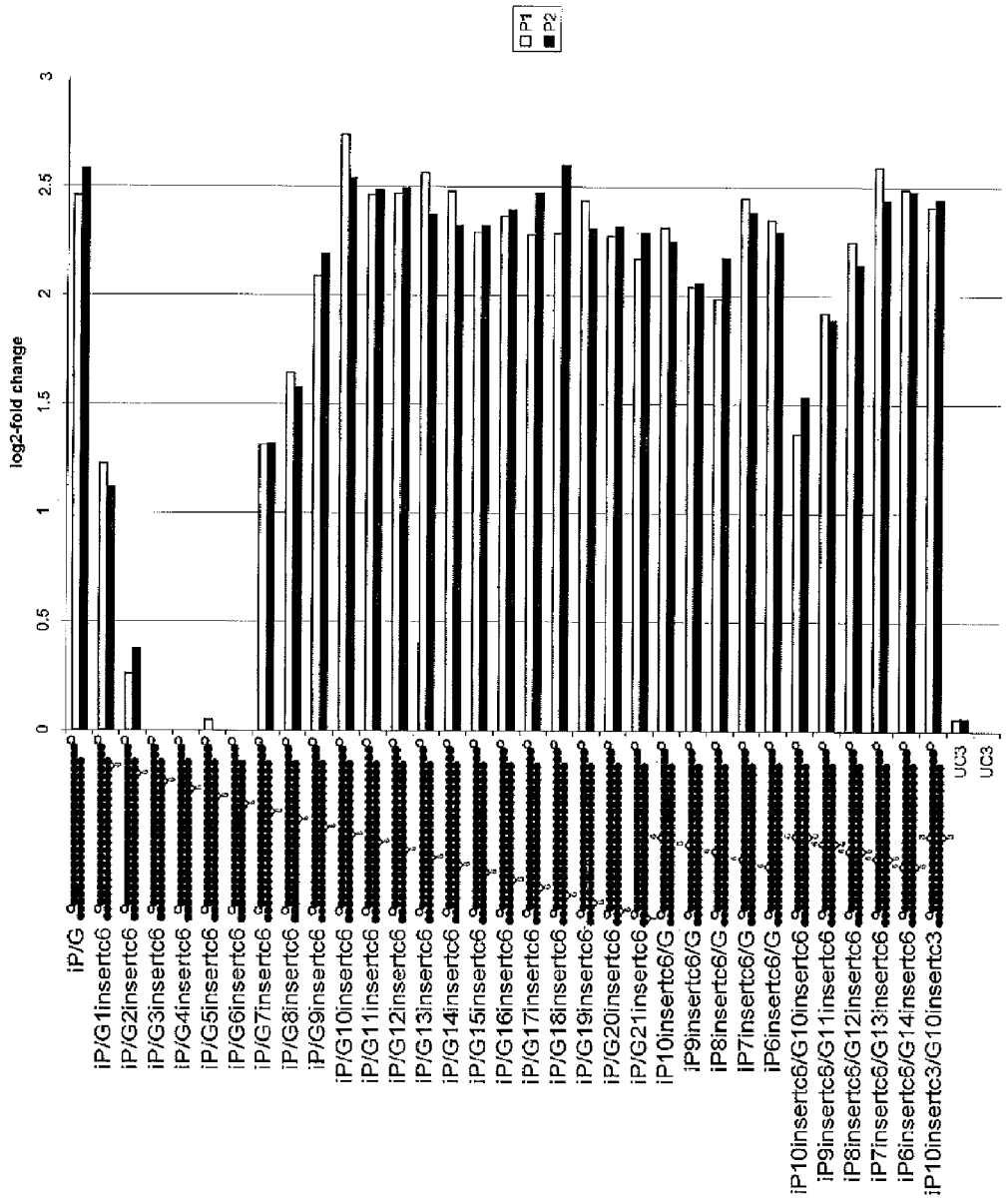
FIG. 20B illustrates knockdown of VAMP3 expression by these segmented microRNAs.

The results of this example are indicated in FIGS. 20A and 20B. A number of the segmented miRNA mimetics of this example showed increased knockdown in comparison to the non-segmented duplex miR-124.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

What is claimed is:

1. A double-stranded segmented miRNA mimetic molecule represented by Formula IV:

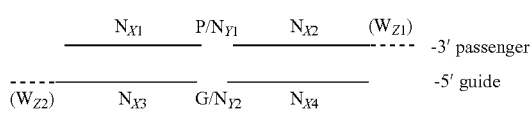

wherein
(a) the molecule comprises a passenger strand and a guide strand where each line and its adjacent "N" represent a contiguous stretch of nucleotides, each of "X1," "X2," "X3" and "X4" represents the number of nucleotides in each stretch, "G/N" represents a discontinuity in the guide strand, "P/N" represents a discontinuity in the passenger strand, "Y1" represents a number of nucleotide positions in the passenger strand discontinuity, "Y2" represents a number of nucleotide positions in the guide strand discontinuity, and each group of dashed lines "-----" and its adjacent "(W)" represents a terminal overhang that is optionally present, and each of "Z1" and "Z2" represents the number of overhanging nucleotides;
(b) X1 and X2 are independently integers from 2 to 24, Y1 is an integer from 0 to 6, provided that the sum of X1, X2 and Y1 is an integer from 16 to 26, X3 is an integer from 2 to 20, X4 is an integer from 6 to 24, Y2 is an integer from 0 to 6, provided that the sum of X3, X4 and Y2 is an integer from 16 to 26; Z1 and Z2 are independently integers from 0 to 4;
(c) $N_{X4}$ comprises sequence having at least 6 contiguous nucleotides of the seed sequence of a miRNA sequence having any of SEQ ID NOs: 1-1090;
(d) $N_{X3}$ and $N_{X4}$ together comprise sequence having at least 50% homology to the miRNA sequence; and
(e) $N_{X1}$ and $N_{X2}$ together comprise sequence having at least 50% complementarity to the miRNA sequence,
wherein each of G/N and P/N independently comprises a nick, gap, non-nucleotide substitution, or non-nucleotide insertion.

2. The miRNA mimetic molecule of claim 1, wherein G/N comprises a nick or gap in the guide strand.

3. The miRNA mimetic molecule of claim 1, wherein P/N comprises a nick or gap in the passenger strand.

4. The miRNA mimetic molecule of claim 1, wherein G/N and P/N are the same.

5. The miRNA mimetic molecule of claim 1, wherein G/N and P/N are different.

6. The miRNA mimetic molecule of claim 1, wherein $N_{X4}$ comprises sequence having at least 7 contiguous nucleotides of the seed sequence of the miRNA.

7. The miRNA mimetic molecule of claim 1, wherein $N_{X4}$ comprises sequence having at least 8 contiguous nucleotides of the seed sequence of the miRNA.

8. The miRNA mimetic molecule of claim 1, wherein $N_{X3}$ and $N_{X4}$ together comprise sequence having at least 60, 70, 80, or 90% homology to the miRNA sequence.

9. The miRNA mimetic molecule of claim 1, wherein $N_{X1}$ and $N_{X2}$ together comprise sequence having at least 60, 70, 80, or 90% complementarity to the miRNA sequence.

10. A composition comprising the miRNA mimetic molecule of claim 1 and a pharmaceutically acceptable carrier, diluent, excipient, adjuvant, emulsifier, buffer, stabilizer, or preservative.

11. The miRNA mimetic molecule of claim 1, wherein the molecule comprises one or more 2'-deoxy modified nucleotides, 2'-O-methyl modified nucleotides, 2'-deoxy-2'-fluoro modified nucleotides or universal base modified nucleotides, or a combination thereof.

12. The miRNA mimetic molecule of claim 1, wherein the molecule comprises one or more phosphorothioate internucleotide linkages.

13. The miRNA mimetic molecule of claim 1, wherein the molecule comprises one or more of a ribonucleotide or a deoxyribonucleotide, or a combination thereof, that is chemically-modified at a nucleic acid sugar, base, or backbone.

14. The miRNA mimetic molecule of claim 1, wherein the molecule comprises one or more locked nucleic acid (LNA) nucleotides.

15. The miRNA mimetic molecule of claim 1, wherein the molecule comprises a ligand.

16. The miRNA mimetic molecule of claim 15, wherein the ligand is a galactose, a galactosamine, a folate, or a cholesterol.

17. The miRNA mimetic molecule of claim 1, wherein Z1 and Z2 are independently 1, 2, or 3.

18. The miRNA mimetic molecule of claim 1, wherein G/N comprises a non-nucleotide substitution or non-nucleotide insertion in the guide strand.

19. The miRNA mimetic molecule of claim 1, wherein P/N comprises a non-nucleotide substitution or non-nucleotide insertion in the passenger stand.

\* \* \* \* \*

SEQUENCE LISTING

```
<160> NUMBER OF SEQ ID NOS: 1310

<210> SEQ ID NO 1
<211> LENGTH: 22
<212> TYPE: RNA
<213> ORGANISM: Homo sapiens

<400> SEQUENCE: 1
ugagguagua gguuguauag uu                                              22

<210> SEQ ID NO 2
<211> LENGTH: 21
<212> TYPE: RNA
<213> ORGANISM: Homo sapiens

<400> SEQUENCE: 2
cuauacaauc uacugucuuu c                                               21

<210> SEQ ID NO 3
<211> LENGTH: 22
<212> TYPE: RNA
<213> ORGANISM: Homo sapiens
```

```
<400> SEQUENCE: 3
cuguacagcc uccuagcuuu cc                                          22

<210> SEQ ID NO 4
<211> LENGTH: 22
<212> TYPE: RNA
<213> ORGANISM: Homo sapiens

<400> SEQUENCE: 4
ugagguagua gguugugugg uu                                          22

<210> SEQ ID NO 5
<211> LENGTH: 22
<212> TYPE: RNA
<213> ORGANISM: Homo sapiens

<400> SEQUENCE: 5
cuauacaacc uacugccuuc cc                                          22

<210> SEQ ID NO 6
<211> LENGTH: 22
<212> TYPE: RNA
<213> ORGANISM: Homo sapiens

<400> SEQUENCE: 6
ugagguagua gguuguaugg uu                                          22

<210> SEQ ID NO 7
<211> LENGTH: 22
<212> TYPE: RNA
<213> ORGANISM: Homo sapiens

<400> SEQUENCE: 7
uagaguuaca cccugggagu ua                                          22

<210> SEQ ID NO 8
<211> LENGTH: 22
<212> TYPE: RNA
<213> ORGANISM: Homo sapiens

<400> SEQUENCE: 8
agagguagua gguugcauag uu                                          22

<210> SEQ ID NO 9
<211> LENGTH: 22
<212> TYPE: RNA
<213> ORGANISM: Homo sapiens

<400> SEQUENCE: 9
cuauacgacc ugcugccuuu cu                                          22

<210> SEQ ID NO 10
<211> LENGTH: 22
<212> TYPE: RNA
<213> ORGANISM: Homo sapiens

<400> SEQUENCE: 10
ugagguagga gguuguauag uu                                          22

<210> SEQ ID NO 11
<211> LENGTH: 22
<212> TYPE: RNA
```

```
<213> ORGANISM: Homo sapiens

<400> SEQUENCE: 11
cuauacggcc uccuagcuuu cc                                              22

<210> SEQ ID NO 12
<211> LENGTH: 22
<212> TYPE: RNA
<213> ORGANISM: Homo sapiens

<400> SEQUENCE: 12
ugagguagua gauuguauag uu                                              22

<210> SEQ ID NO 13
<211> LENGTH: 22
<212> TYPE: RNA
<213> ORGANISM: Homo sapiens

<400> SEQUENCE: 13
cuauacaauc uauugccuuc cc                                              22

<210> SEQ ID NO 14
<211> LENGTH: 22
<212> TYPE: RNA
<213> ORGANISM: Homo sapiens

<400> SEQUENCE: 14
cuauacaguc uacugucuuu cc                                              22

<210> SEQ ID NO 15
<211> LENGTH: 22
<212> TYPE: RNA
<213> ORGANISM: Homo sapiens

<400> SEQUENCE: 15
uagcagcaca uaaugguuug ug                                              22

<210> SEQ ID NO 16
<211> LENGTH: 22
<212> TYPE: RNA
<213> ORGANISM: Homo sapiens

<400> SEQUENCE: 16
caggccauau ugugcugccu ca                                              22

<210> SEQ ID NO 17
<211> LENGTH: 22
<212> TYPE: RNA
<213> ORGANISM: Homo sapiens

<400> SEQUENCE: 17
uagcagcacg uaaauauugg cg                                              22

<210> SEQ ID NO 18
<211> LENGTH: 22
<212> TYPE: RNA
<213> ORGANISM: Homo sapiens

<400> SEQUENCE: 18
ccaguauuaa cugugcugcu ga                                              22

<210> SEQ ID NO 19
<211> LENGTH: 23
```

```
<212> TYPE: RNA
<213> ORGANISM: Homo sapiens

<400> SEQUENCE: 19
caaagugcuu acagugcagg uag                                            23

<210> SEQ ID NO 20
<211> LENGTH: 22
<212> TYPE: RNA
<213> ORGANISM: Homo sapiens

<400> SEQUENCE: 20
acugcaguga aggcacuugu ag                                             22

<210> SEQ ID NO 21
<211> LENGTH: 23
<212> TYPE: RNA
<213> ORGANISM: Homo sapiens

<400> SEQUENCE: 21
uaaggugcau cuagugcaga uag                                            23

<210> SEQ ID NO 22
<211> LENGTH: 23
<212> TYPE: RNA
<213> ORGANISM: Homo sapiens

<400> SEQUENCE: 22
acugcccuaa gugcuccuuc ugg                                            23

<210> SEQ ID NO 23
<211> LENGTH: 22
<212> TYPE: RNA
<213> ORGANISM: Homo sapiens

<400> SEQUENCE: 23
aguuuugcau aguugcacua ca                                             22

<210> SEQ ID NO 24
<211> LENGTH: 23
<212> TYPE: RNA
<213> ORGANISM: Homo sapiens

<400> SEQUENCE: 24
ugugcaaauc uaugcaaaac uga                                            23

<210> SEQ ID NO 25
<211> LENGTH: 23
<212> TYPE: RNA
<213> ORGANISM: Homo sapiens

<400> SEQUENCE: 25
aguuuugcag guuugcaucc agc                                            23

<210> SEQ ID NO 26
<211> LENGTH: 23
<212> TYPE: RNA
<213> ORGANISM: Homo sapiens

<400> SEQUENCE: 26
ugugcaaauc caugcaaaac uga                                            23

<210> SEQ ID NO 27
```

```
<211> LENGTH: 22
<212> TYPE: RNA
<213> ORGANISM: Homo sapiens

<400> SEQUENCE: 27
aguuuugcag guuugcauuu ca                                           22

<210> SEQ ID NO 28
<211> LENGTH: 23
<212> TYPE: RNA
<213> ORGANISM: Homo sapiens

<400> SEQUENCE: 28
uaaagugcuu auagugcagg uag                                          23

<210> SEQ ID NO 29
<211> LENGTH: 22
<212> TYPE: RNA
<213> ORGANISM: Homo sapiens

<400> SEQUENCE: 29
acugcauuau gagcacuuaa ag                                           22

<210> SEQ ID NO 30
<211> LENGTH: 22
<212> TYPE: RNA
<213> ORGANISM: Homo sapiens

<400> SEQUENCE: 30
uagcuuauca gacugauguu ga                                           22

<210> SEQ ID NO 31
<211> LENGTH: 21
<212> TYPE: RNA
<213> ORGANISM: Homo sapiens

<400> SEQUENCE: 31
caacaccagu cgaugggcug u                                            21

<210> SEQ ID NO 32
<211> LENGTH: 22
<212> TYPE: RNA
<213> ORGANISM: Homo sapiens

<400> SEQUENCE: 32
aguucuucag uggcaagcuu ua                                           22

<210> SEQ ID NO 33
<211> LENGTH: 22
<212> TYPE: RNA
<213> ORGANISM: Homo sapiens

<400> SEQUENCE: 33
aagcugccag uugaagaacu gu                                           22

<210> SEQ ID NO 34
<211> LENGTH: 22
<212> TYPE: RNA
<213> ORGANISM: Homo sapiens

<400> SEQUENCE: 34
ggggUuccug gggaugggau uu                                           22
```

```
<210> SEQ ID NO 35
<211> LENGTH: 21
<212> TYPE: RNA
<213> ORGANISM: Homo sapiens

<400> SEQUENCE: 35
aucacauugc cagggauuuc c                                              21

<210> SEQ ID NO 36
<211> LENGTH: 22
<212> TYPE: RNA
<213> ORGANISM: Homo sapiens

<400> SEQUENCE: 36
ugccuacuga gcugauauca gu                                             22

<210> SEQ ID NO 37
<211> LENGTH: 22
<212> TYPE: RNA
<213> ORGANISM: Homo sapiens

<400> SEQUENCE: 37
uggcucaguu cagcaggaac ag                                             22

<210> SEQ ID NO 38
<211> LENGTH: 22
<212> TYPE: RNA
<213> ORGANISM: Homo sapiens

<400> SEQUENCE: 38
ugccuacuga gcugaaacac ag                                             22

<210> SEQ ID NO 39
<211> LENGTH: 21
<212> TYPE: RNA
<213> ORGANISM: Homo sapiens

<400> SEQUENCE: 39
aggcggagac uugggcaauu g                                              21

<210> SEQ ID NO 40
<211> LENGTH: 22
<212> TYPE: RNA
<213> ORGANISM: Homo sapiens

<400> SEQUENCE: 40
cauugcacuu gucucggucu ga                                             22

<210> SEQ ID NO 41
<211> LENGTH: 22
<212> TYPE: RNA
<213> ORGANISM: Homo sapiens

<400> SEQUENCE: 41
uucaaguaau ccaggauagg cu                                             22

<210> SEQ ID NO 42
<211> LENGTH: 22
<212> TYPE: RNA
<213> ORGANISM: Homo sapiens

<400> SEQUENCE: 42
ccuauucuug guuacuugca cg                                             22
```

<210> SEQ ID NO 43
<211> LENGTH: 21
<212> TYPE: RNA
<213> ORGANISM: Homo sapiens

<400> SEQUENCE: 43
uucaaguaau ucaggauagg u                                    21

<210> SEQ ID NO 44
<211> LENGTH: 22
<212> TYPE: RNA
<213> ORGANISM: Homo sapiens

<400> SEQUENCE: 44
ccuguucucc auuacuuggc uc                                   22

<210> SEQ ID NO 45
<211> LENGTH: 22
<212> TYPE: RNA
<213> ORGANISM: Homo sapiens

<400> SEQUENCE: 45
agggcuuagc ugcuugugag ca                                   22

<210> SEQ ID NO 46
<211> LENGTH: 21
<212> TYPE: RNA
<213> ORGANISM: Homo sapiens

<400> SEQUENCE: 46
uucacagugg cuaaguuccg c                                    21

<210> SEQ ID NO 47
<211> LENGTH: 22
<212> TYPE: RNA
<213> ORGANISM: Homo sapiens

<400> SEQUENCE: 47
aaggagcuca cagucuauug ag                                   22

<210> SEQ ID NO 48
<211> LENGTH: 22
<212> TYPE: RNA
<213> ORGANISM: Homo sapiens

<400> SEQUENCE: 48
cacuagauug ugagcccug ga                                    22

<210> SEQ ID NO 49
<211> LENGTH: 22
<212> TYPE: RNA
<213> ORGANISM: Homo sapiens

<400> SEQUENCE: 49
acugauuucu uuugguguuc ag                                   22

<210> SEQ ID NO 50
<211> LENGTH: 22
<212> TYPE: RNA
<213> ORGANISM: Homo sapiens

<400> SEQUENCE: 50
uagcaccauc ugaaaucggu ua                                   22

```
<210> SEQ ID NO 51
<211> LENGTH: 22
<212> TYPE: RNA
<213> ORGANISM: Homo sapiens

<400> SEQUENCE: 51
uguaaacauc cucgacugga ag                                                  22

<210> SEQ ID NO 52
<211> LENGTH: 22
<212> TYPE: RNA
<213> ORGANISM: Homo sapiens

<400> SEQUENCE: 52
cuuucagucg gauguuugca gc                                                  22

<210> SEQ ID NO 53
<211> LENGTH: 21
<212> TYPE: RNA
<213> ORGANISM: Homo sapiens

<400> SEQUENCE: 53
aggcaagaug cuggcauagc u                                                   21

<210> SEQ ID NO 54
<211> LENGTH: 22
<212> TYPE: RNA
<213> ORGANISM: Homo sapiens

<400> SEQUENCE: 54
ugcuaugcca acauauugcc au                                                  22

<210> SEQ ID NO 55
<211> LENGTH: 22
<212> TYPE: RNA
<213> ORGANISM: Homo sapiens

<400> SEQUENCE: 55
uauugcacau uacuaaguug ca                                                  22

<210> SEQ ID NO 56
<211> LENGTH: 22
<212> TYPE: RNA
<213> ORGANISM: Homo sapiens

<400> SEQUENCE: 56
caauuuagug ugugugauau uu                                                  22

<210> SEQ ID NO 57
<211> LENGTH: 21
<212> TYPE: RNA
<213> ORGANISM: Homo sapiens

<400> SEQUENCE: 57
gugcauugua guugcauugc a                                                   21

<210> SEQ ID NO 58
<211> LENGTH: 22
<212> TYPE: RNA
<213> ORGANISM: Homo sapiens

<400> SEQUENCE: 58
```
caauguuucc acagugcauc ac                                    22

<210> SEQ ID NO 59
<211> LENGTH: 23
<212> TYPE: RNA
<213> ORGANISM: Homo sapiens

<400> SEQUENCE: 59
agguugggau cgguugcaau gcu                                   23

<210> SEQ ID NO 60
<211> LENGTH: 22
<212> TYPE: RNA
<213> ORGANISM: Homo sapiens

<400> SEQUENCE: 60
uauugcacuu gucccggccu gu                                    22

<210> SEQ ID NO 61
<211> LENGTH: 22
<212> TYPE: RNA
<213> ORGANISM: Homo sapiens

<400> SEQUENCE: 61
ggguggggau uuguugcauu ac                                    22

<210> SEQ ID NO 62
<211> LENGTH: 23
<212> TYPE: RNA
<213> ORGANISM: Homo sapiens

<400> SEQUENCE: 62
caaagugcug uucgugcagg uag                                   23

<210> SEQ ID NO 63
<211> LENGTH: 22
<212> TYPE: RNA
<213> ORGANISM: Homo sapiens

<400> SEQUENCE: 63
acugcugagc uagcacuucc cg                                    22

<210> SEQ ID NO 64
<211> LENGTH: 22
<212> TYPE: RNA
<213> ORGANISM: Homo sapiens

<400> SEQUENCE: 64
uucaacgggu auuauugag ca                                     22

<210> SEQ ID NO 65
<211> LENGTH: 23
<212> TYPE: RNA
<213> ORGANISM: Homo sapiens

<400> SEQUENCE: 65
uuuggcacua gcacauuuuu gcu                                   23

<210> SEQ ID NO 66
<211> LENGTH: 22
<212> TYPE: RNA
<213> ORGANISM: Homo sapiens

<400> SEQUENCE: 66

| | |
|---|---|
| aaucaugugc agugccaaua ug | 22 |

<210> SEQ ID NO 67
<211> LENGTH: 22
<212> TYPE: RNA
<213> ORGANISM: Homo sapiens

<400> SEQUENCE: 67

| | |
|---|---|
| ugagguagua aguuguauug uu | 22 |

<210> SEQ ID NO 68
<211> LENGTH: 22
<212> TYPE: RNA
<213> ORGANISM: Homo sapiens

<400> SEQUENCE: 68

| | |
|---|---|
| aacccguaga uccgaucuug ug | 22 |

<210> SEQ ID NO 69
<211> LENGTH: 22
<212> TYPE: RNA
<213> ORGANISM: Homo sapiens

<400> SEQUENCE: 69

| | |
|---|---|
| caagcucgcu ucuaugguc ug | 22 |

<210> SEQ ID NO 70
<211> LENGTH: 22
<212> TYPE: RNA
<213> ORGANISM: Homo sapiens

<400> SEQUENCE: 70

| | |
|---|---|
| aacccguaga uccgaacuug ug | 22 |

<210> SEQ ID NO 71
<211> LENGTH: 22
<212> TYPE: RNA
<213> ORGANISM: Homo sapiens

<400> SEQUENCE: 71

| | |
|---|---|
| caagcuugua ucuauaggua ug | 22 |

<210> SEQ ID NO 72
<211> LENGTH: 22
<212> TYPE: RNA
<213> ORGANISM: Homo sapiens

<400> SEQUENCE: 72

| | |
|---|---|
| caguuaucac agugcugaug cu | 22 |

<210> SEQ ID NO 73
<211> LENGTH: 21
<212> TYPE: RNA
<213> ORGANISM: Homo sapiens

<400> SEQUENCE: 73

| | |
|---|---|
| uacaguacug ugauaacuga a | 21 |

<210> SEQ ID NO 74
<211> LENGTH: 24
<212> TYPE: RNA
<213> ORGANISM: Homo sapiens -continued

```
<400> SEQUENCE: 74
gcugguuuca uauggugguu uaga                                      24

<210> SEQ ID NO 75
<211> LENGTH: 23
<212> TYPE: RNA
<213> ORGANISM: Homo sapiens

<400> SEQUENCE: 75
uagcaccauu ugaaaucagu guu                                       23

<210> SEQ ID NO 76
<211> LENGTH: 22
<212> TYPE: RNA
<213> ORGANISM: Homo sapiens

<400> SEQUENCE: 76
cugguuucac augguggcuu ag                                        22

<210> SEQ ID NO 77
<211> LENGTH: 23
<212> TYPE: RNA
<213> ORGANISM: Homo sapiens

<400> SEQUENCE: 77
agcuucuuua cagugcugcc uug                                       23

<210> SEQ ID NO 78
<211> LENGTH: 23
<212> TYPE: RNA
<213> ORGANISM: Homo sapiens

<400> SEQUENCE: 78
agcagcauug uacagggcua uga                                       23

<210> SEQ ID NO 79
<211> LENGTH: 23
<212> TYPE: RNA
<213> ORGANISM: Homo sapiens

<400> SEQUENCE: 79
ucaaaugcuc agacccugu ggu                                        23

<210> SEQ ID NO 80
<211> LENGTH: 22
<212> TYPE: RNA
<213> ORGANISM: Homo sapiens

<400> SEQUENCE: 80
acggauguuu gagcaugugc ua                                        22

<210> SEQ ID NO 81
<211> LENGTH: 23
<212> TYPE: RNA
<213> ORGANISM: Homo sapiens

<400> SEQUENCE: 81
aaaagugcuu acagugcagg uag                                       23

<210> SEQ ID NO 82
<211> LENGTH: 22
<212> TYPE: RNA
<213> ORGANISM: Homo sapiens
```

```
<400> SEQUENCE: 82
cugcaaugua agcacuucuu ac                                              22

<210> SEQ ID NO 83
<211> LENGTH: 23
<212> TYPE: RNA
<213> ORGANISM: Homo sapiens

<400> SEQUENCE: 83
agcagcauug uacagggcua uca                                             23

<210> SEQ ID NO 84
<211> LENGTH: 22
<212> TYPE: RNA
<213> ORGANISM: Homo sapiens

<400> SEQUENCE: 84
ccaauauuac ugugcugcuu ua                                              22

<210> SEQ ID NO 85
<211> LENGTH: 21
<212> TYPE: RNA
<213> ORGANISM: Homo sapiens

<400> SEQUENCE: 85
cugaccuaug aauugacagc c                                               21

<210> SEQ ID NO 86
<211> LENGTH: 22
<212> TYPE: RNA
<213> ORGANISM: Homo sapiens

<400> SEQUENCE: 86
cugccaauuc cauaggucac ag                                              22

<210> SEQ ID NO 87
<211> LENGTH: 22
<212> TYPE: RNA
<213> ORGANISM: Homo sapiens

<400> SEQUENCE: 87
uagguaguuu cauguuguug gg                                              22

<210> SEQ ID NO 88
<211> LENGTH: 22
<212> TYPE: RNA
<213> ORGANISM: Homo sapiens

<400> SEQUENCE: 88
uucaccaccu ucuccaccca gc                                              22

<210> SEQ ID NO 89
<211> LENGTH: 22
<212> TYPE: RNA
<213> ORGANISM: Homo sapiens

<400> SEQUENCE: 89
gguccagagg ggagauaggu uc                                              22

<210> SEQ ID NO 90
<211> LENGTH: 23
<212> TYPE: RNA
```

```
<213> ORGANISM: Homo sapiens

<400> SEQUENCE: 90
cccaguguuc agacuaccug uuc                                              23

<210> SEQ ID NO 91
<211> LENGTH: 22
<212> TYPE: RNA
<213> ORGANISM: Homo sapiens

<400> SEQUENCE: 91
acaguagucu gcacauuggu ua                                               22

<210> SEQ ID NO 92
<211> LENGTH: 22
<212> TYPE: RNA
<213> ORGANISM: Homo sapiens

<400> SEQUENCE: 92
auaagacgag caaaaagcuu gu                                               22

<210> SEQ ID NO 93
<211> LENGTH: 21
<212> TYPE: RNA
<213> ORGANISM: Homo sapiens

<400> SEQUENCE: 93
cuuuuugcgg ucugggcuug c                                                21

<210> SEQ ID NO 94
<211> LENGTH: 22
<212> TYPE: RNA
<213> ORGANISM: Homo sapiens

<400> SEQUENCE: 94
aagcccuuac cccaaaaagu au                                               22

<210> SEQ ID NO 95
<211> LENGTH: 22
<212> TYPE: RNA
<213> ORGANISM: Homo sapiens

<400> SEQUENCE: 95
aaaguucuga gacacuccga cu                                               22

<210> SEQ ID NO 96
<211> LENGTH: 22
<212> TYPE: RNA
<213> ORGANISM: Homo sapiens

<400> SEQUENCE: 96
ucagugcacu acagaacuuu gu                                               22

<210> SEQ ID NO 97
<211> LENGTH: 23
<212> TYPE: RNA
<213> ORGANISM: Homo sapiens

<400> SEQUENCE: 97
uguaaacauc cuacacucuc agc                                              23

<210> SEQ ID NO 98
<211> LENGTH: 22
```

```
<212> TYPE: RNA
<213> ORGANISM: Homo sapiens

<400> SEQUENCE: 98
cugggagaag gcuguuuacu cu                                              22

<210> SEQ ID NO 99
<211> LENGTH: 22
<212> TYPE: RNA
<213> ORGANISM: Homo sapiens

<400> SEQUENCE: 99
uguaaacauc cccgacugga ag                                              22

<210> SEQ ID NO 100
<211> LENGTH: 22
<212> TYPE: RNA
<213> ORGANISM: Homo sapiens

<400> SEQUENCE: 100
cuuucaguca gauguuugcu gc                                              22

<210> SEQ ID NO 101
<211> LENGTH: 22
<212> TYPE: RNA
<213> ORGANISM: Homo sapiens

<400> SEQUENCE: 101
ucuacagugc acgugucucc ag                                              22

<210> SEQ ID NO 102
<211> LENGTH: 22
<212> TYPE: RNA
<213> ORGANISM: Homo sapiens

<400> SEQUENCE: 102
ggagacgcgg cccuguugga gu                                              22

<210> SEQ ID NO 103
<211> LENGTH: 20
<212> TYPE: RNA
<213> ORGANISM: Homo sapiens

<400> SEQUENCE: 103
guguguggaa augcuucugc                                                 20

<210> SEQ ID NO 104
<211> LENGTH: 23
<212> TYPE: RNA
<213> ORGANISM: Homo sapiens

<400> SEQUENCE: 104
uggaagacua gugauuuugu ugu                                             23

<210> SEQ ID NO 105
<211> LENGTH: 22
<212> TYPE: RNA
<213> ORGANISM: Homo sapiens

<400> SEQUENCE: 105
caacaaauca cagucugcca ua                                              22

<210> SEQ ID NO 106
```

-continued

```
<211> LENGTH: 22
<212> TYPE: RNA
<213> ORGANISM: Homo sapiens

<400> SEQUENCE: 106
caacaaaucc cagucuaccu aa                                              22

<210> SEQ ID NO 107
<211> LENGTH: 23
<212> TYPE: RNA
<213> ORGANISM: Homo sapiens

<400> SEQUENCE: 107
uacccuguag auccgaauuu gug                                             23

<210> SEQ ID NO 108
<211> LENGTH: 22
<212> TYPE: RNA
<213> ORGANISM: Homo sapiens

<400> SEQUENCE: 108
caaauucgua ucuaggggaa ua                                              22

<210> SEQ ID NO 109
<211> LENGTH: 23
<212> TYPE: RNA
<213> ORGANISM: Homo sapiens

<400> SEQUENCE: 109
uacccuguag aaccgaauuu gug                                             23

<210> SEQ ID NO 110
<211> LENGTH: 22
<212> TYPE: RNA
<213> ORGANISM: Homo sapiens

<400> SEQUENCE: 110
acagauucga uucuagggga au                                              22

<210> SEQ ID NO 111
<211> LENGTH: 22
<212> TYPE: RNA
<213> ORGANISM: Homo sapiens

<400> SEQUENCE: 111
uggcaguguc uuagcugguu gu                                              22

<210> SEQ ID NO 112
<211> LENGTH: 22
<212> TYPE: RNA
<213> ORGANISM: Homo sapiens

<400> SEQUENCE: 112
caaucagcaa guauacugcc cu                                              22

<210> SEQ ID NO 113
<211> LENGTH: 23
<212> TYPE: RNA
<213> ORGANISM: Homo sapiens

<400> SEQUENCE: 113
aacauucaac gcugucggug agu                                             23
```

```
<210> SEQ ID NO 114
<211> LENGTH: 22
<212> TYPE: RNA
<213> ORGANISM: Homo sapiens

<400> SEQUENCE: 114
accacugacc guugacugua cc                                              22

<210> SEQ ID NO 115
<211> LENGTH: 23
<212> TYPE: RNA
<213> ORGANISM: Homo sapiens

<400> SEQUENCE: 115
aacauucauu gcugucggug ggu                                             23

<210> SEQ ID NO 116
<211> LENGTH: 22
<212> TYPE: RNA
<213> ORGANISM: Homo sapiens

<400> SEQUENCE: 116
aacauucaac cugucgguga gu                                              22

<210> SEQ ID NO 117
<211> LENGTH: 22
<212> TYPE: RNA
<213> ORGANISM: Homo sapiens

<400> SEQUENCE: 117
aaccaucgac cguugagugg ac                                              22

<210> SEQ ID NO 118
<211> LENGTH: 24
<212> TYPE: RNA
<213> ORGANISM: Homo sapiens

<400> SEQUENCE: 118
uuuggcaaug guagaacuca cacu                                            24

<210> SEQ ID NO 119
<211> LENGTH: 21
<212> TYPE: RNA
<213> ORGANISM: Homo sapiens

<400> SEQUENCE: 119
ugguucuaga cuugccaacu a                                               21

<210> SEQ ID NO 120
<211> LENGTH: 22
<212> TYPE: RNA
<213> ORGANISM: Homo sapiens

<400> SEQUENCE: 120
uauggcacug guagaauuca cu                                              22

<210> SEQ ID NO 121
<211> LENGTH: 22
<212> TYPE: RNA
<213> ORGANISM: Homo sapiens

<400> SEQUENCE: 121
gugaauuacc gaagggccau aa                                              22
```

-continued

```
<210> SEQ ID NO 122
<211> LENGTH: 22
<212> TYPE: RNA
<213> ORGANISM: Homo sapiens

<400> SEQUENCE: 122
ggcuacaaca caggacccgg gc                                              22

<210> SEQ ID NO 123
<211> LENGTH: 22
<212> TYPE: RNA
<213> ORGANISM: Homo sapiens

<400> SEQUENCE: 123
ucgugucuug uguugcagcc gg                                              22

<210> SEQ ID NO 124
<211> LENGTH: 22
<212> TYPE: RNA
<213> ORGANISM: Homo sapiens

<400> SEQUENCE: 124
cggcaacaag aaacugccug ag                                              22

<210> SEQ ID NO 125
<211> LENGTH: 23
<212> TYPE: RNA
<213> ORGANISM: Homo sapiens

<400> SEQUENCE: 125
cccaguguuu agacuaucug uuc                                             23

<210> SEQ ID NO 126
<211> LENGTH: 22
<212> TYPE: RNA
<213> ORGANISM: Homo sapiens

<400> SEQUENCE: 126
gugaaauguu uaggaccacu ag                                              22

<210> SEQ ID NO 127
<211> LENGTH: 22
<212> TYPE: RNA
<213> ORGANISM: Homo sapiens

<400> SEQUENCE: 127
uucccuuugu cauccuaugc cu                                              22

<210> SEQ ID NO 128
<211> LENGTH: 22
<212> TYPE: RNA
<213> ORGANISM: Homo sapiens

<400> SEQUENCE: 128
uccuucauuc caccggaguc ug                                              22

<210> SEQ ID NO 129
<211> LENGTH: 21
<212> TYPE: RNA
<213> ORGANISM: Homo sapiens

<400> SEQUENCE: 129
gauuucagug gagugaaguu c                                               21
```

<210> SEQ ID NO 130
<211> LENGTH: 22
<212> TYPE: RNA
<213> ORGANISM: Homo sapiens

<400> SEQUENCE: 130
cugugcgugu gacagcggcu ga                                              22

<210> SEQ ID NO 131
<211> LENGTH: 22
<212> TYPE: RNA
<213> ORGANISM: Homo sapiens

<400> SEQUENCE: 131
uucccuuugu cauccuucgc cu                                              22

<210> SEQ ID NO 132
<211> LENGTH: 21
<212> TYPE: RNA
<213> ORGANISM: Homo sapiens

<400> SEQUENCE: 132
uaacagucuc cagucacggc c                                               21

<210> SEQ ID NO 133
<211> LENGTH: 22
<212> TYPE: RNA
<213> ORGANISM: Homo sapiens

<400> SEQUENCE: 133
accaucgacc guugauugua cc                                              22

<210> SEQ ID NO 134
<211> LENGTH: 22
<212> TYPE: RNA
<213> ORGANISM: Homo sapiens

<400> SEQUENCE: 134
ugccugucua cacuugcugu gc                                              22

<210> SEQ ID NO 135
<211> LENGTH: 22
<212> TYPE: RNA
<213> ORGANISM: Homo sapiens

<400> SEQUENCE: 135
acagcaggca cagacaggca gu                                              22

<210> SEQ ID NO 136
<211> LENGTH: 21
<212> TYPE: RNA
<213> ORGANISM: Homo sapiens

<400> SEQUENCE: 136
augaccuaug aauugacaga c                                               21

<210> SEQ ID NO 137
<211> LENGTH: 22
<212> TYPE: RNA
<213> ORGANISM: Homo sapiens

<400> SEQUENCE: 137
uaaucucagc uggcaacugu ga                                                  22

<210> SEQ ID NO 138
<211> LENGTH: 23
<212> TYPE: RNA
<213> ORGANISM: Homo sapiens

<400> SEQUENCE: 138
uacugcauca ggaacugauu gga                                                 23

<210> SEQ ID NO 139
<211> LENGTH: 21
<212> TYPE: RNA
<213> ORGANISM: Homo sapiens

<400> SEQUENCE: 139
uugugcuuga ucuaaccaug u                                                   21

<210> SEQ ID NO 140
<211> LENGTH: 22
<212> TYPE: RNA
<213> ORGANISM: Homo sapiens

<400> SEQUENCE: 140
augguuccgu caagcaccau gg                                                  22

<210> SEQ ID NO 141
<211> LENGTH: 22
<212> TYPE: RNA
<213> ORGANISM: Homo sapiens

<400> SEQUENCE: 141 cagguucug ucaagcaccg cg                                                   22

<210> SEQ ID NO 142
<211> LENGTH: 21
<212> TYPE: RNA
<213> ORGANISM: Homo sapiens

<400> SEQUENCE: 142
ugauugucca aacgcaauuc u                                                   21

<210> SEQ ID NO 143
<211> LENGTH: 22
<212> TYPE: RNA
<213> ORGANISM: Homo sapiens

<400> SEQUENCE: 143
agaguugagu cuggacgucc cg                                                  22

<210> SEQ ID NO 144
<211> LENGTH: 21
<212> TYPE: RNA
<213> ORGANISM: Homo sapiens

<400> SEQUENCE: 144
ccacaccgua ucugacacuu u                                                   21

<210> SEQ ID NO 145
<211> LENGTH: 22
<212> TYPE: RNA
<213> ORGANISM: Homo sapiens

<400> SEQUENCE: 145

| | |
|---|---|
| accuggcaua caauguagau uu | 22 |

<210> SEQ ID NO 146
<211> LENGTH: 23
<212> TYPE: RNA
<213> ORGANISM: Homo sapiens

<400> SEQUENCE: 146

| | |
|---|---|
| agcuacauug ucugcugggu uuc | 23 |

<210> SEQ ID NO 147
<211> LENGTH: 22
<212> TYPE: RNA
<213> ORGANISM: Homo sapiens

<400> SEQUENCE: 147

| | |
|---|---|
| cucaguagcc aguguagauc cu | 22 |

<210> SEQ ID NO 148
<211> LENGTH: 21
<212> TYPE: RNA
<213> ORGANISM: Homo sapiens

<400> SEQUENCE: 148

| | |
|---|---|
| agcuacaucu ggcuacuggg u | 21 |

<210> SEQ ID NO 149
<211> LENGTH: 22
<212> TYPE: RNA
<213> ORGANISM: Homo sapiens

<400> SEQUENCE: 149

| | |
|---|---|
| cguguauuug acaagcugag uu | 22 |

<210> SEQ ID NO 150
<211> LENGTH: 22
<212> TYPE: RNA
<213> ORGANISM: Homo sapiens

<400> SEQUENCE: 150

| | |
|---|---|
| ugucaguuug ucaaauaccc ca | 22 |

<210> SEQ ID NO 151
<211> LENGTH: 21
<212> TYPE: RNA
<213> ORGANISM: Homo sapiens

<400> SEQUENCE: 151

| | |
|---|---|
| caagucacua gugguuccgu u | 21 |

<210> SEQ ID NO 152
<211> LENGTH: 23
<212> TYPE: RNA
<213> ORGANISM: Homo sapiens

<400> SEQUENCE: 152

| | |
|---|---|
| aaaauggugc ccuagugacu aca | 23 |

<210> SEQ ID NO 153
<211> LENGTH: 22
<212> TYPE: RNA
<213> ORGANISM: Homo sapiens

```
<400> SEQUENCE: 153
caucuuacug ggcagcauug ga                                              22

<210> SEQ ID NO 154
<211> LENGTH: 22
<212> TYPE: RNA
<213> ORGANISM: Homo sapiens

<400> SEQUENCE: 154
uaauacugcc ugguaaugau ga                                              22

<210> SEQ ID NO 155
<211> LENGTH: 22
<212> TYPE: RNA
<213> ORGANISM: Homo sapiens

<400> SEQUENCE: 155
ugagguagua guuuguacag uu                                              22

<210> SEQ ID NO 156
<211> LENGTH: 21
<212> TYPE: RNA
<213> ORGANISM: Homo sapiens

<400> SEQUENCE: 156
cuguacaggc cacugccuug c                                               21

<210> SEQ ID NO 157
<211> LENGTH: 22
<212> TYPE: RNA
<213> ORGANISM: Homo sapiens

<400> SEQUENCE: 157
ugagguagua guuugugcug uu                                              22

<210> SEQ ID NO 158
<211> LENGTH: 22
<212> TYPE: RNA
<213> ORGANISM: Homo sapiens

<400> SEQUENCE: 158
cugcgcaagc uacugccuug cu                                              22

<210> SEQ ID NO 159
<211> LENGTH: 22
<212> TYPE: RNA
<213> ORGANISM: Homo sapiens

<400> SEQUENCE: 159
uggaauguaa agaaguaugu au                                              22

<210> SEQ ID NO 160
<211> LENGTH: 22
<212> TYPE: RNA
<213> ORGANISM: Homo sapiens

<400> SEQUENCE: 160
uagcagcaca ucaugguuua ca                                              22

<210> SEQ ID NO 161
<211> LENGTH: 22
<212> TYPE: RNA
<213> ORGANISM: Homo sapiens
```

```
<400> SEQUENCE: 161
cgaaucauua uuugcugcuc ua                                              22

<210> SEQ ID NO 162
<211> LENGTH: 22
<212> TYPE: RNA
<213> ORGANISM: Homo sapiens

<400> SEQUENCE: 162
uggguuccug gcaugcugau uu                                              22

<210> SEQ ID NO 163
<211> LENGTH: 21
<212> TYPE: RNA
<213> ORGANISM: Homo sapiens

<400> SEQUENCE: 163
aucacauugc cagggauuac c                                               21

<210> SEQ ID NO 164
<211> LENGTH: 22
<212> TYPE: RNA
<213> ORGANISM: Homo sapiens

<400> SEQUENCE: 164
agagcuuagc ugauugguga ac                                              22

<210> SEQ ID NO 165
<211> LENGTH: 21
<212> TYPE: RNA
<213> ORGANISM: Homo sapiens

<400> SEQUENCE: 165
uucacagugg cuaaguucug c                                               21

<210> SEQ ID NO 166
<211> LENGTH: 22
<212> TYPE: RNA
<213> ORGANISM: Homo sapiens

<400> SEQUENCE: 166
uguaaacauc cuacacucag cu                                              22

<210> SEQ ID NO 167
<211> LENGTH: 22
<212> TYPE: RNA
<213> ORGANISM: Homo sapiens

<400> SEQUENCE: 167
cugggaggug gauguuuacu uc                                              22

<210> SEQ ID NO 168
<211> LENGTH: 22
<212> TYPE: RNA
<213> ORGANISM: Homo sapiens

<400> SEQUENCE: 168
uggaguguga caaugguguu ug                                              22

<210> SEQ ID NO 169
<211> LENGTH: 22
<212> TYPE: RNA
```

```
<213> ORGANISM: Homo sapiens

<400> SEQUENCE: 169
aacgccauua ucacacuaaa ua                                              22

<210> SEQ ID NO 170
<211> LENGTH: 22
<212> TYPE: RNA
<213> ORGANISM: Homo sapiens

<400> SEQUENCE: 170
cguguucaca gcggaccuug au                                              22

<210> SEQ ID NO 171
<211> LENGTH: 20
<212> TYPE: RNA
<213> ORGANISM: Homo sapiens

<400> SEQUENCE: 171
uaaggcacgc ggugaaugcc                                                 20

<210> SEQ ID NO 172
<211> LENGTH: 22
<212> TYPE: RNA
<213> ORGANISM: Homo sapiens

<400> SEQUENCE: 172
ucccugagac ccuaacuugu ga                                              22

<210> SEQ ID NO 173
<211> LENGTH: 22
<212> TYPE: RNA
<213> ORGANISM: Homo sapiens

<400> SEQUENCE: 173
acggguuagg cucuugggag cu                                              22

<210> SEQ ID NO 174
<211> LENGTH: 21
<212> TYPE: RNA
<213> ORGANISM: Homo sapiens

<400> SEQUENCE: 174
ucacagugaa ccggucucuu u                                               21

<210> SEQ ID NO 175
<211> LENGTH: 22
<212> TYPE: RNA
<213> ORGANISM: Homo sapiens

<400> SEQUENCE: 175
uucacauugu gcuacugucu gc                                              22

<210> SEQ ID NO 176
<211> LENGTH: 22
<212> TYPE: RNA
<213> ORGANISM: Homo sapiens

<400> SEQUENCE: 176
cagugcaaug uuaaaagggc au                                              22

<210> SEQ ID NO 177
<211> LENGTH: 22
```

```
<212> TYPE: RNA
<213> ORGANISM: Homo sapiens

<400> SEQUENCE: 177
accguggcuu ucgauuguua cu                                        22

<210> SEQ ID NO 178
<211> LENGTH: 22
<212> TYPE: RNA
<213> ORGANISM: Homo sapiens

<400> SEQUENCE: 178
uaacagucua cagccauggu cg                                        22

<210> SEQ ID NO 179
<211> LENGTH: 22
<212> TYPE: RNA
<213> ORGANISM: Homo sapiens

<400> SEQUENCE: 179
uuuggucccc uucaaccagc ug                                        22

<210> SEQ ID NO 180
<211> LENGTH: 23
<212> TYPE: RNA
<213> ORGANISM: Homo sapiens

<400> SEQUENCE: 180
uauggcuuuu uauuccuaug uga                                       23

<210> SEQ ID NO 181
<211> LENGTH: 22
<212> TYPE: RNA
<213> ORGANISM: Homo sapiens

<400> SEQUENCE: 181
uauagggauu ggagccgugg cg                                        22

<210> SEQ ID NO 182
<211> LENGTH: 23
<212> TYPE: RNA
<213> ORGANISM: Homo sapiens

<400> SEQUENCE: 182
uuauugcuua agaauacgcg uag                                       23

<210> SEQ ID NO 183
<211> LENGTH: 23
<212> TYPE: RNA
<213> ORGANISM: Homo sapiens

<400> SEQUENCE: 183
agcugguguu gugaaucagg ccg                                       23

<210> SEQ ID NO 184
<211> LENGTH: 22
<212> TYPE: RNA
<213> ORGANISM: Homo sapiens

<400> SEQUENCE: 184
gcuauuucac gacaccaggg uu                                        22

<210> SEQ ID NO 185
```

```
<211> LENGTH: 22
<212> TYPE: RNA
<213> ORGANISM: Homo sapiens

<400> SEQUENCE: 185
cagugguuuu acccuauggu ag                                              22

<210> SEQ ID NO 186
<211> LENGTH: 21
<212> TYPE: RNA
<213> ORGANISM: Homo sapiens

<400> SEQUENCE: 186
uaccacaggg uagaaccacg g                                               21

<210> SEQ ID NO 187
<211> LENGTH: 22
<212> TYPE: RNA
<213> ORGANISM: Homo sapiens

<400> SEQUENCE: 187
caucuuccag uacaguguug ga                                              22

<210> SEQ ID NO 188
<211> LENGTH: 22
<212> TYPE: RNA
<213> ORGANISM: Homo sapiens

<400> SEQUENCE: 188
uaacacuguc ugguaaagau gg                                              22

<210> SEQ ID NO 189
<211> LENGTH: 21
<212> TYPE: RNA
<213> ORGANISM: Homo sapiens

<400> SEQUENCE: 189
cauaaaguag aaagcacuac u                                               21

<210> SEQ ID NO 190
<211> LENGTH: 23
<212> TYPE: RNA
<213> ORGANISM: Homo sapiens

<400> SEQUENCE: 190
uguaguguuu ccuacuuuau gga                                             23

<210> SEQ ID NO 191
<211> LENGTH: 22
<212> TYPE: RNA
<213> ORGANISM: Homo sapiens

<400> SEQUENCE: 191
ggugcagugc ugcaucucug gu                                              22

<210> SEQ ID NO 192
<211> LENGTH: 21
<212> TYPE: RNA
<213> ORGANISM: Homo sapiens

<400> SEQUENCE: 192
ugagaugaag cacguagcu c                                                21
```

```
<210> SEQ ID NO 193
<211> LENGTH: 22
<212> TYPE: RNA
<213> ORGANISM: Homo sapiens

<400> SEQUENCE: 193
ggauaucauc auauacugua ag                                              22

<210> SEQ ID NO 194
<211> LENGTH: 20
<212> TYPE: RNA
<213> ORGANISM: Homo sapiens

<400> SEQUENCE: 194
uacaguauag augauguacu                                                 20

<210> SEQ ID NO 195
<211> LENGTH: 23
<212> TYPE: RNA
<213> ORGANISM: Homo sapiens

<400> SEQUENCE: 195
guccaguuuu cccaggaauc ccu                                             23

<210> SEQ ID NO 196
<211> LENGTH: 22
<212> TYPE: RNA
<213> ORGANISM: Homo sapiens

<400> SEQUENCE: 196
ggauuccugg aaauacuguu cu                                              22

<210> SEQ ID NO 197
<211> LENGTH: 21
<212> TYPE: RNA
<213> ORGANISM: Homo sapiens

<400> SEQUENCE: 197
ucagugcaug acagaacuug g                                               21

<210> SEQ ID NO 198
<211> LENGTH: 22
<212> TYPE: RNA
<213> ORGANISM: Homo sapiens

<400> SEQUENCE: 198
uugcauaguc acaaaaguga uc                                              22

<210> SEQ ID NO 199
<211> LENGTH: 23
<212> TYPE: RNA
<213> ORGANISM: Homo sapiens

<400> SEQUENCE: 199
caacggaauc ccaaaagcag cug                                             23

<210> SEQ ID NO 200
<211> LENGTH: 22
<212> TYPE: RNA
<213> ORGANISM: Homo sapiens

<400> SEQUENCE: 200
gcugcgcuug gauuucgucc cc                                              22
```

```
<210> SEQ ID NO 201
<211> LENGTH: 23
<212> TYPE: RNA
<213> ORGANISM: Homo sapiens

<400> SEQUENCE: 201
ucuuugguua ucuagcugua uga                                              23

<210> SEQ ID NO 202
<211> LENGTH: 22
<212> TYPE: RNA
<213> ORGANISM: Homo sapiens

<400> SEQUENCE: 202
auaaagcuag auaaccgaaa gu                                               22

<210> SEQ ID NO 203
<211> LENGTH: 24
<212> TYPE: RNA
<213> ORGANISM: Homo sapiens

<400> SEQUENCE: 203
ucccugagac ccuuuaaccu guga                                             24

<210> SEQ ID NO 204
<211> LENGTH: 22
<212> TYPE: RNA
<213> ORGANISM: Homo sapiens

<400> SEQUENCE: 204
acaggugagg uucuugggag cc                                               22

<210> SEQ ID NO 205
<211> LENGTH: 22
<212> TYPE: RNA
<213> ORGANISM: Homo sapiens

<400> SEQUENCE: 205
ucacaaguca ggcucuuggg ac                                               22

<210> SEQ ID NO 206
<211> LENGTH: 21
<212> TYPE: RNA
<213> ORGANISM: Homo sapiens

<400> SEQUENCE: 206
cauuauuacu uuugguacgc g                                                21

<210> SEQ ID NO 207
<211> LENGTH: 22
<212> TYPE: RNA
<213> ORGANISM: Homo sapiens

<400> SEQUENCE: 207
ucguaccgug aguaauaaug cg                                               22

<210> SEQ ID NO 208
<211> LENGTH: 22
<212> TYPE: RNA
<213> ORGANISM: Homo sapiens

<400> SEQUENCE: 208
cugaagcuca gagggcucug au                                               22
```

<210> SEQ ID NO 209
<211> LENGTH: 22
<212> TYPE: RNA
<213> ORGANISM: Homo sapiens

<400> SEQUENCE: 209
ucggauccgu cugagcuugg cu                                            22

<210> SEQ ID NO 210
<211> LENGTH: 22
<212> TYPE: RNA
<213> ORGANISM: Homo sapiens

<400> SEQUENCE: 210
aagcccuuac cccaaaaagc au                                            22

<210> SEQ ID NO 211
<211> LENGTH: 22
<212> TYPE: RNA
<213> ORGANISM: Homo sapiens

<400> SEQUENCE: 211
ugugacuggu ugaccagagg gg                                            22

<210> SEQ ID NO 212
<211> LENGTH: 23
<212> TYPE: RNA
<213> ORGANISM: Homo sapiens

<400> SEQUENCE: 212
acuccauuug uuuugaugau gga                                           23

<210> SEQ ID NO 213
<211> LENGTH: 22
<212> TYPE: RNA
<213> ORGANISM: Homo sapiens

<400> SEQUENCE: 213
caucaucguc ucaaaugagu cu                                            22

<210> SEQ ID NO 214
<211> LENGTH: 22
<212> TYPE: RNA
<213> ORGANISM: Homo sapiens

<400> SEQUENCE: 214
gcuacuucac aacaccaggg cc                                            22

<210> SEQ ID NO 215
<211> LENGTH: 22
<212> TYPE: RNA
<213> ORGANISM: Homo sapiens

<400> SEQUENCE: 215
ugagaacuga auuccauggg uu                                            22

<210> SEQ ID NO 216
<211> LENGTH: 22
<212> TYPE: RNA
<213> ORGANISM: Homo sapiens

<400> SEQUENCE: 216
ccucugaaau ucaguucuuc ag          22

<210> SEQ ID NO 217
<211> LENGTH: 23
<212> TYPE: RNA
<213> ORGANISM: Homo sapiens

<400> SEQUENCE: 217
ucuggcuccg ugucuucacu ccc         23

<210> SEQ ID NO 218
<211> LENGTH: 21
<212> TYPE: RNA
<213> ORGANISM: Homo sapiens

<400> SEQUENCE: 218
agggagggac gggggcugug c           21

<210> SEQ ID NO 219
<211> LENGTH: 22
<212> TYPE: RNA
<213> ORGANISM: Homo sapiens

<400> SEQUENCE: 219
ucucccaacc cuuguaccag ug          22

<210> SEQ ID NO 220
<211> LENGTH: 22
<212> TYPE: RNA
<213> ORGANISM: Homo sapiens

<400> SEQUENCE: 220
cugguacagg ccuggggggac ag         22

<210> SEQ ID NO 221
<211> LENGTH: 22
<212> TYPE: RNA
<213> ORGANISM: Homo sapiens

<400> SEQUENCE: 221
uagguuaucc guguugccuu cg          22

<210> SEQ ID NO 222
<211> LENGTH: 22
<212> TYPE: RNA
<213> ORGANISM: Homo sapiens

<400> SEQUENCE: 222
aaucauacac gguugaccua uu          22

<210> SEQ ID NO 223
<211> LENGTH: 22
<212> TYPE: RNA
<213> ORGANISM: Homo sapiens

<400> SEQUENCE: 223
uggacggaga acugauaagg gu          22

<210> SEQ ID NO 224
<211> LENGTH: 22
<212> TYPE: RNA
<213> ORGANISM: Homo sapiens

<400> SEQUENCE: 224
uggagagaaa ggcaguuccu ga                                       22

<210> SEQ ID NO 225
<211> LENGTH: 22
<212> TYPE: RNA
<213> ORGANISM: Homo sapiens

<400> SEQUENCE: 225
aggggcuggc uuccucugg uc                                        22

<210> SEQ ID NO 226
<211> LENGTH: 22
<212> TYPE: RNA
<213> ORGANISM: Homo sapiens

<400> SEQUENCE: 226
caaagaauuc uccuuuuggg cu                                       22

<210> SEQ ID NO 227
<211> LENGTH: 22
<212> TYPE: RNA
<213> ORGANISM: Homo sapiens

<400> SEQUENCE: 227
gcccaaaggu gaauuuuuug gg                                       22

<210> SEQ ID NO 228
<211> LENGTH: 21
<212> TYPE: RNA
<213> ORGANISM: Homo sapiens

<400> SEQUENCE: 228
caucccuugc augguggagg g                                        21

<210> SEQ ID NO 229
<211> LENGTH: 21
<212> TYPE: RNA
<213> ORGANISM: Homo sapiens

<400> SEQUENCE: 229
cucccacaug caggguuugc a                                        21

<210> SEQ ID NO 230
<211> LENGTH: 22
<212> TYPE: RNA
<213> ORGANISM: Homo sapiens

<400> SEQUENCE: 230
ugauauguuu gauauauuag gu                                       22

<210> SEQ ID NO 231
<211> LENGTH: 22
<212> TYPE: RNA
<213> ORGANISM: Homo sapiens

<400> SEQUENCE: 231
ugggucuuug cgggcgagau ga                                       22

<210> SEQ ID NO 232
<211> LENGTH: 22
<212> TYPE: RNA
<213> ORGANISM: Homo sapiens

```
<400> SEQUENCE: 232
aacuggccua caaaguccca gu                                              22

<210> SEQ ID NO 233
<211> LENGTH: 22
<212> TYPE: RNA
<213> ORGANISM: Homo sapiens

<400> SEQUENCE: 233
uguaacagca acuccaugug ga                                              22

<210> SEQ ID NO 234
<211> LENGTH: 21
<212> TYPE: RNA
<213> ORGANISM: Homo sapiens

<400> SEQUENCE: 234
uagcagcaca gaaauauugg c                                               21

<210> SEQ ID NO 235
<211> LENGTH: 22
<212> TYPE: RNA
<213> ORGANISM: Homo sapiens

<400> SEQUENCE: 235
ccaauauugg cugugcugcu cc                                              22

<210> SEQ ID NO 236
<211> LENGTH: 22
<212> TYPE: RNA
<213> ORGANISM: Homo sapiens

<400> SEQUENCE: 236
uggaauguaa ggaagugugu gg                                              22

<210> SEQ ID NO 237
<211> LENGTH: 22
<212> TYPE: RNA
<213> ORGANISM: Homo sapiens

<400> SEQUENCE: 237
aaaagcuggg uugagagggc ga                                              22

<210> SEQ ID NO 238
<211> LENGTH: 22
<212> TYPE: RNA
<213> ORGANISM: Homo sapiens

<400> SEQUENCE: 238
cgucuuaccc agcaguguuu gg                                              22

<210> SEQ ID NO 239
<211> LENGTH: 23
<212> TYPE: RNA
<213> ORGANISM: Homo sapiens

<400> SEQUENCE: 239
uaauacugcc ggguaaugau gga                                             23

<210> SEQ ID NO 240
<211> LENGTH: 23
<212> TYPE: RNA
<213> ORGANISM: Homo sapiens
```

```
<400> SEQUENCE: 240
uuaaugcuaa ucgugauagg ggu                                           23

<210> SEQ ID NO 241
<211> LENGTH: 22
<212> TYPE: RNA
<213> ORGANISM: Homo sapiens

<400> SEQUENCE: 241
cuccuacaua uuagcauuaa ca                                            22

<210> SEQ ID NO 242
<211> LENGTH: 22
<212> TYPE: RNA
<213> ORGANISM: Homo sapiens

<400> SEQUENCE: 242 ccagugggc ugcuguuauc ug                                             22

<210> SEQ ID NO 243
<211> LENGTH: 21
<212> TYPE: RNA
<213> ORGANISM: Homo sapiens

<400> SEQUENCE: 243
uaaagugcug acagugcaga u                                             21

<210> SEQ ID NO 244
<211> LENGTH: 22
<212> TYPE: RNA
<213> ORGANISM: Homo sapiens

<400> SEQUENCE: 244
ccgcacugug gguacuugcu gc                                            22

<210> SEQ ID NO 245
<211> LENGTH: 22
<212> TYPE: RNA
<213> ORGANISM: Homo sapiens

<400> SEQUENCE: 245
ugaccgauuu cuccuggugu uc                                            22

<210> SEQ ID NO 246
<211> LENGTH: 22
<212> TYPE: RNA
<213> ORGANISM: Homo sapiens

<400> SEQUENCE: 246
uagcaccauu ugaaaucggu ua                                            22

<210> SEQ ID NO 247
<211> LENGTH: 22
<212> TYPE: RNA
<213> ORGANISM: Homo sapiens

<400> SEQUENCE: 247
cugggagagg guuguuuacu cc                                            22

<210> SEQ ID NO 248
<211> LENGTH: 22
<212> TYPE: RNA
```

```
<213> ORGANISM: Homo sapiens

<400> SEQUENCE: 248
caucuuaccg gacagugcug ga                                          22

<210> SEQ ID NO 249
<211> LENGTH: 22
<212> TYPE: RNA
<213> ORGANISM: Homo sapiens

<400> SEQUENCE: 249
uaacacuguc ugguaacgau gu                                          22

<210> SEQ ID NO 250
<211> LENGTH: 23
<212> TYPE: RNA
<213> ORGANISM: Homo sapiens

<400> SEQUENCE: 250
acuuaaacgu ggauguacuu gcu                                         23

<210> SEQ ID NO 251
<211> LENGTH: 23
<212> TYPE: RNA
<213> ORGANISM: Homo sapiens

<400> SEQUENCE: 251
uaagugcuuc cauguuuugg uga                                         23

<210> SEQ ID NO 252
<211> LENGTH: 22
<212> TYPE: RNA
<213> ORGANISM: Homo sapiens

<400> SEQUENCE: 252
agaauugugg cuggacaucu gu                                          22

<210> SEQ ID NO 253
<211> LENGTH: 23
<212> TYPE: RNA
<213> ORGANISM: Homo sapiens

<400> SEQUENCE: 253
uaggcagugu cauuagcuga uug                                         23

<210> SEQ ID NO 254
<211> LENGTH: 22
<212> TYPE: RNA
<213> ORGANISM: Homo sapiens

<400> SEQUENCE: 254
caaucacuaa cuccacugcc au                                          22

<210> SEQ ID NO 255
<211> LENGTH: 23
<212> TYPE: RNA
<213> ORGANISM: Homo sapiens

<400> SEQUENCE: 255
aggcagugua guuagcugau ugc                                         23

<210> SEQ ID NO 256
<211> LENGTH: 22
```

<212> TYPE: RNA
<213> ORGANISM: Homo sapiens

<400> SEQUENCE: 256
aaucacuaac cacacggcca gg                                     22

<210> SEQ ID NO 257
<211> LENGTH: 22
<212> TYPE: RNA
<213> ORGANISM: Homo sapiens

<400> SEQUENCE: 257
ugguuuaccg ucccacauac au                                     22

<210> SEQ ID NO 258
<211> LENGTH: 22
<212> TYPE: RNA
<213> ORGANISM: Homo sapiens

<400> SEQUENCE: 258 uauguggau gguaaaccgc uu                                      22

<210> SEQ ID NO 259
<211> LENGTH: 23
<212> TYPE: RNA
<213> ORGANISM: Homo sapiens

<400> SEQUENCE: 259
cagugcaaua guauugucaa agc                                    23

<210> SEQ ID NO 260
<211> LENGTH: 22
<212> TYPE: RNA
<213> ORGANISM: Homo sapiens

<400> SEQUENCE: 260
cacccguaga accgaccuug cg                                     22

<210> SEQ ID NO 261
<211> LENGTH: 22
<212> TYPE: RNA
<213> ORGANISM: Homo sapiens

<400> SEQUENCE: 261
caagcucgug ucuggguc cg                                       22

<210> SEQ ID NO 262
<211> LENGTH: 21
<212> TYPE: RNA
<213> ORGANISM: Homo sapiens

<400> SEQUENCE: 262 agggccccc cucaauccug u                                       21

<210> SEQ ID NO 263
<211> LENGTH: 22
<212> TYPE: RNA
<213> ORGANISM: Homo sapiens

<400> SEQUENCE: 263 gagguuggg uggaggcucu cc                                      22

<210> SEQ ID NO 264

```
<211> LENGTH: 21
<212> TYPE: RNA
<213> ORGANISM: Homo sapiens

<400> SEQUENCE: 264 acucuuccc uguugcacua c                                           21

<210> SEQ ID NO 265
<211> LENGTH: 22
<212> TYPE: RNA
<213> ORGANISM: Homo sapiens

<400> SEQUENCE: 265
cagugcaaug augaaagggc au                                         22

<210> SEQ ID NO 266
<211> LENGTH: 22
<212> TYPE: RNA
<213> ORGANISM: Homo sapiens

<400> SEQUENCE: 266
uguaaacauc cuugacugga ag                                         22

<210> SEQ ID NO 267
<211> LENGTH: 22
<212> TYPE: RNA
<213> ORGANISM: Homo sapiens

<400> SEQUENCE: 267
cuuucagucg gauguuuaca gc                                         22

<210> SEQ ID NO 268
<211> LENGTH: 22
<212> TYPE: RNA
<213> ORGANISM: Homo sapiens

<400> SEQUENCE: 268
ccuauucuug auuacuuguu uc                                         22

<210> SEQ ID NO 269
<211> LENGTH: 22
<212> TYPE: RNA
<213> ORGANISM: Homo sapiens

<400> SEQUENCE: 269
uuaucagaau cuccagggu ac                                          22

<210> SEQ ID NO 270
<211> LENGTH: 23
<212> TYPE: RNA
<213> ORGANISM: Homo sapiens

<400> SEQUENCE: 270 uccccaggu gugauucuga uuu                                         23

<210> SEQ ID NO 271
<211> LENGTH: 24
<212> TYPE: RNA
<213> ORGANISM: Homo sapiens

<400> SEQUENCE: 271
aauccuugga accuaggugu gagu                                       24
```

```
<210> SEQ ID NO 272
<211> LENGTH: 22
<212> TYPE: RNA
<213> ORGANISM: Homo sapiens

<400> SEQUENCE: 272
aacacaccua uucaaggauu ca                                              22

<210> SEQ ID NO 273
<211> LENGTH: 22
<212> TYPE: RNA
<213> ORGANISM: Homo sapiens

<400> SEQUENCE: 273
cggguggauc acgaugcaau uu                                              22

<210> SEQ ID NO 274
<211> LENGTH: 22
<212> TYPE: RNA
<213> ORGANISM: Homo sapiens

<400> SEQUENCE: 274
aauugcacgg uauccaucug ua                                              22

<210> SEQ ID NO 275
<211> LENGTH: 22
<212> TYPE: RNA
<213> ORGANISM: Homo sapiens

<400> SEQUENCE: 275
uaaugccccu aaaaauccuu au                                              22

<210> SEQ ID NO 276
<211> LENGTH: 22
<212> TYPE: RNA
<213> ORGANISM: Homo sapiens

<400> SEQUENCE: 276
agggacuuuc aggggcagcu gu                                              22

<210> SEQ ID NO 277
<211> LENGTH: 22
<212> TYPE: RNA
<213> ORGANISM: Homo sapiens

<400> SEQUENCE: 277
acuuuaacau ggaagugcuu uc                                              22

<210> SEQ ID NO 278
<211> LENGTH: 23
<212> TYPE: RNA
<213> ORGANISM: Homo sapiens

<400> SEQUENCE: 278
uaagugcuuc cauguuuuag uag                                             23

<210> SEQ ID NO 279
<211> LENGTH: 22
<212> TYPE: RNA
<213> ORGANISM: Homo sapiens

<400> SEQUENCE: 279
uuuaacaugg ggguaccugc ug                                              22
```

```
<210> SEQ ID NO 280
<211> LENGTH: 23
<212> TYPE: RNA
<213> ORGANISM: Homo sapiens

<400> SEQUENCE: 280
uaagugcuuc cauguuucag ugg                                              23

<210> SEQ ID NO 281
<211> LENGTH: 22
<212> TYPE: RNA
<213> ORGANISM: Homo sapiens

<400> SEQUENCE: 281
acuuuaacau ggaggcacuu gc                                               22

<210> SEQ ID NO 282
<211> LENGTH: 23
<212> TYPE: RNA
<213> ORGANISM: Homo sapiens

<400> SEQUENCE: 282
uaagugcuuc cauguuugag ugu                                              23

<210> SEQ ID NO 283
<211> LENGTH: 22
<212> TYPE: RNA
<213> ORGANISM: Homo sapiens

<400> SEQUENCE: 283
acuguugcua auaugcaacu cu                                               22

<210> SEQ ID NO 284
<211> LENGTH: 22
<212> TYPE: RNA
<213> ORGANISM: Homo sapiens

<400> SEQUENCE: 284
aauugcacuu uagcaauggu ga                                               22

<210> SEQ ID NO 285
<211> LENGTH: 21
<212> TYPE: RNA
<213> ORGANISM: Homo sapiens

<400> SEQUENCE: 285
aacauagagg aaauuccacg u                                                21

<210> SEQ ID NO 286
<211> LENGTH: 22
<212> TYPE: RNA
<213> ORGANISM: Homo sapiens

<400> SEQUENCE: 286
agaucgaccg uguuauauuc gc                                               22

<210> SEQ ID NO 287
<211> LENGTH: 21
<212> TYPE: RNA
<213> ORGANISM: Homo sapiens

<400> SEQUENCE: 287
aauaauacau gguugaucuu u                                                21
```

```
<210> SEQ ID NO 288
<211> LENGTH: 22
<212> TYPE: RNA
<213> ORGANISM: Homo sapiens

<400> SEQUENCE: 288
gccugcuggg guggaaccug gu                                            22

<210> SEQ ID NO 289
<211> LENGTH: 20
<212> TYPE: RNA
<213> ORGANISM: Homo sapiens

<400> SEQUENCE: 289
acucaaacug uggggcacu                                                20

<210> SEQ ID NO 290
<211> LENGTH: 23
<212> TYPE: RNA
<213> ORGANISM: Homo sapiens

<400> SEQUENCE: 290
aagugccgcc aucuuugag ugu                                            23

<210> SEQ ID NO 291
<211> LENGTH: 23
<212> TYPE: RNA
<213> ORGANISM: Homo sapiens

<400> SEQUENCE: 291
aaagugcugc gacauuugag cgu                                           23

<210> SEQ ID NO 292
<211> LENGTH: 22
<212> TYPE: RNA
<213> ORGANISM: Homo sapiens

<400> SEQUENCE: 292
acucaaaaug ggggcgcuuu cc                                            22

<210> SEQ ID NO 293
<211> LENGTH: 23
<212> TYPE: RNA
<213> ORGANISM: Homo sapiens

<400> SEQUENCE: 293
gaagugcuuc gauuuugggg ugu                                           23

<210> SEQ ID NO 294
<211> LENGTH: 22
<212> TYPE: RNA
<213> ORGANISM: Homo sapiens

<400> SEQUENCE: 294
uuauaauaca accugauaag ug                                            22

<210> SEQ ID NO 295
<211> LENGTH: 22
<212> TYPE: RNA
<213> ORGANISM: Homo sapiens

<400> SEQUENCE: 295
```
cuuaucagau uguauuguaa uu                                                    22

<210> SEQ ID NO 296
<211> LENGTH: 22
<212> TYPE: RNA
<213> ORGANISM: Homo sapiens

<400> SEQUENCE: 296
uuuguucguu cggcucgcgu ga                                                    22

<210> SEQ ID NO 297
<211> LENGTH: 22
<212> TYPE: RNA
<213> ORGANISM: Homo sapiens

<400> SEQUENCE: 297
guagauucuc cuucuaugag ua                                                    22

<210> SEQ ID NO 298
<211> LENGTH: 21
<212> TYPE: RNA
<213> ORGANISM: Homo sapiens

<400> SEQUENCE: 298
aucauagagg aaaauccacg u                                                     21

<210> SEQ ID NO 299
<211> LENGTH: 22
<212> TYPE: RNA
<213> ORGANISM: Homo sapiens

<400> SEQUENCE: 299
agagguugcc cuuggugaau uc                                                    22

<210> SEQ ID NO 300
<211> LENGTH: 22
<212> TYPE: RNA
<213> ORGANISM: Homo sapiens

<400> SEQUENCE: 300
aucacacaaa ggcaacuuuu gu                                                    22

<210> SEQ ID NO 301
<211> LENGTH: 22
<212> TYPE: RNA
<213> ORGANISM: Homo sapiens

<400> SEQUENCE: 301
cuccugacuc cagguccugu gu                                                    22

<210> SEQ ID NO 302
<211> LENGTH: 21
<212> TYPE: RNA
<213> ORGANISM: Homo sapiens

<400> SEQUENCE: 302
acuggacuug gagucagaag g                                                     21

<210> SEQ ID NO 303
<211> LENGTH: 21
<212> TYPE: RNA
<213> ORGANISM: Homo sapiens

<400> SEQUENCE: 303
ugguagacua uggaacguag g        21

<210> SEQ ID NO 304
<211> LENGTH: 22
<212> TYPE: RNA
<213> ORGANISM: Homo sapiens

<400> SEQUENCE: 304
uauguaacau gguccacuaa cu        22

<210> SEQ ID NO 305
<211> LENGTH: 22
<212> TYPE: RNA
<213> ORGANISM: Homo sapiens

<400> SEQUENCE: 305
ugguugacca uagaacaugc gc        22

<210> SEQ ID NO 306
<211> LENGTH: 22
<212> TYPE: RNA
<213> ORGANISM: Homo sapiens

<400> SEQUENCE: 306
uauguaauau gguccacauc uu        22

<210> SEQ ID NO 307
<211> LENGTH: 22
<212> TYPE: RNA
<213> ORGANISM: Homo sapiens

<400> SEQUENCE: 307
uauacaaggg caagcucucu gu        22

<210> SEQ ID NO 308
<211> LENGTH: 22
<212> TYPE: RNA
<213> ORGANISM: Homo sapiens

<400> SEQUENCE: 308
gaaguuguuc gugguggauu cg        22

<210> SEQ ID NO 309
<211> LENGTH: 22
<212> TYPE: RNA
<213> ORGANISM: Homo sapiens

<400> SEQUENCE: 309
agaucagaag gugauugugg cu        22

<210> SEQ ID NO 310
<211> LENGTH: 22
<212> TYPE: RNA
<213> ORGANISM: Homo sapiens

<400> SEQUENCE: 310
uuauaaagca augagacuga uu        22

<210> SEQ ID NO 311
<211> LENGTH: 22
<212> TYPE: RNA
<213> ORGANISM: Homo sapiens -continued

```
<400> SEQUENCE: 311
uccgucucag uuacuuuaua gc                                      22

<210> SEQ ID NO 312
<211> LENGTH: 22
<212> TYPE: RNA
<213> ORGANISM: Homo sapiens

<400> SEQUENCE: 312
ucucugggcc ugugucuuag gc                                      22

<210> SEQ ID NO 313
<211> LENGTH: 23
<212> TYPE: RNA
<213> ORGANISM: Homo sapiens

<400> SEQUENCE: 313
gcaaagcaca cggccugcag aga                                     23

<210> SEQ ID NO 314
<211> LENGTH: 22
<212> TYPE: RNA
<213> ORGANISM: Homo sapiens

<400> SEQUENCE: 314
cuggcccucu cugcccuucc gu                                      22

<210> SEQ ID NO 315
<211> LENGTH: 21
<212> TYPE: RNA
<213> ORGANISM: Homo sapiens

<400> SEQUENCE: 315
aggggugcua ucugugauug a                                       21

<210> SEQ ID NO 316
<211> LENGTH: 23
<212> TYPE: RNA
<213> ORGANISM: Homo sapiens

<400> SEQUENCE: 316
ucucacacag aaaucgcacc cgu                                     23

<210> SEQ ID NO 317
<211> LENGTH: 21
<212> TYPE: RNA
<213> ORGANISM: Homo sapiens

<400> SEQUENCE: 317
gaacggcuuc auacaggagu u                                       21

<210> SEQ ID NO 318
<211> LENGTH: 22
<212> TYPE: RNA
<213> ORGANISM: Homo sapiens

<400> SEQUENCE: 318
cuccuauaug augccuuucu uc                                      22

<210> SEQ ID NO 319
<211> LENGTH: 22
<212> TYPE: RNA
<213> ORGANISM: Homo sapiens
```

```
<400> SEQUENCE: 319
aggugguccg uggcgcguuc gc                                          22

<210> SEQ ID NO 320
<211> LENGTH: 21
<212> TYPE: RNA
<213> ORGANISM: Homo sapiens

<400> SEQUENCE: 320
cacauuacac ggucgaccuc u                                           21

<210> SEQ ID NO 321
<211> LENGTH: 20
<212> TYPE: RNA
<213> ORGANISM: Homo sapiens

<400> SEQUENCE: 321
ccucugggcc cuuccuccag                                             20

<210> SEQ ID NO 322
<211> LENGTH: 21
<212> TYPE: RNA
<213> ORGANISM: Homo sapiens

<400> SEQUENCE: 322
ucgaggagcu cacagucuag u                                           21

<210> SEQ ID NO 323
<211> LENGTH: 21
<212> TYPE: RNA
<213> ORGANISM: Homo sapiens

<400> SEQUENCE: 323
cuagacugaa gcuccuugag g                                           21

<210> SEQ ID NO 324
<211> LENGTH: 23
<212> TYPE: RNA
<213> ORGANISM: Homo sapiens

<400> SEQUENCE: 324
uauggcuuuu cauuccuaug uga                                         23

<210> SEQ ID NO 325
<211> LENGTH: 22
<212> TYPE: RNA
<213> ORGANISM: Homo sapiens

<400> SEQUENCE: 325
auguagggcu aaaagccaug gg                                          22

<210> SEQ ID NO 326
<211> LENGTH: 22
<212> TYPE: RNA
<213> ORGANISM: Homo sapiens

<400> SEQUENCE: 326
aaguucuguu auacacucag gc                                          22

<210> SEQ ID NO 327
<211> LENGTH: 22
<212> TYPE: RNA
```

```
<213> ORGANISM: Homo sapiens

<400> SEQUENCE: 327
ucagugcauc acagaacuuu gu                                        22

<210> SEQ ID NO 328
<211> LENGTH: 22
<212> TYPE: RNA
<213> ORGANISM: Homo sapiens

<400> SEQUENCE: 328
cuagguaugg ucccagggau cc                                        22

<210> SEQ ID NO 329
<211> LENGTH: 21
<212> TYPE: RNA
<213> ORGANISM: Homo sapiens

<400> SEQUENCE: 329
gccccugggc cuauccuaga a                                         21

<210> SEQ ID NO 330
<211> LENGTH: 23
<212> TYPE: RNA
<213> ORGANISM: Homo sapiens

<400> SEQUENCE: 330
cgcauccccu agggcauugg ugu                                       23

<210> SEQ ID NO 331
<211> LENGTH: 20
<212> TYPE: RNA
<213> ORGANISM: Homo sapiens

<400> SEQUENCE: 331
acugccccag gugcugcugg                                           20

<210> SEQ ID NO 332
<211> LENGTH: 22
<212> TYPE: RNA
<213> ORGANISM: Homo sapiens

<400> SEQUENCE: 332
aacaauaucc uggugcugag ug                                        22

<210> SEQ ID NO 333
<211> LENGTH: 22
<212> TYPE: RNA
<213> ORGANISM: Homo sapiens

<400> SEQUENCE: 333
uccagcauca gugauuuugu ug                                        22

<210> SEQ ID NO 334
<211> LENGTH: 23
<212> TYPE: RNA
<213> ORGANISM: Homo sapiens

<400> SEQUENCE: 334
ucccuguccu ccaggagcuc acg                                       23

<210> SEQ ID NO 335
<211> LENGTH: 23
```

```
<212> TYPE: RNA
<213> ORGANISM: Homo sapiens

<400> SEQUENCE: 335
ugagcgccuc gacgacagag ccg                                            23

<210> SEQ ID NO 336
<211> LENGTH: 23
<212> TYPE: RNA
<213> ORGANISM: Homo sapiens

<400> SEQUENCE: 336
ucaagagcaa uaacgaaaaa ugu                                            23

<210> SEQ ID NO 337
<211> LENGTH: 22
<212> TYPE: RNA
<213> ORGANISM: Homo sapiens

<400> SEQUENCE: 337
uuuuucauua uugcuccuga cc                                             22

<210> SEQ ID NO 338
<211> LENGTH: 22
<212> TYPE: RNA
<213> ORGANISM: Homo sapiens

<400> SEQUENCE: 338
uuuggucccc uucaaccagc ua                                             22

<210> SEQ ID NO 339
<211> LENGTH: 23
<212> TYPE: RNA
<213> ORGANISM: Homo sapiens

<400> SEQUENCE: 339
ccuaguaggu guccaguaag ugu                                            23

<210> SEQ ID NO 340
<211> LENGTH: 22
<212> TYPE: RNA
<213> ORGANISM: Homo sapiens

<400> SEQUENCE: 340
gcugacuccu aguccagggc uc                                             22

<210> SEQ ID NO 341
<211> LENGTH: 23
<212> TYPE: RNA
<213> ORGANISM: Homo sapiens

<400> SEQUENCE: 341
ugucugcccg caugccugcc ucu                                            23

<210> SEQ ID NO 342
<211> LENGTH: 20
<212> TYPE: RNA
<213> ORGANISM: Homo sapiens

<400> SEQUENCE: 342
auuccuagaa auuguucaua                                                20

<210> SEQ ID NO 343
```

```
<211> LENGTH: 22
<212> TYPE: RNA
<213> ORGANISM: Homo sapiens

<400> SEQUENCE: 343
uagguaguuu ccuguuguug gg                                              22

<210> SEQ ID NO 344
<211> LENGTH: 22
<212> TYPE: RNA
<213> ORGANISM: Homo sapiens

<400> SEQUENCE: 344
ucgacagcac gacacugccu uc                                              22

<210> SEQ ID NO 345
<211> LENGTH: 22
<212> TYPE: RNA
<213> ORGANISM: Homo sapiens

<400> SEQUENCE: 345
acuggacuua gggucagaag gc                                              22

<210> SEQ ID NO 346
<211> LENGTH: 23
<212> TYPE: RNA
<213> ORGANISM: Homo sapiens

<400> SEQUENCE: 346
ugaggggcag agagcgagac uuu                                             23

<210> SEQ ID NO 347
<211> LENGTH: 23
<212> TYPE: RNA
<213> ORGANISM: Homo sapiens

<400> SEQUENCE: 347
agcucggucu gaggccccuc agu                                             23

<210> SEQ ID NO 348
<211> LENGTH: 22
<212> TYPE: RNA
<213> ORGANISM: Homo sapiens

<400> SEQUENCE: 348
cagcagcaau ucauguuuug aa                                              22

<210> SEQ ID NO 349
<211> LENGTH: 21
<212> TYPE: RNA
<213> ORGANISM: Homo sapiens

<400> SEQUENCE: 349
caaaacguga ggcgcugcua u                                               21

<210> SEQ ID NO 350
<211> LENGTH: 23
<212> TYPE: RNA
<213> ORGANISM: Homo sapiens

<400> SEQUENCE: 350
aaugacacga ucacucccgu uga                                             23
```

```
<210> SEQ ID NO 351
<211> LENGTH: 22
<212> TYPE: RNA
<213> ORGANISM: Homo sapiens

<400> SEQUENCE: 351
aucgggaaug ucguguccgc cc                                              22

<210> SEQ ID NO 352
<211> LENGTH: 23
<212> TYPE: RNA
<213> ORGANISM: Homo sapiens

<400> SEQUENCE: 352
uaaggugcau cuagugcagu uag                                             23

<210> SEQ ID NO 353
<211> LENGTH: 22
<212> TYPE: RNA
<213> ORGANISM: Homo sapiens

<400> SEQUENCE: 353
ugcccuaaau gccccuucug gc                                              22

<210> SEQ ID NO 354
<211> LENGTH: 23
<212> TYPE: RNA
<213> ORGANISM: Homo sapiens

<400> SEQUENCE: 354
caaagugcuc auagugcagg uag                                             23

<210> SEQ ID NO 355
<211> LENGTH: 22
<212> TYPE: RNA
<213> ORGANISM: Homo sapiens

<400> SEQUENCE: 355
acuguaguau gggcacuucc ag                                              22

<210> SEQ ID NO 356
<211> LENGTH: 22
<212> TYPE: RNA
<213> ORGANISM: Homo sapiens

<400> SEQUENCE: 356
uugcauaugu aggaugucccc au                                             22

<210> SEQ ID NO 357
<211> LENGTH: 22
<212> TYPE: RNA
<213> ORGANISM: Homo sapiens

<400> SEQUENCE: 357
uaauacuguc ugguaaaacc gu                                              22

<210> SEQ ID NO 358
<211> LENGTH: 22
<212> TYPE: RNA
<213> ORGANISM: Homo sapiens

<400> SEQUENCE: 358
uggcagugua uuguuagcug gu                                              22
```

```
<210> SEQ ID NO 359
<211> LENGTH: 22
<212> TYPE: RNA
<213> ORGANISM: Homo sapiens

<400> SEQUENCE: 359
uuuugcgaug uguuccuaau au                                              22

<210> SEQ ID NO 360
<211> LENGTH: 21
<212> TYPE: RNA
<213> ORGANISM: Homo sapiens

<400> SEQUENCE: 360
ugucuugcag gccgucaugc a                                               21

<210> SEQ ID NO 361
<211> LENGTH: 22
<212> TYPE: RNA
<213> ORGANISM: Homo sapiens

<400> SEQUENCE: 361
caggucgucu ugcagggcuu cu                                              22

<210> SEQ ID NO 362
<211> LENGTH: 22
<212> TYPE: RNA
<213> ORGANISM: Homo sapiens

<400> SEQUENCE: 362
aucaugaugg gcuccucggu gu                                              22

<210> SEQ ID NO 363
<211> LENGTH: 22
<212> TYPE: RNA
<213> ORGANISM: Homo sapiens

<400> SEQUENCE: 363
aacacaccug guuaaccucu uu                                              22

<210> SEQ ID NO 364
<211> LENGTH: 22
<212> TYPE: RNA
<213> ORGANISM: Homo sapiens

<400> SEQUENCE: 364
aaaccguuac cauuacugag uu                                              22

<210> SEQ ID NO 365
<211> LENGTH: 22
<212> TYPE: RNA
<213> ORGANISM: Homo sapiens

<400> SEQUENCE: 365
aacuguuugc agaggaaacu ga                                              22

<210> SEQ ID NO 366
<211> LENGTH: 22
<212> TYPE: RNA
<213> ORGANISM: Homo sapiens

<400> SEQUENCE: 366
cucaucugca aagaaguaag ug                                              22
```

```
<210> SEQ ID NO 367
<211> LENGTH: 23
<212> TYPE: RNA
<213> ORGANISM: Homo sapiens

<400> SEQUENCE: 367
agguuacccg agcaacuuug cau                                        23

<210> SEQ ID NO 368
<211> LENGTH: 22
<212> TYPE: RNA
<213> ORGANISM: Homo sapiens

<400> SEQUENCE: 368
gaauguugcu cggugaaccc cu                                         22

<210> SEQ ID NO 369
<211> LENGTH: 23
<212> TYPE: RNA
<213> ORGANISM: Homo sapiens

<400> SEQUENCE: 369
acuucaccug guccacuagc cgu                                        23

<210> SEQ ID NO 370
<211> LENGTH: 21
<212> TYPE: RNA
<213> ORGANISM: Homo sapiens

<400> SEQUENCE: 370
aauauaacac agauggccug u                                          21

<210> SEQ ID NO 371
<211> LENGTH: 22
<212> TYPE: RNA
<213> ORGANISM: Homo sapiens

<400> SEQUENCE: 371
aucauagagg aaaauccaug uu                                         22

<210> SEQ ID NO 372
<211> LENGTH: 22
<212> TYPE: RNA
<213> ORGANISM: Homo sapiens

<400> SEQUENCE: 372
aagacgggag gaaagaaggg ag                                         22

<210> SEQ ID NO 373
<211> LENGTH: 21
<212> TYPE: RNA
<213> ORGANISM: Homo sapiens

<400> SEQUENCE: 373
ucacuccucu ccucccgucu u                                          21

<210> SEQ ID NO 374
<211> LENGTH: 22
<212> TYPE: RNA
<213> ORGANISM: Homo sapiens

<400> SEQUENCE: 374
```

```
ucaggcucag uccccucccg au                                              22

<210> SEQ ID NO 375
<211> LENGTH: 22
<212> TYPE: RNA
<213> ORGANISM: Homo sapiens

<400> SEQUENCE: 375
agaggcuggc cgugaugaau uc                                              22

<210> SEQ ID NO 376
<211> LENGTH: 22
<212> TYPE: RNA
<213> ORGANISM: Homo sapiens

<400> SEQUENCE: 376
gucauacacg gcucuccucu cu                                              22

<210> SEQ ID NO 377
<211> LENGTH: 22
<212> TYPE: RNA
<213> ORGANISM: Homo sapiens

<400> SEQUENCE: 377
uccuguacug agcugccccg ag                                              22

<210> SEQ ID NO 378
<211> LENGTH: 21
<212> TYPE: RNA
<213> ORGANISM: Homo sapiens

<400> SEQUENCE: 378
cggggcagcu caguacagga u                                               21

<210> SEQ ID NO 379
<211> LENGTH: 22
<212> TYPE: RNA
<213> ORGANISM: Homo sapiens

<400> SEQUENCE: 379
aaucauacag ggacauccag uu                                              22

<210> SEQ ID NO 380
<211> LENGTH: 21
<212> TYPE: RNA
<213> ORGANISM: Homo sapiens

<400> SEQUENCE: 380
cccagauaau ggcacucuca a                                               21

<210> SEQ ID NO 381
<211> LENGTH: 21
<212> TYPE: RNA
<213> ORGANISM: Homo sapiens

<400> SEQUENCE: 381
uugaaaggcu auuucuuggu c                                               21

<210> SEQ ID NO 382
<211> LENGTH: 22
<212> TYPE: RNA
<213> ORGANISM: Homo sapiens

<400> SEQUENCE: 382
```

```
gugacaucac auauacggca gc                                              22

<210> SEQ ID NO 383
<211> LENGTH: 20
<212> TYPE: RNA
<213> ORGANISM: Homo sapiens

<400> SEQUENCE: 383
ccauggaucu ccaggugggu                                                 20

<210> SEQ ID NO 384
<211> LENGTH: 22
<212> TYPE: RNA
<213> ORGANISM: Homo sapiens

<400> SEQUENCE: 384
caaccuggag gacuccaugc ug                                              22

<210> SEQ ID NO 385
<211> LENGTH: 22
<212> TYPE: RNA
<213> ORGANISM: Homo sapiens

<400> SEQUENCE: 385 agugggggaac ccuuccauga gg                                             22

<210> SEQ ID NO 386
<211> LENGTH: 22
<212> TYPE: RNA
<213> ORGANISM: Homo sapiens

<400> SEQUENCE: 386
cuuaugcaag auucccuucu ac                                              22

<210> SEQ ID NO 387
<211> LENGTH: 21
<212> TYPE: RNA
<213> ORGANISM: Homo sapiens

<400> SEQUENCE: 387
gugucuuuug cucugcaguc a                                               21

<210> SEQ ID NO 388
<211> LENGTH: 22
<212> TYPE: RNA
<213> ORGANISM: Homo sapiens

<400> SEQUENCE: 388
ugagaacuga auuccauagg cu                                              22

<210> SEQ ID NO 389
<211> LENGTH: 22
<212> TYPE: RNA
<213> ORGANISM: Homo sapiens

<400> SEQUENCE: 389
ugcccugugg acucaguucu gg                                              22

<210> SEQ ID NO 390
<211> LENGTH: 22
<212> TYPE: RNA
<213> ORGANISM: Homo sapiens
```

-continued

```
<400> SEQUENCE: 390
uuccuaugca uauacuucuu ug                                              22

<210> SEQ ID NO 391
<211> LENGTH: 20
<212> TYPE: RNA
<213> ORGANISM: Homo sapiens

<400> SEQUENCE: 391
agagguauag ggcaugggaa                                                 20

<210> SEQ ID NO 392
<211> LENGTH: 23
<212> TYPE: RNA
<213> ORGANISM: Homo sapiens

<400> SEQUENCE: 392
aggaccugcg ggacaagauu cuu                                             23

<210> SEQ ID NO 393
<211> LENGTH: 22
<212> TYPE: RNA
<213> ORGANISM: Homo sapiens

<400> SEQUENCE: 393
uuguacaugg uaggcuuuca uu                                              22

<210> SEQ ID NO 394
<211> LENGTH: 22
<212> TYPE: RNA
<213> ORGANISM: Homo sapiens

<400> SEQUENCE: 394
ugaaggucua cugugugcca gg                                              22

<210> SEQ ID NO 395
<211> LENGTH: 23
<212> TYPE: RNA
<213> ORGANISM: Homo sapiens

<400> SEQUENCE: 395
ucuuggagua ggucauuggg ugg                                             23

<210> SEQ ID NO 396
<211> LENGTH: 21
<212> TYPE: RNA
<213> ORGANISM: Homo sapiens

<400> SEQUENCE: 396
cuggauggcu ccuccauguc u                                               21

<210> SEQ ID NO 397
<211> LENGTH: 22
<212> TYPE: RNA
<213> ORGANISM: Homo sapiens

<400> SEQUENCE: 397
ugaaacauac acgggaaacc uc                                              22

<210> SEQ ID NO 398
<211> LENGTH: 22
<212> TYPE: RNA
<213> ORGANISM: Homo sapiens
```

<400> SEQUENCE: 398
aaacaaacau ggugcacuuc uu                                          22

<210> SEQ ID NO 399
<211> LENGTH: 22
<212> TYPE: RNA
<213> ORGANISM: Homo sapiens

<400> SEQUENCE: 399
ugaguauuac auggccaauc uc                                          22

<210> SEQ ID NO 400
<211> LENGTH: 22
<212> TYPE: RNA
<213> ORGANISM: Homo sapiens

<400> SEQUENCE: 400
cgggguuuug agggcgagau ga                                          22

<210> SEQ ID NO 401
<211> LENGTH: 22
<212> TYPE: RNA
<213> ORGANISM: Homo sapiens

<400> SEQUENCE: 401
aacuggcccu caaagucccg cu                                          22

<210> SEQ ID NO 402
<211> LENGTH: 21
<212> TYPE: RNA
<213> ORGANISM: Homo sapiens

<400> SEQUENCE: 402
cagcagcaca cugugguuug u                                           21

<210> SEQ ID NO 403
<211> LENGTH: 22
<212> TYPE: RNA
<213> ORGANISM: Homo sapiens

<400> SEQUENCE: 403
caaaccacac ugugguguua ga                                          22

<210> SEQ ID NO 404
<211> LENGTH: 23
<212> TYPE: RNA
<213> ORGANISM: Homo sapiens

<400> SEQUENCE: 404
aacauucauu guugucggug ggu                                         23

<210> SEQ ID NO 405
<211> LENGTH: 23
<212> TYPE: RNA
<213> ORGANISM: Homo sapiens

<400> SEQUENCE: 405
cacucagccu ugagggcacu uuc                                         23

<210> SEQ ID NO 406
<211> LENGTH: 22
<212> TYPE: RNA

```
<213> ORGANISM: Homo sapiens

<400> SEQUENCE: 406
aagugcuguc auagcugagg uc                                          22

<210> SEQ ID NO 407
<211> LENGTH: 23
<212> TYPE: RNA
<213> ORGANISM: Homo sapiens

<400> SEQUENCE: 407
uuucaagcca gggggcguuu uuc                                         23

<210> SEQ ID NO 408
<211> LENGTH: 21
<212> TYPE: RNA
<213> ORGANISM: Homo sapiens

<400> SEQUENCE: 408
aaagugcuuc cuuuuugagg g                                           21

<210> SEQ ID NO 409
<211> LENGTH: 24
<212> TYPE: RNA
<213> ORGANISM: Homo sapiens

<400> SEQUENCE: 409
uucuccaaaa gaaagcacuu ucug                                        24

<210> SEQ ID NO 410
<211> LENGTH: 22
<212> TYPE: RNA
<213> ORGANISM: Homo sapiens

<400> SEQUENCE: 410
gagugccuuc uuuuggagcg uu                                          22

<210> SEQ ID NO 411
<211> LENGTH: 22
<212> TYPE: RNA
<213> ORGANISM: Homo sapiens

<400> SEQUENCE: 411
uucuccaaaa gggagcacuu uc                                          22

<210> SEQ ID NO 412
<211> LENGTH: 22
<212> TYPE: RNA
<213> ORGANISM: Homo sapiens

<400> SEQUENCE: 412
aagugccucc uuuuagagug uu                                          22

<210> SEQ ID NO 413
<211> LENGTH: 22
<212> TYPE: RNA
<213> ORGANISM: Homo sapiens

<400> SEQUENCE: 413
aagugcuucc uuuuagaggg uu                                          22

<210> SEQ ID NO 414
<211> LENGTH: 22
```

```
<212> TYPE: RNA
<213> ORGANISM: Homo sapiens

<400> SEQUENCE: 414
cucuagaggg aagcgcuuuc ug                                              22

<210> SEQ ID NO 415
<211> LENGTH: 22
<212> TYPE: RNA
<213> ORGANISM: Homo sapiens

<400> SEQUENCE: 415
aaagugcauc uuuuuagagg au                                              22

<210> SEQ ID NO 416
<211> LENGTH: 21
<212> TYPE: RNA
<213> ORGANISM: Homo sapiens

<400> SEQUENCE: 416
cuccagaggg aaguacuuuc u                                               21

<210> SEQ ID NO 417
<211> LENGTH: 22
<212> TYPE: RNA
<213> ORGANISM: Homo sapiens

<400> SEQUENCE: 417
aaagugcuuc ccuuuggacu gu                                              22

<210> SEQ ID NO 418
<211> LENGTH: 23
<212> TYPE: RNA
<213> ORGANISM: Homo sapiens

<400> SEQUENCE: 418
cucuugaggg aagcacuuuc ugu                                             23

<210> SEQ ID NO 419
<211> LENGTH: 22
<212> TYPE: RNA
<213> ORGANISM: Homo sapiens

<400> SEQUENCE: 419
gaaagugcuu ccuuuuagag gc                                              22

<210> SEQ ID NO 420
<211> LENGTH: 22
<212> TYPE: RNA
<213> ORGANISM: Homo sapiens

<400> SEQUENCE: 420
aaagugcauc cuuuuagagg uu                                              22

<210> SEQ ID NO 421
<211> LENGTH: 21
<212> TYPE: RNA
<213> ORGANISM: Homo sapiens

<400> SEQUENCE: 421
cuccagaggg augcacuuuc u                                               21

<210> SEQ ID NO 422
```

```
<211> LENGTH: 22
<212> TYPE: RNA
<213> ORGANISM: Homo sapiens

<400> SEQUENCE: 422
gaaggcgcuu cccuuuagag cg                                              22

<210> SEQ ID NO 423
<211> LENGTH: 23
<212> TYPE: RNA
<213> ORGANISM: Homo sapiens

<400> SEQUENCE: 423
gaacgcgcuu cccuauagag ggu                                             23

<210> SEQ ID NO 424
<211> LENGTH: 22
<212> TYPE: RNA
<213> ORGANISM: Homo sapiens

<400> SEQUENCE: 424
cucuagaggg aagcacuuuc uc                                              22

<210> SEQ ID NO 425
<211> LENGTH: 21
<212> TYPE: RNA
<213> ORGANISM: Homo sapiens

<400> SEQUENCE: 425
gaaagcgcuu cucuuuagag g                                               21

<210> SEQ ID NO 426
<211> LENGTH: 21
<212> TYPE: RNA
<213> ORGANISM: Homo sapiens

<400> SEQUENCE: 426
aaagugcuuc cuuuuagagg g                                               21

<210> SEQ ID NO 427
<211> LENGTH: 22
<212> TYPE: RNA
<213> ORGANISM: Homo sapiens

<400> SEQUENCE: 427
caaagcgcuc cccuuuagag gu                                              22

<210> SEQ ID NO 428
<211> LENGTH: 22
<212> TYPE: RNA
<213> ORGANISM: Homo sapiens

<400> SEQUENCE: 428
cucuagaggg aagcacuuuc ug                                              22

<210> SEQ ID NO 429
<211> LENGTH: 22
<212> TYPE: RNA
<213> ORGANISM: Homo sapiens

<400> SEQUENCE: 429
aaagugcuuc cuuuuagagg gu                                              22
```

```
<210> SEQ ID NO 430
<211> LENGTH: 23
<212> TYPE: RNA
<213> ORGANISM: Homo sapiens

<400> SEQUENCE: 430
ucucuggagg gaagcacuuu cug                                              23

<210> SEQ ID NO 431
<211> LENGTH: 23
<212> TYPE: RNA
<213> ORGANISM: Homo sapiens

<400> SEQUENCE: 431
caaagcgcuu cucuuuagag ugu                                              23

<210> SEQ ID NO 432
<211> LENGTH: 22
<212> TYPE: RNA
<213> ORGANISM: Homo sapiens

<400> SEQUENCE: 432
cuacaaaggg aagcacuuuc uc                                               22

<210> SEQ ID NO 433
<211> LENGTH: 21
<212> TYPE: RNA
<213> ORGANISM: Homo sapiens

<400> SEQUENCE: 433
gaaggcgcuu cccuuuggag u                                                21

<210> SEQ ID NO 434
<211> LENGTH: 22
<212> TYPE: RNA
<213> ORGANISM: Homo sapiens

<400> SEQUENCE: 434
ccucuagaug gaagcacugu cu                                               22

<210> SEQ ID NO 435
<211> LENGTH: 22
<212> TYPE: RNA
<213> ORGANISM: Homo sapiens

<400> SEQUENCE: 435
aucgugcauc ccuuuagagu gu                                               22

<210> SEQ ID NO 436
<211> LENGTH: 22
<212> TYPE: RNA
<213> ORGANISM: Homo sapiens

<400> SEQUENCE: 436
caaagugccu cccuuuagag ug                                               22

<210> SEQ ID NO 437
<211> LENGTH: 22
<212> TYPE: RNA
<213> ORGANISM: Homo sapiens

<400> SEQUENCE: 437
aacgcacuuc ccuuuagagu gu                                               22
```

```
<210> SEQ ID NO 438
<211> LENGTH: 20
<212> TYPE: RNA
<213> ORGANISM: Homo sapiens

<400> SEQUENCE: 438
cuacaaaggg aagcccuuuc                                              20

<210> SEQ ID NO 439
<211> LENGTH: 22
<212> TYPE: RNA
<213> ORGANISM: Homo sapiens

<400> SEQUENCE: 439
aaagugcuuc ucuuuggugg gu                                           22

<210> SEQ ID NO 440
<211> LENGTH: 22
<212> TYPE: RNA
<213> ORGANISM: Homo sapiens

<400> SEQUENCE: 440
ucgugcaucc cuuuagagug uu                                           22

<210> SEQ ID NO 441
<211> LENGTH: 24
<212> TYPE: RNA
<213> ORGANISM: Homo sapiens

<400> SEQUENCE: 441
acaaagugcu ucccuuuaga gugu                                         24

<210> SEQ ID NO 442
<211> LENGTH: 22
<212> TYPE: RNA
<213> ORGANISM: Homo sapiens

<400> SEQUENCE: 442
aucuggaggu aagaagcacu uu                                           22

<210> SEQ ID NO 443
<211> LENGTH: 18
<212> TYPE: RNA
<213> ORGANISM: Homo sapiens

<400> SEQUENCE: 443
ugcuuccuuu cagagggu                                                18

<210> SEQ ID NO 444
<211> LENGTH: 21
<212> TYPE: RNA
<213> ORGANISM: Homo sapiens

<400> SEQUENCE: 444
aaagcgcuuc ccuucagagu g                                            21

<210> SEQ ID NO 445
<211> LENGTH: 20
<212> TYPE: RNA
<213> ORGANISM: Homo sapiens

<400> SEQUENCE: 445
cugcaaaggg aagcccuuuc                                              20
```

```
<210> SEQ ID NO 446
<211> LENGTH: 22
<212> TYPE: RNA
<213> ORGANISM: Homo sapiens

<400> SEQUENCE: 446
gaaagcgcuu cccuuugcug ga                                              22

<210> SEQ ID NO 447
<211> LENGTH: 21
<212> TYPE: RNA
<213> ORGANISM: Homo sapiens

<400> SEQUENCE: 447
caaagcgcuu cccuuuggag c                                               21

<210> SEQ ID NO 448
<211> LENGTH: 22
<212> TYPE: RNA
<213> ORGANISM: Homo sapiens

<400> SEQUENCE: 448
aucgugcauc cuuuuagagu gu                                              22

<210> SEQ ID NO 449
<211> LENGTH: 22
<212> TYPE: RNA
<213> ORGANISM: Homo sapiens

<400> SEQUENCE: 449
acaaagugcu ucccuuuaga gu                                              22

<210> SEQ ID NO 450
<211> LENGTH: 22
<212> TYPE: RNA
<213> ORGANISM: Homo sapiens

<400> SEQUENCE: 450
aaaaugguuc ccuuuagagu gu                                              22

<210> SEQ ID NO 451
<211> LENGTH: 22
<212> TYPE: RNA
<213> ORGANISM: Homo sapiens

<400> SEQUENCE: 451
aaagugcauc cuuuuagagu gu                                              22

<210> SEQ ID NO 452
<211> LENGTH: 23
<212> TYPE: RNA
<213> ORGANISM: Homo sapiens

<400> SEQUENCE: 452
uucucgagga aagaagcacu uuc                                             23

<210> SEQ ID NO 453
<211> LENGTH: 21
<212> TYPE: RNA
<213> ORGANISM: Homo sapiens

<400> SEQUENCE: 453
```
uuaagacuug cagugauguu u                                                21

<210> SEQ ID NO 454
<211> LENGTH: 22
<212> TYPE: RNA
<213> ORGANISM: Homo sapiens

<400> SEQUENCE: 454
aacaucacag caagucugug cu                                               22

<210> SEQ ID NO 455
<211> LENGTH: 23
<212> TYPE: RNA
<213> ORGANISM: Homo sapiens

<400> SEQUENCE: 455
uaauccuugc uaccugggug aga                                              23

<210> SEQ ID NO 456
<211> LENGTH: 22
<212> TYPE: RNA
<213> ORGANISM: Homo sapiens

<400> SEQUENCE: 456
augcaccugg gcaaggauuc ug                                               22

<210> SEQ ID NO 457
<211> LENGTH: 22
<212> TYPE: RNA
<213> ORGANISM: Homo sapiens

<400> SEQUENCE: 457
aauccuuugu cccuggguga ga                                               22

<210> SEQ ID NO 458
<211> LENGTH: 22
<212> TYPE: RNA
<213> ORGANISM: Homo sapiens

<400> SEQUENCE: 458
aaugcacccg ggcaaggauu cu                                               22

<210> SEQ ID NO 459
<211> LENGTH: 21
<212> TYPE: RNA
<213> ORGANISM: Homo sapiens

<400> SEQUENCE: 459
auccuugcua ucugggugcu a                                                21

<210> SEQ ID NO 460
<211> LENGTH: 22
<212> TYPE: RNA
<213> ORGANISM: Homo sapiens

<400> SEQUENCE: 460
aaugcaccug ggcaaggauu ca                                               22

<210> SEQ ID NO 461
<211> LENGTH: 23
<212> TYPE: RNA
<213> ORGANISM: Homo sapiens

<400> SEQUENCE: 461

```
uagcagcggg aacaguucug cag                                            23

<210> SEQ ID NO 462
<211> LENGTH: 22
<212> TYPE: RNA
<213> ORGANISM: Homo sapiens

<400> SEQUENCE: 462
agacccuggu cugcacucua uc                                             22

<210> SEQ ID NO 463
<211> LENGTH: 22
<212> TYPE: RNA
<213> ORGANISM: Homo sapiens

<400> SEQUENCE: 463
gggagccagg aaguauugau gu                                             22

<210> SEQ ID NO 464
<211> LENGTH: 22
<212> TYPE: RNA
<213> ORGANISM: Homo sapiens

<400> SEQUENCE: 464
cgucaacacu ugcugguuuc cu                                             22

<210> SEQ ID NO 465
<211> LENGTH: 18
<212> TYPE: RNA
<213> ORGANISM: Homo sapiens

<400> SEQUENCE: 465
uucacaggga ggugucau                                                  18

<210> SEQ ID NO 466
<211> LENGTH: 23
<212> TYPE: RNA
<213> ORGANISM: Homo sapiens

<400> SEQUENCE: 466
uaaauuucac cuuucugaga agg                                            23

<210> SEQ ID NO 467
<211> LENGTH: 21
<212> TYPE: RNA
<213> ORGANISM: Homo sapiens

<400> SEQUENCE: 467
uaaggcaccc uucugaguag a                                              21

<210> SEQ ID NO 468
<211> LENGTH: 21
<212> TYPE: RNA
<213> ORGANISM: Homo sapiens

<400> SEQUENCE: 468
uuuugcaccu uuuggaguga a                                              21

<210> SEQ ID NO 469
<211> LENGTH: 23
<212> TYPE: RNA
<213> ORGANISM: Homo sapiens
```

```
<400> SEQUENCE: 469
uacuccagag ggcgucacuc aug                                    23

<210> SEQ ID NO 470
<211> LENGTH: 23
<212> TYPE: RNA
<213> ORGANISM: Homo sapiens

<400> SEQUENCE: 470
ugauuguagc cuuuuggagu aga                                    23

<210> SEQ ID NO 471
<211> LENGTH: 21
<212> TYPE: RNA
<213> ORGANISM: Homo sapiens

<400> SEQUENCE: 471
uacugcagac aguggcaauc a                                      21

<210> SEQ ID NO 472
<211> LENGTH: 22
<212> TYPE: RNA
<213> ORGANISM: Homo sapiens

<400> SEQUENCE: 472
ugauugguac gucugugggu ag                                     22

<210> SEQ ID NO 473
<211> LENGTH: 22
<212> TYPE: RNA
<213> ORGANISM: Homo sapiens

<400> SEQUENCE: 473
uacucaggag aguggcaauc ac                                     22

<210> SEQ ID NO 474
<211> LENGTH: 21
<212> TYPE: RNA
<213> ORGANISM: Homo sapiens

<400> SEQUENCE: 474
auugacacuu cugugaguag a                                      21

<210> SEQ ID NO 475
<211> LENGTH: 22
<212> TYPE: RNA
<213> ORGANISM: Homo sapiens

<400> SEQUENCE: 475
caugccuuga guguaggacc gu                                     22

<210> SEQ ID NO 476
<211> LENGTH: 22
<212> TYPE: RNA
<213> ORGANISM: Homo sapiens

<400> SEQUENCE: 476
ccucccacac ccaaggcuug ca                                     22

<210> SEQ ID NO 477
<211> LENGTH: 22
<212> TYPE: RNA
<213> ORGANISM: Homo sapiens
```

```
<400> SEQUENCE: 477
uaugugccuu uggacuacau cg                                    22

<210> SEQ ID NO 478
<211> LENGTH: 21
<212> TYPE: RNA
<213> ORGANISM: Homo sapiens

<400> SEQUENCE: 478
gcaguccaug ggcauauaca c                                     21

<210> SEQ ID NO 479
<211> LENGTH: 22
<212> TYPE: RNA
<213> ORGANISM: Homo sapiens

<400> SEQUENCE: 479
ggagaaauua uccuuggugu gu                                    22

<210> SEQ ID NO 480
<211> LENGTH: 22
<212> TYPE: RNA
<213> ORGANISM: Homo sapiens

<400> SEQUENCE: 480
auucugcauu uuuagcaagu uc                                    22

<210> SEQ ID NO 481
<211> LENGTH: 22
<212> TYPE: RNA
<213> ORGANISM: Homo sapiens

<400> SEQUENCE: 481
ucaguaaaug uuuauuagau ga                                    22

<210> SEQ ID NO 482
<211> LENGTH: 22
<212> TYPE: RNA
<213> ORGANISM: Homo sapiens

<400> SEQUENCE: 482
ucagcaaaca uuuauugugu gc                                    22

<210> SEQ ID NO 483
<211> LENGTH: 22
<212> TYPE: RNA
<213> ORGANISM: Homo sapiens

<400> SEQUENCE: 483
aaucguacag ggucauccac uu                                    22

<210> SEQ ID NO 484
<211> LENGTH: 21
<212> TYPE: RNA
<213> ORGANISM: Homo sapiens

<400> SEQUENCE: 484
gcgacccacu cuugguuucc a                                     21

<210> SEQ ID NO 485
<211> LENGTH: 21
<212> TYPE: RNA
```

```
<213> ORGANISM: Homo sapiens

<400> SEQUENCE: 485
aacaggugac ugguuagaca a                                              21

<210> SEQ ID NO 486
<211> LENGTH: 21
<212> TYPE: RNA
<213> ORGANISM: Homo sapiens

<400> SEQUENCE: 486
aaaacgguga gauuuuguuu u                                              21

<210> SEQ ID NO 487
<211> LENGTH: 21
<212> TYPE: RNA
<213> ORGANISM: Homo sapiens

<400> SEQUENCE: 487
gcuaguccug acucagccag u                                              21

<210> SEQ ID NO 488
<211> LENGTH: 22
<212> TYPE: RNA
<213> ORGANISM: Homo sapiens

<400> SEQUENCE: 488
agggacggga cgcggugcag ug                                             22

<210> SEQ ID NO 489
<211> LENGTH: 22
<212> TYPE: RNA
<213> ORGANISM: Homo sapiens

<400> SEQUENCE: 489
uauugcacuc gucccggccu cc                                             22

<210> SEQ ID NO 490
<211> LENGTH: 21
<212> TYPE: RNA
<213> ORGANISM: Homo sapiens

<400> SEQUENCE: 490
aggguaagcu gaaccucuga u                                              21

<210> SEQ ID NO 491
<211> LENGTH: 22
<212> TYPE: RNA
<213> ORGANISM: Homo sapiens

<400> SEQUENCE: 491
gaugagcuca uuguaauaug ag                                             22

<210> SEQ ID NO 492
<211> LENGTH: 22
<212> TYPE: RNA
<213> ORGANISM: Homo sapiens

<400> SEQUENCE: 492
auauuaccau uagcucaucu uu                                             22

<210> SEQ ID NO 493
<211> LENGTH: 23
```

```
<212> TYPE: RNA
<213> ORGANISM: Homo sapiens

<400> SEQUENCE: 493
guuugcacgg gugggccuug ucu                                           23

<210> SEQ ID NO 494
<211> LENGTH: 19
<212> TYPE: RNA
<213> ORGANISM: Homo sapiens

<400> SEQUENCE: 494
ugagcugcug uaccaaaau                                                19

<210> SEQ ID NO 495
<211> LENGTH: 21
<212> TYPE: RNA
<213> ORGANISM: Homo sapiens

<400> SEQUENCE: 495
uaaaguaaau augcaccaaa a                                             21

<210> SEQ ID NO 496
<211> LENGTH: 22
<212> TYPE: RNA
<213> ORGANISM: Homo sapiens

<400> SEQUENCE: 496
caaaguuuaa gauccuugaa gu                                            22

<210> SEQ ID NO 497
<211> LENGTH: 20
<212> TYPE: RNA
<213> ORGANISM: Homo sapiens

<400> SEQUENCE: 497
aaaguagcug uaccauuugc                                               20

<210> SEQ ID NO 498
<211> LENGTH: 19
<212> TYPE: RNA
<213> ORGANISM: Homo sapiens

<400> SEQUENCE: 498
agguugacau acguuuccc                                                19

<210> SEQ ID NO 499
<211> LENGTH: 19
<212> TYPE: RNA
<213> ORGANISM: Homo sapiens

<400> SEQUENCE: 499
aggcacggug ucagcaggc                                                19

<210> SEQ ID NO 500
<211> LENGTH: 19
<212> TYPE: RNA
<213> ORGANISM: Homo sapiens

<400> SEQUENCE: 500
gggcgccugu gaucccaac                                                19

<210> SEQ ID NO 501
```

```
<211> LENGTH: 23
<212> TYPE: RNA
<213> ORGANISM: Homo sapiens

<400> SEQUENCE: 501
aguauguucu uccaggacag aac                                              23

<210> SEQ ID NO 502
<211> LENGTH: 20
<212> TYPE: RNA
<213> ORGANISM: Homo sapiens

<400> SEQUENCE: 502
auguauaaau guauacacac                                                  20

<210> SEQ ID NO 503
<211> LENGTH: 22
<212> TYPE: RNA
<213> ORGANISM: Homo sapiens

<400> SEQUENCE: 503
gaaaucaagc gugggugaga cc                                               22

<210> SEQ ID NO 504
<211> LENGTH: 21
<212> TYPE: RNA
<213> ORGANISM: Homo sapiens

<400> SEQUENCE: 504
gcgacccaua cuugguuuca g                                                21

<210> SEQ ID NO 505
<211> LENGTH: 21
<212> TYPE: RNA
<213> ORGANISM: Homo sapiens

<400> SEQUENCE: 505
aguuaaugaa uccuggaaag u                                                21

<210> SEQ ID NO 506
<211> LENGTH: 22
<212> TYPE: RNA
<213> ORGANISM: Homo sapiens

<400> SEQUENCE: 506
cgaaaacagc aauuaccuuu gc                                               22

<210> SEQ ID NO 507
<211> LENGTH: 21
<212> TYPE: RNA
<213> ORGANISM: Homo sapiens

<400> SEQUENCE: 507
ugaguuggcc aucugaguga g                                                21

<210> SEQ ID NO 508
<211> LENGTH: 20
<212> TYPE: RNA
<213> ORGANISM: Homo sapiens

<400> SEQUENCE: 508
guccgcucgg cgguggccca                                                  20
```

```
<210> SEQ ID NO 509
<211> LENGTH: 24
<212> TYPE: RNA
<213> ORGANISM: Homo sapiens

<400> SEQUENCE: 509
cugaagugau guguaacuga ucag                                         24

<210> SEQ ID NO 510
<211> LENGTH: 23
<212> TYPE: RNA
<213> ORGANISM: Homo sapiens

<400> SEQUENCE: 510
ugagugugug ugugugagug ugu                                          23

<210> SEQ ID NO 511
<211> LENGTH: 22
<212> TYPE: RNA
<213> ORGANISM: Homo sapiens

<400> SEQUENCE: 511
cacgcucaug cacacaccca ca                                           22

<210> SEQ ID NO 512
<211> LENGTH: 19
<212> TYPE: RNA
<213> ORGANISM: Homo sapiens

<400> SEQUENCE: 512
gagccaguug gacaggagc                                               19

<210> SEQ ID NO 513
<211> LENGTH: 22
<212> TYPE: RNA
<213> ORGANISM: Homo sapiens

<400> SEQUENCE: 513
auucuaauuu cuccacgucu uu                                           22

<210> SEQ ID NO 514
<211> LENGTH: 22
<212> TYPE: RNA
<213> ORGANISM: Homo sapiens

<400> SEQUENCE: 514
aagaugugga aaaauuggaa uc                                           22

<210> SEQ ID NO 515
<211> LENGTH: 21
<212> TYPE: RNA
<213> ORGANISM: Homo sapiens

<400> SEQUENCE: 515
uagauaaaau auuggguaccu g                                           21

<210> SEQ ID NO 516
<211> LENGTH: 21
<212> TYPE: RNA
<213> ORGANISM: Homo sapiens

<400> SEQUENCE: 516
cuucuugugc ucuaggauug u                                            21
```

<210> SEQ ID NO 517
<211> LENGTH: 23
<212> TYPE: RNA
<213> ORGANISM: Homo sapiens

<400> SEQUENCE: 517
uucauuuggu auaaaccgcg auu                                           23

<210> SEQ ID NO 518
<211> LENGTH: 22
<212> TYPE: RNA
<213> ORGANISM: Homo sapiens

<400> SEQUENCE: 518
uugagaauga ugaaucauua gg                                            22

<210> SEQ ID NO 519
<211> LENGTH: 21
<212> TYPE: RNA
<213> ORGANISM: Homo sapiens

<400> SEQUENCE: 519
ucuuguguuc ucuagaucag u                                             21

<210> SEQ ID NO 520
<211> LENGTH: 23
<212> TYPE: RNA
<213> ORGANISM: Homo sapiens

<400> SEQUENCE: 520
uuacaguugu ucaaccaguu acu                                           23

<210> SEQ ID NO 521
<211> LENGTH: 22
<212> TYPE: RNA
<213> ORGANISM: Homo sapiens

<400> SEQUENCE: 521
uaacugguug aacaacugaa cc                                            22

<210> SEQ ID NO 522
<211> LENGTH: 21
<212> TYPE: RNA
<213> ORGANISM: Homo sapiens

<400> SEQUENCE: 522
caaagaggaa ggucccauua c                                             21

<210> SEQ ID NO 523
<211> LENGTH: 22
<212> TYPE: RNA
<213> ORGANISM: Homo sapiens

<400> SEQUENCE: 523
uuaugguuug ccugggacug ag                                            22

<210> SEQ ID NO 524
<211> LENGTH: 19
<212> TYPE: RNA
<213> ORGANISM: Homo sapiens

<400> SEQUENCE: 524
ugggcguauc uguaugcua                                                19

<210> SEQ ID NO 525
<211> LENGTH: 22
<212> TYPE: RNA
<213> ORGANISM: Homo sapiens

<400> SEQUENCE: 525
caaaacuggc aauuacuuuu gc                                            22

<210> SEQ ID NO 526
<211> LENGTH: 22
<212> TYPE: RNA
<213> ORGANISM: Homo sapiens

<400> SEQUENCE: 526
uaugcauugu auuuuaggu cc                                             22

<210> SEQ ID NO 527
<211> LENGTH: 21
<212> TYPE: RNA
<213> ORGANISM: Homo sapiens

<400> SEQUENCE: 527
uuuccauagg ugaugaguca c                                             21

<210> SEQ ID NO 528
<211> LENGTH: 22
<212> TYPE: RNA
<213> ORGANISM: Homo sapiens

<400> SEQUENCE: 528
aaaaguaauu gugguuuugg cc                                            22

<210> SEQ ID NO 529
<211> LENGTH: 22
<212> TYPE: RNA
<213> ORGANISM: Homo sapiens

<400> SEQUENCE: 529
caagaaccuc aguugcuuuu gu                                            22

<210> SEQ ID NO 530
<211> LENGTH: 21
<212> TYPE: RNA
<213> ORGANISM: Homo sapiens

<400> SEQUENCE: 530
uuggccacaa ugggguuagaa c                                            21

<210> SEQ ID NO 531
<211> LENGTH: 22
<212> TYPE: RNA
<213> ORGANISM: Homo sapiens

<400> SEQUENCE: 531
ugagaaccac gucugcucug ag                                            22

<210> SEQ ID NO 532
<211> LENGTH: 24
<212> TYPE: RNA
<213> ORGANISM: Homo sapiens

<400> SEQUENCE: 532

```
ucagaacaaa ugccgguucc caga                                          24

<210> SEQ ID NO 533
<211> LENGTH: 23
<212> TYPE: RNA
<213> ORGANISM: Homo sapiens

<400> SEQUENCE: 533
agugccugag ggaguaagag ccc                                           23

<210> SEQ ID NO 534
<211> LENGTH: 22
<212> TYPE: RNA
<213> ORGANISM: Homo sapiens

<400> SEQUENCE: 534
ugucuuacuc ccucaggcac au                                            22

<210> SEQ ID NO 535
<211> LENGTH: 22
<212> TYPE: RNA
<213> ORGANISM: Homo sapiens

<400> SEQUENCE: 535
gagcuuauuc auaaaagugc ag                                            22

<210> SEQ ID NO 536
<211> LENGTH: 21
<212> TYPE: RNA
<213> ORGANISM: Homo sapiens

<400> SEQUENCE: 536
uaauuuuaug uauaagcuag u                                             21

<210> SEQ ID NO 537
<211> LENGTH: 20
<212> TYPE: RNA
<213> ORGANISM: Homo sapiens

<400> SEQUENCE: 537
agaccauggg uucucauugu                                               20

<210> SEQ ID NO 538
<211> LENGTH: 22
<212> TYPE: RNA
<213> ORGANISM: Homo sapiens

<400> SEQUENCE: 538
uugugucaau augcgaugau gu                                            22

<210> SEQ ID NO 539
<211> LENGTH: 25
<212> TYPE: RNA
<213> ORGANISM: Homo sapiens

<400> SEQUENCE: 539
aggcaccagc caggcauugc ucagc                                         25

<210> SEQ ID NO 540
<211> LENGTH: 19
<212> TYPE: RNA
<213> ORGANISM: Homo sapiens

<400> SEQUENCE: 540
```

-continued

| | |
|---|---|
| ugucucugcu gggguuucu | 19 |

<210> SEQ ID NO 541
<211> LENGTH: 21
<212> TYPE: RNA
<213> ORGANISM: Homo sapiens

<400> SEQUENCE: 541

| | |
|---|---|
| gaagugugcc guguguguc u | 21 |

<210> SEQ ID NO 542
<211> LENGTH: 21
<212> TYPE: RNA
<213> ORGANISM: Homo sapiens

<400> SEQUENCE: 542

| | |
|---|---|
| aagccugccc ggcuccucgg g | 21 |

<210> SEQ ID NO 543
<211> LENGTH: 22
<212> TYPE: RNA
<213> ORGANISM: Homo sapiens

<400> SEQUENCE: 543

| | |
|---|---|
| ugugucacuc gaugaccacu gu | 22 |

<210> SEQ ID NO 544
<211> LENGTH: 22
<212> TYPE: RNA
<213> ORGANISM: Homo sapiens

<400> SEQUENCE: 544

| | |
|---|---|
| uacgucaucg uugucaucgu ca | 22 |

<210> SEQ ID NO 545
<211> LENGTH: 20
<212> TYPE: RNA
<213> ORGANISM: Homo sapiens

<400> SEQUENCE: 545

| | |
|---|---|
| guugugucag uuuaucaaac | 20 |

<210> SEQ ID NO 546
<211> LENGTH: 22
<212> TYPE: RNA
<213> ORGANISM: Homo sapiens

<400> SEQUENCE: 546

| | |
|---|---|
| aaaaguaauu gcgaguuuua cc | 22 |

<210> SEQ ID NO 547
<211> LENGTH: 23
<212> TYPE: RNA
<213> ORGANISM: Homo sapiens

<400> SEQUENCE: 547

| | |
|---|---|
| acuuacagac aagagccuug cuc | 23 |

<210> SEQ ID NO 548
<211> LENGTH: 22
<212> TYPE: RNA
<213> ORGANISM: Homo sapiens

<400> SEQUENCE: 548
uggucuagga uuguuggagg ag                                                22

<210> SEQ ID NO 549
<211> LENGTH: 23
<212> TYPE: RNA
<213> ORGANISM: Homo sapiens

<400> SEQUENCE: 549
gacacgggcg acagcugcgg ccc                                               23

<210> SEQ ID NO 550
<211> LENGTH: 22
<212> TYPE: RNA
<213> ORGANISM: Homo sapiens

<400> SEQUENCE: 550
cacacacugc aauuacuuuu gc                                                22

<210> SEQ ID NO 551
<211> LENGTH: 19
<212> TYPE: RNA
<213> ORGANISM: Homo sapiens

<400> SEQUENCE: 551
aggcugcgga auucaggac                                                    19

<210> SEQ ID NO 552
<211> LENGTH: 23
<212> TYPE: RNA
<213> ORGANISM: Homo sapiens

<400> SEQUENCE: 552
uaaaucccau ggugccuucu ccu                                               23

<210> SEQ ID NO 553
<211> LENGTH: 21
<212> TYPE: RNA
<213> ORGANISM: Homo sapiens

<400> SEQUENCE: 553
aaacuacuga aaaucaaaga u                                                 21

<210> SEQ ID NO 554
<211> LENGTH: 21
<212> TYPE: RNA
<213> ORGANISM: Homo sapiens

<400> SEQUENCE: 554
guucaaaucc agaucuauaa c                                                 21

<210> SEQ ID NO 555
<211> LENGTH: 25
<212> TYPE: RNA
<213> ORGANISM: Homo sapiens

<400> SEQUENCE: 555 aggggugggug uugggacagc uccgu                                            25

<210> SEQ ID NO 556
<211> LENGTH: 20
<212> TYPE: RNA
<213> ORGANISM: Homo sapiens

```
<400> SEQUENCE: 556
aggguguuuc ucucaucucu                                              20

<210> SEQ ID NO 557
<211> LENGTH: 21
<212> TYPE: RNA
<213> ORGANISM: Homo sapiens

<400> SEQUENCE: 557
ugagcuaaau gugugcuggg a                                            21

<210> SEQ ID NO 558
<211> LENGTH: 23
<212> TYPE: RNA
<213> ORGANISM: Homo sapiens

<400> SEQUENCE: 558
gcgaggaccc cucggggucu gac                                          23

<210> SEQ ID NO 559
<211> LENGTH: 25
<212> TYPE: RNA
<213> ORGANISM: Homo sapiens

<400> SEQUENCE: 559
gcugggcagg gcuucugagc uccuu                                        25

<210> SEQ ID NO 560
<211> LENGTH: 20
<212> TYPE: RNA
<213> ORGANISM: Homo sapiens

<400> SEQUENCE: 560
aggaauguuc cuucuuugcc                                              20

<210> SEQ ID NO 561
<211> LENGTH: 23
<212> TYPE: RNA
<213> ORGANISM: Homo sapiens

<400> SEQUENCE: 561
gaacgccugu ucuugccagg ugg                                          23

<210> SEQ ID NO 562
<211> LENGTH: 22
<212> TYPE: RNA
<213> ORGANISM: Homo sapiens

<400> SEQUENCE: 562
gggggucccc ggugcucgga uc                                           22

<210> SEQ ID NO 563
<211> LENGTH: 22
<212> TYPE: RNA
<213> ORGANISM: Homo sapiens

<400> SEQUENCE: 563
uccgagccug ggucucccuc uu                                           22

<210> SEQ ID NO 564
<211> LENGTH: 22
<212> TYPE: RNA
```

```
<213> ORGANISM: Homo sapiens

<400> SEQUENCE: 564
acucaaaacc cuucagugac uu                                              22

<210> SEQ ID NO 565
<211> LENGTH: 22
<212> TYPE: RNA
<213> ORGANISM: Homo sapiens

<400> SEQUENCE: 565
agucauugga ggguuugagc ag                                              22

<210> SEQ ID NO 566
<211> LENGTH: 22
<212> TYPE: RNA
<213> ORGANISM: Homo sapiens

<400> SEQUENCE: 566
aaaaguaauu gcgguuuuug cc                                              22

<210> SEQ ID NO 567
<211> LENGTH: 22
<212> TYPE: RNA
<213> ORGANISM: Homo sapiens

<400> SEQUENCE: 567
caaaaaucuc aauuacuuuu gc                                              22

<210> SEQ ID NO 568
<211> LENGTH: 22
<212> TYPE: RNA
<213> ORGANISM: Homo sapiens

<400> SEQUENCE: 568
agacuuccca uuugaaggug gc                                              22

<210> SEQ ID NO 569
<211> LENGTH: 23
<212> TYPE: RNA
<213> ORGANISM: Homo sapiens

<400> SEQUENCE: 569
aaacucuacu uguccuucug agu                                             23

<210> SEQ ID NO 570
<211> LENGTH: 24
<212> TYPE: RNA
<213> ORGANISM: Homo sapiens

<400> SEQUENCE: 570
gaccuggaca uguuugugcc cagu                                            24

<210> SEQ ID NO 571
<211> LENGTH: 20
<212> TYPE: RNA
<213> ORGANISM: Homo sapiens

<400> SEQUENCE: 571
auggagauag auauagaaau                                                 20

<210> SEQ ID NO 572
<211> LENGTH: 21
```

```
<212> TYPE: RNA
<213> ORGANISM: Homo sapiens

<400> SEQUENCE: 572
ggcuagcaac agcgcuuacc u                                              21

<210> SEQ ID NO 573
<211> LENGTH: 21
<212> TYPE: RNA
<213> ORGANISM: Homo sapiens

<400> SEQUENCE: 573
acagucugcu gagguuggag c                                              21

<210> SEQ ID NO 574
<211> LENGTH: 23
<212> TYPE: RNA
<213> ORGANISM: Homo sapiens

<400> SEQUENCE: 574
aucccuugca ggggcuguug ggu                                            23

<210> SEQ ID NO 575
<211> LENGTH: 22
<212> TYPE: RNA
<213> ORGANISM: Homo sapiens

<400> SEQUENCE: 575
uaguaccagu accuuguguu ca                                             22

<210> SEQ ID NO 576
<211> LENGTH: 21
<212> TYPE: RNA
<213> ORGANISM: Homo sapiens

<400> SEQUENCE: 576
cacaagguau ugguauuacc u                                              21

<210> SEQ ID NO 577
<211> LENGTH: 21
<212> TYPE: RNA
<213> ORGANISM: Homo sapiens

<400> SEQUENCE: 577 aggggggaaag uucuauaguc c                                             21

<210> SEQ ID NO 578
<211> LENGTH: 22
<212> TYPE: RNA
<213> ORGANISM: Homo sapiens

<400> SEQUENCE: 578
gacuauagaa cuuuccccu ca                                              22

<210> SEQ ID NO 579
<211> LENGTH: 19
<212> TYPE: RNA
<213> ORGANISM: Homo sapiens

<400> SEQUENCE: 579
agcugucuga aaaugucuu                                                 19

<210> SEQ ID NO 580
```

```
<211> LENGTH: 22
<212> TYPE: RNA
<213> ORGANISM: Homo sapiens

<400> SEQUENCE: 580
gugagucucu aagaaaagag ga                                              22

<210> SEQ ID NO 581
<211> LENGTH: 22
<212> TYPE: RNA
<213> ORGANISM: Homo sapiens

<400> SEQUENCE: 581
augcugacau auuuacuaga gg                                              22

<210> SEQ ID NO 582
<211> LENGTH: 21
<212> TYPE: RNA
<213> ORGANISM: Homo sapiens

<400> SEQUENCE: 582
ucuaguaaga guggcagucg a                                               21

<210> SEQ ID NO 583
<211> LENGTH: 21
<212> TYPE: RNA
<213> ORGANISM: Homo sapiens

<400> SEQUENCE: 583
uggguuuacg uugggagaac u                                               21

<210> SEQ ID NO 584
<211> LENGTH: 22
<212> TYPE: RNA
<213> ORGANISM: Homo sapiens

<400> SEQUENCE: 584
guucucccaa cguaagccca gc                                              22

<210> SEQ ID NO 585
<211> LENGTH: 22
<212> TYPE: RNA
<213> ORGANISM: Homo sapiens

<400> SEQUENCE: 585
aguauucugu accagggaag gu                                              22

<210> SEQ ID NO 586
<211> LENGTH: 21
<212> TYPE: RNA
<213> ORGANISM: Homo sapiens

<400> SEQUENCE: 586
agaccuggcc cagaccucag c                                               21

<210> SEQ ID NO 587
<211> LENGTH: 20
<212> TYPE: RNA
<213> ORGANISM: Homo sapiens

<400> SEQUENCE: 587
gugcauugcu guugcauugc                                                 20
```

```
<210> SEQ ID NO 588
<211> LENGTH: 22
<212> TYPE: RNA
<213> ORGANISM: Homo sapiens

<400> SEQUENCE: 588
cagugccucg gcagugcagc cc                                    22

<210> SEQ ID NO 589
<211> LENGTH: 19
<212> TYPE: RNA
<213> ORGANISM: Homo sapiens

<400> SEQUENCE: 589
gugucugcuu ccuguggga                                        19

<210> SEQ ID NO 590
<211> LENGTH: 23
<212> TYPE: RNA
<213> ORGANISM: Homo sapiens

<400> SEQUENCE: 590
cuaauaguau cuaccacaau aaa                                   23

<210> SEQ ID NO 591
<211> LENGTH: 22
<212> TYPE: RNA
<213> ORGANISM: Homo sapiens

<400> SEQUENCE: 591
aaccagcacc ccaacuuugg ac                                    22

<210> SEQ ID NO 592
<211> LENGTH: 23
<212> TYPE: RNA
<213> ORGANISM: Homo sapiens

<400> SEQUENCE: 592
acuugggcac ugaaacaaug ucc                                   23

<210> SEQ ID NO 593
<211> LENGTH: 23
<212> TYPE: RNA
<213> ORGANISM: Homo sapiens

<400> SEQUENCE: 593
ugugcuugcu cgucccgccc gca                                   23

<210> SEQ ID NO 594
<211> LENGTH: 24
<212> TYPE: RNA
<213> ORGANISM: Homo sapiens

<400> SEQUENCE: 594 acuggggcu uucgggcucu gcgu                                   24

<210> SEQ ID NO 595
<211> LENGTH: 25
<212> TYPE: RNA
<213> ORGANISM: Homo sapiens

<400> SEQUENCE: 595
agggaucgcg ggcggguggc ggccu                                 25
```

```
<210> SEQ ID NO 596
<211> LENGTH: 23
<212> TYPE: RNA
<213> ORGANISM: Homo sapiens

<400> SEQUENCE: 596
aucgcugcgg uugcgagcgc ugu                                               23

<210> SEQ ID NO 597
<211> LENGTH: 21
<212> TYPE: RNA
<213> ORGANISM: Homo sapiens

<400> SEQUENCE: 597
augauccagg aaccugccuc u                                                 21

<210> SEQ ID NO 598
<211> LENGTH: 24
<212> TYPE: RNA
<213> ORGANISM: Homo sapiens

<400> SEQUENCE: 598
aaagacauag gauagaguca ccuc                                              24

<210> SEQ ID NO 599
<211> LENGTH: 22
<212> TYPE: RNA
<213> ORGANISM: Homo sapiens

<400> SEQUENCE: 599
gucccucucc aaaugugucu ug                                                22

<210> SEQ ID NO 600
<211> LENGTH: 22
<212> TYPE: RNA
<213> ORGANISM: Homo sapiens

<400> SEQUENCE: 600
acuuguaugc uagcucaggu ag                                                22

<210> SEQ ID NO 601
<211> LENGTH: 19
<212> TYPE: RNA
<213> ORGANISM: Homo sapiens

<400> SEQUENCE: 601
aguguggcuu ucuuagagc                                                    19

<210> SEQ ID NO 602
<211> LENGTH: 19
<212> TYPE: RNA
<213> ORGANISM: Homo sapiens

<400> SEQUENCE: 602
ucuaggcugg uacugcuga                                                    19

<210> SEQ ID NO 603
<211> LENGTH: 19
<212> TYPE: RNA
<213> ORGANISM: Homo sapiens

<400> SEQUENCE: 603
aagcagcugc cucugaggc                                                    19
```

<210> SEQ ID NO 604
<211> LENGTH: 21
<212> TYPE: RNA
<213> ORGANISM: Homo sapiens

<400> SEQUENCE: 604
guggcugcac ucacuuccuu c                                              21

<210> SEQ ID NO 605
<211> LENGTH: 19
<212> TYPE: RNA
<213> ORGANISM: Homo sapiens

<400> SEQUENCE: 605
aagugugcag ggcacuggu                                                 19

<210> SEQ ID NO 606
<211> LENGTH: 22
<212> TYPE: RNA
<213> ORGANISM: Homo sapiens

<400> SEQUENCE: 606
aaaccugugu uguucaagag uc                                             22

<210> SEQ ID NO 607
<211> LENGTH: 21
<212> TYPE: RNA
<213> ORGANISM: Homo sapiens

<400> SEQUENCE: 607
aggaggcagc gcucucagga c                                              21

<210> SEQ ID NO 608
<211> LENGTH: 22
<212> TYPE: RNA
<213> ORGANISM: Homo sapiens

<400> SEQUENCE: 608
uuuaggauaa gcuugacuuu ug                                             22

<210> SEQ ID NO 609
<211> LENGTH: 21
<212> TYPE: RNA
<213> ORGANISM: Homo sapiens

<400> SEQUENCE: 609
aauggcgcca cuaggguugu g                                              21

<210> SEQ ID NO 610
<211> LENGTH: 22
<212> TYPE: RNA
<213> ORGANISM: Homo sapiens

<400> SEQUENCE: 610
aaaaguaauu gugguuuuug cc                                             22

<210> SEQ ID NO 611
<211> LENGTH: 22
<212> TYPE: RNA
<213> ORGANISM: Homo sapiens

<400> SEQUENCE: 611

```
caaaaaccac aguuucuuuu gc                                    22

<210> SEQ ID NO 612
<211> LENGTH: 24
<212> TYPE: RNA
<213> ORGANISM: Homo sapiens

<400> SEQUENCE: 612
ugccuggguc ucuggccugc gcgu                                  24

<210> SEQ ID NO 613
<211> LENGTH: 21
<212> TYPE: RNA
<213> ORGANISM: Homo sapiens

<400> SEQUENCE: 613
ucccacguug uggcccagca g                                     21

<210> SEQ ID NO 614
<211> LENGTH: 22
<212> TYPE: RNA
<213> ORGANISM: Homo sapiens

<400> SEQUENCE: 614
aggcggggcg ccgcgggacc gc                                    22

<210> SEQ ID NO 615
<211> LENGTH: 22
<212> TYPE: RNA
<213> ORGANISM: Homo sapiens

<400> SEQUENCE: 615
aggcagugua uuguuagcug gc                                    22

<210> SEQ ID NO 616
<211> LENGTH: 22
<212> TYPE: RNA
<213> ORGANISM: Homo sapiens

<400> SEQUENCE: 616
cagccacaac uacccugcca cu                                    22

<210> SEQ ID NO 617
<211> LENGTH: 21
<212> TYPE: RNA
<213> ORGANISM: Homo sapiens

<400> SEQUENCE: 617
guguugaaac aaucucuacu g                                     21

<210> SEQ ID NO 618
<211> LENGTH: 21
<212> TYPE: RNA
<213> ORGANISM: Homo sapiens

<400> SEQUENCE: 618
uaguagaccg uauagcguac g                                     21

<210> SEQ ID NO 619
<211> LENGTH: 22
<212> TYPE: RNA
<213> ORGANISM: Homo sapiens

<400> SEQUENCE: 619
```
uauguaacac gguccacuaa cc							22

<210> SEQ ID NO 620
<211> LENGTH: 22
<212> TYPE: RNA
<213> ORGANISM: Homo sapiens

<400> SEQUENCE: 620 ugugggccg cagaacaugu gc							22

<210> SEQ ID NO 621
<211> LENGTH: 22
<212> TYPE: RNA
<213> ORGANISM: Homo sapiens

<400> SEQUENCE: 621
uaugucugcu gaccaucacc uu							22

<210> SEQ ID NO 622
<211> LENGTH: 22
<212> TYPE: RNA
<213> ORGANISM: Homo sapiens

<400> SEQUENCE: 622 auaaucaug guuaaccucu uu							22

<210> SEQ ID NO 623
<211> LENGTH: 21
<212> TYPE: RNA
<213> ORGANISM: Homo sapiens

<400> SEQUENCE: 623
aauauuauac agucaaccuc u							21

<210> SEQ ID NO 624
<211> LENGTH: 21
<212> TYPE: RNA
<213> ORGANISM: Homo sapiens

<400> SEQUENCE: 624
ugacaacuau ggaugagcuc u							21

<210> SEQ ID NO 625
<211> LENGTH: 23
<212> TYPE: RNA
<213> ORGANISM: Homo sapiens

<400> SEQUENCE: 625
ggcagguucu cacccucucu agg							23

<210> SEQ ID NO 626
<211> LENGTH: 25
<212> TYPE: RNA
<213> ORGANISM: Homo sapiens

<400> SEQUENCE: 626
ggcggaggga aguagguccg uuggu							25

<210> SEQ ID NO 627
<211> LENGTH: 22
<212> TYPE: RNA
<213> ORGANISM: Homo sapiens

```
<400> SEQUENCE: 627
cuugguucag ggagggucccc ca                                           22

<210> SEQ ID NO 628
<211> LENGTH: 22
<212> TYPE: RNA
<213> ORGANISM: Homo sapiens

<400> SEQUENCE: 628
uacccauugc auaucggagu ug                                            22

<210> SEQ ID NO 629
<211> LENGTH: 23
<212> TYPE: RNA
<213> ORGANISM: Homo sapiens

<400> SEQUENCE: 629
aucaacagac auuaauuggg cgc                                           23

<210> SEQ ID NO 630
<211> LENGTH: 23
<212> TYPE: RNA
<213> ORGANISM: Homo sapiens

<400> SEQUENCE: 630
ucggggauca ucaugucacg aga                                           23

<210> SEQ ID NO 631
<211> LENGTH: 22
<212> TYPE: RNA
<213> ORGANISM: Homo sapiens

<400> SEQUENCE: 631
ugugacagau ugauaacuga aa                                            22

<210> SEQ ID NO 632
<211> LENGTH: 22
<212> TYPE: RNA
<213> ORGANISM: Homo sapiens

<400> SEQUENCE: 632
uuugugaccu gguccacuaa cc                                            22

<210> SEQ ID NO 633
<211> LENGTH: 23
<212> TYPE: RNA
<213> ORGANISM: Homo sapiens

<400> SEQUENCE: 633
caagucuuau uugagcaccu guu                                           23

<210> SEQ ID NO 634
<211> LENGTH: 23
<212> TYPE: RNA
<213> ORGANISM: Homo sapiens

<400> SEQUENCE: 634
aggaagcccu ggaggggcug gag                                           23

<210> SEQ ID NO 635
<211> LENGTH: 21
<212> TYPE: RNA
<213> ORGANISM: Homo sapiens
```

```
<400> SEQUENCE: 635
uccgguucuc agggcuccac c                                            21

<210> SEQ ID NO 636
<211> LENGTH: 23
<212> TYPE: RNA
<213> ORGANISM: Homo sapiens

<400> SEQUENCE: 636
ugucacucgg cucggcccac uac                                          23

<210> SEQ ID NO 637
<211> LENGTH: 23
<212> TYPE: RNA
<213> ORGANISM: Homo sapiens

<400> SEQUENCE: 637
ugcaccaugg uugucugagc aug                                          23

<210> SEQ ID NO 638
<211> LENGTH: 23
<212> TYPE: RNA
<213> ORGANISM: Homo sapiens

<400> SEQUENCE: 638
ucugcucaua ccccaugguu ucu                                          23

<210> SEQ ID NO 639
<211> LENGTH: 19
<212> TYPE: RNA
<213> ORGANISM: Homo sapiens

<400> SEQUENCE: 639
gugaggacuc gggaggugg                                               19

<210> SEQ ID NO 640
<211> LENGTH: 21
<212> TYPE: RNA
<213> ORGANISM: Homo sapiens

<400> SEQUENCE: 640
ccccaccucc ucucuccuca g                                            21

<210> SEQ ID NO 641
<211> LENGTH: 22
<212> TYPE: RNA
<213> ORGANISM: Homo sapiens

<400> SEQUENCE: 641
aaaagcuggg uugagagggc aa                                           22

<210> SEQ ID NO 642
<211> LENGTH: 20
<212> TYPE: RNA
<213> ORGANISM: Homo sapiens

<400> SEQUENCE: 642
aaaagcuggg uugagagggu                                              20

<210> SEQ ID NO 643
<211> LENGTH: 22
<212> TYPE: RNA
```

<213> ORGANISM: Homo sapiens

<400> SEQUENCE: 643
uuagggcccu ggcuccaucu cc  22

<210> SEQ ID NO 644
<211> LENGTH: 21
<212> TYPE: RNA
<213> ORGANISM: Homo sapiens

<400> SEQUENCE: 644
cuccguuugc cuguuucgcu g  21

<210> SEQ ID NO 645
<211> LENGTH: 22
<212> TYPE: RNA
<213> ORGANISM: Homo sapiens

<400> SEQUENCE: 645
ucaaaacuga ggggcauuuu cu  22

<210> SEQ ID NO 646
<211> LENGTH: 22
<212> TYPE: RNA
<213> ORGANISM: Homo sapiens

<400> SEQUENCE: 646
cuuggcaccu agcaagcacu ca  22

<210> SEQ ID NO 647
<211> LENGTH: 24
<212> TYPE: RNA
<213> ORGANISM: Homo sapiens

<400> SEQUENCE: 647
uugcagcugc cugggaguga cuuc  24

<210> SEQ ID NO 648
<211> LENGTH: 22
<212> TYPE: RNA
<213> ORGANISM: Homo sapiens

<400> SEQUENCE: 648
acccuaucaa uauugucucu gc  22

<210> SEQ ID NO 649
<211> LENGTH: 23
<212> TYPE: RNA
<213> ORGANISM: Homo sapiens

<400> SEQUENCE: 649
uagugcaaua uugcuuauag ggu  23

<210> SEQ ID NO 650
<211> LENGTH: 21
<212> TYPE: RNA
<213> ORGANISM: Homo sapiens

<400> SEQUENCE: 650
agaggauacc cuuuguaugu u  21

<210> SEQ ID NO 651
<211> LENGTH: 25

```
<212> TYPE: RNA
<213> ORGANISM: Homo sapiens

<400> SEQUENCE: 651
uaggcagugu auugcuagcg gcugu                                           25

<210> SEQ ID NO 652
<211> LENGTH: 23
<212> TYPE: RNA
<213> ORGANISM: Homo sapiens

<400> SEQUENCE: 652
uugcuaguug cacuccucuc ugu                                             23

<210> SEQ ID NO 653
<211> LENGTH: 22
<212> TYPE: RNA
<213> ORGANISM: Homo sapiens

<400> SEQUENCE: 653
ucuacaaagg aaagcgcuuu cu                                              22

<210> SEQ ID NO 654
<211> LENGTH: 22
<212> TYPE: RNA
<213> ORGANISM: Homo sapiens

<400> SEQUENCE: 654
ugagaccucu ggguucugag cu                                              22

<210> SEQ ID NO 655
<211> LENGTH: 23
<212> TYPE: RNA
<213> ORGANISM: Homo sapiens

<400> SEQUENCE: 655
cugggaucuc cggggucuug guu                                             23

<210> SEQ ID NO 656
<211> LENGTH: 22
<212> TYPE: RNA
<213> ORGANISM: Homo sapiens

<400> SEQUENCE: 656
acuccagccc cacagccuca gc                                              22

<210> SEQ ID NO 657
<211> LENGTH: 22
<212> TYPE: RNA
<213> ORGANISM: Homo sapiens

<400> SEQUENCE: 657
ggggcugggg ccggggccga gc                                              22

<210> SEQ ID NO 658
<211> LENGTH: 23
<212> TYPE: RNA
<213> ORGANISM: Homo sapiens

<400> SEQUENCE: 658
caguaacaaa gauucauccu ugu                                             23

<210> SEQ ID NO 659
```

```
<211> LENGTH: 20
<212> TYPE: RNA
<213> ORGANISM: Homo sapiens

<400> SEQUENCE: 659
gucccugagu guauguggug                                              20

<210> SEQ ID NO 660
<211> LENGTH: 22
<212> TYPE: RNA
<213> ORGANISM: Homo sapiens

<400> SEQUENCE: 660
uucauucggc uguccagaug ua                                           22

<210> SEQ ID NO 661
<211> LENGTH: 21
<212> TYPE: RNA
<213> ORGANISM: Homo sapiens

<400> SEQUENCE: 661
auuugugcuu ggcucuguca c                                            21

<210> SEQ ID NO 662
<211> LENGTH: 22
<212> TYPE: RNA
<213> ORGANISM: Homo sapiens

<400> SEQUENCE: 662
gcagcagggu gaaacugaca ca                                           22

<210> SEQ ID NO 663
<211> LENGTH: 22
<212> TYPE: RNA
<213> ORGANISM: Homo sapiens

<400> SEQUENCE: 663
gcaggugcuc acuuguccuc cu                                           22

<210> SEQ ID NO 664
<211> LENGTH: 22
<212> TYPE: RNA
<213> ORGANISM: Homo sapiens

<400> SEQUENCE: 664
gcagagugca aacaauuuug ac                                           22

<210> SEQ ID NO 665
<211> LENGTH: 21
<212> TYPE: RNA
<213> ORGANISM: Homo sapiens

<400> SEQUENCE: 665
uggaggagaa ggaaggugau g                                            21

<210> SEQ ID NO 666
<211> LENGTH: 23
<212> TYPE: RNA
<213> ORGANISM: Homo sapiens

<400> SEQUENCE: 666
uccaguacca cgugucaggg cca                                          23
```

```
<210> SEQ ID NO 667
<211> LENGTH: 23
<212> TYPE: RNA
<213> ORGANISM: Homo sapiens

<400> SEQUENCE: 667
uggugcggag agggcccaca gug                                              23

<210> SEQ ID NO 668
<211> LENGTH: 20
<212> TYPE: RNA
<213> ORGANISM: Homo sapiens

<400> SEQUENCE: 668
cuguaugccc ucaccgcuca                                                  20

<210> SEQ ID NO 669
<211> LENGTH: 24
<212> TYPE: RNA
<213> ORGANISM: Homo sapiens

<400> SEQUENCE: 669
agcagaagca gggagguucu ccca                                             24

<210> SEQ ID NO 670
<211> LENGTH: 22
<212> TYPE: RNA
<213> ORGANISM: Homo sapiens

<400> SEQUENCE: 670
ugcaacgaac cugagccacu ga                                               22

<210> SEQ ID NO 671
<211> LENGTH: 22
<212> TYPE: RNA
<213> ORGANISM: Homo sapiens

<400> SEQUENCE: 671
uauacaaggg cagacucucu cu                                               22

<210> SEQ ID NO 672
<211> LENGTH: 23
<212> TYPE: RNA
<213> ORGANISM: Homo sapiens

<400> SEQUENCE: 672
cgggucggag uuagcucaag cgg                                              23

<210> SEQ ID NO 673
<211> LENGTH: 21
<212> TYPE: RNA
<213> ORGANISM: Homo sapiens

<400> SEQUENCE: 673
cgcgggugcu uacugacccu u                                                21

<210> SEQ ID NO 674
<211> LENGTH: 21
<212> TYPE: RNA
<213> ORGANISM: Homo sapiens

<400> SEQUENCE: 674
cacugugucc uuucugcgua g                                                21
```

<210> SEQ ID NO 675
<211> LENGTH: 21
<212> TYPE: RNA
<213> ORGANISM: Homo sapiens

<400> SEQUENCE: 675
ccaccaccgu gucugacacu u                                              21

<210> SEQ ID NO 676
<211> LENGTH: 22
<212> TYPE: RNA
<213> ORGANISM: Homo sapiens

<400> SEQUENCE: 676
uuuugcaaua uguuccugaa ua                                             22

<210> SEQ ID NO 677
<211> LENGTH: 22
<212> TYPE: RNA
<213> ORGANISM: Homo sapiens

<400> SEQUENCE: 677
uugggaucau uuugcaucca ua                                             22

<210> SEQ ID NO 678
<211> LENGTH: 22
<212> TYPE: RNA
<213> ORGANISM: Homo sapiens

<400> SEQUENCE: 678
cugcccuggc ccgagggacc ga                                             22

<210> SEQ ID NO 679
<211> LENGTH: 21
<212> TYPE: RNA
<213> ORGANISM: Homo sapiens

<400> SEQUENCE: 679
uacuuggaaa ggcaucaguu g                                              21

<210> SEQ ID NO 680
<211> LENGTH: 22
<212> TYPE: RNA
<213> ORGANISM: Homo sapiens

<400> SEQUENCE: 680
ugcaacuuac cugagucauu ga                                             22

<210> SEQ ID NO 681
<211> LENGTH: 22
<212> TYPE: RNA
<213> ORGANISM: Homo sapiens

<400> SEQUENCE: 681
acacagggcu guugugaaga cu                                             22

<210> SEQ ID NO 682
<211> LENGTH: 21
<212> TYPE: RNA
<213> ORGANISM: Homo sapiens

<400> SEQUENCE: 682
uacucaaaaa gcugucaguc a                                              21

<210> SEQ ID NO 683
<211> LENGTH: 22
<212> TYPE: RNA
<213> ORGANISM: Homo sapiens

<400> SEQUENCE: 683
gacugacacc ucuuugggug aa                                             22

<210> SEQ ID NO 684
<211> LENGTH: 22
<212> TYPE: RNA
<213> ORGANISM: Homo sapiens

<400> SEQUENCE: 684
cacuggcucc uuucugggua ga                                             22

<210> SEQ ID NO 685
<211> LENGTH: 25
<212> TYPE: RNA
<213> ORGANISM: Homo sapiens

<400> SEQUENCE: 685
aaaggauucu gcugucgguc ccacu                                          25

<210> SEQ ID NO 686
<211> LENGTH: 22
<212> TYPE: RNA
<213> ORGANISM: Homo sapiens

<400> SEQUENCE: 686
uggugggcac agaaucugga cu                                             22

<210> SEQ ID NO 687
<211> LENGTH: 21
<212> TYPE: RNA
<213> ORGANISM: Homo sapiens

<400> SEQUENCE: 687
uuaauaucgg acaaccauug u                                              21

<210> SEQ ID NO 688
<211> LENGTH: 22
<212> TYPE: RNA
<213> ORGANISM: Homo sapiens

<400> SEQUENCE: 688
uauaccucag uuuuaucagg ug                                             22

<210> SEQ ID NO 689
<211> LENGTH: 21
<212> TYPE: RNA
<213> ORGANISM: Homo sapiens

<400> SEQUENCE: 689
ccuggaaaca cugagguugu g                                              21

<210> SEQ ID NO 690
<211> LENGTH: 22
<212> TYPE: RNA
<213> ORGANISM: Homo sapiens

<400> SEQUENCE: 690

-continued uggauuucuu ugugaaucac ca        22

<210> SEQ ID NO 691
<211> LENGTH: 22
<212> TYPE: RNA
<213> ORGANISM: Homo sapiens

<400> SEQUENCE: 691
uggugguuua caaaguaauu ca        22

<210> SEQ ID NO 692
<211> LENGTH: 23
<212> TYPE: RNA
<213> ORGANISM: Homo sapiens

<400> SEQUENCE: 692
aaggagcuua caaucuagcu ggg       23

<210> SEQ ID NO 693
<211> LENGTH: 22
<212> TYPE: RNA
<213> ORGANISM: Homo sapiens

<400> SEQUENCE: 693
caacuagacu gugagcuucu ag        22

<210> SEQ ID NO 694
<211> LENGTH: 22
<212> TYPE: RNA
<213> ORGANISM: Homo sapiens

<400> SEQUENCE: 694
gugugcggaa augcuucugc ua        22

<210> SEQ ID NO 695
<211> LENGTH: 21
<212> TYPE: RNA
<213> ORGANISM: Homo sapiens

<400> SEQUENCE: 695
ugauauguuu gauauugggu u         21

<210> SEQ ID NO 696
<211> LENGTH: 22
<212> TYPE: RNA
<213> ORGANISM: Homo sapiens

<400> SEQUENCE: 696
ugcggggcua gggcuaacag ca        22

<210> SEQ ID NO 697
<211> LENGTH: 22
<212> TYPE: RNA
<213> ORGANISM: Homo sapiens

<400> SEQUENCE: 697
cuguugccac uaaccucaac cu        22

<210> SEQ ID NO 698
<211> LENGTH: 22
<212> TYPE: RNA
<213> ORGANISM: Homo sapiens

<400> SEQUENCE: 698

```
uccauuacac uacccugccu cu                                              22

<210> SEQ ID NO 699
<211> LENGTH: 22
<212> TYPE: RNA
<213> ORGANISM: Homo sapiens

<400> SEQUENCE: 699
aggcagcggg guguagugga ua                                              22

<210> SEQ ID NO 700
<211> LENGTH: 20
<212> TYPE: RNA
<213> ORGANISM: Homo sapiens

<400> SEQUENCE: 700
guagaggaga uggcgcaggg                                                 20

<210> SEQ ID NO 701
<211> LENGTH: 21
<212> TYPE: RNA
<213> ORGANISM: Homo sapiens

<400> SEQUENCE: 701
uccucuucuc ccuccuccca g                                               21

<210> SEQ ID NO 702
<211> LENGTH: 22
<212> TYPE: RNA
<213> ORGANISM: Homo sapiens

<400> SEQUENCE: 702
gugaacgggc gccaucccga gg                                              22

<210> SEQ ID NO 703
<211> LENGTH: 20
<212> TYPE: RNA
<213> ORGANISM: Homo sapiens

<400> SEQUENCE: 703
accaggaggc ugaggccccu                                                 20

<210> SEQ ID NO 704
<211> LENGTH: 21
<212> TYPE: RNA
<213> ORGANISM: Homo sapiens

<400> SEQUENCE: 704
gcaggaacuu gugagucucc u                                               21

<210> SEQ ID NO 705
<211> LENGTH: 22
<212> TYPE: RNA
<213> ORGANISM: Homo sapiens

<400> SEQUENCE: 705
aaacauucgc ggugcacuuc uu                                              22

<210> SEQ ID NO 706
<211> LENGTH: 22
<212> TYPE: RNA
<213> ORGANISM: Homo sapiens
```

```
<400> SEQUENCE: 706
auauaauaca accugcuaag ug                                        22

<210> SEQ ID NO 707
<211> LENGTH: 22
<212> TYPE: RNA
<213> ORGANISM: Homo sapiens

<400> SEQUENCE: 707
cuuagcaggu uguauuauca uu                                        22

<210> SEQ ID NO 708
<211> LENGTH: 20
<212> TYPE: RNA
<213> ORGANISM: Homo sapiens

<400> SEQUENCE: 708
cggcucuggg ucuguggga                                            20

<210> SEQ ID NO 709
<211> LENGTH: 23
<212> TYPE: RNA
<213> ORGANISM: Homo sapiens

<400> SEQUENCE: 709
cagugcaaug auauugucaa agc                                       23

<210> SEQ ID NO 710
<211> LENGTH: 22
<212> TYPE: RNA
<213> ORGANISM: Homo sapiens

<400> SEQUENCE: 710
aaaucucugc aggcaaaugu ga                                        22

<210> SEQ ID NO 711
<211> LENGTH: 22
<212> TYPE: RNA
<213> ORGANISM: Homo sapiens

<400> SEQUENCE: 711
auaagacgaa caaaagguuu gu                                        22

<210> SEQ ID NO 712
<211> LENGTH: 20
<212> TYPE: RNA
<213> ORGANISM: Homo sapiens

<400> SEQUENCE: 712
ggggagcugu ggaagcagua                                           20

<210> SEQ ID NO 713
<211> LENGTH: 25
<212> TYPE: RNA
<213> ORGANISM: Homo sapiens

<400> SEQUENCE: 713 cugugaggg acagaaccag gauuc                                      25

<210> SEQ ID NO 714
<211> LENGTH: 23
<212> TYPE: RNA
<213> ORGANISM: Homo sapiens
```

```
<400> SEQUENCE: 714
gcagcagaga auaggacuac guc                                          23

<210> SEQ ID NO 715
<211> LENGTH: 20
<212> TYPE: RNA
<213> ORGANISM: Homo sapiens

<400> SEQUENCE: 715
agagucuugu gaugucuugc                                              20

<210> SEQ ID NO 716
<211> LENGTH: 22
<212> TYPE: RNA
<213> ORGANISM: Homo sapiens

<400> SEQUENCE: 716
uacugcagac guggcaauca ug                                           22

<210> SEQ ID NO 717
<211> LENGTH: 22
<212> TYPE: RNA
<213> ORGANISM: Homo sapiens

<400> SEQUENCE: 717
ugugcgcagg gagaccucuc cc                                           22

<210> SEQ ID NO 718
<211> LENGTH: 22
<212> TYPE: RNA
<213> ORGANISM: Homo sapiens

<400> SEQUENCE: 718
ugucuacuac uggagacacu gg                                           22

<210> SEQ ID NO 719
<211> LENGTH: 23
<212> TYPE: RNA
<213> ORGANISM: Homo sapiens

<400> SEQUENCE: 719
ccaguuaccg cuuccgcuac cgc                                          23

<210> SEQ ID NO 720
<211> LENGTH: 22
<212> TYPE: RNA
<213> ORGANISM: Homo sapiens

<400> SEQUENCE: 720
acaguagagg gaggaaucgc ag                                           22

<210> SEQ ID NO 721
<211> LENGTH: 22
<212> TYPE: RNA
<213> ORGANISM: Homo sapiens

<400> SEQUENCE: 721
auccgcgcuc ugacucucug cc                                           22

<210> SEQ ID NO 722
<211> LENGTH: 22
<212> TYPE: RNA
```

<213> ORGANISM: Homo sapiens

<400> SEQUENCE: 722
ugcccuuaaa ggugaacccca gu       22

<210> SEQ ID NO 723
<211> LENGTH: 24
<212> TYPE: RNA
<213> ORGANISM: Homo sapiens

<400> SEQUENCE: 723 ugggggagcug aggcucuggg ggug       24

<210> SEQ ID NO 724
<211> LENGTH: 21
<212> TYPE: RNA
<213> ORGANISM: Homo sapiens

<400> SEQUENCE: 724
aaggcagggc ccccgcuccc c       21

<210> SEQ ID NO 725
<211> LENGTH: 23
<212> TYPE: RNA
<213> ORGANISM: Homo sapiens

<400> SEQUENCE: 725
cacccggcug ugugcacaug ugc       23

<210> SEQ ID NO 726
<211> LENGTH: 22
<212> TYPE: RNA
<213> ORGANISM: Homo sapiens

<400> SEQUENCE: 726
ucuucucugu uuuggccaug ug       22

<210> SEQ ID NO 727
<211> LENGTH: 21
<212> TYPE: RNA
<213> ORGANISM: Homo sapiens

<400> SEQUENCE: 727
cugacuguug ccguccucca g       21

<210> SEQ ID NO 728
<211> LENGTH: 22
<212> TYPE: RNA
<213> ORGANISM: Homo sapiens

<400> SEQUENCE: 728
aaauuauugu acaucggaug ag       22

<210> SEQ ID NO 729
<211> LENGTH: 21
<212> TYPE: RNA
<213> ORGANISM: Homo sapiens

<400> SEQUENCE: 729
auguaugugu gcaugugcau g       21

<210> SEQ ID NO 730
<211> LENGTH: 21

```
<212> TYPE: RNA
<213> ORGANISM: Homo sapiens

<400> SEQUENCE: 730
uugcucacug uucuucccua g                                              21

<210> SEQ ID NO 731
<211> LENGTH: 21
<212> TYPE: RNA
<213> ORGANISM: Homo sapiens

<400> SEQUENCE: 731
aagcauucuu ucauugguug g                                              21

<210> SEQ ID NO 732
<211> LENGTH: 22
<212> TYPE: RNA
<213> ORGANISM: Homo sapiens

<400> SEQUENCE: 732
uuuccggcuc gcguggugu gu                                              22

<210> SEQ ID NO 733
<211> LENGTH: 21
<212> TYPE: RNA
<213> ORGANISM: Homo sapiens

<400> SEQUENCE: 733
ccgucgccgc cacccgagcc g                                              21

<210> SEQ ID NO 734
<211> LENGTH: 23
<212> TYPE: RNA
<213> ORGANISM: Homo sapiens

<400> SEQUENCE: 734
gagggucuug ggagggaugu gac                                            23

<210> SEQ ID NO 735
<211> LENGTH: 27
<212> TYPE: RNA
<213> ORGANISM: Homo sapiens

<400> SEQUENCE: 735
cacuguaggu gauggugaga gugggca                                        27

<210> SEQ ID NO 736
<211> LENGTH: 23
<212> TYPE: RNA
<213> ORGANISM: Homo sapiens

<400> SEQUENCE: 736
ccugcagcga cuugauggcu ucc                                            23

<210> SEQ ID NO 737
<211> LENGTH: 22
<212> TYPE: RNA
<213> ORGANISM: Homo sapiens

<400> SEQUENCE: 737
guggguacgg cccagugggg gg                                             22

<210> SEQ ID NO 738
```

```
<211> LENGTH: 22
<212> TYPE: RNA
<213> ORGANISM: Homo sapiens

<400> SEQUENCE: 738 ugagcccug ugccgccccc ag                                              22

<210> SEQ ID NO 739
<211> LENGTH: 26
<212> TYPE: RNA
<213> ORGANISM: Homo sapiens

<400> SEQUENCE: 739
gugagggcau gcaggccugg augggg                                         26

<210> SEQ ID NO 740
<211> LENGTH: 22
<212> TYPE: RNA
<213> ORGANISM: Homo sapiens

<400> SEQUENCE: 740
ucaccagccc uguguucccu ag                                             22

<210> SEQ ID NO 741
<211> LENGTH: 20
<212> TYPE: RNA
<213> ORGANISM: Homo sapiens

<400> SEQUENCE: 741
cgugccaccc uuuucccag                                                 20

<210> SEQ ID NO 742
<211> LENGTH: 21
<212> TYPE: RNA
<213> ORGANISM: Homo sapiens

<400> SEQUENCE: 742
gugggcgggg gcaggugugu g                                              21

<210> SEQ ID NO 743
<211> LENGTH: 20
<212> TYPE: RNA
<213> ORGANISM: Homo sapiens

<400> SEQUENCE: 743
ucacaccugc cucgcccccc                                                20

<210> SEQ ID NO 744
<211> LENGTH: 23
<212> TYPE: RNA
<213> ORGANISM: Homo sapiens

<400> SEQUENCE: 744
cucucaccac ugcccuccca cag                                            23

<210> SEQ ID NO 745
<211> LENGTH: 20
<212> TYPE: RNA
<213> ORGANISM: Homo sapiens

<400> SEQUENCE: 745
gugucugggc ggacagcugc                                                20
```

```
<210> SEQ ID NO 746
<211> LENGTH: 20
<212> TYPE: RNA
<213> ORGANISM: Homo sapiens

<400> SEQUENCE: 746
ugagcccugu ccucccgcag                                              20

<210> SEQ ID NO 747
<211> LENGTH: 22
<212> TYPE: RNA
<213> ORGANISM: Homo sapiens

<400> SEQUENCE: 747
ucggccugac cacccacccc ac                                           22

<210> SEQ ID NO 748
<211> LENGTH: 22
<212> TYPE: RNA
<213> ORGANISM: Homo sapiens

<400> SEQUENCE: 748
ccucuucccc uugucucucc ag                                           22

<210> SEQ ID NO 749
<211> LENGTH: 21
<212> TYPE: RNA
<213> ORGANISM: Homo sapiens

<400> SEQUENCE: 749
uccuucugcu ccgucccca g                                             21

<210> SEQ ID NO 750
<211> LENGTH: 20
<212> TYPE: RNA
<213> ORGANISM: Homo sapiens

<400> SEQUENCE: 750
cuuccucguc ugucugcccc                                              20

<210> SEQ ID NO 751
<211> LENGTH: 22
<212> TYPE: RNA
<213> ORGANISM: Homo sapiens

<400> SEQUENCE: 751
cuccugagcc auucugagcc uc                                           22

<210> SEQ ID NO 752
<211> LENGTH: 24
<212> TYPE: RNA
<213> ORGANISM: Homo sapiens

<400> SEQUENCE: 752
agccugauua aacacaugcu cuga                                         24

<210> SEQ ID NO 753
<211> LENGTH: 21
<212> TYPE: RNA
<213> ORGANISM: Homo sapiens

<400> SEQUENCE: 753
gugccagcug cagugggga g                                             21
```

```
<210> SEQ ID NO 754
<211> LENGTH: 21
<212> TYPE: RNA
<213> ORGANISM: Homo sapiens

<400> SEQUENCE: 754
cccggagcca ggaugcagcu c                                           21

<210> SEQ ID NO 755
<211> LENGTH: 22
<212> TYPE: RNA
<213> ORGANISM: Homo sapiens

<400> SEQUENCE: 755
gguggcccgg ccgugccuga gg                                          22

<210> SEQ ID NO 756
<211> LENGTH: 21
<212> TYPE: RNA
<213> ORGANISM: Homo sapiens

<400> SEQUENCE: 756
ucguggccug gucuccauua u                                           21

<210> SEQ ID NO 757
<211> LENGTH: 20
<212> TYPE: RNA
<213> ORGANISM: Homo sapiens

<400> SEQUENCE: 757
ucugcagggu uugcuuugag                                             20

<210> SEQ ID NO 758
<211> LENGTH: 21
<212> TYPE: RNA
<213> ORGANISM: Homo sapiens

<400> SEQUENCE: 758
uguucaugua gauguuuaag c                                           21

<210> SEQ ID NO 759
<211> LENGTH: 21
<212> TYPE: RNA
<213> ORGANISM: Homo sapiens

<400> SEQUENCE: 759
uggcagggag gcugggaggg g                                           21

<210> SEQ ID NO 760
<211> LENGTH: 18
<212> TYPE: RNA
<213> ORGANISM: Homo sapiens

<400> SEQUENCE: 760
ucagcuggcc cucauuuc                                               18

<210> SEQ ID NO 761
<211> LENGTH: 20
<212> TYPE: RNA
<213> ORGANISM: Homo sapiens

<400> SEQUENCE: 761
ucacuguuca gacaggcgga                                             20
```

```
<210> SEQ ID NO 762
<211> LENGTH: 22
<212> TYPE: RNA
<213> ORGANISM: Homo sapiens

<400> SEQUENCE: 762
aaaaacugag acuacuuuug ca                                          22

<210> SEQ ID NO 763
<211> LENGTH: 22
<212> TYPE: RNA
<213> ORGANISM: Homo sapiens

<400> SEQUENCE: 763
aaaaguaauu gcggucuuug gu                                          22

<210> SEQ ID NO 764
<211> LENGTH: 22
<212> TYPE: RNA
<213> ORGANISM: Homo sapiens

<400> SEQUENCE: 764
ucugggcaac aaagugagac cu                                          22

<210> SEQ ID NO 765
<211> LENGTH: 21
<212> TYPE: RNA
<213> ORGANISM: Homo sapiens

<400> SEQUENCE: 765
ugcaggacca agaugagccc u                                           21

<210> SEQ ID NO 766
<211> LENGTH: 22
<212> TYPE: RNA
<213> ORGANISM: Homo sapiens

<400> SEQUENCE: 766
ugcuggauca gugguucgag uc                                          22

<210> SEQ ID NO 767
<211> LENGTH: 23
<212> TYPE: RNA
<213> ORGANISM: Homo sapiens

<400> SEQUENCE: 767
uggaguccag gaaucugcau uuu                                         23

<210> SEQ ID NO 768
<211> LENGTH: 19
<212> TYPE: RNA
<213> ORGANISM: Homo sapiens

<400> SEQUENCE: 768
uggauuuuug gaucaggga                                              19

<210> SEQ ID NO 769
<211> LENGTH: 24
<212> TYPE: RNA
<213> ORGANISM: Homo sapiens

<400> SEQUENCE: 769
```
uggcccugac ugaagaccag cagu                          24

<210> SEQ ID NO 770
<211> LENGTH: 22
<212> TYPE: RNA
<213> ORGANISM: Homo sapiens

<400> SEQUENCE: 770
aaaaguacuu gcggauuuug cu                            22

<210> SEQ ID NO 771
<211> LENGTH: 22
<212> TYPE: RNA
<213> ORGANISM: Homo sapiens

<400> SEQUENCE: 771 ugggugucu ggagauuugu gc                             22

<210> SEQ ID NO 772
<211> LENGTH: 22
<212> TYPE: RNA
<213> ORGANISM: Homo sapiens

<400> SEQUENCE: 772
ugugagguug gcauuguugu cu                            22

<210> SEQ ID NO 773
<211> LENGTH: 21
<212> TYPE: RNA
<213> ORGANISM: Homo sapiens

<400> SEQUENCE: 773
uuaggccgca gaucugggug a                             21

<210> SEQ ID NO 774
<211> LENGTH: 17
<212> TYPE: RNA
<213> ORGANISM: Homo sapiens

<400> SEQUENCE: 774
uucaaguaau ucaggug                                  17

<210> SEQ ID NO 775
<211> LENGTH: 22
<212> TYPE: RNA
<213> ORGANISM: Homo sapiens

<400> SEQUENCE: 775
uucuggaauu cugugugagg ga                            22

<210> SEQ ID NO 776
<211> LENGTH: 22
<212> TYPE: RNA
<213> ORGANISM: Homo sapiens

<400> SEQUENCE: 776
aaaaguauuu gcggguuuug uc                            22

<210> SEQ ID NO 777
<211> LENGTH: 21
<212> TYPE: RNA
<213> ORGANISM: Homo sapiens

<400> SEQUENCE: 777
uugggacaua cuuaugcuaa a                                         21

<210> SEQ ID NO 778
<211> LENGTH: 22
<212> TYPE: RNA
<213> ORGANISM: Homo sapiens

<400> SEQUENCE: 778
uuuagagacg gggucuugcu cu                                        22

<210> SEQ ID NO 779
<211> LENGTH: 22
<212> TYPE: RNA
<213> ORGANISM: Homo sapiens

<400> SEQUENCE: 779
uuugaggcua cagugagaug ug                                        22

<210> SEQ ID NO 780
<211> LENGTH: 22
<212> TYPE: RNA
<213> ORGANISM: Homo sapiens

<400> SEQUENCE: 780
uuuucaacuc uaaugggaga ga                                        22

<210> SEQ ID NO 781
<211> LENGTH: 22
<212> TYPE: RNA
<213> ORGANISM: Homo sapiens

<400> SEQUENCE: 781
aacuggauca auuauaggag ug                                        22

<210> SEQ ID NO 782
<211> LENGTH: 19
<212> TYPE: RNA
<213> ORGANISM: Homo sapiens

<400> SEQUENCE: 782
aaaaacugua auuacuuuu                                            19

<210> SEQ ID NO 783
<211> LENGTH: 26
<212> TYPE: RNA
<213> ORGANISM: Homo sapiens

<400> SEQUENCE: 783
aaguaguugg uuuguaugag augguu                                    26

<210> SEQ ID NO 784
<211> LENGTH: 21
<212> TYPE: RNA
<213> ORGANISM: Homo sapiens

<400> SEQUENCE: 784
aagugaucua aaggccuaca u                                         21

<210> SEQ ID NO 785
<211> LENGTH: 19
<212> TYPE: RNA
<213> ORGANISM: Homo sapiens

<400> SEQUENCE: 785
aauggauuuu uggagcagg                                                19

<210> SEQ ID NO 786
<211> LENGTH: 22
<212> TYPE: RNA
<213> ORGANISM: Homo sapiens

<400> SEQUENCE: 786
acccgucccg uucguccccg ga                                            22

<210> SEQ ID NO 787
<211> LENGTH: 27
<212> TYPE: RNA
<213> ORGANISM: Homo sapiens

<400> SEQUENCE: 787
accuucuugu auaagcacug ugcuaaa                                       27

<210> SEQ ID NO 788
<211> LENGTH: 22
<212> TYPE: RNA
<213> ORGANISM: Homo sapiens

<400> SEQUENCE: 788
acgcccuucc cccccuucuu ca                                            22

<210> SEQ ID NO 789
<211> LENGTH: 21
<212> TYPE: RNA
<213> ORGANISM: Homo sapiens

<400> SEQUENCE: 789
acggugcugg auguggccuu u                                             21

<210> SEQ ID NO 790
<211> LENGTH: 21
<212> TYPE: RNA
<213> ORGANISM: Homo sapiens

<400> SEQUENCE: 790
acucuagcug ccaaaggcgc u                                             21

<210> SEQ ID NO 791
<211> LENGTH: 21
<212> TYPE: RNA
<213> ORGANISM: Homo sapiens

<400> SEQUENCE: 791
agagaagaag aucagccugc a                                             21

<210> SEQ ID NO 792
<211> LENGTH: 24
<212> TYPE: RNA
<213> ORGANISM: Homo sapiens

<400> SEQUENCE: 792
agccuggaag cuggagccug cagu                                          24

<210> SEQ ID NO 793
<211> LENGTH: 23
<212> TYPE: RNA
<213> ORGANISM: Homo sapiens

```
<400> SEQUENCE: 793
aggaugagca agaaaguag auu                                          23

<210> SEQ ID NO 794
<211> LENGTH: 22
<212> TYPE: RNA
<213> ORGANISM: Homo sapiens

<400> SEQUENCE: 794
aggcauugac uucucacuag cu                                          22

<210> SEQ ID NO 795
<211> LENGTH: 21
<212> TYPE: RNA
<213> ORGANISM: Homo sapiens

<400> SEQUENCE: 795
agugaaugau ggguucugac c                                           21

<210> SEQ ID NO 796
<211> LENGTH: 21
<212> TYPE: RNA
<213> ORGANISM: Homo sapiens

<400> SEQUENCE: 796
aguuaggauu aggucgugga a                                           21

<210> SEQ ID NO 797
<211> LENGTH: 21
<212> TYPE: RNA
<213> ORGANISM: Homo sapiens

<400> SEQUENCE: 797
auauaugaug acuuagcuuu u                                           21

<210> SEQ ID NO 798
<211> LENGTH: 18
<212> TYPE: RNA
<213> ORGANISM: Homo sapiens

<400> SEQUENCE: 798
aucccaccuc ugccacca                                               18

<210> SEQ ID NO 799
<211> LENGTH: 22
<212> TYPE: RNA
<213> ORGANISM: Homo sapiens

<400> SEQUENCE: 799
aaaacuguaa uuacuuuugu ac                                          22

<210> SEQ ID NO 800
<211> LENGTH: 19
<212> TYPE: RNA
<213> ORGANISM: Homo sapiens

<400> SEQUENCE: 800
auggauaagg cuuuggcuu                                              19

<210> SEQ ID NO 801
<211> LENGTH: 22
<212> TYPE: RNA
```

```
<213> ORGANISM: Homo sapiens

<400> SEQUENCE: 801
augggugaau uuguagaagg au                                              22

<210> SEQ ID NO 802
<211> LENGTH: 22
<212> TYPE: RNA
<213> ORGANISM: Homo sapiens

<400> SEQUENCE: 802
augguacccu ggcauacuga gu                                              22

<210> SEQ ID NO 803
<211> LENGTH: 22
<212> TYPE: RNA
<213> ORGANISM: Homo sapiens

<400> SEQUENCE: 803
caaaaguaau uguggauuuu gu                                              22

<210> SEQ ID NO 804
<211> LENGTH: 21
<212> TYPE: RNA
<213> ORGANISM: Homo sapiens

<400> SEQUENCE: 804
caaagguauu uguggguuuuu g                                              21

<210> SEQ ID NO 805
<211> LENGTH: 22
<212> TYPE: RNA
<213> ORGANISM: Homo sapiens

<400> SEQUENCE: 805
caggaugugg ucaguguug uu                                               22

<210> SEQ ID NO 806
<211> LENGTH: 22
<212> TYPE: RNA
<213> ORGANISM: Homo sapiens

<400> SEQUENCE: 806
ccaaaacugc aguuacuuuu gc                                              22

<210> SEQ ID NO 807
<211> LENGTH: 23
<212> TYPE: RNA
<213> ORGANISM: Homo sapiens

<400> SEQUENCE: 807
ccucagggcu guagaacagg gcu                                             23

<210> SEQ ID NO 808
<211> LENGTH: 21
<212> TYPE: RNA
<213> ORGANISM: Homo sapiens

<400> SEQUENCE: 808
ccuguugaag uguaaucccc a                                               21

<210> SEQ ID NO 809
<211> LENGTH: 18
```

```
<212> TYPE: RNA
<213> ORGANISM: Homo sapiens

<400> SEQUENCE: 809
cgggcguggu ggugggg                                              18

<210> SEQ ID NO 810
<211> LENGTH: 22
<212> TYPE: RNA
<213> ORGANISM: Homo sapiens

<400> SEQUENCE: 810
cuggacugag ccgugcuacu gg                                        22

<210> SEQ ID NO 811
<211> LENGTH: 23
<212> TYPE: RNA
<213> ORGANISM: Homo sapiens

<400> SEQUENCE: 811
cuggagauau ggaagagcug ugu                                       23

<210> SEQ ID NO 812
<211> LENGTH: 26
<212> TYPE: RNA
<213> ORGANISM: Homo sapiens

<400> SEQUENCE: 812
gaugaugaug gcagcaaauu cugaaa                                    26

<210> SEQ ID NO 813
<211> LENGTH: 25
<212> TYPE: RNA
<213> ORGANISM: Homo sapiens

<400> SEQUENCE: 813
gggcgacaaa gcaagacucu uucuu                                     25

<210> SEQ ID NO 814
<211> LENGTH: 18
<212> TYPE: RNA
<213> ORGANISM: Homo sapiens

<400> SEQUENCE: 814
gucccuguuc aggcgcca                                             18

<210> SEQ ID NO 815
<211> LENGTH: 22
<212> TYPE: RNA
<213> ORGANISM: Homo sapiens

<400> SEQUENCE: 815
aaaaguaauc gcgguuuuug uc                                        22

<210> SEQ ID NO 816
<211> LENGTH: 17
<212> TYPE: RNA
<213> ORGANISM: Homo sapiens

<400> SEQUENCE: 816 guggggaga ggcuguc                                               17

<210> SEQ ID NO 817
```

```
<211> LENGTH: 20
<212> TYPE: RNA
<213> ORGANISM: Homo sapiens

<400> SEQUENCE: 817
uaaagagccc uguggagaca                                              20

<210> SEQ ID NO 818
<211> LENGTH: 17
<212> TYPE: RNA
<213> ORGANISM: Homo sapiens

<400> SEQUENCE: 818
uaagugcuuc caugcuu                                                 17

<210> SEQ ID NO 819
<211> LENGTH: 17
<212> TYPE: RNA
<213> ORGANISM: Homo sapiens

<400> SEQUENCE: 819
uaauugcuuc cauguuu                                                 17

<210> SEQ ID NO 820
<211> LENGTH: 22
<212> TYPE: RNA
<213> ORGANISM: Homo sapiens

<400> SEQUENCE: 820
uacguagaua uauauguauu uu                                           22

<210> SEQ ID NO 821
<211> LENGTH: 22
<212> TYPE: RNA
<213> ORGANISM: Homo sapiens

<400> SEQUENCE: 821
uagcaaaaac ugcaguuacu uu                                           22

<210> SEQ ID NO 822
<211> LENGTH: 22
<212> TYPE: RNA
<213> ORGANISM: Homo sapiens

<400> SEQUENCE: 822
aaaaguaauu gcggauuuug cc                                           22

<210> SEQ ID NO 823
<211> LENGTH: 22
<212> TYPE: RNA
<213> ORGANISM: Homo sapiens

<400> SEQUENCE: 823
uaguacugug cauaucaucu au                                           22

<210> SEQ ID NO 824
<211> LENGTH: 17
<212> TYPE: RNA
<213> ORGANISM: Homo sapiens

<400> SEQUENCE: 824
ucauauugcu ucuuucu                                                 17
```

```
<210> SEQ ID NO 825
<211> LENGTH: 17
<212> TYPE: RNA
<213> ORGANISM: Homo sapiens

<400> SEQUENCE: 825
ucccuguucg ggcgcca                                                  17

<210> SEQ ID NO 826
<211> LENGTH: 17
<212> TYPE: RNA
<213> ORGANISM: Homo sapiens

<400> SEQUENCE: 826
ucgccuccuc cucuccc                                                  17

<210> SEQ ID NO 827
<211> LENGTH: 20
<212> TYPE: RNA
<213> ORGANISM: Homo sapiens

<400> SEQUENCE: 827
ucguuugccu uuucugcuu                                                20

<210> SEQ ID NO 828
<211> LENGTH: 22
<212> TYPE: RNA
<213> ORGANISM: Homo sapiens

<400> SEQUENCE: 828
ucuauacaga cccuggcuuu uc                                            22

<210> SEQ ID NO 829
<211> LENGTH: 21
<212> TYPE: RNA
<213> ORGANISM: Homo sapiens

<400> SEQUENCE: 829
uggacugccc ugaucuggag a                                             21

<210> SEQ ID NO 830
<211> LENGTH: 25
<212> TYPE: RNA
<213> ORGANISM: Homo sapiens

<400> SEQUENCE: 830
ugggaacggg uuccggcaga cgcug                                         25

<210> SEQ ID NO 831
<211> LENGTH: 22
<212> TYPE: RNA
<213> ORGANISM: Homo sapiens

<400> SEQUENCE: 831
agaaggaaau ugaauucauu ua                                            22

<210> SEQ ID NO 832
<211> LENGTH: 22
<212> TYPE: RNA
<213> ORGANISM: Homo sapiens

<400> SEQUENCE: 832
cggaugagca aagaaagugg uu                                            22
```

<210> SEQ ID NO 833
<211> LENGTH: 17
<212> TYPE: RNA
<213> ORGANISM: Homo sapiens

<400> SEQUENCE: 833
ucccaccgcu gccaccc                                                    17

<210> SEQ ID NO 834
<211> LENGTH: 18
<212> TYPE: RNA
<213> ORGANISM: Homo sapiens

<400> SEQUENCE: 834
gcaugggugg uucagugg                                                   18

<210> SEQ ID NO 835
<211> LENGTH: 24
<212> TYPE: RNA
<213> ORGANISM: Homo sapiens

<400> SEQUENCE: 835
acuggcuagg gaaaaugauu ggau                                            24

<210> SEQ ID NO 836
<211> LENGTH: 23
<212> TYPE: RNA
<213> ORGANISM: Homo sapiens

<400> SEQUENCE: 836
uauucauuua uccccagccu aca                                             23

<210> SEQ ID NO 837
<211> LENGTH: 18
<212> TYPE: RNA
<213> ORGANISM: Homo sapiens

<400> SEQUENCE: 837
acguuggcuc ugguggug                                                   18

<210> SEQ ID NO 838
<211> LENGTH: 22
<212> TYPE: RNA
<213> ORGANISM: Homo sapiens

<400> SEQUENCE: 838
acucggcgug gcgucggucg ug                                              22

<210> SEQ ID NO 839
<211> LENGTH: 22
<212> TYPE: RNA
<213> ORGANISM: Homo sapiens

<400> SEQUENCE: 839
uucacaagga ggugucauuu au                                              22

<210> SEQ ID NO 840
<211> LENGTH: 22
<212> TYPE: RNA
<213> ORGANISM: Homo sapiens

<400> SEQUENCE: 840
uucucaagga ggugucguuu au                                              22

```
<210> SEQ ID NO 841
<211> LENGTH: 18
<212> TYPE: RNA
<213> ORGANISM: Homo sapiens

<400> SEQUENCE: 841
cagggaggug aaugugau                                                 18

<210> SEQ ID NO 842
<211> LENGTH: 19
<212> TYPE: RNA
<213> ORGANISM: Homo sapiens

<400> SEQUENCE: 842
gaugaugcug cugaugcug                                                19

<210> SEQ ID NO 843
<211> LENGTH: 17
<212> TYPE: RNA
<213> ORGANISM: Homo sapiens

<400> SEQUENCE: 843
ucucgcuggg gccucca                                                  17

<210> SEQ ID NO 844
<211> LENGTH: 21
<212> TYPE: RNA
<213> ORGANISM: Homo sapiens

<400> SEQUENCE: 844
uaggacacau ggucuacuuc u                                             21

<210> SEQ ID NO 845
<211> LENGTH: 24
<212> TYPE: RNA
<213> ORGANISM: Homo sapiens

<400> SEQUENCE: 845
ccagacagaa uucuaugcac uuuc                                          24

<210> SEQ ID NO 846
<211> LENGTH: 22
<212> TYPE: RNA
<213> ORGANISM: Homo sapiens

<400> SEQUENCE: 846
cucggcgcgg ggcgcgggcu cc                                            22

<210> SEQ ID NO 847
<211> LENGTH: 21
<212> TYPE: RNA
<213> ORGANISM: Homo sapiens

<400> SEQUENCE: 847
gcccuccgcc cgugcacccc g                                             21

<210> SEQ ID NO 848
<211> LENGTH: 22
<212> TYPE: RNA
<213> ORGANISM: Homo sapiens

<400> SEQUENCE: 848
```

```
gcccgcgugu ggagccaggu gu                                              22

<210> SEQ ID NO 849
<211> LENGTH: 22
<212> TYPE: RNA
<213> ORGANISM: Homo sapiens

<400> SEQUENCE: 849
aaaaccgucu aguuacaguu gu                                              22

<210> SEQ ID NO 850
<211> LENGTH: 23
<212> TYPE: RNA
<213> ORGANISM: Homo sapiens

<400> SEQUENCE: 850
cggcccgggc ugcugcuguu ccu                                             23

<210> SEQ ID NO 851
<211> LENGTH: 21
<212> TYPE: RNA
<213> ORGANISM: Homo sapiens

<400> SEQUENCE: 851
uccugcgcgu cccagaugcc c                                               21

<210> SEQ ID NO 852
<211> LENGTH: 23
<212> TYPE: RNA
<213> ORGANISM: Homo sapiens

<400> SEQUENCE: 852
ucauagcccu guacaaugcu gcu                                             23

<210> SEQ ID NO 853
<211> LENGTH: 19
<212> TYPE: RNA
<213> ORGANISM: Homo sapiens

<400> SEQUENCE: 853
aaaagcuggg uugagagga                                                  19

<210> SEQ ID NO 854
<211> LENGTH: 18
<212> TYPE: RNA
<213> ORGANISM: Homo sapiens

<400> SEQUENCE: 854
uccagugccc uccucucc                                                   18

<210> SEQ ID NO 855
<211> LENGTH: 27
<212> TYPE: RNA
<213> ORGANISM: Homo sapiens

<400> SEQUENCE: 855
auugaucauc gacacuucga acgcaau                                         27

<210> SEQ ID NO 856
<211> LENGTH: 18
<212> TYPE: RNA
<213> ORGANISM: Homo sapiens

<400> SEQUENCE: 856
```

-continued ugaggcagua gauugaau					18

<210> SEQ ID NO 857
<211> LENGTH: 21
<212> TYPE: RNA
<213> ORGANISM: Homo sapiens

<400> SEQUENCE: 857
cggcggggac ggcgauuggu c					21

<210> SEQ ID NO 858
<211> LENGTH: 21
<212> TYPE: RNA
<213> ORGANISM: Homo sapiens

<400> SEQUENCE: 858
ugagugccgg ugccugcccu g					21

<210> SEQ ID NO 859
<211> LENGTH: 22
<212> TYPE: RNA
<213> ORGANISM: Homo sapiens

<400> SEQUENCE: 859
cgcaggggcc gggugcucac cg				22

<210> SEQ ID NO 860
<211> LENGTH: 21
<212> TYPE: RNA
<213> ORGANISM: Homo sapiens

<400> SEQUENCE: 860
ccaguccugu gccugccgcc u					21

<210> SEQ ID NO 861
<211> LENGTH: 23
<212> TYPE: RNA
<213> ORGANISM: Homo sapiens

<400> SEQUENCE: 861
ugaguaccgc caugucuguu ggg				23

<210> SEQ ID NO 862
<211> LENGTH: 20
<212> TYPE: RNA
<213> ORGANISM: Homo sapiens

<400> SEQUENCE: 862
caccaggcau uguggucucc					20

<210> SEQ ID NO 863
<211> LENGTH: 22
<212> TYPE: RNA
<213> ORGANISM: Homo sapiens

<400> SEQUENCE: 863
uacccagagc augcagugug aa				22

<210> SEQ ID NO 864
<211> LENGTH: 22
<212> TYPE: RNA
<213> ORGANISM: Homo sapiens

<400> SEQUENCE: 864 ucugccccu ccgcugcugc ca                                        22

<210> SEQ ID NO 865
<211> LENGTH: 22
<212> TYPE: RNA
<213> ORGANISM: Homo sapiens

<400> SEQUENCE: 865
cccugugccc ggcccacuuc ug                                       22

<210> SEQ ID NO 866
<211> LENGTH: 22
<212> TYPE: RNA
<213> ORGANISM: Homo sapiens

<400> SEQUENCE: 866
ggaggggucc cgcacuggga gg                                       22

<210> SEQ ID NO 867
<211> LENGTH: 22
<212> TYPE: RNA
<213> ORGANISM: Homo sapiens

<400> SEQUENCE: 867
accuugccuu gcugcccggg cc                                       22

<210> SEQ ID NO 868
<211> LENGTH: 20
<212> TYPE: RNA
<213> ORGANISM: Homo sapiens

<400> SEQUENCE: 868
ccccagggcg acgcggcggg                                          20

<210> SEQ ID NO 869
<211> LENGTH: 22
<212> TYPE: RNA
<213> ORGANISM: Homo sapiens

<400> SEQUENCE: 869
ucaggccagg cacaguggcu ca                                       22

<210> SEQ ID NO 870
<211> LENGTH: 19
<212> TYPE: RNA
<213> ORGANISM: Homo sapiens

<400> SEQUENCE: 870
accgugcaaa gguagcaua                                           19

<210> SEQ ID NO 871
<211> LENGTH: 25
<212> TYPE: RNA
<213> ORGANISM: Homo sapiens

<400> SEQUENCE: 871
cccccacaac cgcgcuugac uagcu                                    25

<210> SEQ ID NO 872
<211> LENGTH: 20
<212> TYPE: RNA
<213> ORGANISM: Homo sapiens

```
<400> SEQUENCE: 872
ccuccugccc uccuugcugu                                              20

<210> SEQ ID NO 873
<211> LENGTH: 22
<212> TYPE: RNA
<213> ORGANISM: Homo sapiens

<400> SEQUENCE: 873
cucccacugc uucacuugac ua                                           22

<210> SEQ ID NO 874
<211> LENGTH: 20
<212> TYPE: RNA
<213> ORGANISM: Homo sapiens

<400> SEQUENCE: 874
uguuuugaua acaguaaugu                                              20

<210> SEQ ID NO 875
<211> LENGTH: 23
<212> TYPE: RNA
<213> ORGANISM: Homo sapiens

<400> SEQUENCE: 875
guguuaauua aaccucuauu uac                                          23

<210> SEQ ID NO 876
<211> LENGTH: 23
<212> TYPE: RNA
<213> ORGANISM: Homo sapiens

<400> SEQUENCE: 876
cuguaauaua aauuuaauuu auu                                          23

<210> SEQ ID NO 877
<211> LENGTH: 22
<212> TYPE: RNA
<213> ORGANISM: Homo sapiens

<400> SEQUENCE: 877
uuggggaaac ggccgcugag ug                                           22

<210> SEQ ID NO 878
<211> LENGTH: 22
<212> TYPE: RNA
<213> ORGANISM: Homo sapiens

<400> SEQUENCE: 878
uagucccuuc cuugaagcgg uc                                           22

<210> SEQ ID NO 879
<211> LENGTH: 21
<212> TYPE: RNA
<213> ORGANISM: Homo sapiens

<400> SEQUENCE: 879
cgagccucaa gcaagggacu u                                            21

<210> SEQ ID NO 880
<211> LENGTH: 22
<212> TYPE: RNA
```

```
<213> ORGANISM: Homo sapiens

<400> SEQUENCE: 880
agcuuccaug acuccugaug ga                                    22

<210> SEQ ID NO 881
<211> LENGTH: 22
<212> TYPE: RNA
<213> ORGANISM: Homo sapiens

<400> SEQUENCE: 881
caucagaauu cauggaggcu ag                                    22

<210> SEQ ID NO 882
<211> LENGTH: 21
<212> TYPE: RNA
<213> ORGANISM: Homo sapiens

<400> SEQUENCE: 882
gguucuuagc auaggagguc u                                     21

<210> SEQ ID NO 883
<211> LENGTH: 21
<212> TYPE: RNA
<213> ORGANISM: Homo sapiens

<400> SEQUENCE: 883
ccucccaugc caagaacucc c                                     21

<210> SEQ ID NO 884
<211> LENGTH: 21
<212> TYPE: RNA
<213> ORGANISM: Homo sapiens

<400> SEQUENCE: 884
uguucucuuu gccaaggaca g                                     21

<210> SEQ ID NO 885
<211> LENGTH: 22
<212> TYPE: RNA
<213> ORGANISM: Homo sapiens

<400> SEQUENCE: 885
gcuggugcaa aaguaauggc gg                                    22

<210> SEQ ID NO 886
<211> LENGTH: 22
<212> TYPE: RNA
<213> ORGANISM: Homo sapiens

<400> SEQUENCE: 886
ucugcaagug ucagaggcga gg                                    22

<210> SEQ ID NO 887
<211> LENGTH: 21
<212> TYPE: RNA
<213> ORGANISM: Homo sapiens

<400> SEQUENCE: 887
ugacagcgcc cugccuggcu c                                     21

<210> SEQ ID NO 888
<211> LENGTH: 22
```

<212> TYPE: RNA
<213> ORGANISM: Homo sapiens

<400> SEQUENCE: 888
gagagcagug uguguugccu gg					22

<210> SEQ ID NO 889
<211> LENGTH: 22
<212> TYPE: RNA
<213> ORGANISM: Homo sapiens

<400> SEQUENCE: 889
gggacccagg gagagacgua ag					22

<210> SEQ ID NO 890
<211> LENGTH: 21
<212> TYPE: RNA
<213> ORGANISM: Homo sapiens

<400> SEQUENCE: 890
cuuccgcccc gccgggcguc g						21

<210> SEQ ID NO 891
<211> LENGTH: 19
<212> TYPE: RNA
<213> ORGANISM: Homo sapiens

<400> SEQUENCE: 891
ggggccuggc ggugggcgg						19

<210> SEQ ID NO 892
<211> LENGTH: 21
<212> TYPE: RNA
<213> ORGANISM: Homo sapiens

<400> SEQUENCE: 892
guuagggcca acaucucuug g						21

<210> SEQ ID NO 893
<211> LENGTH: 20
<212> TYPE: RNA
<213> ORGANISM: Homo sapiens

<400> SEQUENCE: 893
auauggguuu acuaguuggu						20

<210> SEQ ID NO 894
<211> LENGTH: 22
<212> TYPE: RNA
<213> ORGANISM: Homo sapiens

<400> SEQUENCE: 894
ugccuggaac auaguaggga cu					22

<210> SEQ ID NO 895
<211> LENGTH: 21
<212> TYPE: RNA
<213> ORGANISM: Homo sapiens

<400> SEQUENCE: 895
auaggacuca uauagugcca g						21

<210> SEQ ID NO 896

-continued

```
<211> LENGTH: 23
<212> TYPE: RNA
<213> ORGANISM: Homo sapiens

<400> SEQUENCE: 896
ugugacugca uuaugaaaau ucu                                           23

<210> SEQ ID NO 897
<211> LENGTH: 20
<212> TYPE: RNA
<213> ORGANISM: Homo sapiens

<400> SEQUENCE: 897
uggcuuuuaa cuuugauggc                                               20

<210> SEQ ID NO 898
<211> LENGTH: 21
<212> TYPE: RNA
<213> ORGANISM: Homo sapiens

<400> SEQUENCE: 898
cacagcaagu guagacaggc a                                             21

<210> SEQ ID NO 899
<211> LENGTH: 22
<212> TYPE: RNA
<213> ORGANISM: Homo sapiens

<400> SEQUENCE: 899
uaaauagagu aggcaaagga ca                                            22

<210> SEQ ID NO 900
<211> LENGTH: 22
<212> TYPE: RNA
<213> ORGANISM: Homo sapiens

<400> SEQUENCE: 900
guugggacaa gaggacgguc uu                                            22

<210> SEQ ID NO 901
<211> LENGTH: 17
<212> TYPE: RNA
<213> ORGANISM: Homo sapiens

<400> SEQUENCE: 901
cagagaauug uuuaauc                                                  17

<210> SEQ ID NO 902
<211> LENGTH: 21
<212> TYPE: RNA
<213> ORGANISM: Homo sapiens

<400> SEQUENCE: 902
uucgcgggcg aaggcaaagu c                                             21

<210> SEQ ID NO 903
<211> LENGTH: 23
<212> TYPE: RNA
<213> ORGANISM: Homo sapiens

<400> SEQUENCE: 903
auggccaaaa cugcaguuau uuu                                           23
```

```
<210> SEQ ID NO 904
<211> LENGTH: 20
<212> TYPE: RNA
<213> ORGANISM: Homo sapiens

<400> SEQUENCE: 904
uagaggaagc uguggagaga                                                    20

<210> SEQ ID NO 905
<211> LENGTH: 22
<212> TYPE: RNA
<213> ORGANISM: Homo sapiens

<400> SEQUENCE: 905
ugagggacag augccagaag ca                                                 22

<210> SEQ ID NO 906
<211> LENGTH: 22
<212> TYPE: RNA
<213> ORGANISM: Homo sapiens

<400> SEQUENCE: 906
caucuggcau ccgucacaca ga                                                 22

<210> SEQ ID NO 907
<211> LENGTH: 23
<212> TYPE: RNA
<213> ORGANISM: Homo sapiens

<400> SEQUENCE: 907
aucagggcuu guggaauggg aag                                                23

<210> SEQ ID NO 908
<211> LENGTH: 23
<212> TYPE: RNA
<213> ORGANISM: Homo sapiens

<400> SEQUENCE: 908
ucuggcaagu aaaaaacucu cau                                                23

<210> SEQ ID NO 909
<211> LENGTH: 22
<212> TYPE: RNA
<213> ORGANISM: Homo sapiens

<400> SEQUENCE: 909
gcaguagugu agagauuggu uu                                                 22

<210> SEQ ID NO 910
<211> LENGTH: 21
<212> TYPE: RNA
<213> ORGANISM: Homo sapiens

<400> SEQUENCE: 910
uacccagucu ccggugcagc c                                                  21

<210> SEQ ID NO 911
<211> LENGTH: 21
<212> TYPE: RNA
<213> ORGANISM: Homo sapiens

<400> SEQUENCE: 911
gcugcaccgg agacugggua a                                                  21
```

```
<210> SEQ ID NO 912
<211> LENGTH: 23
<212> TYPE: RNA
<213> ORGANISM: Homo sapiens

<400> SEQUENCE: 912
ucgaggacug guggaagggc cuu                                              23

<210> SEQ ID NO 913
<211> LENGTH: 24
<212> TYPE: RNA
<213> ORGANISM: Homo sapiens

<400> SEQUENCE: 913
uggguagaga aggagcucag agga                                             24

<210> SEQ ID NO 914
<211> LENGTH: 22
<212> TYPE: RNA
<213> ORGANISM: Homo sapiens

<400> SEQUENCE: 914
uaaagaacuc uuaaaaccca au                                               22

<210> SEQ ID NO 915
<211> LENGTH: 19
<212> TYPE: RNA
<213> ORGANISM: Homo sapiens

<400> SEQUENCE: 915
acuggacuug gaggcagaa                                                   19

<210> SEQ ID NO 916
<211> LENGTH: 23
<212> TYPE: RNA
<213> ORGANISM: Homo sapiens

<400> SEQUENCE: 916
ugauggauaa aagacuacau auu                                              23

<210> SEQ ID NO 917
<211> LENGTH: 22
<212> TYPE: RNA
<213> ORGANISM: Homo sapiens

<400> SEQUENCE: 917
ugccuaggcu gagacugcag ug                                               22

<210> SEQ ID NO 918
<211> LENGTH: 23
<212> TYPE: RNA
<213> ORGANISM: Homo sapiens

<400> SEQUENCE: 918
auacacauac acgcaacaca cau                                              23

<210> SEQ ID NO 919
<211> LENGTH: 23
<212> TYPE: RNA
<213> ORGANISM: Homo sapiens

<400> SEQUENCE: 919
cugacugaau agguaggguc auu                                              23
```

<210> SEQ ID NO 920
<211> LENGTH: 22
<212> TYPE: RNA
<213> ORGANISM: Homo sapiens

<400> SEQUENCE: 920
accugagguu gugcauuucu aa                                           22

<210> SEQ ID NO 921
<211> LENGTH: 24
<212> TYPE: RNA
<213> ORGANISM: Homo sapiens

<400> SEQUENCE: 921
ucuguagccu gggagcaaug gggu                                         24

<210> SEQ ID NO 922
<211> LENGTH: 24
<212> TYPE: RNA
<213> ORGANISM: Homo sapiens

<400> SEQUENCE: 922
uguggacagu gagguagagg gagu                                         24

<210> SEQ ID NO 923
<211> LENGTH: 23
<212> TYPE: RNA
<213> ORGANISM: Homo sapiens

<400> SEQUENCE: 923
uaggagcuca acagaugccu guu                                          23

<210> SEQ ID NO 924
<211> LENGTH: 22
<212> TYPE: RNA
<213> ORGANISM: Homo sapiens

<400> SEQUENCE: 924
agcuuuuggg aauucaggua gu                                           22

<210> SEQ ID NO 925
<211> LENGTH: 21
<212> TYPE: RNA
<213> ORGANISM: Homo sapiens

<400> SEQUENCE: 925
caaaagugau cgugguuuuu g                                            21

<210> SEQ ID NO 926
<211> LENGTH: 19
<212> TYPE: RNA
<213> ORGANISM: Homo sapiens

<400> SEQUENCE: 926
gagggcgggu ggaggagga                                               19

<210> SEQ ID NO 927
<211> LENGTH: 22
<212> TYPE: RNA
<213> ORGANISM: Homo sapiens

<400> SEQUENCE: 927

```
aaggccuuuc ugaaccuuca ga                                          22

<210> SEQ ID NO 928
<211> LENGTH: 25
<212> TYPE: RNA
<213> ORGANISM: Homo sapiens

<400> SEQUENCE: 928
auaacauugu aaagcgcuuc uuucg                                       25

<210> SEQ ID NO 929
<211> LENGTH: 23
<212> TYPE: RNA
<213> ORGANISM: Homo sapiens

<400> SEQUENCE: 929
caaagacugc aauuacuuuu gcg                                         23

<210> SEQ ID NO 930
<211> LENGTH: 22
<212> TYPE: RNA
<213> ORGANISM: Homo sapiens

<400> SEQUENCE: 930
aggggaccaa agagauauau ag                                          22

<210> SEQ ID NO 931
<211> LENGTH: 22
<212> TYPE: RNA
<213> ORGANISM: Homo sapiens

<400> SEQUENCE: 931
auauaccugu ucggucucuu ua                                          22

<210> SEQ ID NO 932
<211> LENGTH: 24
<212> TYPE: RNA
<213> ORGANISM: Homo sapiens

<400> SEQUENCE: 932
agauauuuug aguguuugga auug                                        24

<210> SEQ ID NO 933
<211> LENGTH: 22
<212> TYPE: RNA
<213> ORGANISM: Homo sapiens

<400> SEQUENCE: 933
ggcgacaaaa cgagacccug uc                                          22

<210> SEQ ID NO 934
<211> LENGTH: 22
<212> TYPE: RNA
<213> ORGANISM: Homo sapiens

<400> SEQUENCE: 934
caugcuagga uagaaagaau gg                                          22

<210> SEQ ID NO 935
<211> LENGTH: 24
<212> TYPE: RNA
<213> ORGANISM: Homo sapiens

<400> SEQUENCE: 935
```

| | |
|---|---|
| gguugggcag ugaggagggu guga | 24 |

<210> SEQ ID NO 936
<211> LENGTH: 22
<212> TYPE: RNA
<213> ORGANISM: Homo sapiens

<400> SEQUENCE: 936

| | |
|---|---|
| agcuacaguu acuuuugcac ca | 22 |

<210> SEQ ID NO 937
<211> LENGTH: 22
<212> TYPE: RNA
<213> ORGANISM: Homo sapiens

<400> SEQUENCE: 937

| | |
|---|---|
| uggaaaaaac uggugugugc uu | 22 |

<210> SEQ ID NO 938
<211> LENGTH: 23
<212> TYPE: RNA
<213> ORGANISM: Homo sapiens

<400> SEQUENCE: 938

| | |
|---|---|
| uuuguaugga uaugugugug uau | 23 |

<210> SEQ ID NO 939
<211> LENGTH: 22
<212> TYPE: RNA
<213> ORGANISM: Homo sapiens

<400> SEQUENCE: 939

| | |
|---|---|
| cugggagau ccucgagguu gg | 22 |

<210> SEQ ID NO 940
<211> LENGTH: 21
<212> TYPE: RNA
<213> ORGANISM: Homo sapiens

<400> SEQUENCE: 940

| | |
|---|---|
| ggugggcaa ugggaucagg u | 21 |

<210> SEQ ID NO 941
<211> LENGTH: 22
<212> TYPE: RNA
<213> ORGANISM: Homo sapiens

<400> SEQUENCE: 941

| | |
|---|---|
| uguguuagaa uagggcaau aa | 22 |

<210> SEQ ID NO 942
<211> LENGTH: 23
<212> TYPE: RNA
<213> ORGANISM: Homo sapiens

<400> SEQUENCE: 942

| | |
|---|---|
| ggggaaagcg aguagggaca uuu | 23 |

<210> SEQ ID NO 943
<211> LENGTH: 22
<212> TYPE: RNA
<213> ORGANISM: Homo sapiens

```
<400> SEQUENCE: 943
gauaucagcu caguaggcac cg                                              22

<210> SEQ ID NO 944
<211> LENGTH: 22
<212> TYPE: RNA
<213> ORGANISM: Homo sapiens

<400> SEQUENCE: 944
cagaagggga guugggagca ga                                              22

<210> SEQ ID NO 945
<211> LENGTH: 21
<212> TYPE: RNA
<213> ORGANISM: Homo sapiens

<400> SEQUENCE: 945
ccaggcucug cagugggaac u                                               21

<210> SEQ ID NO 946
<211> LENGTH: 22
<212> TYPE: RNA
<213> ORGANISM: Homo sapiens

<400> SEQUENCE: 946
aaagaucugg aagugggaga ca                                              22

<210> SEQ ID NO 947
<211> LENGTH: 22
<212> TYPE: RNA
<213> ORGANISM: Homo sapiens

<400> SEQUENCE: 947
uucagccagg cuagugcagu cu                                              22

<210> SEQ ID NO 948
<211> LENGTH: 22
<212> TYPE: RNA
<213> ORGANISM: Homo sapiens

<400> SEQUENCE: 948
aagggcuucc ucucugcagg ac                                              22

<210> SEQ ID NO 949
<211> LENGTH: 22
<212> TYPE: RNA
<213> ORGANISM: Homo sapiens

<400> SEQUENCE: 949
uaggauuaca agugucggcc ac                                              22

<210> SEQ ID NO 950
<211> LENGTH: 22
<212> TYPE: RNA
<213> ORGANISM: Homo sapiens

<400> SEQUENCE: 950
agagcugaga cuagaaagcc ca                                              22

<210> SEQ ID NO 951
<211> LENGTH: 23
<212> TYPE: RNA
<213> ORGANISM: Homo sapiens
```

```
<400> SEQUENCE: 951
cugauaagaa cagaggccca gau                                              23

<210> SEQ ID NO 952
<211> LENGTH: 23
<212> TYPE: RNA
<213> ORGANISM: Homo sapiens

<400> SEQUENCE: 952
uuagggagua aagggugggg gag                                              23

<210> SEQ ID NO 953
<211> LENGTH: 22
<212> TYPE: RNA
<213> ORGANISM: Homo sapiens

<400> SEQUENCE: 953
uauaaaauga gggcaguaag ac                                               22

<210> SEQ ID NO 954
<211> LENGTH: 22
<212> TYPE: RNA
<213> ORGANISM: Homo sapiens

<400> SEQUENCE: 954
ugugacuuua agggaaaugg cg                                               22

<210> SEQ ID NO 955
<211> LENGTH: 22
<212> TYPE: RNA
<213> ORGANISM: Homo sapiens

<400> SEQUENCE: 955
agguggaugc aaugugaccu ca                                               22

<210> SEQ ID NO 956
<211> LENGTH: 23
<212> TYPE: RNA
<213> ORGANISM: Homo sapiens

<400> SEQUENCE: 956
cgcagacaau gccuacuggc cua                                              23

<210> SEQ ID NO 957
<211> LENGTH: 19
<212> TYPE: RNA
<213> ORGANISM: Homo sapiens

<400> SEQUENCE: 957
aucccaccac ugccaccau                                                   19

<210> SEQ ID NO 958
<211> LENGTH: 22
<212> TYPE: RNA
<213> ORGANISM: Homo sapiens

<400> SEQUENCE: 958
aggauuucag aaauacuggu gu                                               22

<210> SEQ ID NO 959
<211> LENGTH: 17
<212> TYPE: RNA
```

```
<213> ORGANISM: Homo sapiens

<400> SEQUENCE: 959
gaguucuaca gucagac                                              17

<210> SEQ ID NO 960
<211> LENGTH: 22
<212> TYPE: RNA
<213> ORGANISM: Homo sapiens

<400> SEQUENCE: 960
uaggacugug cuuggcacau ag                                        22

<210> SEQ ID NO 961
<211> LENGTH: 22
<212> TYPE: RNA
<213> ORGANISM: Homo sapiens

<400> SEQUENCE: 961 cuggguucu gagacagaca gu                                         22

<210> SEQ ID NO 962
<211> LENGTH: 24
<212> TYPE: RNA
<213> ORGANISM: Homo sapiens

<400> SEQUENCE: 962
agauguaugg aaucuguaua uauc                                      24

<210> SEQ ID NO 963
<211> LENGTH: 19
<212> TYPE: RNA
<213> ORGANISM: Homo sapiens

<400> SEQUENCE: 963 uggguuuug caguccuua                                             19

<210> SEQ ID NO 964
<211> LENGTH: 22
<212> TYPE: RNA
<213> ORGANISM: Homo sapiens

<400> SEQUENCE: 964
aaaggaggaa auaggcaggc ca                                        22

<210> SEQ ID NO 965
<211> LENGTH: 23
<212> TYPE: RNA
<213> ORGANISM: Homo sapiens

<400> SEQUENCE: 965
gggauggaug accggugacg ugc                                       23

<210> SEQ ID NO 966
<211> LENGTH: 23
<212> TYPE: RNA
<213> ORGANISM: Homo sapiens

<400> SEQUENCE: 966
agguuguccg uggugaguuc gca                                       23

<210> SEQ ID NO 967
<211> LENGTH: 22
```

<210> SEQ ID NO 967
<211> LENGTH: 22
<212> TYPE: RNA
<213> ORGANISM: Homo sapiens

<400> SEQUENCE: 967
cccaauacac ggucgaccuc uu                                    22

<210> SEQ ID NO 968
<211> LENGTH: 23
<212> TYPE: RNA
<213> ORGANISM: Homo sapiens

<400> SEQUENCE: 968
uagugaguua gagaugcaga gcc                                   23

<210> SEQ ID NO 969
<211> LENGTH: 22
<212> TYPE: RNA
<213> ORGANISM: Homo sapiens

<400> SEQUENCE: 969
cggggagaga acgcagugac gu                                    22

<210> SEQ ID NO 970
<211> LENGTH: 19
<212> TYPE: RNA
<213> ORGANISM: Homo sapiens

<400> SEQUENCE: 970
acuggccugg gacuaccgg                                        19

<210> SEQ ID NO 971
<211> LENGTH: 21
<212> TYPE: RNA
<213> ORGANISM: Homo sapiens

<400> SEQUENCE: 971
ugcacggcac uggggacacg u                                     21

<210> SEQ ID NO 972
<211> LENGTH: 17
<212> TYPE: RNA
<213> ORGANISM: Homo sapiens

<400> SEQUENCE: 972
ggggcgcggc cggaucg                                          17

<210> SEQ ID NO 973
<211> LENGTH: 22
<212> TYPE: RNA
<213> ORGANISM: Homo sapiens

<400> SEQUENCE: 973
agaaggggug aaauuuaaac gu                                    22

<210> SEQ ID NO 974
<211> LENGTH: 25
<212> TYPE: RNA
<213> ORGANISM: Homo sapiens

<400> SEQUENCE: 974
cuuccagacg cuccgcccca cgucg                                 25

<210> SEQ ID NO 975

```
<211> LENGTH: 22
<212> TYPE: RNA
<213> ORGANISM: Homo sapiens

<400> SEQUENCE: 975 ugggcggag cuuccggagg cc                                              22

<210> SEQ ID NO 976
<211> LENGTH: 23
<212> TYPE: RNA
<213> ORGANISM: Homo sapiens

<400> SEQUENCE: 976
aaaaguaacu gcgguuuuug ccu                                            23

<210> SEQ ID NO 977
<211> LENGTH: 19
<212> TYPE: RNA
<213> ORGANISM: Homo sapiens

<400> SEQUENCE: 977
aucgggcccu cggcgccgg                                                 19

<210> SEQ ID NO 978
<211> LENGTH: 17
<212> TYPE: RNA
<213> ORGANISM: Homo sapiens

<400> SEQUENCE: 978
gcuucuguag uguaguc                                                   17

<210> SEQ ID NO 979
<211> LENGTH: 22
<212> TYPE: RNA
<213> ORGANISM: Homo sapiens

<400> SEQUENCE: 979
gccucucucg gagucgcucg ga                                             22

<210> SEQ ID NO 980
<211> LENGTH: 24
<212> TYPE: RNA
<213> ORGANISM: Homo sapiens

<400> SEQUENCE: 980
ugaggggccu cagaccgagc uuuu                                           24

<210> SEQ ID NO 981
<211> LENGTH: 23
<212> TYPE: RNA
<213> ORGANISM: Homo sapiens

<400> SEQUENCE: 981
agaagaaggc ggucggucug cgg                                            23

<210> SEQ ID NO 982
<211> LENGTH: 23
<212> TYPE: RNA
<213> ORGANISM: Homo sapiens

<400> SEQUENCE: 982
ucaacaaaau cacugaugcu gga                                            23
```

```
<210> SEQ ID NO 983
<211> LENGTH: 23
<212> TYPE: RNA
<213> ORGANISM: Homo sapiens

<400> SEQUENCE: 983
ucagcaccag gauauuguug gag                                          23

<210> SEQ ID NO 984
<211> LENGTH: 22
<212> TYPE: RNA
<213> ORGANISM: Homo sapiens

<400> SEQUENCE: 984
caggcgucug ucuacguggc uu                                           22

<210> SEQ ID NO 985
<211> LENGTH: 21
<212> TYPE: RNA
<213> ORGANISM: Homo sapiens

<400> SEQUENCE: 985
ucacgcggag agauggcuuu g                                            21

<210> SEQ ID NO 986
<211> LENGTH: 20
<212> TYPE: RNA
<213> ORGANISM: Homo sapiens

<400> SEQUENCE: 986
uuggccaugg ggcugcgcgg                                              20

<210> SEQ ID NO 987
<211> LENGTH: 23
<212> TYPE: RNA
<213> ORGANISM: Homo sapiens

<400> SEQUENCE: 987
agaggcuuug ugcggauacg ggg                                          23

<210> SEQ ID NO 988
<211> LENGTH: 21
<212> TYPE: RNA
<213> ORGANISM: Homo sapiens

<400> SEQUENCE: 988
cccuuggguc ugaugggua g                                             21

<210> SEQ ID NO 989
<211> LENGTH: 18
<212> TYPE: RNA
<213> ORGANISM: Homo sapiens

<400> SEQUENCE: 989
aaagcugggu ugagaagg                                                18

<210> SEQ ID NO 990
<211> LENGTH: 23
<212> TYPE: RNA
<213> ORGANISM: Homo sapiens

<400> SEQUENCE: 990
uguggaaggu agacggccag aga                                          23
```

```
<210> SEQ ID NO 991
<211> LENGTH: 22
<212> TYPE: RNA
<213> ORGANISM: Homo sapiens

<400> SEQUENCE: 991
uggaagguag acggccagag ag                                              22

<210> SEQ ID NO 992
<211> LENGTH: 23
<212> TYPE: RNA
<213> ORGANISM: Homo sapiens

<400> SEQUENCE: 992
uggggacgua gcuggccaga cag                                             23

<210> SEQ ID NO 993
<211> LENGTH: 23
<212> TYPE: RNA
<213> ORGANISM: Homo sapiens

<400> SEQUENCE: 993
ucugggaggu uguagcagug gaa                                             23

<210> SEQ ID NO 994
<211> LENGTH: 22
<212> TYPE: RNA
<213> ORGANISM: Homo sapiens

<400> SEQUENCE: 994
uccugcguag gaucugagga gu                                              22

<210> SEQ ID NO 995
<211> LENGTH: 21
<212> TYPE: RNA
<213> ORGANISM: Homo sapiens

<400> SEQUENCE: 995
ggccagccac caggagggcu g                                               21

<210> SEQ ID NO 996
<211> LENGTH: 17
<212> TYPE: RNA
<213> ORGANISM: Homo sapiens

<400> SEQUENCE: 996
cgcgccgggc ccgguu                                                     17

<210> SEQ ID NO 997
<211> LENGTH: 18
<212> TYPE: RNA
<213> ORGANISM: Homo sapiens

<400> SEQUENCE: 997
cggggcggca ggggccuc                                                   18

<210> SEQ ID NO 998
<211> LENGTH: 21
<212> TYPE: RNA
<213> ORGANISM: Homo sapiens

<400> SEQUENCE: 998
uaaaaacugc aauuacuuuc a                                               21
```

<210> SEQ ID NO 999
<211> LENGTH: 23
<212> TYPE: RNA
<213> ORGANISM: Homo sapiens

<400> SEQUENCE: 999
ggaggcgcag gcucggaaag gcg                                           23

<210> SEQ ID NO 1000
<211> LENGTH: 22
<212> TYPE: RNA
<213> ORGANISM: Homo sapiens

<400> SEQUENCE: 1000
guggaguccu ggggaaugga ga                                            22

<210> SEQ ID NO 1001
<211> LENGTH: 23
<212> TYPE: RNA
<213> ORGANISM: Homo sapiens

<400> SEQUENCE: 1001
agggacugcc uuaggagaaa guu                                           23

<210> SEQ ID NO 1002
<211> LENGTH: 22
<212> TYPE: RNA
<213> ORGANISM: Homo sapiens

<400> SEQUENCE: 1002
caccuugcgc uacucagguc ug                                            22

<210> SEQ ID NO 1003
<211> LENGTH: 17
<212> TYPE: RNA
<213> ORGANISM: Homo sapiens

<400> SEQUENCE: 1003
gggauaugaa gaaaaau                                                  17

<210> SEQ ID NO 1004
<211> LENGTH: 22
<212> TYPE: RNA
<213> ORGANISM: Homo sapiens

<400> SEQUENCE: 1004
uucucaagag ggaggcaauc au                                            22

<210> SEQ ID NO 1005
<211> LENGTH: 21
<212> TYPE: RNA
<213> ORGANISM: Homo sapiens

<400> SEQUENCE: 1005
auugacaccu cugugagugg a                                             21

<210> SEQ ID NO 1006
<211> LENGTH: 22
<212> TYPE: RNA
<213> ORGANISM: Homo sapiens

<400> SEQUENCE: 1006
uggaagggag aagagcuuua au 22

<210> SEQ ID NO 1007
<211> LENGTH: 25
<212> TYPE: RNA
<213> ORGANISM: Homo sapiens

<400> SEQUENCE: 1007
gaacccauga gguugaggcu gcagu 25

<210> SEQ ID NO 1008
<211> LENGTH: 18
<212> TYPE: RNA
<213> ORGANISM: Homo sapiens

<400> SEQUENCE: 1008
cagugcaaug uuuuccuu 18

<210> SEQ ID NO 1009
<211> LENGTH: 17
<212> TYPE: RNA
<213> ORGANISM: Homo sapiens

<400> SEQUENCE: 1009
augugggcuc aggcuca 17

<210> SEQ ID NO 1010
<211> LENGTH: 16
<212> TYPE: RNA
<213> ORGANISM: Homo sapiens

<400> SEQUENCE: 1010
ugccuuccug ucugug 16

<210> SEQ ID NO 1011
<211> LENGTH: 25
<212> TYPE: RNA
<213> ORGANISM: Homo sapiens

<400> SEQUENCE: 1011
acuggacuug gagucagaag agugg 25

<210> SEQ ID NO 1012
<211> LENGTH: 17
<212> TYPE: RNA
<213> ORGANISM: Homo sapiens

<400> SEQUENCE: 1012
cagccugaca ggaacag 17

<210> SEQ ID NO 1013
<211> LENGTH: 17
<212> TYPE: RNA
<213> ORGANISM: Homo sapiens

<400> SEQUENCE: 1013
gggagucuac agcaggg 17

<210> SEQ ID NO 1014
<211> LENGTH: 20
<212> TYPE: RNA
<213> ORGANISM: Homo sapiens

<400> SEQUENCE: 1014

-continued

| | |
|---|---|
| ucccacuacu ucacuuguga | 20 |

<210> SEQ ID NO 1015
<211> LENGTH: 18
<212> TYPE: RNA
<213> ORGANISM: Homo sapiens

<400> SEQUENCE: 1015

| | |
|---|---|
| gcuggugaca ugagaggc | 18 |

<210> SEQ ID NO 1016
<211> LENGTH: 22
<212> TYPE: RNA
<213> ORGANISM: Homo sapiens

<400> SEQUENCE: 1016

| | |
|---|---|
| cugggacagg aggaggaggc ag | 22 |

<210> SEQ ID NO 1017
<211> LENGTH: 18
<212> TYPE: RNA
<213> ORGANISM: Homo sapiens

<400> SEQUENCE: 1017

| | |
|---|---|
| ugggagcugg acuacuuc | 18 |

<210> SEQ ID NO 1018
<211> LENGTH: 17
<212> TYPE: RNA
<213> ORGANISM: Homo sapiens

<400> SEQUENCE: 1018

| | |
|---|---|
| ccggcauguc cagggca | 17 |

<210> SEQ ID NO 1019
<211> LENGTH: 18
<212> TYPE: RNA
<213> ORGANISM: Homo sapiens

<400> SEQUENCE: 1019

| | |
|---|---|
| ccagugug gc ucagcgag | 18 |

<210> SEQ ID NO 1020
<211> LENGTH: 17
<212> TYPE: RNA
<213> ORGANISM: Homo sapiens

<400> SEQUENCE: 1020

| | |
|---|---|
| uucugagcug aggacag | 17 |

<210> SEQ ID NO 1021
<211> LENGTH: 18
<212> TYPE: RNA
<213> ORGANISM: Homo sapiens

<400> SEQUENCE: 1021

| | |
|---|---|
| ccuagacacc uccaguuc | 18 |

<210> SEQ ID NO 1022
<211> LENGTH: 17
<212> TYPE: RNA
<213> ORGANISM: Homo sapiens

```
<400> SEQUENCE: 1022
uggagagaaa ggcagua                                                  17

<210> SEQ ID NO 1023
<211> LENGTH: 18
<212> TYPE: RNA
<213> ORGANISM: Homo sapiens

<400> SEQUENCE: 1023
cuggagucua ggauucca                                                 18

<210> SEQ ID NO 1024
<211> LENGTH: 19
<212> TYPE: RNA
<213> ORGANISM: Homo sapiens

<400> SEQUENCE: 1024
aauguuuuuu ccuguuccc                                                19

<210> SEQ ID NO 1025
<211> LENGTH: 18
<212> TYPE: RNA
<213> ORGANISM: Homo sapiens

<400> SEQUENCE: 1025
ucccuggagu uucuucuu                                                 18

<210> SEQ ID NO 1026
<211> LENGTH: 16
<212> TYPE: RNA
<213> ORGANISM: Homo sapiens

<400> SEQUENCE: 1026
gcagcauuca uguccc                                                   16

<210> SEQ ID NO 1027
<211> LENGTH: 18
<212> TYPE: RNA
<213> ORGANISM: Homo sapiens

<400> SEQUENCE: 1027
gaaagagagc ugagugug                                                 18

<210> SEQ ID NO 1028
<211> LENGTH: 19
<212> TYPE: RNA
<213> ORGANISM: Homo sapiens

<400> SEQUENCE: 1028
ggccuuguuc cugucccca                                                19

<210> SEQ ID NO 1029
<211> LENGTH: 20
<212> TYPE: RNA
<213> ORGANISM: Homo sapiens

<400> SEQUENCE: 1029
agcccccugg ccccaaaccc                                               20

<210> SEQ ID NO 1030
<211> LENGTH: 18
<212> TYPE: RNA
<213> ORGANISM: Homo sapiens
```

```
<400> SEQUENCE: 1030
ccgcuuucug agcuggac                                              18

<210> SEQ ID NO 1031
<211> LENGTH: 17
<212> TYPE: RNA
<213> ORGANISM: Homo sapiens

<400> SEQUENCE: 1031
ggugaggcua gcuggug                                               17

<210> SEQ ID NO 1032
<211> LENGTH: 18
<212> TYPE: RNA
<213> ORGANISM: Homo sapiens

<400> SEQUENCE: 1032
cucugggaaa ugggacag                                              18

<210> SEQ ID NO 1033
<211> LENGTH: 17
<212> TYPE: RNA
<213> ORGANISM: Homo sapiens

<400> SEQUENCE: 1033
cacugugggu acaugcu                                               17

<210> SEQ ID NO 1034
<211> LENGTH: 17
<212> TYPE: RNA
<213> ORGANISM: Homo sapiens

<400> SEQUENCE: 1034
ucccugagca aagccac                                               17

<210> SEQ ID NO 1035
<211> LENGTH: 18
<212> TYPE: RNA
<213> ORGANISM: Homo sapiens

<400> SEQUENCE: 1035
gggauucugu agcuuccu                                              18

<210> SEQ ID NO 1036
<211> LENGTH: 17
<212> TYPE: RNA
<213> ORGANISM: Homo sapiens

<400> SEQUENCE: 1036
acauugccag ggaguuu                                               17

<210> SEQ ID NO 1037
<211> LENGTH: 21
<212> TYPE: RNA
<213> ORGANISM: Homo sapiens

<400> SEQUENCE: 1037
cugugggcuc agcgcguggg g                                          21

<210> SEQ ID NO 1038
<211> LENGTH: 21
<212> TYPE: RNA
```

```
<213> ORGANISM: Homo sapiens

<400> SEQUENCE: 1038
uuagcggugg accgcccugc g                                             21

<210> SEQ ID NO 1039
<211> LENGTH: 18
<212> TYPE: RNA
<213> ORGANISM: Homo sapiens

<400> SEQUENCE: 1039
cagccccaca gccucaga                                                 18

<210> SEQ ID NO 1040
<211> LENGTH: 20
<212> TYPE: RNA
<213> ORGANISM: Homo sapiens

<400> SEQUENCE: 1040
cccugagacc cuaaccuuaa                                               20

<210> SEQ ID NO 1041
<211> LENGTH: 18
<212> TYPE: RNA
<213> ORGANISM: Homo sapiens

<400> SEQUENCE: 1041
aucugaccug augaaggu                                                 18

<210> SEQ ID NO 1042
<211> LENGTH: 18
<212> TYPE: RNA
<213> ORGANISM: Homo sapiens

<400> SEQUENCE: 1042
ccagaggugg ggacugag                                                 18

<210> SEQ ID NO 1043
<211> LENGTH: 17
<212> TYPE: RNA
<213> ORGANISM: Homo sapiens

<400> SEQUENCE: 1043
ccccgccacc gccuugg                                                  17

<210> SEQ ID NO 1044
<211> LENGTH: 22
<212> TYPE: RNA
<213> ORGANISM: Homo sapiens

<400> SEQUENCE: 1044
caguuggguc uaggggucag ga                                            22

<210> SEQ ID NO 1045
<211> LENGTH: 19
<212> TYPE: RNA
<213> ORGANISM: Homo sapiens

<400> SEQUENCE: 1045
cuuggggcau ggaguccca                                                19

<210> SEQ ID NO 1046
<211> LENGTH: 18
```

```
<212> TYPE: RNA
<213> ORGANISM: Homo sapiens

<400> SEQUENCE: 1046
agggcauguc caggggu                                                  18

<210> SEQ ID NO 1047
<211> LENGTH: 17
<212> TYPE: RNA
<213> ORGANISM: Homo sapiens

<400> SEQUENCE: 1047
ccugagaaaa gggccaa                                                  17

<210> SEQ ID NO 1048
<211> LENGTH: 23
<212> TYPE: RNA
<213> ORGANISM: Homo sapiens

<400> SEQUENCE: 1048
gccuggagcu acuccaccau cuc                                           23

<210> SEQ ID NO 1049
<211> LENGTH: 17
<212> TYPE: RNA
<213> ORGANISM: Homo sapiens

<400> SEQUENCE: 1049
caguguucag agaugga                                                  17

<210> SEQ ID NO 1050
<211> LENGTH: 19
<212> TYPE: RNA
<213> ORGANISM: Homo sapiens

<400> SEQUENCE: 1050
ggccacugag ucagcacca                                                19

<210> SEQ ID NO 1051
<211> LENGTH: 18
<212> TYPE: RNA
<213> ORGANISM: Homo sapiens

<400> SEQUENCE: 1051
uugcacuugu cucaguga                                                 18

<210> SEQ ID NO 1052
<211> LENGTH: 20
<212> TYPE: RNA
<213> ORGANISM: Homo sapiens

<400> SEQUENCE: 1052
uguuccucug ucucccagac                                               20

<210> SEQ ID NO 1053
<211> LENGTH: 19
<212> TYPE: RNA
<213> ORGANISM: Homo sapiens

<400> SEQUENCE: 1053
ggcuugcaug ggggacugg                                                19

<210> SEQ ID NO 1054
```

```
<211> LENGTH: 16
<212> TYPE: RNA
<213> ORGANISM: Homo sapiens

<400> SEQUENCE: 1054
aggaaacagg gaccca                                                    16

<210> SEQ ID NO 1055
<211> LENGTH: 19
<212> TYPE: RNA
<213> ORGANISM: Homo sapiens

<400> SEQUENCE: 1055
cugugggcuc agcucuggg                                                 19

<210> SEQ ID NO 1056
<211> LENGTH: 16
<212> TYPE: RNA
<213> ORGANISM: Homo sapiens

<400> SEQUENCE: 1056
cuaggaggcc uuggcc                                                    16

<210> SEQ ID NO 1057
<211> LENGTH: 16
<212> TYPE: RNA
<213> ORGANISM: Homo sapiens

<400> SEQUENCE: 1057
uccagcucgg uggcac                                                    16

<210> SEQ ID NO 1058
<211> LENGTH: 17
<212> TYPE: RNA
<213> ORGANISM: Homo sapiens

<400> SEQUENCE: 1058
gacauucaga cuaccug                                                   17

<210> SEQ ID NO 1059
<211> LENGTH: 21
<212> TYPE: RNA
<213> ORGANISM: Homo sapiens

<400> SEQUENCE: 1059
auccccagau acaauggaca a                                              21

<210> SEQ ID NO 1060
<211> LENGTH: 21
<212> TYPE: RNA
<213> ORGANISM: Homo sapiens

<400> SEQUENCE: 1060
ggcuccuccu cucaggaugu g                                              21

<210> SEQ ID NO 1061
<211> LENGTH: 21
<212> TYPE: RNA
<213> ORGANISM: Homo sapiens

<400> SEQUENCE: 1061
gcaggcacag acagcccugg c                                              21
```

```
<210> SEQ ID NO 1062
<211> LENGTH: 18
<212> TYPE: RNA
<213> ORGANISM: Homo sapiens

<400> SEQUENCE: 1062
auucuaagug ccuuggcc                                                 18

<210> SEQ ID NO 1063
<211> LENGTH: 17
<212> TYPE: RNA
<213> ORGANISM: Homo sapiens

<400> SEQUENCE: 1063
acucagucau ggucauu                                                  17

<210> SEQ ID NO 1064
<211> LENGTH: 20
<212> TYPE: RNA
<213> ORGANISM: Homo sapiens

<400> SEQUENCE: 1064
ucagggaguc aggggagggc                                               20

<210> SEQ ID NO 1065
<211> LENGTH: 19
<212> TYPE: RNA
<213> ORGANISM: Homo sapiens

<400> SEQUENCE: 1065
gggggaagaa aaggugggg                                                19

<210> SEQ ID NO 1066
<211> LENGTH: 18
<212> TYPE: RNA
<213> ORGANISM: Homo sapiens

<400> SEQUENCE: 1066
cauucaacua gugauugu                                                 18

<210> SEQ ID NO 1067
<211> LENGTH: 18
<212> TYPE: RNA
<213> ORGANISM: Homo sapiens

<400> SEQUENCE: 1067
guguucucug auggacag                                                 18

<210> SEQ ID NO 1068
<211> LENGTH: 17
<212> TYPE: RNA
<213> ORGANISM: Homo sapiens

<400> SEQUENCE: 1068
cucagugacu caugugc                                                  17

<210> SEQ ID NO 1069
<211> LENGTH: 17
<212> TYPE: RNA
<213> ORGANISM: Homo sapiens

<400> SEQUENCE: 1069
ccaauuacca cuucuuu                                                  17
```

<210> SEQ ID NO 1070
<211> LENGTH: 18
<212> TYPE: RNA
<213> ORGANISM: Homo sapiens

<400> SEQUENCE: 1070
cagcaguccc uccccug                                                  18

<210> SEQ ID NO 1071
<211> LENGTH: 18
<212> TYPE: RNA
<213> ORGANISM: Homo sapiens

<400> SEQUENCE: 1071
gggucccggg gagggggg                                                 18

<210> SEQ ID NO 1072
<211> LENGTH: 21
<212> TYPE: RNA
<213> ORGANISM: Homo sapiens

<400> SEQUENCE: 1072
gcaguucuga gcacaguaca c                                             21

<210> SEQ ID NO 1073
<211> LENGTH: 16
<212> TYPE: RNA
<213> ORGANISM: Homo sapiens

<400> SEQUENCE: 1073
cucuccuccc ggcuuc                                                   16

<210> SEQ ID NO 1074
<211> LENGTH: 18
<212> TYPE: RNA
<213> ORGANISM: Homo sapiens

<400> SEQUENCE: 1074
cuaggggguu ugcccuug                                                 18

<210> SEQ ID NO 1075
<211> LENGTH: 21
<212> TYPE: RNA
<213> ORGANISM: Homo sapiens

<400> SEQUENCE: 1075
gaguguaguu cugagcagag c                                             21

<210> SEQ ID NO 1076
<211> LENGTH: 18
<212> TYPE: RNA
<213> ORGANISM: Homo sapiens

<400> SEQUENCE: 1076
uaaaauuugc auccagga                                                 18

<210> SEQ ID NO 1077
<211> LENGTH: 18
<212> TYPE: RNA
<213> ORGANISM: Homo sapiens

<400> SEQUENCE: 1077
gcggcgaguc cgacucau                                                 18

<210> SEQ ID NO 1078
<211> LENGTH: 17
<212> TYPE: RNA
<213> ORGANISM: Homo sapiens

<400> SEQUENCE: 1078
uggggcucag cgaguuu                                                  17

<210> SEQ ID NO 1079
<211> LENGTH: 18
<212> TYPE: RNA
<213> ORGANISM: Homo sapiens

<400> SEQUENCE: 1079
gggcucacau caccccau                                                 18

<210> SEQ ID NO 1080
<211> LENGTH: 17
<212> TYPE: RNA
<213> ORGANISM: Homo sapiens

<400> SEQUENCE: 1080
accccacucc ugguacc                                                  17

<210> SEQ ID NO 1081
<211> LENGTH: 19
<212> TYPE: RNA
<213> ORGANISM: Homo sapiens

<400> SEQUENCE: 1081
ucucccuuga gggcacuuu                                                19

<210> SEQ ID NO 1082
<211> LENGTH: 17
<212> TYPE: RNA
<213> ORGANISM: Homo sapiens

<400> SEQUENCE: 1082
uugucugcug aguuucc                                                  17

<210> SEQ ID NO 1083
<211> LENGTH: 18
<212> TYPE: RNA
<213> ORGANISM: Homo sapiens

<400> SEQUENCE: 1083
ccccugggcc ggccuugg                                                 18

<210> SEQ ID NO 1084
<211> LENGTH: 19
<212> TYPE: RNA
<213> ORGANISM: Homo sapiens

<400> SEQUENCE: 1084
gcauugugca gggcuauca                                                19

<210> SEQ ID NO 1085
<211> LENGTH: 19
<212> TYPE: RNA
<213> ORGANISM: Homo sapiens

<400> SEQUENCE: 1085
ugcccuccuu ucuucccuc                                                19

<210> SEQ ID NO 1086
<211> LENGTH: 16
<212> TYPE: RNA
<213> ORGANISM: Homo sapiens

<400> SEQUENCE: 1086
uucagcagga acagcu                                                   16

<210> SEQ ID NO 1087
<211> LENGTH: 19
<212> TYPE: RNA
<213> ORGANISM: Homo sapiens

<400> SEQUENCE: 1087
ccugagaccc uaguuccac                                                19

<210> SEQ ID NO 1088
<211> LENGTH: 19
<212> TYPE: RNA
<213> ORGANISM: Homo sapiens

<400> SEQUENCE: 1088
ccucagauca gagccuugc                                                19

<210> SEQ ID NO 1089
<211> LENGTH: 18
<212> TYPE: RNA
<213> ORGANISM: Homo sapiens

<400> SEQUENCE: 1089
aauccuugcu accugggu                                                 18

<210> SEQ ID NO 1090
<211> LENGTH: 17
<212> TYPE: RNA
<213> ORGANISM: Homo sapiens

<400> SEQUENCE: 1090
ccaguuuucc caggauu                                                  17

<210> SEQ ID NO 1091
<211> LENGTH: 22
<212> TYPE: RNA
<213> ORGANISM: Artificial Sequence
<220> FEATURE:
<223> OTHER INFORMATION: Synthetic

<400> SEQUENCE: 1091
uuaaggcacg cggugaaugc ca                                            22

<210> SEQ ID NO 1092
<211> LENGTH: 22
<212> TYPE: RNA
<213> ORGANISM: Artificial Sequence
<220> FEATURE:
<223> OTHER INFORMATION: Synthetic

<400> SEQUENCE: 1092
gcauucaccg cgugccuua aau                                            22

<210> SEQ ID NO 1093
<211> LENGTH: 10

<212> TYPE: RNA
<213> ORGANISM: Artificial Sequence
<220> FEATURE:
<223> OTHER INFORMATION: Synthetic

<400> SEQUENCE: 1093
uuaaggcacg                                                          10

<210> SEQ ID NO 1094
<211> LENGTH: 12
<212> TYPE: RNA
<213> ORGANISM: Artificial Sequence
<220> FEATURE:
<223> OTHER INFORMATION: Synthetic

<400> SEQUENCE: 1094
cggugaaugc ca                                                       12

<210> SEQ ID NO 1095
<211> LENGTH: 11
<212> TYPE: RNA
<213> ORGANISM: Artificial Sequence
<220> FEATURE:
<223> OTHER INFORMATION: Synthetic

<400> SEQUENCE: 1095
ggugaaugcc a                                                        11

<210> SEQ ID NO 1096
<211> LENGTH: 10
<212> TYPE: RNA
<213> ORGANISM: Artificial Sequence
<220> FEATURE:
<223> OTHER INFORMATION: Synthetic

<400> SEQUENCE: 1096
gcauucaccg                                                          10

<210> SEQ ID NO 1097
<211> LENGTH: 12
<212> TYPE: RNA
<213> ORGANISM: Artificial Sequence
<220> FEATURE:
<223> OTHER INFORMATION: Synthetic

<400> SEQUENCE: 1097
cgugccuuaa au                                                       12

<210> SEQ ID NO 1098
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 10
<223> OTHER INFORMATION: inverted abasic at 3' end

<400> SEQUENCE: 1098
uuaaggcacg                                                          10

<210> SEQ ID NO 1099
<211> LENGTH: 10
<212> TYPE: RNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: 10
<223> OTHER INFORMATION: Cy3 fluorescent dye molecule at 3' end

<400> SEQUENCE: 1099
uuaaggcacg                                                              10

<210> SEQ ID NO 1100
<211> LENGTH: 58
<212> TYPE: RNA
<213> ORGANISM: Artificial Sequence
<220> FEATURE:
<223> OTHER INFORMATION: Synthetic

<400> SEQUENCE: 1100
gcguucaccg cggaccuuga uuuaaauguc cauacaauua aggcacgcgg ugaaugcc       58

<210> SEQ ID NO 1101
<211> LENGTH: 58
<212> TYPE: RNA
<213> ORGANISM: Artificial Sequence
<220> FEATURE:
<223> OTHER INFORMATION: Synthetic

<400> SEQUENCE: 1101
gcguucaccg cggaccuuga uuuaaauguc cauacaauua aggcacgcgg ugaaugcc       58

<210> SEQ ID NO 1102
<211> LENGTH: 10
<212> TYPE: RNA
<213> ORGANISM: Artificial Sequence
<220> FEATURE:
<223> OTHER INFORMATION: Synthetic

<400> SEQUENCE: 1102
ggugaaugcc                                                              10

<210> SEQ ID NO 1103
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: Locked nucleic acid

<400> SEQUENCE: 1103
uuaaggcacg                                                              10

<210> SEQ ID NO 1104
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: Locked nucleic acid

<400> SEQUENCE: 1104 cggugaaugcca                                                            12
```

-continued

```
<210> SEQ ID NO 1105
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 2
<223> OTHER INFORMATION: Locked nucleic acid

<400> SEQUENCE: 1105 gcauucaccgcg                                                              12

<210> SEQ ID NO 1106
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3
<223> OTHER INFORMATION: Locked nucleic acid

<400> SEQUENCE: 1106
ugccuuaaau                                                                10

<210> SEQ ID NO 1107
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 2
<223> OTHER INFORMATION: Locked nucleic acid

<400> SEQUENCE: 1107
gcauucaccg                                                                10

<210> SEQ ID NO 1108
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: Locked nucleic acid

<400> SEQUENCE: 1108
cgugccuuaa au                                                             12

<210> SEQ ID NO 1109
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 2
<223> OTHER INFORMATION: Locked nucleic acid

<400> SEQUENCE: 1109
ugccuuaaau                                                                10
```

```
<210> SEQ ID NO 1110
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 4
<223> OTHER INFORMATION: Locked nucleic acid

<400> SEQUENCE: 1110
ggugaaugcc a                                                              11

<210> SEQ ID NO 1111
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: Locked nucleic acid

<400> SEQUENCE: 1111
uuaaggcacg c                                                              11

<210> SEQ ID NO 1112
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 3
<223> OTHER INFORMATION: Locked nucleic acid

<400> SEQUENCE: 1112
gugaaugcca                                                                10

<210> SEQ ID NO 1113
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: Locked nucleic acid

<400> SEQUENCE: 1113
uuaaggcacg cg                                                             12

<210> SEQ ID NO 1114
<211> LENGTH: 13
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 5
<223> OTHER INFORMATION: Locked nucleic acid

<400> SEQUENCE: 1114
uuaaggcacg cgg                                                            13
```

<210> SEQ ID NO 1115
<211> LENGTH: 20
<212> TYPE: RNA
<213> ORGANISM: Artificial Sequence
<220> FEATURE:
<223> OTHER INFORMATION: Synthetic

<400> SEQUENCE: 1115
uuaaggcacg cggugaaugc                                              20

<210> SEQ ID NO 1116
<211> LENGTH: 18
<212> TYPE: RNA
<213> ORGANISM: Artificial Sequence
<220> FEATURE:
<223> OTHER INFORMATION: Synthetic

<400> SEQUENCE: 1116
uuaaggcacg cggugaau                                                18

<210> SEQ ID NO 1117
<211> LENGTH: 11
<212> TYPE: RNA
<213> ORGANISM: Artificial Sequence
<220> FEATURE:
<223> OTHER INFORMATION: Synthetic

<400> SEQUENCE: 1117
uuaaggcacg c                                                       11

<210> SEQ ID NO 1118
<211> LENGTH: 11
<212> TYPE: RNA
<213> ORGANISM: Artificial Sequence
<220> FEATURE:
<223> OTHER INFORMATION: Synthetic

<400> SEQUENCE: 1118
ggugaaugcc a                                                       11

<210> SEQ ID NO 1119
<211> LENGTH: 10
<212> TYPE: RNA
<213> ORGANISM: Artificial Sequence
<220> FEATURE:
<223> OTHER INFORMATION: Synthetic

<400> SEQUENCE: 1119
gcaucuaccg                                                         10

<210> SEQ ID NO 1120
<211> LENGTH: 12
<212> TYPE: RNA
<213> ORGANISM: Artificial Sequence
<220> FEATURE:
<223> OTHER INFORMATION: Synthetic

<400> SEQUENCE: 1120
cgguagaugc ca                                                      12

<210> SEQ ID NO 1121
<211> LENGTH: 12
<212> TYPE: RNA
<213> ORGANISM: Artificial Sequence
<220> FEATURE:

<223> OTHER INFORMATION: Synthetic

<400> SEQUENCE: 1121
cgucgcuuaa au                                                            12

<210> SEQ ID NO 1122
<211> LENGTH: 10
<212> TYPE: RNA
<213> ORGANISM: Artificial Sequence
<220> FEATURE:
<223> OTHER INFORMATION: Synthetic

<400> SEQUENCE: 1122
uuaagcgacg                                                               10

<210> SEQ ID NO 1123
<211> LENGTH: 12
<212> TYPE: RNA
<213> ORGANISM: Artificial Sequence
<220> FEATURE:
<223> OTHER INFORMATION: Synthetic

<400> SEQUENCE: 1123
cgugccuaua au                                                            12

<210> SEQ ID NO 1124
<211> LENGTH: 11
<212> TYPE: RNA
<213> ORGANISM: Artificial Sequence
<220> FEATURE:
<223> OTHER INFORMATION: Synthetic

<400> SEQUENCE: 1124
uauaggcacg c                                                             11

<210> SEQ ID NO 1125
<211> LENGTH: 10
<212> TYPE: RNA
<213> ORGANISM: Artificial Sequence
<220> FEATURE:
<223> OTHER INFORMATION: Synthetic

<400> SEQUENCE: 1125
gugaaugcca                                                               10

<210> SEQ ID NO 1126
<211> LENGTH: 22
<212> TYPE: RNA
<213> ORGANISM: Artificial Sequence
<220> FEATURE:
<223> OTHER INFORMATION: Synthetic

<400> SEQUENCE: 1126
gcauucaccg cgucgcuuaa au                                                 22

<210> SEQ ID NO 1127
<211> LENGTH: 12
<212> TYPE: RNA
<213> ORGANISM: Artificial Sequence
<220> FEATURE:
<223> OTHER INFORMATION: Synthetic

<400> SEQUENCE: 1127
uuaagcgacg cg                                                            12

```
<210> SEQ ID NO 1128
<211> LENGTH: 12
<212> TYPE: RNA
<213> ORGANISM: Artificial Sequence
<220> FEATURE:
<223> OTHER INFORMATION: Synthetic

<400> SEQUENCE: 1128
uauaggcacg cg                                                          12

<210> SEQ ID NO 1129
<211> LENGTH: 10
<212> TYPE: RNA
<213> ORGANISM: Artificial Sequence
<220> FEATURE:
<223> OTHER INFORMATION: Synthetic

<400> SEQUENCE: 1129
uggcaguguc                                                             10

<210> SEQ ID NO 1130
<211> LENGTH: 12
<212> TYPE: RNA
<213> ORGANISM: Artificial Sequence
<220> FEATURE:
<223> OTHER INFORMATION: Synthetic

<400> SEQUENCE: 1130
uuagcucgug gu                                                          12

<210> SEQ ID NO 1131
<211> LENGTH: 11
<212> TYPE: RNA
<213> ORGANISM: Artificial Sequence
<220> FEATURE:
<223> OTHER INFORMATION: Synthetic

<400> SEQUENCE: 1131
uggcaguguc u                                                           11

<210> SEQ ID NO 1132
<211> LENGTH: 11
<212> TYPE: RNA
<213> ORGANISM: Artificial Sequence
<220> FEATURE:
<223> OTHER INFORMATION: Synthetic

<400> SEQUENCE: 1132
uagcucgugg u                                                           11

<210> SEQ ID NO 1133
<211> LENGTH: 15
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1
<223> OTHER INFORMATION: Inverted abasic at 5' end

<400> SEQUENCE: 1133
acgcggugaa ugcca                                                       15

<210> SEQ ID NO 1134
<211> LENGTH: 14
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: 1
<223> OTHER INFORMATION: Inverted abasic at 5' end

<400> SEQUENCE: 1134
cgcggugaau gcca                                                      14

<210> SEQ ID NO 1135
<211> LENGTH: 13
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1
<223> OTHER INFORMATION: Inverted abasic at 5' end

<400> SEQUENCE: 1135
gcggugaaug cca                                                       13

<210> SEQ ID NO 1136
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 10
<223> OTHER INFORMATION: Inverted abasic at 3' end

<400> SEQUENCE: 1136
uuaaggcacg                                                           10

<210> SEQ ID NO 1137
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1
<223> OTHER INFORMATION: Inverted abasic at 5' end

<400> SEQUENCE: 1137
cggugaaugc ca                                                        12

<210> SEQ ID NO 1138
<211> LENGTH: 11
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 10
<223> OTHER INFORMATION: Inverted abasic at 3' end

<400> SEQUENCE: 1138
uuaaggcacg c                                                         11

<210> SEQ ID NO 1139
<211> LENGTH: 11
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1
<223> OTHER INFORMATION: Inverted abasic at 5' end

<400> SEQUENCE: 1139
ggugaaugcc a                                                            11

<210> SEQ ID NO 1140
<211> LENGTH: 12
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 10
<223> OTHER INFORMATION: Inverted abasic at 3' end

<400> SEQUENCE: 1140
uuaaggcacg cg                                                           12

<210> SEQ ID NO 1141
<211> LENGTH: 10
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 1
<223> OTHER INFORMATION: Inverted abasic at 5' end

<400> SEQUENCE: 1141
gugaaugcca                                                              10

<210> SEQ ID NO 1142
<211> LENGTH: 13
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 10
<223> OTHER INFORMATION: Inverted abasic at 3' end

<400> SEQUENCE: 1142
uuaaggcacg cgg                                                          13

<210> SEQ ID NO 1143
<211> LENGTH: 15
<212> TYPE: RNA
<213> ORGANISM: Artificial Sequence
<220> FEATURE:
<223> OTHER INFORMATION: Synthetic

<400> SEQUENCE: 1143
acgcggugaa ugcca                                                        15

<210> SEQ ID NO 1144
<211> LENGTH: 14
<212> TYPE: RNA
<213> ORGANISM: Artificial Sequence
<220> FEATURE:
```

<223> OTHER INFORMATION: Synthetic

<400> SEQUENCE: 1144
cgcggugaau gcca                                                            14

<210> SEQ ID NO 1145
<211> LENGTH: 13
<212> TYPE: RNA
<213> ORGANISM: Artificial Sequence
<220> FEATURE:
<223> OTHER INFORMATION: Synthetic

<400> SEQUENCE: 1145
gcggugaaug cca                                                             13

<210> SEQ ID NO 1146
<211> LENGTH: 12
<212> TYPE: RNA
<213> ORGANISM: Artificial Sequence
<220> FEATURE:
<223> OTHER INFORMATION: Synthetic

<400> SEQUENCE: 1146
uuaaggcacg cg                                                              12

<210> SEQ ID NO 1147
<211> LENGTH: 13
<212> TYPE: RNA
<213> ORGANISM: Artificial Sequence
<220> FEATURE:
<223> OTHER INFORMATION: Synthetic

<400> SEQUENCE: 1147
uuaaggcacg cgg                                                             13

<210> SEQ ID NO 1148
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by two abasic groups

<400> SEQUENCE: 1148
gcauucaccg ugccuuaaau                                                      20

<210> SEQ ID NO 1149
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by two abasic groups

<400> SEQUENCE: 1149
uuaaggcacg gugaaugcca                                                      20

<210> SEQ ID NO 1150
<211> LENGTH: 19
<212> TYPE: RNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by three abasic groups

<400> SEQUENCE: 1150
gcauucacgu gccuuaaau                                                   19

<210> SEQ ID NO 1151
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by three abasic groups

<400> SEQUENCE: 1151
uuaaggcacg ugaaugcca                                                   19

<210> SEQ ID NO 1152
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by four abasic groups

<400> SEQUENCE: 1152 gcauccgug ccuuaaau                                                     18

<210> SEQ ID NO 1153
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by four abasic groups

<400> SEQUENCE: 1153
uuaaggcacu gaaugcca                                                    18

<210> SEQ ID NO 1154
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by five abasic groups

<400> SEQUENCE: 1154
gcauucgugc cuuaaau                                                     17

<210> SEQ ID NO 1155
<211> LENGTH: 17
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by five abasic groups

<400> SEQUENCE: 1155
uuaaggcacg aaugcca                                                17

<210> SEQ ID NO 1156
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by two abasic groups

<400> SEQUENCE: 1156
uuaaggcacg gugaaugcca                                             20

<210> SEQ ID NO 1157
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by three abasic groups

<400> SEQUENCE: 1157
gcauucgcgu gccuuaaau                                              19

<210> SEQ ID NO 1158
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by three abasic groups

<400> SEQUENCE: 1158
uuaaggcacg ugaaugcca                                              19

<210> SEQ ID NO 1159
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by four abasic groups

<400> SEQUENCE: 1159
gcauugcgug ccuuaaau                                               18

<210> SEQ ID NO 1160
<211> LENGTH: 18
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by four abasic groups

<400> SEQUENCE: 1160
uuaaggcacg gaaugcca                                                   18

<210> SEQ ID NO 1161
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by five abasic groups

<400> SEQUENCE: 1161
gcaugcgugc cuuaaau                                                    17

<210> SEQ ID NO 1162
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by five abasic groups

<400> SEQUENCE: 1162
uuaaggcacg aaugcca                                                    17

<210> SEQ ID NO 1163
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by two abasic groups

<400> SEQUENCE: 1163
uuaaggcacg gugaaugcca                                                 20

<210> SEQ ID NO 1164
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by three abasic groups

<400> SEQUENCE: 1164
uuaaggcagg ugaaugcca                                                  19

<210> SEQ ID NO 1165
```

```
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by four abasic groups

<400> SEQUENCE: 1165
uuaaggcagu gaaugcca                                                       18

<210> SEQ ID NO 1166
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by an abasic group

<400> SEQUENCE: 1166
gcauucaccc gugccuuaaa u                                                   21

<210> SEQ ID NO 1167
<211> LENGTH: 16
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by six abasic groups

<400> SEQUENCE: 1167
gcaucgugcc uuaaau                                                         16

<210> SEQ ID NO 1168
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by an abasic group

<400> SEQUENCE: 1168
gcauucacgc gugccuuaaa u                                                   21

<210> SEQ ID NO 1169
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by two abasic groups

<400> SEQUENCE: 1169
gcauucagcg ugccuuaaau                                                     20
```

```
<210> SEQ ID NO 1170
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by three abasic groups

<400> SEQUENCE: 1170
gcauucgcgu gccuuaaau                                                   19

<210> SEQ ID NO 1171
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by four abasic groups

<400> SEQUENCE: 1171
gcauugcgug ccuuaaau                                                    18

<210> SEQ ID NO 1172
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by five abasic groups

<400> SEQUENCE: 1172
gcaugcgugc cuuaaau                                                     17

<210> SEQ ID NO 1173
<211> LENGTH: 16
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)...(4)
<223> OTHER INFORMATION: bases linked by six abasic groups

<400> SEQUENCE: 1173
gcagcgugcc uuaaau                                                      16

<210> SEQ ID NO 1174
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by two abasic groups

<400> SEQUENCE: 1174
uuaaggcacg cugaaugcca                                                  20
```

<210> SEQ ID NO 1175
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by three abasic groups

<400> SEQUENCE: 1175
uuaaggcacg cgaaugcca                                            19

<210> SEQ ID NO 1176
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by four abasic groups

<400> SEQUENCE: 1176
uuaaggcacg caaugcca                                             18

<210> SEQ ID NO 1177
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by five abasic groups

<400> SEQUENCE: 1177
uuaaggcacg caugcca                                              17

<210> SEQ ID NO 1178
<211> LENGTH: 11
<212> TYPE: RNA
<213> ORGANISM: Artificial Sequence
<220> FEATURE:
<223> OTHER INFORMATION: Synthetic

<400> SEQUENCE: 1178
gugccuuaaa u                                                    11

<210> SEQ ID NO 1179
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by C3 group

<400> SEQUENCE: 1179
gcauucaccg ugccuuaaau                                           20

<210> SEQ ID NO 1180
<211> LENGTH: 20

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C3 group

<400> SEQUENCE: 1180
uuaaggcacg gugaaugcca                                                   20

<210> SEQ ID NO 1181
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by C3 group

<400> SEQUENCE: 1181
gcauucacgu gccuuaaau                                                    19

<210> SEQ ID NO 1182
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C3 group

<400> SEQUENCE: 1182
uuaaggcacg ugaaugcca                                                    19

<210> SEQ ID NO 1183
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C3 group

<400> SEQUENCE: 1183 gcauccgug ccuuaaau                                                      18

<210> SEQ ID NO 1184
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C3 group

<400> SEQUENCE: 1184
uuaaggcacg gaaugcca                                                     18

<210> SEQ ID NO 1185
```

```
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C3 group

<400> SEQUENCE: 1185
gcauucgugc cuuaaau                                               17

<210> SEQ ID NO 1186
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C3 group

<400> SEQUENCE: 1186
uuaaggcacg aaugcca                                               17

<210> SEQ ID NO 1187
<211> LENGTH: 16
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C3 group

<400> SEQUENCE: 1187
gcauucugcc uuaaau                                                16

<210> SEQ ID NO 1188
<211> LENGTH: 16
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by C3 group

<400> SEQUENCE: 1188
uuaaggcaga augcca                                                16

<210> SEQ ID NO 1189
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C6 group

<400> SEQUENCE: 1189
uuaaggcacg gugaaugcca                                            20
```

```
<210> SEQ ID NO 1190
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C6 group

<400> SEQUENCE: 1190
uuaaggcacg ugaaugcca                                                19

<210> SEQ ID NO 1191
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C6 group

<400> SEQUENCE: 1191
uuaaggcacg gaaugcca                                                 18

<210> SEQ ID NO 1192
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C6 group

<400> SEQUENCE: 1192
uuaaggcacg aaugcca                                                  17

<210> SEQ ID NO 1193
<211> LENGTH: 16
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by C6 group

<400> SEQUENCE: 1193
uuaaggcaga augcca                                                   16

<210> SEQ ID NO 1194
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: 21
<223> OTHER INFORMATION: C6 group on 3' end

<400> SEQUENCE: 1194
gcauucaccg cgugccuuaa a                                             21
```

```
<210> SEQ ID NO 1195
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)...(21)
<223> OTHER INFORMATION: bases linked by C3 group

<400> SEQUENCE: 1195
gcauucaccg cgugccuuaa u                                              21

<210> SEQ ID NO 1196
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)...(20)
<223> OTHER INFORMATION: bases linked by C3 group

<400> SEQUENCE: 1196
gcauucaccg cgugccuuaa u                                              21

<210> SEQ ID NO 1197
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)...(19)
<223> OTHER INFORMATION: bases linked by C3 group

<400> SEQUENCE: 1197
gcauucaccg cgugccuuaa u                                              21

<210> SEQ ID NO 1198
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)...(18)
<223> OTHER INFORMATION: bases linked by C3 group

<400> SEQUENCE: 1198
gcauucaccg cgugccuaaa u                                              21

<210> SEQ ID NO 1199
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)...(17)
<223> OTHER INFORMATION: bases linked by C3 group

<400> SEQUENCE: 1199
gcauucaccg cgugccuaaa u                                              21
```

<210> SEQ ID NO 1200
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)...(16)
<223> OTHER INFORMATION: bases linked by C3 group

<400> SEQUENCE: 1200
gcauucaccg cgugcuuaaa u                                              21

<210> SEQ ID NO 1201
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)...(15)
<223> OTHER INFORMATION: bases linked by C3 group

<400> SEQUENCE: 1201
gcauucaccg cgugcuuaaa u                                              21

<210> SEQ ID NO 1202
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)...(14)
<223> OTHER INFORMATION: bases linked by C3 group

<400> SEQUENCE: 1202
gcauucaccg cguccuuaaa u                                              21

<210> SEQ ID NO 1203
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)...(13)
<223> OTHER INFORMATION: bases linked by C3 group

<400> SEQUENCE: 1203
gcauucaccg cggccuuaaa u                                              21

<210> SEQ ID NO 1204
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by C3 group

<400> SEQUENCE: 1204
gcauucaccg cugccuuaaa u    21

<210> SEQ ID NO 1205
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C3 group

<400> SEQUENCE: 1205
gcauucaccg gugccuuaaa u    21

<210> SEQ ID NO 1206
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C3 group

<400> SEQUENCE: 1206
gcauucaccc gugccuuaaa u    21

<210> SEQ ID NO 1207
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by C3 group

<400> SEQUENCE: 1207
gcauucacgc gugccuuaaa u    21

<210> SEQ ID NO 1208
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by C3 group

<400> SEQUENCE: 1208
gcauucacgc gugccuuaaa u    21

<210> SEQ ID NO 1209
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C3 group

<400> SEQUENCE: 1209
gcauucccgc gugccuuaaa u					21

<210> SEQ ID NO 1210
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by C3 group

<400> SEQUENCE: 1210
gcauuaccgc gugccuuaaa u					21

<210> SEQ ID NO 1211
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by C3 group

<400> SEQUENCE: 1211
gcaucaccgc gugccuuaaa u					21

<210> SEQ ID NO 1212
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)...(4)
<223> OTHER INFORMATION: bases linked by C3 group

<400> SEQUENCE: 1212
gcaucaccgc gugccuuaaa u					21

<210> SEQ ID NO 1213
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)...(3)
<223> OTHER INFORMATION: bases linked by C3 group

<400> SEQUENCE: 1213
gcuucaccgc gugccuuaaa u					21

<210> SEQ ID NO 1214
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: bases linked by C3 group -continued

<400> SEQUENCE: 1214
gauucaccgc gugccuuaaa u					21

<210> SEQ ID NO 1215
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(1)
<223> OTHER INFORMATION: C3 group at 5' end

<400> SEQUENCE: 1215
cauucaccgc gugccuuaaa u					21

<210> SEQ ID NO 1216
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(1)
<223> OTHER INFORMATION: C3 group at 5' end

<400> SEQUENCE: 1216
uaaggcacgc ggugaaugcc a					21

<210> SEQ ID NO 1217
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: bases linked by C3 group

<400> SEQUENCE: 1217
uaaggcacgc ggugaaugcc a					21

<210> SEQ ID NO 1218
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)...(3)
<223> OTHER INFORMATION: bases linked by C3 group

<400> SEQUENCE: 1218
uuaaggcacg cggugaaugc ca					22

<210> SEQ ID NO 1219
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)...(4)
<223> OTHER INFORMATION: bases linked by C3 group

<400> SEQUENCE: 1219
uuaggcacgc ggugaaugcc a                                              21

<210> SEQ ID NO 1220
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by C3 group

<400> SEQUENCE: 1220
uuaagcacgc ggugaaugcc a                                              21

<210> SEQ ID NO 1221
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by C3 group

<400> SEQUENCE: 1221
uuaagcacgc ggugaaugcc a                                              21

<210> SEQ ID NO 1222
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C3 group

<400> SEQUENCE: 1222
uuaaggacgc ggugaaugcc a                                              21

<210> SEQ ID NO 1223
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by C3 group

<400> SEQUENCE: 1223
uuaaggccgc ggugaaugcc a                                              21

<210> SEQ ID NO 1224
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)

<223> OTHER INFORMATION: bases linked by C3 group

<400> SEQUENCE: 1224
uuaaggcagc ggugaaugcc a                                                    21

<210> SEQ ID NO 1225
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C3 group

<400> SEQUENCE: 1225
uuaaggcacc ggugaaugcc a                                                    21

<210> SEQ ID NO 1226
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C3 group

<400> SEQUENCE: 1226
uuaaggcacg ggugaaugcc a                                                    21

<210> SEQ ID NO 1227
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by C3 group

<400> SEQUENCE: 1227
uuaaggcacg cgugaaugcc a                                                    21

<210> SEQ ID NO 1228
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)...(13)
<223> OTHER INFORMATION: bases linked by C3 group

<400> SEQUENCE: 1228
uuaaggcacg cgugaaugcc a                                                    21

<210> SEQ ID NO 1229
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)...(14)
<223> OTHER INFORMATION: bases linked by C3 group

<400> SEQUENCE: 1229
uuaaggcacg cgggaaugcc a                                              21

<210> SEQ ID NO 1230
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)...(15)
<223> OTHER INFORMATION: bases linked by C3 group

<400> SEQUENCE: 1230
uuaaggcacg cgguaaugcc a                                              21

<210> SEQ ID NO 1231
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)...(16)
<223> OTHER INFORMATION: bases linked by C3 group

<400> SEQUENCE: 1231
uuaaggcacg cggugaugcc a                                              21

<210> SEQ ID NO 1232
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)...(17)
<223> OTHER INFORMATION: bases linked by C3 group

<400> SEQUENCE: 1232
uuaaggcacg cggugaugcc a                                              21

<210> SEQ ID NO 1233
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)...(18)
<223> OTHER INFORMATION: bases linked by C3 group

<400> SEQUENCE: 1233
uuaaggcacg cggugaagcc a                                              21

<210> SEQ ID NO 1234
<211> LENGTH: 21
<212> TYPE: RNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (18)...(19)
<223> OTHER INFORMATION: bases linked by C3 group

<400> SEQUENCE: 1234
uuaaggcacg cggugaaucc a                                              21

<210> SEQ ID NO 1235
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)...(20)
<223> OTHER INFORMATION: bases linked by C3 group

<400> SEQUENCE: 1235
uuaaggcacg cggugaaugc a                                              21

<210> SEQ ID NO 1236
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)...(21)
<223> OTHER INFORMATION: bases linked by C3 group

<400> SEQUENCE: 1236
uuaaggcacg cggugaaugc a                                              21

<210> SEQ ID NO 1237
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)...(21)
<223> OTHER INFORMATION: C6 group at 3' end

<400> SEQUENCE: 1237
gcauucaccg cgugccuuaa a                                              21

<210> SEQ ID NO 1238
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)...(21)
<223> OTHER INFORMATION: bases linked by C6 group

<400> SEQUENCE: 1238
gcauucaccg cgugccuuaa u                                              21

<210> SEQ ID NO 1239
<211> LENGTH: 21
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (19)...(20)
<223> OTHER INFORMATION: bases linked by C6 group

<400> SEQUENCE: 1239
gcauucaccg cgugccuuaa u                                              21

<210> SEQ ID NO 1240
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)...(19)
<223> OTHER INFORMATION: bases linked by C6 group

<400> SEQUENCE: 1240
gcauucaccg cgugccuuaa u                                              21

<210> SEQ ID NO 1241
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)...(18)
<223> OTHER INFORMATION: bases linked by C6 group

<400> SEQUENCE: 1241
gcauucaccg cgugccuaaa u                                              21

<210> SEQ ID NO 1242
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)...(17)
<223> OTHER INFORMATION: bases linked by C6 group

<400> SEQUENCE: 1242
gcauucaccg cgugccuaaa u                                              21

<210> SEQ ID NO 1243
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)...(16)
<223> OTHER INFORMATION: bases linked by C6 group

<400> SEQUENCE: 1243
gcauucaccg cgugcuuaaa u                                              21

<210> SEQ ID NO 1244
<211> LENGTH: 21
<212> TYPE: RNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (14)...(15)
<223> OTHER INFORMATION: bases linked by C6 group

<400> SEQUENCE: 1244
gcauucaccg cgugcuuaaa u                                              21

<210> SEQ ID NO 1245
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)...(14)
<223> OTHER INFORMATION: bases linked by C6 group

<400> SEQUENCE: 1245
gcauucaccg cguccuuaaa u                                              21

<210> SEQ ID NO 1246
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)...(13)
<223> OTHER INFORMATION: bases linked by C6 group

<400> SEQUENCE: 1246
gcauucaccg cggccuuaaa u                                              21

<210> SEQ ID NO 1247
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by C6 group

<400> SEQUENCE: 1247
gcauucaccg cugccuuaaa u                                              21

<210> SEQ ID NO 1248
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C6 group

<400> SEQUENCE: 1248
gcauucaccg gugccuuaaa u                                              21

<210> SEQ ID NO 1249
<211> LENGTH: 21
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C6 group

<400> SEQUENCE: 1249
gcauucaccc gugccuuaaa u                                                    21

<210> SEQ ID NO 1250
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by C6 group

<400> SEQUENCE: 1250
gcauucacgc gugccuuaaa u                                                    21

<210> SEQ ID NO 1251
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by C6 group

<400> SEQUENCE: 1251
gcauucacgc gugccuuaaa u                                                    21

<210> SEQ ID NO 1252
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C6 group

<400> SEQUENCE: 1252
gcauucccgc gugccuuaaa u                                                    21

<210> SEQ ID NO 1253
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by C6 group

<400> SEQUENCE: 1253
gcauuaccgc gugccuuaaa u                                                    21

<210> SEQ ID NO 1254
<211> LENGTH: 21
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by C6 group

<400> SEQUENCE: 1254
gcaucaccgc gugccuuaaa u                                              21

<210> SEQ ID NO 1255
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)...(4)
<223> OTHER INFORMATION: bases linked by C6 group

<400> SEQUENCE: 1255
gcaucaccgc gugccuuaaa u                                              21

<210> SEQ ID NO 1256
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)...(3)
<223> OTHER INFORMATION: bases linked by C6 group

<400> SEQUENCE: 1256
gcuucaccgc gugccuuaaa u                                              21

<210> SEQ ID NO 1257
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: bases linked by C6 group

<400> SEQUENCE: 1257
gauucaccgc gugccuuaaa u                                              21

<210> SEQ ID NO 1258
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(1)
<223> OTHER INFORMATION: C6 group at 5' end

<400> SEQUENCE: 1258
cauucaccgc gugccuuaaa u                                              21

<210> SEQ ID NO 1259
<211> LENGTH: 21
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(1)
<223> OTHER INFORMATION: C6 group at 5' end

<400> SEQUENCE: 1259
uaaggcacgc ggugaaugcc a                                              21

<210> SEQ ID NO 1260
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: bases linked by C6 group

<400> SEQUENCE: 1260
uaaggcacgc ggugaaugcc a                                              21

<210> SEQ ID NO 1261
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)...(3)
<223> OTHER INFORMATION: bases linked by C6 group

<400> SEQUENCE: 1261
uuaggcacgc ggugaaugcc a                                              21

<210> SEQ ID NO 1262
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)...(4)
<223> OTHER INFORMATION: bases linked by C6 group

<400> SEQUENCE: 1262
uuaggcacgc ggugaaugcc a                                              21

<210> SEQ ID NO 1263
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by C6 group

<400> SEQUENCE: 1263
uuaagcacgc ggugaaugcc a                                              21

<210> SEQ ID NO 1264
```

```
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by C6 group

<400> SEQUENCE: 1264
uuaagcacgc ggugaaugcc a                                              21

<210> SEQ ID NO 1265
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C6 group

<400> SEQUENCE: 1265
uuaaggacgc ggugaaugcc a                                              21

<210> SEQ ID NO 1266
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by C6 group

<400> SEQUENCE: 1266
uuaaggccgc ggugaaugcc a                                              21

<210> SEQ ID NO 1267
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by C6 group

<400> SEQUENCE: 1267
uuaaggcagc ggugaaugcc a                                              21

<210> SEQ ID NO 1268
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C6 group

<400> SEQUENCE: 1268
uuaaggcacc ggugaaugcc a                                              21
```

```
<210> SEQ ID NO 1269
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C6 group

<400> SEQUENCE: 1269
uuaaggcacg ggugaaugcc a                                              21

<210> SEQ ID NO 1270
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by C6 group

<400> SEQUENCE: 1270
uuaaggcacg cgugaaugcc a                                              21

<210> SEQ ID NO 1271
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)...(13)
<223> OTHER INFORMATION: bases linked by C6 group

<400> SEQUENCE: 1271
uuaaggcacg cgugaaugcc a                                              21

<210> SEQ ID NO 1272
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)...(14)
<223> OTHER INFORMATION: bases linked by C6 group

<400> SEQUENCE: 1272
uuaaggcacg cgggaaugcc a                                              21

<210> SEQ ID NO 1273
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)...(15)
<223> OTHER INFORMATION: bases linked by C6 group

<400> SEQUENCE: 1273
uuaaggcacg cgguaaugcc a                                              21
```

```
<210> SEQ ID NO 1274
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)...(16)
<223> OTHER INFORMATION: bases linked by C6 group

<400> SEQUENCE: 1274
uuaaggcacg cggugaugcc a                                              21

<210> SEQ ID NO 1275
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)...(17)
<223> OTHER INFORMATION: bases linked by C6 group

<400> SEQUENCE: 1275
uuaaggcacg cggugaugcc a                                              21

<210> SEQ ID NO 1276
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)...(18)
<223> OTHER INFORMATION: bases linked by C6 group

<400> SEQUENCE: 1276
uuaaggcacg cggugaagcc a                                              21

<210> SEQ ID NO 1277
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)...(19)
<223> OTHER INFORMATION: bases linked by C6 group

<400> SEQUENCE: 1277
uuaaggcacg cggugaaucc a                                              21

<210> SEQ ID NO 1278
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)...(20)
<223> OTHER INFORMATION: bases linked by C6 group

<400> SEQUENCE: 1278
uuaaggcacg cggugaaugc a                                              21
```

<210> SEQ ID NO 1279
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)...(21)
<223> OTHER INFORMATION: bases linked by C6 group

<400> SEQUENCE: 1279
uuaaggcacg cggugaaugc a    21

<210> SEQ ID NO 1280
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(2)
<223> OTHER INFORMATION: bases linked by C6 group

<400> SEQUENCE: 1280
uuaaggcacg cggugaaugc ca    22

<210> SEQ ID NO 1281
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)...(3)
<223> OTHER INFORMATION: bases linked by C6 group

<400> SEQUENCE: 1281
uuaaggcacg cggugaaugc ca    22

<210> SEQ ID NO 1282
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)...(4)
<223> OTHER INFORMATION: bases linked by C6 group

<400> SEQUENCE: 1282
uuaaggcacg cggugaaugc ca    22

<210> SEQ ID NO 1283
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)...(5)
<223> OTHER INFORMATION: bases linked by C6 group

<400> SEQUENCE: 1283
uuaaggcacg cggugaaugc ca					22

<210> SEQ ID NO 1284
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)...(6)
<223> OTHER INFORMATION: bases linked by C6 group

<400> SEQUENCE: 1284
uuaaggcacg cggugaaugc ca					22

<210> SEQ ID NO 1285
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C6 group

<400> SEQUENCE: 1285
uuaaggcacg cggugaaugc ca					22

<210> SEQ ID NO 1286
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by C6 group

<400> SEQUENCE: 1286
uuaaggcacg cggugaaugc ca					22

<210> SEQ ID NO 1287
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)
<223> OTHER INFORMATION: bases linked by C6 group

<400> SEQUENCE: 1287
uuaaggcacg cggugaaugc ca					22

<210> SEQ ID NO 1288
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C6 group

<400> SEQUENCE: 1288
uuaaggcacg cggugaaugc ca                                                    22

<210> SEQ ID NO 1289
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C6 group

<400> SEQUENCE: 1289
uuaaggcacg cggugaaugc ca                                                    22

<210> SEQ ID NO 1290
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)...(12)
<223> OTHER INFORMATION: bases linked by C6 group

<400> SEQUENCE: 1290
uuaaggcacg cggugaaugc ca                                                    22

<210> SEQ ID NO 1291
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)...(13)
<223> OTHER INFORMATION: bases linked by C6 group

<400> SEQUENCE: 1291
uuaaggcacg cggugaaugc ca                                                    22

<210> SEQ ID NO 1292
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)...(14)
<223> OTHER INFORMATION: bases linked by C6 group

<400> SEQUENCE: 1292
uuaaggcacg cggugaaugc ca                                                    22

<210> SEQ ID NO 1293
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)...(15)
<223> OTHER INFORMATION: bases linked by C6 group

```
<400> SEQUENCE: 1293
uuaaggcacg cggugaaugc ca                                              22

<210> SEQ ID NO 1294
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)...(16)
<223> OTHER INFORMATION: bases linked by C6 group

<400> SEQUENCE: 1294
uuaaggcacg cggugaaugc ca                                              22

<210> SEQ ID NO 1295
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)...(17)
<223> OTHER INFORMATION: bases linked by C6 group

<400> SEQUENCE: 1295
uuaaggcacg cggugaaugc ca                                              22

<210> SEQ ID NO 1296
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)...(18)
<223> OTHER INFORMATION: bases linked by C6 group

<400> SEQUENCE: 1296
uuaaggcacg cggugaaugc ca                                              22

<210> SEQ ID NO 1297
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)...(19)
<223> OTHER INFORMATION: bases linked by C6 group

<400> SEQUENCE: 1297
uuaaggcacg cggugaaugc ca                                              22

<210> SEQ ID NO 1298
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)...(20)
<223> OTHER INFORMATION: bases linked by C6 group
```

<400> SEQUENCE: 1298
uuaaggcacg cggugaaugc ca                                            22

<210> SEQ ID NO 1299
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)...(21)
<223> OTHER INFORMATION: bases linked by C6 group

<400> SEQUENCE: 1299
uuaaggcacg cggugaaugc ca                                            22

<210> SEQ ID NO 1300
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)...(21)
<223> OTHER INFORMATION: bases linked by C6 group

<400> SEQUENCE: 1300
uuaaggcacg cggugaaugc ca                                            22

<210> SEQ ID NO 1301
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C6 group

<400> SEQUENCE: 1301
gcauucaccg cgugccuuaa au                                            22

<210> SEQ ID NO 1302
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)...(10)
<223> OTHER INFORMATION: bases linked by C6 group

<400> SEQUENCE: 1302
gcauucaccg cgugccuuaa au                                            22

<210> SEQ ID NO 1303
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)...(9)

<223> OTHER INFORMATION: bases linked by C6 group

<400> SEQUENCE: 1303
gcauucaccg cgugccuuaa au                                              22

<210> SEQ ID NO 1304
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)...(8)
<223> OTHER INFORMATION: bases linked by C6 group

<400> SEQUENCE: 1304
gcauucaccg cgugccuuaa au                                              22

<210> SEQ ID NO 1305
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)...(7)
<223> OTHER INFORMATION: bases linked by C6 group

<400> SEQUENCE: 1305
gcauucaccg cgugccuuaa au                                              22

<210> SEQ ID NO 1306
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C3 group

<400> SEQUENCE: 1306
gcauucaccg cgugccuuaa au                                              22

<210> SEQ ID NO 1307
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)...(11)
<223> OTHER INFORMATION: bases linked by C3 group

<400> SEQUENCE: 1307
uuaaggcacg cggugaaugc ca                                              22

<210> SEQ ID NO 1308
<211> LENGTH: 44
<212> TYPE: RNA
<213> ORGANISM: Artificial Sequence
<220> FEATURE:
<223> OTHER INFORMATION: Synthetic

<400> SEQUENCE: 1308

```
ucgagcauau acuggcauuc accgcgugcc uuaauuguuu aaaa                          44

<210> SEQ ID NO 1309
<211> LENGTH: 44
<212> TYPE: RNA
<213> ORGANISM: Artificial Sequence
<220> FEATURE:
<223> OTHER INFORMATION: Synthetic

<400> SEQUENCE: 1309
ucgagcauau acuuaauguu uucaaacgcc uuaauuguuu aaaa                          44

<210> SEQ ID NO 1310
<211> LENGTH: 43
<212> TYPE: RNA
<213> ORGANISM: Artificial Sequence
<220> FEATURE:
<223> OTHER INFORMATION: Synthetic

<400> SEQUENCE: 1310
ucgagcauau acuuaauguu uuaaaccgcu uaauuguuua aaa                           43
```